United States Patent
Zhou et al.

(10) Patent No.: US 11,873,503 B2
(45) Date of Patent: Jan. 16, 2024

(54) NUCLEOTIDE SEQUENCES AND CORRESPONDING POLYPEPTIDES CONFERRING MODULATED GROWTH RATE AND BIOMASS IN PLANTS GROWN IN SALINE AND OXIDATIVE CONDITIONS

(71) Applicant: Ceres, Inc., Thousand Oaks, CA (US)

(72) Inventors: Fasong Zhou, Oxnard, CA (US); Kenneth A. Feldmann, Tucson, AZ (US); Julissa Sosa, Northridge, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 17/813,816

(22) Filed: Jul. 20, 2022

(65) Prior Publication Data

US 2023/0116932 A1    Apr. 20, 2023

Related U.S. Application Data

(60) Division of application No. 17/063,395, filed on Oct. 5, 2020, now Pat. No. 11,447,792, which is a division of application No. 16/694,109, filed on Nov. 25, 2019, now Pat. No. 11,034,972, which is a division of application No. 16/265,525, filed on Feb. 1, 2019, now Pat. No. 10,619,166, which is a division of application No. 15/962,986, filed on Apr. 25, 2018, now Pat. No. 10,233,461, which is a division of application No. 15/679,052, filed on Aug. 16, 2017, now Pat. No. 10,006,043, which is a division of application No. 13/465,841, filed on May 7, 2012, now Pat. No. 9,765,355, which is a division of application No. 11/858,117, filed on Sep. 19, 2007, now abandoned, which is a continuation-in-part of application No. PCT/US2007/006544, filed on Mar. 14, 2007.

(60) Provisional application No. 60/782,735, filed on Mar. 14, 2006.

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8271* (2013.01)

(58) Field of Classification Search
None
See application file for complete search history.

(56) References Cited

U.S. PATENT DOCUMENTS

| | | | |
|---|---|---|---|
| 6,281,411 B1 | 8/2001 | Adams et al. | |
| 6,867,351 B2 | 3/2005 | da Costa e Silva et al. | |
| 9,765,355 B2 | 9/2017 | Zhou et al. | |
| 10,006,043 B2 | 6/2018 | Zhou et al. | |
| 10,233,461 B2 | 3/2019 | Zhou et al. | |
| 10,619,166 B2 | 4/2020 | Zhou et al. | |
| 11,028,405 B2 | 6/2021 | Zhou et al. | |
| 11,034,972 B2 | 6/2021 | Zhou et al. | |
| 11,142,772 B2 | 10/2021 | Zhou et al. | |
| 11,447,792 B2 | 9/2022 | Zhou et al. | |
| 11,459,581 B2 | 10/2022 | Zhou et al. | |
| 11,667,926 B2 | 6/2023 | Zhou et al. | |
| 11,674,149 B2 | 6/2023 | Zhou et al. | |
| 2004/0034888 A1* | 2/2004 | Liu ........................ | C07H 21/04 536/23.6 |
| 2006/0107345 A1 | 5/2006 | Alexandrov et al. | |
| 2006/0150283 A1 | 7/2006 | Alexandrov et al. | |
| 2007/0214517 A1 | 9/2007 | Alexandrov et al. | |
| 2013/0042367 A1 | 2/2013 | Nadzan et al. | |
| 2015/0259699 A1 | 9/2015 | Nadzan et al. | |
| 2017/0037426 A1* | 2/2017 | Alexandrov ....... | C12N 15/8271 |
| 2018/0223303 A1 | 8/2018 | Alexandrov et al. | |
| 2020/0165625 A1 | 5/2020 | Zhou et al. | |
| 2020/0181636 A1 | 6/2020 | Zhou et al. | |
| 2021/0130841 A1 | 5/2021 | Zhou et al. | |
| 2021/0317469 A1 | 10/2021 | Zhou et al. | |
| 2021/0348184 A1 | 11/2021 | Zhou et al. | |
| 2023/0132139 A1 | 4/2023 | Zhou et al. | |

FOREIGN PATENT DOCUMENTS

| | | |
|---|---|---|
| EP | 1033405 A2 | 9/2000 |
| WO | WO 1999/061616 A2 | 12/1999 |
| WO | WO 2001/055433 | 8/2001 |
| WO | WO 2004/092326 A2 | 10/2004 |
| WO | WO 20041092326 A3 | 10/2004 |

(Continued)

OTHER PUBLICATIONS

Keskin et al. (Protein Science, 13:1043-1055, 2004).*
Thornton et al. (Nature structural Biology, structural genomics supplement, Nov. 2000).*
Ngo et al., (The Protein Folding Problem and Tertiary Structure Prediction, K. Merz., and S. Le Grand (eds.) pp. 492-495,1994).*
Guo et al. (PNAS, 101: 9205-9210, 2004 ).*
Wells (Biochemistry 29:8509-8517, 1990).*
Kang et al. (Cell death and differentiation, 13:84-95, 2006).*
Rhoads et al. (The FASEB Journal, 11:331-340, 1997).*
Doerks et al., (TIG, 14:248-250, 1998).*
Smith et al. (Nature Biotechnology, 15:1222-1223, 1997).*
Bork et al. (TIG, 12:425-427, 1996).*
U.S. Appl. No. 17/813,842, filed Jul. 20, 2022, Zhou et al.
U.S. Appl. No. 17/064,117, filed Oct. 6, 2020, Zhou et al.
U.S. Appl. No. 17/220,681, filed Apr. 1, 2021, Zhou et al.
U.S. Appl. No. 17/221,604, filed Apr. 2, 2021, Zhou et al.

(Continued)

*Primary Examiner* — Vinod Kumar
(74) *Attorney, Agent, or Firm* — Dentons US LLP

(57) ABSTRACT

The present invention relates to isolated nucleic acid molecules and their corresponding encoded polypeptides able confer the trait of improved plant size, vegetative growth, growth rate, seedling vigor and/or biomass in plants challenged with saline and/or oxidative stress conditions. The present invention further relates to the use of these nucleic acid molecules and polypeptides in making transgenic plants, plant cells, plant materials or seeds of a plant having plant size, vegetative growth, growth rate, seedling vigor and/or biomass that are improved in saline and/or oxidative stress conditions with respect to wild-type plants grown under similar conditions.

10 Claims, 18 Drawing Sheets

Specification includes a Sequence Listing.

(56) References Cited

FOREIGN PATENT DOCUMENTS

WO   WO 2006/026756 A2   3/2006

OTHER PUBLICATIONS

Aroca et al., "The role of aquaporins and membrane damage in chilling and hydrogen peroxide induced changes in the hydraulic conductance of maize roots", Plant Physiol., 137(1):341-53, 2005, Epub. Dec. 10, 2004.
Aviv et al., "Runaway cell death, but not basal disease resistance, in Isd1 is SAand NIM1/NPR1-dependent", Plant J., 29(3):381-91, 2002.
Borsani et al., "Evidence for the role of salicylic acid in the oxidative damage generated by NaCl and osmotic stress in Arabidopsis seedlings," Plant Physiol., 126:1024-1030, 2001.
Brisson et al., "Function of Oxidative CROSS-Linking of Cell Wall Structural Proteins in Plant Disease Resistance," Plant Cell, 6(12):1703-1712, 1994.
Cao et al., "Characterization of an Arabidopsis mutant that is nonresponsive to inducers of systemic acquired-resistance," Plant Cell, 6:1583-1592, 1994.
Dat et al., "Changes in salicylic acid and antioxidants during induced thermotolerance in mustard seedlings," Plant Physiol., 118:1455-1461, 1998.
Delaney et al., "A central role of salicylic acid in plant-disease resistance," Science, 266:1247-1250, 1994.
Kim et al.,, "Effects of salicylic acid on paraquat tolerance in Arabidopsis thaliana plants," J. Plant Biol., 46:31-37, 2003.
Lamb et al., "The oxidative burst in plant disease resistance," Annu. Rev. Plant Physiol. Plant Mol. Biol., 48:251-275, Jun. 1997.
Larkindale et al., "Protection against heat stress-induced oxidative damage in Arabidopsis involves calcium, abscisic acid, ethylene, and salicylic acid," Plant Physiol., 128:682-695, 2002.
Lee et al., "Rapid accumulation of hydrogen peroxide in cucumber roots due to exposure to low temperature appears to mediate decreases in water transport, "J. Exp. Bot., 55(403):1733-41, Epub. Jun. 18, 2004.
Levine et al., "H2O2 from the oxidative burst orchestrates the plant hypersensitivedisease resistance response," Cell, 18,79(4):583-93, 1994.
Luna et al., "Drought controls on H2O2 accumulation, catalase (CAT) activity and CAT gene expression in wheat," J Exp Bot., 56(411):417-23, 2005, Epub. Nov. 29, 2004. 2004.
Martinez et al., "Salicylic acid regulates flowering time and links defence responses and reproductive development," Plant J, 37:209-217, 2004.
Noctor et al., "Drought and oxidative load in the leaves of C3 plants: a predominant role forphotorespiration?" Ann Bot (Lond), 89:841-50, 2002.
Rusterucci et al., "The disease resistance signaling components EDS1 and PAD4 are essential regulators of the cell death pathway controlled by LSD1 in Arabidopsis," Plant Cell, 2001.
Scott et al., "Salicylate accumulation inhibits growth at chilling temperature in Arabidopsis," Plant Physiol., 135:1040-1049, 2004.
Senaratna et al., "Acetyl salicylic acid (Aspirin) and salicylic acid induce multiple stress tolerance in bean and tomato plants," Plant Growth Regul., 30:157-161, 2000.
Surplus et al., "Ultraviolet-B-induced responses in Arabidopsis thaliana: role of salicylic acid and reactive oxygen species in the regulation of transcripts encoding photosynthetic and acidic pathogenesis-related proteins," Plant Cell Environ., 21:685-694, 1998.
Zhou et al., "High humidity suppresses ssi4-mediated cell death and disease resistance upstream of MAP kinase activation, H2O2 production and defense gene expression," Plant J, 39(6):920-32, 2004.
Zhou et al., "Proton extrusion is an essential signaling component in the HR of epidermal single cells in the barley-powdery mildew interaction," Plant J., 23(2):245-54, 2000.
Ngo et al., The Protein Folder Problem and Tertiary Structure Prediction, K. Merz., and S. Le Grand (eds.), 492-495, 1994.
NCBI GenBank Accession No. NP 179785 (Aug. 21, 2001).
NCBI GenBank Accession No. NP 665906 (Jan. 29, 2002).
NCBI GenBank Accession No. NP665305 (Jan. 29, 2002).
NCBI GenBank Accession No. NP567957 (Jan. 30, 2002).
NCBI GenBank Accession No. NP 566785 (Jan. 29, 2002).
NCBI GenBank Accession No. NP_567754 (Jan. 29, 2002).
NCBI GenBank Accession No. NM 129505 (Aug. 21, 2001).
NCBI GenBank Accession No. NM '119581 (Jan. 30, 2002).
NCBI GenBank Accession No. BT018295 (Oct. 27, 2004).
NCBI GenBank Accession No. NM_127763 (Nov. 4, 2005).
NCBI GenBank Accession No. BT003928 (Feb. 14, 2003).
NCBI GenBank Accession No. AY086786 (Jan. 27, 2006).
NCBI GenBank Accession No. AY092961 (Apr. 21, 2002).
NCBI GenBank Accession No. AF410323 (Aug. 27, 2001).
USPTO: Office Action regarding U.S. Appl. No. 16/265,525, dated Sep. 20, 2019.
Response to Office Action regarding U.S. Appl. No. 16/265,525, filed Nov. 19, 2019.
Supplemental Response to Office Action regarding U.S. Appl. No. 16/265,525, filed Nov. 27, 2019.
USPTO: Notice of Allowance regarding U.S. Appl. No. 16/265,525, dated Dec. 4, 2019.

\* cited by examiner

| | | | | | |
|---|---|---|---|---|---|
| SEQ ID NO: 55 | KHEAVMKRER | ELAYAFNYDG | | | 253 |
| SEQ ID NO: 96 | LHSRRHAGG- | YSPIDFNGGDD | | | 309 |
| SEQ ID NO: 100 | LDELXXVSG- | TTASGV | VRLPFLDGHG | WFNDFG | 310 |
| SEQ ID NO: 66 | LERQSNYSS- | CCTESLGGE- | MSFSSTSD | LRRWLR | 355 |
| SEQ ID NO: 95 | SEQRSTVSS- | SCAESLGGEP | SPSSTTD | LRRWLR | 361 |
| SEQ ID NO: 93 | SEQRSTVSSL | SCAESVGGEP | VSPSSTTD | LRRWLR | 373 |
| SEQ ID NO: 107 | SEQRSNVSS- | SCAESLGGDV | WSPSSTTD | LRRWLR | 291 |

Figure 2

| SEQ-ID-NO-42 | MGKKGSMFS | A | KRVFTPHS | KEKCLSNNNC | EPEIKSENKE | KKKKGFGKKL | 49 |
| --- | --- | --- | --- | --- | --- | --- | --- |
| SEQ-ID-NO-47 | MERKKGWFE | RI | KRLFI SEP | KQK-PKP | -DKKVK | SKRWLVGKLK | 41 |
| SEQ-ID-NO-44 | MKKKKSWFS | LN | KRLFI WDT | H--STQ | -DKKEK | RRKWI FGRLK | 58 |
| SEQ-ID-NO-54 | MKKKKSWFN | LN | KRFFLFET | ---LIN | -AQKDN | RRKWMFGRIFR | 37 |
| SEQ-ID-NO-43 | MGRATRWFK | GLFG | -------- | ---KP | -SSCSG | TDSGTISNRL | 31 |
| SEQ-ID-NO-41 | --------- | ---- | -------- | -------- | -------- | ---------- | 1 |
| SEQ-ID-NO-45 | MGFFGRLFG | SKKKS | -------- | ---CRA | -ASSRD | KRRWSFI TTRS | 32 |
| SEQ-ID-NO-50 | MGKASKWFR | AN | GLKKFDP | PLDHPCT | -TRSKD | KRRWSFVKSR | 41 |
| SEQ-ID-NO-59 | MGWASRWLR | GLL | GGGKKPN | SGS-GDP | -KPARE | KKKWGFGKSF | 40 |
| SEQ-ID-NO-55 | MGWAPRWLR | GLL | GGGRKA- | ---AVT | -KPAKE | KKLMGFGKSF | 36 |
| SEQ-ID-NO-58 | MGWAPRWLR | GLL | GGGNKA- | ---AET | -KPVKE | KRRWSFGKSF | 36 |

| SEQ-ID-NO-42 | RNGETNSFLP | I FRQPSSIEK | -------- | LSE-EREHNL | VFRPPTPTDR | 90 |
| --- | --- | --- | --- | --- | --- | --- |
| SEQ-ID-NO-47 | TCHSFA---- | LPAFEPEPAT | -----GC | LRCAEEEQS | -KHAVA | 75 |
| SEQ-ID-NO-44 | SKRLPS---- | -KAPLPSK | ------T | LSEAEQEQS | -KHALT | 69 |
| SEQ-ID-NO-54 | TKRL PS---- | -KAPSFPR | -----GTT | KYETEEDQK | -KHALT | 68 |
| SEQ-ID-NO-43 | DRSLCD---SY | ETIPPNISEK | -----DS | AGEEEKERR | -THAI A | 73 |
| SEQ-ID-NO-41 | --------- | ---------- | -------- | ---------- | ---------- | 1 |
| SEQ-ID-NO-45 | --------- | -APAVTS | -----V | VEQNGLDAD | -KHAI A | 61 |
| SEQ-ID-NO-50 | SNSSKR--- | QQDIEASKTS | -----AS | GQEFEEDPN | -KHAVA | 78 |
| SEQ-ID-NO-59 | REKDHCHCQR | PPFFSAAVQR | -----Y | SDEGDDEQS | -KRAIA | 84 |
| SEQ-ID-NO-55 | REKSPAHPFF | RPRTPSVQPT | AVTFRRAYTA | PDEADDEQS | -KRAIA | 80 |
| SEQ-ID-NO-58 | REKAPAPYAA | RPPTPPVQPT | AVTFRRGYAPA | PDEADDEQS | -KRAIA | 80 |

| SEQ-ID-NO-42 | ANSSSI SVAS | PLMRPASFKV | PSQRYVSSPK | PI SPRVAYPQ | VHYPKPPSFK | 140 |
| --- | --- | --- | --- | --- | --- | --- |
| SEQ-ID-NO-47 | VAL-SAAE | AAVA-AHAA | EVVRLTGPPS | PAPAPAR | -E | 113 |
| SEQ-ID-NO-44 | VALA-SAAE | AAVA-AHAA | EVVRLTGCRN | ENSEESQPVK | TRNGAPOSTY | 119 |
| SEQ-ID-NO-54 | VALAAPAAE | AAVT-AHAAQ | EVVRLTGNCA | PRAKEEQ | TNDVKPDCSS | 115 |
| SEQ-ID-NO-43 | VAAAAASAAE | AAVAAAAKAAA | AVVRLQGQGK | SGPLGGG | - | 110 |
| SEQ-ID-NO-41 | --------- | ---------- | ---------- | ---------- | ---------- | 1 |
| SEQ-ID-NO-45 | VAAATAAVAE | AALIAAHAA | EVVRLTSGNG | GRNWGGG | GNSSVFOI GR | 108 |
| SEQ-ID-NO-50 | VAAATAAVAE | AAVAAACAAA | EVVRLTSSGR | CVNNSVA | --NV | 117 |
| SEQ-ID-NO-59 | VAAATAAVAE | AAVAAACAAA | AVVRLTSSGR | CAPAAAK | - | 121 |
| SEQ-ID-NO-55 | VAAATAAVAE | AAVAAAGAAA | AVVRLTSSGR | CPPAAAK | - | 117 |
| SEQ-ID-NO-58 | VAAATAAVAE | AAVAAAGAAA | AVVRLTSSGR | CAPAAAK | - | 117 |

| | | | |
|---|---|---|---|
| SEQ ID NO: 42 | FNRFA | | 517 |
| SEQ ID NO: 47 | FGSEAALHOM | QMEHYTPIR | 475 |
| SEQ ID NO: 44 | CSLPNWDROA | FFK | 460 |
| SEQ ID NO: 54 | | | 364 |
| SEQ ID NO: 43 | | | 383 |
| SEQ ID NO: 41 | YTSFFSSNPL | FFQ | 252 |
| SEQ ID NO: 45 | HSSFLV | | 403 |
| SEQ ID NO: 50 | V | | 477 |
| SEQ ID NO: 59 | | | 464 |
| SEQ ID NO: 65 | | | 457 |
| SEQ ID NO: 68 | | | 455 |

[Sequence alignment figure showing SEQ ID NOs: 135, 141, 147, 145, 140, 149, 151 across multiple alignment blocks]

| | | | | | | |
|---|---|---|---|---|---|---|
| SEQ-ID-NO-35 | MRGFPVPVTS | WSSAALLGRS | ISSARDAAEA | SSPITAAEMV | RVAKEVANAA | 50 |
| SEQ-ID-NO-36 | -----MESRL | LRSAALLARA | ARLARAAATS | TGRAVTAE-- | HLAEVVASAA | 43 |
| SEQ-ID-NO-35 | DACGVSGKKL | LEAAEALSRS | DTDAEPRRRA | AERIFDAASM | VAKEADASGA | 100 |
| SEQ-ID-NO-36 | GDRGFPSGAL | RQAALALARS | -SAPEARPRA | TAEVVRAAAM | VFRAAQEAGS | 92 |
| SEQ-ID-NO-35 | SGLSDAAQNL | TCATYAFSVA | ASGWGSLPES | STSGRDAGDL | LTEPLLGSCQ | 150 |
| SEQ-ID-NO-36 | PGVAEVAGDL | AHAAHDCVRA | ------LVES | GPAAERPRCL | LR--LWRRKN | 134 |
| SEQ-ID-NO-35 | DKNEKMTGEG | KDFSEM---- | RNSAADSDPL | QQSEIKESSL | FGKCKELLNY | 196 |
| SEQ-ID-NO-36 | RHNKNAAGEA | DLEAPLLHPH | ERPSSSSSPI | GASLSEIIEL | SESERDFINY | 184 |
| SEQ-ID-NO-35 | GFLGGPALLP | YL--GSGLRK | TVSPCSPSVF | HYIFSSWWIC | ---------- | 235 |
| SEQ-ID-NO-36 | GMFGALAIFP | YLTRTGGLKS | AYSPLSPSTF | HIIFCTWWIC | VGLDVLCGNR | 234 |
| SEQ-ID-NO-35 | ---------- | ---------- | ---------- | ---------- | ---------- | 235 |
| SEQ-ID-NO-36 | GRAMMKNILA | FILAFYARAS | ARLAILGVSL | LVILYSHLEL | APNEIYTLYI | 284 |
| SEQ-ID-NO-35 | VVGSHEQGDL | KILHIDRITS | HPND---K | 260 | | |
| SEQ-ID-NO-36 | LLGAATCMHL | LVWAMDYMSR | APGDAAD | 311 | | |

SEQUENCE LISTING

```
Sequence total quantity: 168
SEQ ID NO: 1            moltype = DNA  length = 2343
FEATURE                 Location/Qualifiers
source                  1..2343
                        mol_type = other DNA
                        organism = Panicum virgatum
misc_feature            1..2343
                        note = Ceres CLONE ID no.1792354
misc_feature            1..2343
                        note = Encodes the peptide sequence at SEQ ID NO. 2
SEQUENCE: 1
agtgactagt gagctcactc cctcctcctt cccacttgac tctgcccgcc agctactgaa   60
ccaaccaaca aatacctccg ggctccctcc ggctttgcca ctcccatgga ttggaggttg   120
gaggcctgaa gggggaggtg ggtcgccgga cagggacggg gagacggcga gagggcgttc   180
cgcaggagcc gttcccgtgc ttcctccacc gaccgggccg acgcgccgcg ccgctgtttc   240
aggttccaga atttcaagta ttggccgctt taggatacta tgggaaagtc cccggggaag   300
tggatcaagt ctgtgctctt ggggaagaaa tcgactaaat ccggttctac caaggcaaat   360
gagtcgaagg ctacaaataa caatggacac tcagctgggg aggagcgtgc attttctgaa   420
aattctccag tgatctctga gccggtgctt gttgaagccc acaaaaatgg agctgtttca   480
gttaatggga aggctgaaga tgtcaatttg ccaagtgaca gggctggcca acaagatctg   540
cagaaccaaa gtattgttga gtccgaaaca tcagttcctg ggcaattggg agaagaccaa   600
gctgcagtga aggcacaggc agcatttcgc ggttacctag cacgaaggtc attccgtgca   660
ttgaaaggta tcataagact ccaggtactg attcgagggc atcttgtaag gagacaggct   720
gtttcaaccc ttcgaactac ttggttgatt gtgaagtttc aatctctagt tcgtggaaga   780
aatgtcagac tctctggtgc tgacattcaa ctcaatgtga agcttggcca acataacctt   840
ggtggcacta gatcatctga tgcatggaaa gagaagttat cttcaaatgc ctatgttcgg   900
aagcttctgt cttcaccaat agtgctagaa cctcttcact tccagtatga caagagggat   960
cccaattcaa cctataactg gctagagaga tggaccatag gctgcatctg gaagcctgtt   1020
tttcaaccaa aaagagttcc tgatgggaaa ctgctggtaa ggaaggctag ttatgcaatg   1080
gaaactgaat cagccaagtt aaagcgcaac attaggaagg gctctgctgc tacagttgag   1140
agtttccata caagagtgac tggtgaatct gagaaactta aacgtaatcc aaagaaattc   1200
tcaaacttcc ctgctgactc agtaccagat agccagttat ctgaacttga gaaggttaaa   1260
aggaacctga ggaaggtaac tgattccatg gctgaagcct caaagatctc tagttccagg   1320
gttgattcct caaaggtatc tgattctaca cctgatgctc caaagtatc taatcctgtg   1380
gccgaaatct caaagacatc tagtctcctg aacgggatct ctgaccatca agacagccaa   1440
tgtgaaaaag cactacagaa tacacgtgag gcttcatttc ctcttgaaac tcaagattac   1500
tctggcaatg gtcagctatt ggaatattca gatatggata acttcgactt ggtacctggt   1560
ttgaaaagtg atctggaaac tcagcttgat tcagtttcta taggagaaaa tgttgatgag   1620
cccactgttg gtgcttcagc agctgaaggt atgccactgc agaacattga tgagcccatt   1680
agtttaggga agaagagga agcaaggtcc aaggaagagc atctgtctaa tggaagcctt   1740
agaactggca agagaaagtc ttcatcccca tacaaatcag aatatgtgga aaacgggact   1800
cacactactc ctgctcagcc aaggaagcca agctatatgg ctgcaacgga gtctgcgaag   1860
gcgaaattac gagcacagaa ttcacccagg gtggattctg attcatcagc agaaaagaat   1920
ggcttcactc gacgccactc tcttccttcc ggtacaaaca gtagggcgat caaagctgaa   1980
tggaagcgct gaggaggcat tgacttgaat tgaatagtgc gattgtctga atctctgctg   2040
ggtgaactct gccgctgctt gctcctttt atttatcctg cgatgtaaag agaagacatt   2100
gtccctgtat tgaacaatct ttgtgatgag tgcgtctggt tcagtctgtg gtaggttcac   2160
gtgccaggcc tagtgccccg ttcattgtat agtcacagtt ctctcgggat tgaaatcgat   2220
tcctcgtgta agctgatgtt aggactgcag tctgatcgaa taacatcatc cgcttgcaca   2280
ctgccttaag cccttaattg atatgatacc gggcaatttc gtgaaaaaaa aaaaaaaaaa   2340
aaa                                                                 2343
```

```
SEQ ID NO: 2            moltype = AA   length = 570
FEATURE                 Location/Qualifiers
source                  1..570
                        mol_type = protein
                        organism = Panicum virgatum
REGION                  1..570
                        note = Ceres CLONE ID no.1792354
REGION                  1..570
                        note = Score of 822.8 for HMM of FIGURE 5.
REGION                  106..126
                        note = Pfam Name: IQ Pfam Description: IQ
                        calmodulin-binding motif
SEQUENCE: 2
MGKSPGKWIK SVLLGKKSTK SGSTKANESK ATNNNGHSAG EERAFSENSP VISEPVLVEA   60
HKNGAVSVNG KAEDVNLPSD RAGQQDLQNQ SIVESETSVP GQLGEDQAAV KAQAAFRGYL  120
ARRSFRALKG IIRLQVLIRG HLVRRQAVST LRTTWLIVKF QSLVRGRNVR LSGADIQLNV  180
KLGQHNLGGT RSSDAWKEKL SSNAYVRKLL SSPIVLEPLH FQYDKRDPNS TYNWLERWTI  240
GCIWKPVFQP KRVPDGKLLV RKASYAMETE SAKLKRNIRK GSAATVESFH TRVTGESEKL  300
KRNPKKFSNF PADSVPDSQL SELEKVKRNL RKVTDSMAEA SKISSSRVDS SKVSDSTPDA  360
PKVSNPVAEI SKTSSLLNGI SDHQDSQCEK ALQNTREASF PLETQDYSGN GQLLEYSDMD  420
NFDLVPGLKS DLETQLDSVS IGENVDEPTV GASAAEGMPL QNIDEPISLG KKEEARSKEE  480
HLSNGSLRTG KRKSSSPYKS EYVENGTHTT PAQPRKPSYM AATESAKAKL RAQNSPRVDS  540
DSSAEKNGFT RRHSLPSGTN SRAIKAEWKR                                   570

SEQ ID NO: 3            moltype = DNA   length = 2278
FEATURE                 Location/Qualifiers
source                  1..2278
                        mol_type = other DNA
                        organism = Gossypium hirsutum
misc_feature            1..2278
                        note = Ceres CLONE ID no.1925477
misc_feature            1..2278
                        note = Encodes the peptide sequence at SEQ ID NO 4
SEQUENCE: 3
cccgctccat tgatgtcact aaccctaatt atacttacac acctacttct cttgtgattc     60
attttacaca tttaatttct gaaggccgtt ttcatctctt tcttagcttt tatttagttt    120
taaattcact ccaaaaaaaa aaaaaaaaac actgcacggg aatctcttgt tcgaggaatc    180
cttcacggta cgaaattcgt tcttcagatc tctgaatgct cactgtttaa ctgttccttg    240
gtttttcttc tggtaatgg cagcttagta gcgaacaagg acttcaaatt tgctgcattt    300
ttcagatttc cagatttaga aacttggaat tttaattatt tttgggtcta acggagatgg    360
gaaaatctcc agcaaaatgg atcaagacct tacttcttgg gaagaaatct tcaaagtcca    420
gtttctcaaa aggaaagag aagctgaaat ctgcaaataa aggtaggtt ttggtttctt      480
ccaaggtgac tgtgtctgac ctatcagtgg atcctccatc aatttcagca cctattctag    540
tgaatagcgc taggaatgtg gtggactctg agaagggtat acctgcccaa ttgccaaatg    600
atggggcaaa tattccatct ccaaaagtgg atggaaatga tgccacaact ggtaatttgg    660
gtaacccaga aaatcctgat aggattgggc ttgacccagc tctgtgacg gtacaggctg     720
ctttcagagg ttatctggct cgcagggcat ttcgaaccct caagggcatt ataaggctgc    780
aagcagttat tcgtggtcac ttggttagaa acaagctgt tgctactta tgctgtacat      840
ggggaattgt taagttgcaa gcactagctc gtggtcaaaa ggtcagatgt tcagatattg    900
ccatggaaat acaagaaaaa catctaagac tgcttcaagg ttctaaaagc tcggattcta    960
ttggagtgag cacatcttct aaggtgaaga atttatcaaa taatgtgttt gttcagaagc   1020
ttttggcctc atcaccttct gtattacctc tacaacttca atatgttcca gaggagccta   1080
actcatcctg gcagtggctt ctacgatgga caatgtcaca tttttgggta tcccctttaa   1140
aaccaggtag gagtggaaag acaaaacgaa gtattcagaa actgtccaat gcaaaagttg   1200
ttaatggatc tagtcattct accttggagc atgaaaaaaa caaacgaggt gtgaggagag   1260
tttctggcaa ctcagcagca gattcagttc ggaagcatcc acaaaatgag cttgagaggg   1320
ttaagcgcag tttacgaaag cttttctgact cttcaaagga ggtttctgat aagtctgaag   1380
ttttttaatga gaaaacaaag aagactccga aaaaaacttc taattctaat gaccctgatt   1440
tttcagaaca ggaatccgct gagaagataa gagatgtgac tgcaacacta tcagaactgt   1500
caattcttga ggcagatctg aaaatttccc tagaagatcc ttctcttggt gagcctaatc   1560
tctgtcctgc agttgatttg tcacctgctg aaaacaatcg taaacttgag gtaatagagg   1620
agttaatctc taaagacaag caggttggtg atgagagctc aaacacaagc caaagaagag   1680
cttcttttccc tgcaaaaatt gataatcagg cgaatgggtt aaatctcatg ccaaaagttgc  1740
ccagttatat ggcagcaact gaatctgcaa aagctagact taggggtcaa ggctccccaa   1800
tgtttacccc ggaggctgtt gagaaaaatg ggttaaacag gcgatattct ctgccatctt   1860
caacctatag taatacaagt tcacagtccc cacatggtca aagacgggtt cgagtagctg   1920
gcaaaggtgc taacatcagt gacaaatctc aatcatcctc taaagatgct aatgataagg   1980
ttgtcagagc tgagtggagg aggtaattct tgcatgggga attgtttcga tgaagtttca   2040
atggagtttg tgcacggatg ctacttaaca aaacttccct tatgtgttgt aaacttctga   2100
tgtttggttg tagaagcagg agagtgaatc atctaatctt ttgttgcttg gtgtatcttt   2160
ttaagtttcc ttggcacttt caggtttgta gatgggtaaa tatttgtaga tgttacagtt   2220
ggttatttgg tttatttggt tcgtttgtgt ttgtacgcaa aaaaaaaaaa aaaaaaaa     2278

SEQ ID NO: 4            moltype = AA   length = 549
FEATURE                 Location/Qualifiers
source                  1..549
                        mol_type = protein
                        organism = Gossypium hirsutum
```

| REGION | 1..549 |
| | note = Ceres CLONE ID no.1925477 |
| REGION | 1..549 |
| | note = Score of 1112.9 for HMM of FIGURE 5. |
| REGION | 1..549 |
| | note = Functional Homolog Of Ceres CLONE ID no. 1792354 at SEQ ID NO. 2 |
| REGION | 113..133 |
| | note = Pfam Name: IQ Pfam Description: IQ calmodulin-binding motif |

SEQUENCE: 4

```
MGKSPAKWIK TLLLGKKSSK SSFSKGKEKL KSANKGEVLV SSKVTVSDLS VDPPSISAPI    60
LVNSARNVVD SEKGIPAQLP NDGANIPSPK VDGNDATTGN FGNPENPDRI GLDPAAVTVQ   120
AAFRGYLARR AFRTLKGIIR LQAVIRGHLV RRQAVATLCC TWGIVKLQAL ARGQKVRCSD   180
IAMEIQEKHL RLLQGSKSSD SIGVSTSSKV KNLSNNVFVQ KLLASSPSVL PLQLQYVPEE   240
PNSSWQWLLR WTMSHFWVSP LKPVRSGKTK RSIQKLSNAK VVNGSSHSTL EHEKNKRGVR   300
RVSGNSAADS VRKHPQNELE RVKRSLRKLS DSSKEVSDKS EVFNEKTKKT PKKTSNSNDP   360
DFSEQESAEK IRDVTATLSE LSILEADLKI SLEDPSLGEP NLCPAVDLSP AENNRKLEVI   420
EELISKDKQV GDESSNTSQR RASFPAKIDN QANGLNLMPK VPSYMAATES AKARLRGQGS   480
PMFTPEAVEK NGLNRRYSLP SSTYSNTSSQ SPHGQRRVRV AGKGANISDK SQSSSKDAND   540
KVVRAEWRR                                                          549
```

| SEQ ID NO: 5 | moltype = DNA length = 1908 |
| FEATURE | Location/Qualifiers |
| source | 1..1908 |
| | mol_type = other DNA |
| | organism = Populus balsamifera |
| | sub_species = trichocarpa |
| misc_feature | 1..1908 |
| | note = Ceres ANNOT ID no.1521592 |
| misc_feature | 1..1908 |
| | note = Encodes the peptide sequence at SEQ ID NO 6 |

SEQUENCE: 5

```
atggggagaa aatcacctgc gaaatggata aagactgttt tgtttggaaa gaagtcttcc     60
aaatctctta ttgtcaaagg aagggagaga actgtgaatg acaaagagac attggttgct    120
gtcagagccg tggaagctga tgtgacctca gttcctccgg tggtcaagcc gacagccccc    180
actaccacta atatcactga aaggatgtta gagctagaga gcaggaaaac tacagaatca    240
tcacgtgatg gaggtatatt gtcaactgga aatcaagatg caaatcattc tcaattatac    300
actcctgatg ctcctccatc tgatgctgac aaaataaggc ttgatgaagc tgcgacaatg    360
gcacaagccg catttagggg ttacttggct cgccgagcat ttcgagctct taaaggcata    420
ataaggcttc aggctcttat ccgtggacac ttggttagaa ggcaagctgt tgctactctc    480
tgctgtgtgc tcggagttgt caagttacag gctcttgctc gaggaagaat ggttaggaat    540
tcagagattg gctatgaggt tcataaatta tgcagccaag taaaactgcc ggagggcaag    600
cttgcagatt ctagtggagt tggtatacaa atggccaagc tgtcatcaaa tgcttttgtt    660
cgcaagcttc ttgctccatc acctgctgta atgcctttgc aactccccta tgattccatg    720
gaaccaaact cagttgcaaa ctggttagag tgctggtcag cgtcctcttt ctggaaacca    780
gttcccaac caaaaaaaat tacttgctca aaaactcaga gaaagcagag taatggtcaa    840
atagtggaag ctgaaactgg taggccaaag cgcactgttc ggagggtccc tgctgcaaat    900
gttgacagta cctcagtaca agcagcctct gaatttgaga aacccaagcg caatttgagg    960
aaagtttcaa gccatccagc tgattcagca gaaaattcac agattgagct tgaaaaggta   1020
aagcgcagct taagaaaggt taataacccc gttataagaa actctgctca ttcagaggtt   1080
gaaaatgaaa agccaaagca aggtctagaa aaggtatctg gcacttcagg tgataatgtt   1140
ttgggatgga gcgtaagtaa ttcagctgag aagatgaaga agaagctac cttgacaaca   1200
tccaatgtac ctgatgtggt gaagaatgat ccaaacttga tgtccaagtt gcctgatgca   1260
gagacagctg atgaacctgt agaaatgatc aaggcattgg aatcatcaca tgacgatcaa   1320
gctgtggtag aatctaaagc ttcagtagat actggtggta tagttgagaa atgcaaaata   1380
aatgggaagt ccatacacca ggatgatcca acaagcaatg aaaatcacaa aactgccaag   1440
aaaccttcat tcacaatgaa accagaacgt gccgagaatg ggctacagag cagtcccacc   1500
ctccctagct acatggcagc aactgaatct gcaaaggcaa agctgagaat gcaaggctcc   1560
ccaagattta gtgaagatcg agttgagaaa aataacatca cccgtcgtca ttctctgccc   1620
tcttcaacta atagcaaaat cagctccgag tccccgagga cacaaagagc agttcatggt   1680
agtggcaaag gggggaataa gagtgacaag tcttttattgt cttcaagaga tggaaatgct   1740
aagggagccc aaccagagtg gaagagatca tggtgtagca gtgaaacatg gtctatagcc   1800
ggaagggggg gaataaagag aaaagaagga aaaaaaata aaagtccacc aatgacaaac   1860
caaccaccta acattgacac gcgtcgcccc aaaataaaga ggacatga                1908
```

| SEQ ID NO: 6 | moltype = AA length = 589 |
| FEATURE | Location/Qualifiers |
| source | 1..589 |
| | mol_type = protein |
| | note = subspecies = trichocarpa |
| | organism = Populus balsamifera |
| REGION | 1..589 |
| | note = Ceres ANNOT ID no.1521592 |
| REGION | 1..589 |
| | note = Score of 1414.1 for HMM of FIGURE 5. |
| REGION | 1..589 |
| | note = Functional Homolog Of Ceres CLONE ID no. 1792354 at SEQ ID NO. 2 |

```
                           REGION                       115..135
                                                        note = Pfam Name: IQ Pfam Description: IQ
                                                           calmodulin-binding motif
                           SEQUENCE: 6
                           MGRKSPAKWI KTVLFGKKSS KSLIVKGRER TVNDKETLVA VRAVEADVTS VPPVVKPTAP    60
                           TTTNITERML ELESRETTES SRDGGILSTG NQDANHSQLY TPDAPPSDAD KIRLDEAATM   120
                           AQAAFRGYLA RRAFRALKGI IRLQALIRGH LVRRQAVATL CCVLGVVKLQ ALARGRMVRN   180
                           SEIGYEVHKL CSQVKLPEGK LADSSGVGIQ MAKLSSNAFV RKLLAPSPAV MPLQLPYDSM   240
                           EPNSVANWLE CWSASSFWKP VPQPKKITCS KTQRKQSNGQ IVEAETGRPK RTVRRVPAAN   300
                           VDSTSVQAAS EFEKPKRNLR KVSSHPADSA ENSQIELEKV KRSLRKVNNP VIENSAHSEV   360
                           ENEKPKQGLE KVSGTSGDNV LGWSVSNSAE KMKKEATLTT SNVPDVVKND PNLMSKLPDA   420
                           ETADEPVEMI KALESSHDDQ AVVESKASVD TGGIVENMQI NGKSIHQDDP TSNENHKTAK   480
                           KPSFTMKPER AENGLQSSPT LPSYMAATES AKAKLRMQGS PRFSEDRVEK NNITRRHSLP   540
                           SSTNSKISSE SPRTQRAVHG SGKGGNKSDK SLLSSRDGNA KGAQPEWKR             589

SEQ ID NO: 7                moltype = DNA   length = 2059
                           FEATURE                     Location/Qualifiers
                           source                      1..2059
                                                        mol_type = other DNA
                                                        organism = Glycine max
                           misc_feature                1..2059
                                                        note = Ceres CLONE ID no.463594
                           misc_feature                1..2059
                                                        note = Encodes the peptide sequence at SEQ ID NO 8
                           SEQUENCE: 7
                           attgtttggt tctggttctc aggaatggta gatttgaggt gaagacgttc cacattggtc     60
                           aggtcccgat ctcacgatgg ggaagtcacc aggaaaatgg atcaaaactg tactgttcgg    120
                           gaaaaagtca tctaaatcaa atatttcaaa aggcagagag aagcttgtta atcaaaaagg    180
                           agtagtagtt acctccaagg tgccagaaac tggtttggct ttagaaccaa cctccgatac    240
                           tattgccaga catgaggaag atccagagct ggaaaataaa gaagcagaaa atgtttttac    300
                           cgggaatcaa gaaatagaca cagtgggatc aattaatgaa gatgctgcac tagatccaga    360
                           gaaaatgagg ctggagaaag cagctacaaa ggcacaagct gctttcaggg gttatttggc    420
                           tcggagagca tttagggctc taaaaggaat aataaggttg caagcactca tccgtgggca    480
                           cttggttagg agacaagctg ttgttacatt atgctcaatg tatgtattg tcaagtttca    540
                           agcacttgtt cgtggaggaa tagtagaca gtctaatgtt ggatctgaaa tccatgagaa    600
                           gtccaatata ttgaaccctc tggatggcaa gcttgtcaag ccaaatgcta tgttcacgaa    660
                           aattaccaag ctgtctgcaa atgctttcat tcggaagctt cttacttcgt caactacaat    720
                           aatggcgctg cggttgcaat atgttcccgg cgatccaaat tcagtcctaa gttggttgga    780
                           gcgctggtca gcatctcact tttgaaaacc agttccccaa cccaagaaaa ttcgagatac    840
                           taagtctcag agaaagcatg gcaatatttc agttggagat actcatgtga gcaagtcaaa    900
                           acgaatcaac aggaagcttc ctactgcaag ttttgactcg gtcccagtgc aagcaaatcc    960
                           tgaatttgaa aaaccaaaac gaaacacaag gaaaatttca aaccaatcct cagatcctca   1020
                           tgtgcaggaa aacccacaaa gtgagcttga aagattaaa cgtaacttga gaaaggttta   1080
                           taacccagtt gttgagaatg ctgttccgtc agaagttgaa tccgaaatgc aaaggatca    1140
                           tttggaaaag gtaacagtta cctcatgcct tgctgtttca gagcaagagg tcattagttc   1200
                           taatgagaag atcaagaagg aagcaatatt aactgttcc agtgtgccag atatagaaac    1260
                           tactccaaga ctttcagtta gtaaggaggt gtctgacaca ccaagcagtt atcaagtgac   1320
                           tgtggaatca aaaccattga ctgagattac aactaaagat aaaaacattt ctgtttctga   1380
                           cgaagtaaaa aatgagccca tagatttacc agagcctatt tgtaaagatg aaaattctca   1440
                           cttaacaaat ggagatttga gtcacaagga agatcaaata ggcagtgaaa accagaaacc   1500
                           aaaccaaaaa gcctcaattg tagcaaagca ggaacgtgca gagaatggta tacagaataag   1560
                           tccaacatta ccgagttaca tggcagcaac tgaatctgca aaggcaaagt tgagggcaca   1620
                           aggatcccca agatttggac aggatggaag tgaaagaaac aaccatactc ggcgacattc   1680
                           tctgccatcc tcaactaaca gcaaaattaa ttcaccttca cctaggacac agagaccagt   1740
                           tcaatcaggt ggcaaaggtg gccacagaag tgacagaact gtatcatctt ctagagatgg   1800
                           gaatggaaag gtaattcaag cagagtggag gcggtaattt gaggaaggcc gatgttctgt   1860
                           aggaacatga ggagggcgaa accgtgtgtg gtttatatgt atctttgatg agaattgttg   1920
                           aatggatagg actataggtg tgcttgaatt caggttattt cttcatttgc tgcatttggg   1980
                           gctttgaggg tgatttgtac attataggtt tctagttttg catgatgcaa ctataactaa   2040
                           atttaattat gttttaagc                                                 2059

SEQ ID NO: 8                moltype = AA   length = 586
                           FEATURE                     Location/Qualifiers
                           source                      1..586
                                                        mol_type = protein
                                                        organism = Glycine max
                           REGION                      1..586
                                                        note = Ceres CLONE ID no.463594
                           REGION                      1..586
                                                        note = Score of 730.7 for HMM of FIGURE 5.
                           REGION                      1..586
                                                        note = Functional Homolog Of Ceres CLONE ID no. 1792354 at
                                                           SEQ ID NO. 2
                           REGION                      100..120
                                                        note = Pfam Name: IQ Pfam Description: IQ
                                                           calmodulin-binding motif
                           SEQUENCE: 8
                           MGKSPGKWIK TVLFGKKSSK SNISKGREKL VNQKGVVVTS KVPETGLALE PTSDTIARHE    60
                           EDPELENKEA ENVLPGNQEI DTVGSINEDA ALDPEKMRLE EAATKAQAAF RGYLARRAFR   120
```

```
ALKGIIRLQA  LIRGHLVRRQ  AVVTLCSMYG  IVKFQALVRG  GIVRQSNVGS  EIHEKSNILN  180
PLDGKLVKPN  AMFTKITKLS  ANAFIRKLLT  SSTTIMALRL  QYVPGDPNSV  LSWLERWSAS  240
HFWKPVPQPK  KIRDTKSQRK  HGNISVGDTH  VSKSKRINRK  LPTASFDSVP  VQANPEFEKP  300
KRNTRKISNQ  SSDPHVQENP  QSELEKIKRN  LRKVYNPVVE  NAVPSEVESE  MPKDHLEKVT  360
VTSCLAVSEQ  EVISSNEKIK  KEAILTVSSV  PDIETTPRLS  VSKEVSDTPS  SYQVTVESKP  420
LTEITTKDKN  ISVSDEVKNE  PIDLPEPICK  DENSHLTNGD  LSHKEDQIGS  ENQKPNQKAS  480
IVAKQERAEN  GIQNSPTLPS  YMAATESAKA  KLRAQGSPRF  GQDGSERNNH  TRRHSLPSST  540
NSKINSPSPR  TQRPVQSGGK  GGHRSDRTVS  SSRDGNGKVI  QAEWRR                  586

SEQ ID NO: 9            moltype = AA   length = 587
FEATURE                 Location/Qualifiers
source                  1..587
                        mol_type = protein
                        organism = Arabidopsis thaliana
REGION                  1..587
                        note = Public GI ID no.22330633
REGION                  1..587
                        note = Score of 545.5 for HMM of FIGURE 5.
REGION                  1..587
                        note = Functional Homolog Of Ceres CLONE ID no. 1792354 at
                          SEQ ID NO. 2
REGION                  113..132
                        note = Pfam Name: IQ Pfam Description: IQ
                          calmodulin-binding motif
SEQUENCE: 9
MGKSTKWLKN  VLLGKKTSKS  SGSKDKERVV  SGKEVLVTSK  VEESDVVSDL  PSFEVAETNT   60
VDRSGGMLET  QNVGPEEISD  DEIELPEGKS  TDSQNVAPVQ  DHSLSDAERI  QREIAATSVQ  120
AAFRGYLARR  AFWALKGIIR  LQALIRGHLV  RRQAVATLFS  VMGIVRLQAF  ARGREIRKSD  180
IGVQVYRKCR  LQLLQGNKLA  NPTDAYLGIK  KLTANAFAQK  LLASSPKVLP  VHAYDTSNPN  240
SNLIWLENWS  ASCFWKPVPQ  PKKTISRKPQ  NRLLVEAESA  KPKKSVRKVP  ASNFESSSVQ  300
TSFEFEKPKR  SFRKVSSQSI  EPPAVEDPQI  ELEKVKRSLR  KVHNPVVESS  IQPQRSPRKE  360
VEKPKLGVEK  TRESSYPLVH  ETAEEPVNVC  DEKKQEISE   QPEEEVHALE  MEVHTPGPLE  420
TNEALDSSLV  NQIDSNEKAM  VEEKPSMEKD  TKEEKTPKPN  NKENSAGKEN  QKSRKKGSAT  480
SKTEREESNG  HHETSPSIPS  YMQATKSAKA  KLRLQGSPKS  AEQDGTEKAT  VPRRHSLPSP  540
GNGRITSHSP  RTTRLANSGD  KTGNKKEKPL  LSSREGNAKT  TPAERKR                 587

SEQ ID NO: 10           moltype = DNA   length = 2049
FEATURE                 Location/Qualifiers
source                  1..2049
                        mol_type = other DNA
                        organism = Zea mays
misc_feature            1..2049
                        note = Ceres CLONE ID no.345954
misc_feature            1..2049
                        note = Encodes the peptide sequence at SEQ ID NO 11
SEQUENCE: 10
gttttttcgcc gagcagttcg cgtgctcccc tccacaggcc gacgcggcga cgccgctgtt   60
tcaggttctg gaatttccag tgcgggtgca ttaggctgct atgggcaagt cgccggggaa  120
gtggatcaaa tcggtgcttt tggggaagaa atctaccaag tcaggtccta ccaagtcgaa  180
tgaatctaag gctgacaaca acagatactc gaccggggag gaccgcacat tgtctgagag  240
ttctcctgtg atttctgagc cggtactagt taacatccac aagaacgtag ctatcaatgg  300
gaaggctgca gatgccagtg atagggcacg gcaacaagat ccgcagagcc aaagcgttgt  360
tgagtccaga tcatcggctc cagctgctca gctgggagaa gatcaagctg cagcgaaggc  420
acaggcagcc tttcgtggtt acctggcacg aaggtcattc cgtgcattaa aaggtatcgt  480
aagactccag gcgctgattc gagggtatct tgtaaggagg caggctgtat caaccccttcg  540
cgcaacatgg ttgattgtga agtttcaggc tctagttcgt ggaagaaatg ttagactctc  600
tggcagtcgc atgcagctca atgtgaagtt tggtcagagt aactttgggg gtgttagatc  660
gtctgatgca tggaaagaga agctatcttc aaatgcttat gttcggaagc ttctgtcttc  720
accaattgtt ttagaacctc ttcacttcca gtatgacaag agggatccca attcaaccta  780
taactggttt gagagatgga ccataggttg catctggaag cctgcttttc aacccaaaag  840
agttgctgat gggaaaccac tggtaaagaa ggctagttat gcaatggaaa ctcaatcagc  900
caagttaaaa cgcaacattc ggaagggttc tgctgctatc gctgggagtt ccatacatc   960
tggtgaatct gataaagtaa aaaggaatcc aagaatttc tctagcttcc ctgctgattc  1020
agtaccagat agccagttat ctgaacttga aaggttaaga aggaacctca ggaaggtaac  1080
tgattcgatg gctcaagcct caaagatatc tagttccagg gttgattcct cgaaggtatg  1140
taattctaca gctgaggttc caaaggaatc taatcctgtg gcagaaatct caaagatacg  1200
tagtctcctg aatgggatct ctgaccatca ggatattcaa tgtgagaata cacgtgaatc  1260
ttcatttcct cttggaactc aagaagactc tgacaatgat catctattgc gatattcaaa  1320
tatgatagc ttgacttgg tacctggttt gaaaagtgat caggaaattc agctggattc  1380
ggtttctata ggagaaaatg ttgatgatcc cactgttgtt gctccagcag ttgaagaaat  1440
gtcaccgcaa acattgata cggaagacaa tgtttatgc aagaaagagg aagcaaggtc  1500
caaggaagag cacttgtcta atggaagcct tagaactagc aagaggaagt cttcattccc  1560
caacaaatca gaatatgtag aaaatgggac tcacgcact cctgttcagc aacgcagcc  1620
aagctatatg gctgcaacgg agtccgcaaa ggcgaaattg gagcccaaa attcacccag  1680
tctggattct gattcagcgg cagaaaagaa tggtttcacc cgacgccact ctcttccttc  1740
cagtacaaag agtagagcac ttaaagctga atggaagcgc tgaagaggca acccatcgtc  1800
cacttgaatt gaattgtgca ctgctctgaa acttcgctgg atgaactcga ccggtcttgt  1860
cccatgttct tgctgtattg aacaaccccct tgtgaagttg cgattctggt tcagtttgtc  1920
gtaggttcat gtgcaaccac tagtgccttg tgtcgtatat tgcatggttc ttgtcgaagg  1980
```

```
aacaatgcct gcgaaagctg atgttaggac tgcattaact gaataacatc acccagttgc 2040
ccaggtctt                                                         2049

SEQ ID NO: 11           moltype = AA  length = 560
FEATURE                 Location/Qualifiers
source                  1..560
                        mol_type = protein
                        organism = Zea mays
REGION                  1..560
                        note = Ceres CLONE ID no.345954
REGION                  1..560
                        note = Score of 757.6 for HMM of FIGURE 5.
REGION                  1..560
                        note = Functional Homolog Of Ceres CLONE ID no. 1792354 at
                          SEQ ID NO. 2
REGION                  101..121
                        note = Pfam Name: IQ Pfam Description: IQ
                          calmodulin-binding motif
SEQUENCE: 11
MGKSPGKWIK SVLLGKKSTK SGPTKSNESK ADNNRYSTGE DRTLSESSPV ISEPVLVNIH  60
KNVAINGKAA DASDRARQQD PQSQSVVESR SSAPAAQLGE DQAAAKAQAA FRGYLARRSF 120
RALKGIVRLQ ALIRGYLVRR QAVSTLRATW LIVKFQALVR GRNVRLSGSR MQLNVKFGQS 180
NFGGVRSSDA WKEKLSSNAY VRKLLSSPIV LEPLHFQYDK RDPNSTYNWF ERWTIGCIWK 240
PAFQPKRVAD GKPLVKKASY AMETQSAKLK RNIRKGSAAI AGSFHTSGES DKVKRNPKNF 300
SSFPADSVPD SQLSELEKVK RNLRKVTDSM AEASKISSSR VDSSKVCNST AEVPKESNPV 360
AEISKIRSLL NGISDHQDIQ CENTRESSFP LGTQEDSDND HLLRYSNMDS LDLVPGLKSD 420
QEIQLDSVSI GENVDDPTVV APAVEEMSPQ NIDTEDNVLC KKEEARSKEE HLSNGSLRTS 480
KRKSSFPNKS EYVENGTHAT PVQPTQPSYM AATESAKAKL RAQNSPSLDS DSAAEKNGFT 540
RRHSLPSSTK SRALKAEWKR                                            560

SEQ ID NO: 12           moltype = DNA  length = 2049
FEATURE                 Location/Qualifiers
source                  1..2049
                        mol_type = other DNA
                        organism = Zea mays
misc_feature            1..2049
                        note = Ceres CLONE ID no.345954
misc_feature            1..2049
                        note = Encodes the peptide sequence at SEQ ID NO 11
SEQUENCE: 12
gttttttcgcc gagcagttcg cgtgctcccc tccacaggcc gacgcggcga cgccgctgtt  60
tcaggttctg gaatttccag tgcgggtgca ttaggctgct atgggcaagt cgccgggaa  120
gtggatcaaa tcggtgcttt tggggaagaa atctaccagt tcaggtccta ccaagtccaa 180
tgaatctaag gctgacaaca acagatactc gaccggggag gaccgcacat tgtctgagag 240
ttctcctgtg atttctgagc cggtactagt taacatccac aagaacgtag ctatcaatgg 300
gaaggctgca gatgccagtg ataggggcacg gcaacaagat ccgcagagcc aaagcgttgt 360
tgagtccaga tcatcggctc cagctgctca gctggagaga gatcaagctg cagcgaaggc 420
acaggcagcc tttcgtggtt acctggcacg aaggtcattc cgtgcattaa aaggtatcgt 480
aagactccag gcgctgattc gagggtatct tgtaaggagg caggctgtat caacccttcg 540
cgcaacatgg ttgattgtga agtttcaggc tctagttcgt ggaagaaatg ttagactctc 600
tggcagtcgc atgcagctca atgtgaagtt tggtcagagt aactttgggg gtgttagatc 660
gtctgatgca tggaaagaga agctatcttc aaatgctttt gttcggaagc ttctgtcttc 720
accaattgtt ttagaacctc ttcacttcca gtatgacaag agggatccca attcaaccta 780
taactggttt gagagatgga ccataggttg catctggaag cctgctttc aacccaaaag 840
agttgctgat gggaaaccac tggtaaagaa ggctagttat gcaatggaaa ctcaatcagc 900
caagttaaaa cgcaacattc ggaagggttc tgctgctatc gctgggagtt tccatacatc 960
tggtgaatct gataaagtaa aaaggaatcc aaagaatttc tctagcttcc ctgctgattc 1020
agtaccagat agccagttat ctgaacttga aaaggttaaa aggaacctca ggaaggtaac 1080
tgattcgatg gctgaagcct caaagatatc tagttccagg gttgattcct cgaaggtatg 1140
taattctaca gctgaggttc caaaggaatc taatcctgtg gcagaaatct caaagatacg 1200
tagtctcctg aatgggatct ctgaccatca ggatattcaa tgtgagaata cacgtgaatc 1260
ttcatttcct cttggaactc aagaagactc tgacaatgat catctattgc gatattcaaa 1320
tatggatagc ttggacttgg tacctggttt gaaaagtgat caggaaattc agctggattc 1380
ggttttctata ggagaaaatg ttgatgatcc cactgttgtt gctccagcag ttgaagaaat 1440
gtcaccgcaa acattgata cggaagacaa tgtttttatgc aagaaagagg aagcaaggtc 1500
caaggaagag cacttgtcta atggaagcct tagaactagc aagaggaagt cttcattccc 1560
caacaaatca gaatatgtag aaaatgggac tcacgctact cctgttcagc aacgcagcc 1620
aagctatatg gctgcaacgg agtccgcaaa ggcgaaattc gagcccaga attcaccag 1680
tctggattct gattcagcgg cagaaaagaa tggtttcacc gcgccact ctcttccttc 1740
cagtacaaag agtagagcac ttaaagctga atggaagcgc tgaagaggca acccatcgtc 1800
cacttgaatt gaattgtgca ctgctctgaa acttcgctgg atgaactcga ccggtcttgt 1860
cccatgttct tgctgtattg aacacccct tgtgaagttg cgattctggt tcagttttgtc 1920
gtaggttcat gtgcaaccac tagtgccttg tgtcgtatat tgcatggttc ttgtcgaagg 1980
aacaatgcct gcgaaagctg atgttaggac tgcattaact gaataacatc acccagttgc 2040
ccaggtctt                                                         2049
```

```
SEQ ID NO: 13            moltype = AA  length = 574
FEATURE                  Location/Qualifiers
source                   1..574
                         mol_type = protein
                         organism = Zea mays
REGION                   1..574
                         note = Ceres LOCUS ID no. Os01m05025_AP003288
REGION                   1..574
                         note = Score of 858.7for HMM of FIGURE 5.
REGION                   1..574
                         note = Functional Homolog Of Ceres CLONE ID no. 1792354 at
                           SEQ ID NO. 2
REGION                   98..118
                         note = Pfam Name: IQ Pfam Description: IQ
                           calmodulin-binding motif
SEQUENCE: 13
MGKSPAKWIK SVLLGKKSAK SNSTKAKDLA KAANNKPVLS EDPPVISEPA LVNSHNDGNA    60
ENCKLPNGVA VEAMGQGVEN QNIVGSKAPT SPEKLSEELA AVKAQAAFRG YLARRAFRAL   120
KGIIRLQALI RGHLVRRQAA STLRVTWLIV KLQALVRGRN VRLSGASIQF VVKSGQHKFL   180
SDKPSDAWKE KVSSNAYVRK LLSSSIGLEA LHLQYDKRDP NSLYNWLERW TISQIWKSSS   240
QPKKVADGKP QVRKASYAME TESAKLKRNV RKSSAVTVDS FQTNMTVEPE KIKRNSRKFS   300
SSAADSVPDS QLSELEKVKR NLRKVTNSMA EASKISSSRA DASKVSSSMA DASKVSSSTA   360
DASKVSDSVA QIPPSLVNGI SDHQDNQCEE AQQNACVSFP PETQELHSGI LLEDNSHMNL   420
LEPDLISNPE TPFTSILTWE KFNDSTADAQ EVEVLPLQNI DNEDNFPENG VLGKKEKPRS   480
KEEPLSNGNL KTSKRRSSFS TKSDYPENGA QNTPVPRRKP SYMAATESAK AKLRGQNSPR   540
LDSDSPADMN GFTRRQSLPS STNNRAIRAE WRRW                              574

SEQ ID NO: 14            moltype = AA  length = 582
FEATURE                  Location/Qualifiers
source                   1..582
                         mol_type = protein
                         note = subspecies = indica
                         organism = Oryza sativa
REGION                   1..582
                         note = Public GI ID no.125527495
REGION                   1..582
                         note = Score of 851.5 for HMM of FIGURE 5.
REGION                   1..582
                         note = Functional Homolog Of Ceres CLONE ID no. 1792354 at
                           SEQ ID NO. 2
REGION                   98..118
                         note = Pfam Name: IQ Pfam Description: IQ
                           calmodulin-binding motif
SEQUENCE: 14
MGKSPAKWIK SVLLGKKSAK SNSTKAKDLA KAANNKPVLS EDPPVISEPA LVNSHNDGNA    60
ENCKLPNGVA VEAMGQGVEN QNIVGSKAPT SPEKLSEELA AVKAQAAFRG YLARRAFRAL   120
KGIIRLQALI RGHLVRRQAA STLRVTWLIV KLQALVRGRN VRLSGASIQF VVKSGQHKFL   180
SDKPSDAWKE KVSSNAYVRK LLSSSIGLEA LHLQYDKRDP NSLYNWLERW TISQIWKSSS   240
QPKKVADGKP QVRKASYAME TESAKLKRNV RKSSAVTVDS FQTNMTVEPE KIKRNSRKFS   300
SSAADSVPDS QLSELEKVKR NLRKVTNSMA EASKISSSRA DASKVSSSMA DASKVSSSTA   360
DASKVSDSVA QIPPSLVNGI SDHQDNQCEE AQQNACVSFP PETQELHSGI LLEDNSHMNL   420
LEPDLISNPE TPFTSILTWE KFNDSTADAQ EVEVLPLQNI DNEDNFPENG VLGKKEKPRS   480
KEEPLSNGNL KTSKRRSSFS TKSDYPENGA QNTPVPRRKP SYMAATESAK AKLRGQNSPR   540
LDSDSPADMN GFTRRQSLPS STNSKLNPHS PHTQGPIYFK FD                      582

SEQ ID NO: 15            moltype = AA  length = 580
FEATURE                  Location/Qualifiers
source                   1..580
                         mol_type = protein
                         note = subspecies = indica
                         organism = Oryza sativa
REGION                   1..580
                         note = Public GI ID no.125553119
REGION                   1..580
                         note = Score of 656.4 for HMM of FIGURE 5.
REGION                   1..580
                         note = Functional Homolog Of Ceres CLONE ID no. 1792354 at
                           SEQ ID NO. 2
SEQUENCE: 15
MGKSPAKWIK SVLFGKKSSR SGSTKAKDLS KGSNNKGYAA AGKDAGFESS PVISEPVLVT    60
PHNNEAVQEV GRGENSSLQG EVVVRDVSQD LEKQNTVVSD ASNDPERLRE EQAAVKAQAA   120
FRGYLHGIGP GTSGIPCVER NHKTPSPDSW ASRKEASRCN SSCNMVDCEV SSSSPWLTRP   180
HTRNMCPNLL ALKPHKQPIM LYKSYKSGKR DAWKEKLSSN AFARKLLASP ILVEALHFQY   240
DERDPNSAFN WLERWTIGRV WRPISHPKRA AVTDAKPHTR KASYAMETES GKLKRNSRRS   300
SAAPVESSQT NMAMETEKSR RNPRKFTSST ADSVPESQLT ELEKVKRNLR KVTNSMAEAS   360
KVSTPATEIP ERQEVQCEKP QRTAEEVPNY PEIQEPQNGN LLENAKTDIL VPDLQPEPEV   420
```

```
PSYQVETEEK VAELTVADPA VETMPLQDIH NEENALVNDM EQRSKEEPLS TESLKSSKRR   480
SSFSTKTEYP ENGSKNSPAV PSYMAATQSA KAKLRGQNLP RLSSDSAEKN GFTRRHSLPS   540
SNGKLNSHSP RTQRPTHAGG KEGVKADKSM LSSRDASGKL                        580

SEQ ID NO: 16           moltype = DNA   length = 2368
FEATURE                 Location/Qualifiers
source                  1..2368
                        mol_type = other DNA
                        organism = Zea mays
misc_feature            1..2368
                        note = Ceres CLONE ID no.236431
misc_feature            1..2368
                        note = Encodes the peptide sequence at SEQ ID NO 17
SEQUENCE: 16
agctgattta ttttctctcg ctctcgcctt cgcggcgctg cctgcgcagt actacgagct    60
agcaggctag cagcaccagg accaggagcc tcttcccaca cttccgctct tcctctctct   120
ctttcctctc gagaatggtt gtgtaggcgg gcgcaggagg gaggagagag aggggagcta   180
gctagggttt tgcgtcgccg ccttctgtta cccttaggcc ctgaaccccct ccggtccagt   240
gcggcggcgg attaggctcc gatggggaag tctccggcga agtggatcaa gtccgtgctc   300
ttcggtaaaa agtcgtcgtc gaggtccggc tccaccaagg ccaaggattt atcgaagggt   360
accactaaca aagcggcggc tgctgctgct gccgggaagg agcctgcgtt ctctgagagc   420
tctccggtca tctcggagcc tgtgcttgtt agcgcccaca acaatgagac cgcgcgggag   480
gccgctaagg gtgagaattc cagcgtgcaa gaagtgccag tgactgatgt tagtcaagac   540
ttggagaagc agggcactgt tgggtctgat acgtctaatg atgctgagag gttgagggaa   600
gagcaagcgg ccgtgaaggc acaagctgcc ttccgtggtt atctggcacg ccgagcattc   660
cgtgccctga aagggatcat aagactacag gcactgattc ggggacattc tgtaaggagg   720
caagctgttt caactctccg tgctacatgg ttgattgtga agtttcaagc ccttgtccgt   780
ggaaggaacg ttagactttc taaagtttcc attcaaccaa ctacggaact tcccaacag    840
aacttcgggg gttctaaacc tggttcctgg aaggagaagt tgtcttcaaa tgcatttgct   900
cggaagcttc tctcttcacc aatttgtggtt gaggctcttc atgtccagta tgatgagatg   960
gaccctaatt cggccttcaa ttggttagag aggtggacag taagtcatgt ctggaagcct  1020
atttcccaac caaagagagt tggtgctgat actaagcctc ataaggaa ggccagttat    1080
gcaatggaaa cagagtcagc gaaattaaag cgtaatgcac ggaagagccc tgcagtgcca  1140
tttgagcctt ctcaaacaaa caccaccatt gaaaatgaga agcaaagacg gaatccaagg  1200
aaattaagta gcactcctgc tgagtcagtt cccgatgcc agttaacaga acttgagaag   1260
gttaaacgta gccttaggaa ggttactagt tccatggttg aaacctcaaa ggtgcctagc  1320
ccaacaactg agattcctga ccgtcaagag gtacaatgtg agagaccact aagaagtgca  1380
aagcaagctc aattcatgt tgagaatcaa gaacctcaga atgttaatct atcggacaat   1440
gcaaagatgg atattctggt accagatatc cagcctgagt tggaagttgc ttcagatcta  1500
gtcacaatca caaatgaaga aaaagttgat gagacaccgt ctgttgttgc tccagcgact  1560
gaaattatgc cactgcaaga catcaacagc gaagaaaatg ctttggtgaa tgatgtggaa  1620
gagagatcca agaagaaca tccatctact gataacctga aaggcagcaa gaggaggtct  1680
tcattctcag ttaagcctga aaatccagaa agtggctcca aaaattctcc agctctgcca  1740
agctacatgg ctgctacaca atctgcaaag gcgaaactgc gggggaattg ttccaccaaga 1800
cttagctctg attcagcaga gaaaaacggg ttcactcgtc gtcactccct tccgtcccct  1860
aacaatggta agataatttc acattctcca cgtacgcaaa ggccaaccca tgctggtggc  1920
aaggacggag caaaaggcga caaggctatg ctgtcatcaa ggatgcgag cgagagacca   1980
ctgaaagctg agtggagacg ctgaggtggc gaatcaaaac cccaaacccct ccatttggtt  2040
agtgcaacta tttgggttgg tggatggcgt ctgcagtttg ctccgattgt tttgcttgtg  2100
atgtaaaaaa gacgttatca tcatcatccg aggcgatgaa cgggttcagc tttgttgtga  2160
tgaatctgct gggagtcaac ttatttacag ggttttgatt catgcctttt gtgatgtata  2220
gctgaagtat tttcccggtt tgttttgttt tcccagaccc ccagactccc ccctcccct   2280
cctgcttgct gagagggctg ctgattgtag agaacgag aacctgtatg gattgagttg    2340
aacagaacaa tcttagtccc gtttggtc                                     2368

SEQ ID NO: 17           moltype = AA   length = 580
FEATURE                 Location/Qualifiers
source                  1..580
                        mol_type = protein
                        organism = Zea mays
REGION                  1..580
                        note = Ceres CLONE ID no.236431
REGION                  1..580
                        note = Score of 1099.7 for HMM of FIGURE 5.
REGION                  1..580
                        note = Functional Homolog Of Ceres CLONE ID no. 1792354 at
                          SEQ ID NO. 2
REGION                  114..134
                        note = Pfam Name: IQ Pfam Description: IQ
                          calmodulin-binding motif
SEQUENCE: 17
MGKSPAKWIK SVLFGKKSSS RSGSTKAKDL SKGTTNKAAA AAAGKEPAF SESSPVISEP     60
VLVSAHNNET AREAAKGENS SVQEVPVTDV SQDLEKQGTV GSDTSNDAER LREEQAAVKA   120
QAAFRGYLAR RAFRALKGII RLQALIRGHL VRRQAVSTLR ATWLIVKFQA LVRGRNVRLS   180
KVSIQPTTEL SQQNFGGSKP GSWKEKLSSN AFARKLLSSP IVVEALHVQY DEMDPNSAFN   240
WLERWTVSHV WKPISQPKRV GADTKPHTRK ASYAMETESA KLKRNARKSP AVPFEPSQTN   300
TTIENEKTRR NPRKLSSTPA ESVPDGQLTE LEKVKRSLRK VTSSMVETSK VPSPTTEIPD   360
RQEVQCERPL RSAKQAPIHV ENQEPQNVNL SDNAKMDILV PDIQPDVEVA SDLVTITNEE   420
KVDETPSVVA PATEIMPLQD INSEENALVN DVEERSKEEH PSTDNLKGSK RRSSFSVKPE   480
```

```
YPENGSKNSP ALPSYMAATQ SAKAKLRGNC SPRLSSDSAE KNGFTRRHSL PSPNNGKIIS   540
HSPRTQRPTH AGGKDGAKGD KAMLSSRDAS ERPLKAEWRR                        580

SEQ ID NO: 18           moltype = DNA  length = 2129
FEATURE                 Location/Qualifiers
source                  1..2129
                        mol_type = other DNA
                        organism = Triticum aestivum
misc_feature            1..2129
                        note = Ceres CLONE ID no.908518
misc_feature            1..2129
                        note = Encodes the peptide sequence at SEQ ID NO 19
SEQUENCE: 18
agaacctctc tctctcctct gctccacgcc acagaagaga acaaacagta ggaggagcgc   60
tctccttcgg ccgcgagcgt ctgcgtcccg caatggaggc gtgatggttg gcgcggatag   120
aggggtagcg ggacagggaa ggtgagcaat ctgccgggag agcgccgacg ccccgcccag   180
tccagcccag gtccagaatt tccggtgttt gagcagtttt agtaggctgc tatggggaag   240
tccccggcca agtggataaa gtccgtgctc tcgggaaga aatcaacaaa atccaattct    300
accaaggcaa aggatcttcc agcaaaggct gcaaacagca acggatgcac tgctgggaag   360
gagcctgaat cctctgataa ttctccccte atctcggagc cggtacttgt tagctcccac   420
aatgtgtctg aaatttccaa cttgcccaat gggagggcaa tcgaaaacat ggttagagtt   480
gggtccgaca cgcaaattag tccagagaaa ctgagagaag aactagcagc agtgaaggcg   540
caagccgctt ttcgaggtta cctggcacgc agggccttcc gcgcattaaa aggtatcatc   600
agacttcagg cactgattcg agggcatctt gtaaggaggc agccgtttc aaccttcgt    660
ggaacatggt tgattgtgaa gtttcaagct ctagttcgtg gaaagaatgt tagattttct   720
agtgctgcca cgcaattagc tgtgaagttt ggtcaacata agtatggggg tgacaagtcg   780
tcggatgcat ggaaggagaa gctatcttca catccatatg ttcgaaagct tctgtcttca   840
ccaatttttgg tacaagctct tcacgttcag tatgatgaga caaaccccaa ttcagccctc   900
aactggctga agagatggac aataagctgc atctggaagc ctgttccaa accaaaaata    960
gttactgacg ggaaaccaca agtaaggagg gccagttatg ccatggaaac tcactcagca   1020
aagtaaagc gcaatgttcg gaagtcttct actgccactg ttgagactca ggcaaatacc   1080
gttgaatctg aaaaatggaa aagaaaccca cggaaattga atggctcacc tgctgattca   1140
gtaccagaca gccagttatc tgaacttgag aaggttaaaa ggaaccttaa gaaggcagct   1200
aactccatgg ctgaagcctc taagatatct accaaggctg atgttgaa ggtacctaat     1260
tccatagctg atgagctgaa gatacttggt tccatggctg aactatcaaa aaaatccagc   1320
ataccaaacg gtatctctga ccatcaagac agcgaatgcg agaaagcact agagagtaca   1380
cgtgaggctg tgtttcctct tggaactcaa gattctcaca gtgcaatct tttggaaaat   1440
tcaaatataa gtaagttggt acctgacata aaatatgatc tagaagcatc attcttaggg   1500
gacaaagtta atgaaccac tactgtcgct caagcagatg aagtcataca actgcagaac   1560
cttgataacg gatatgatat tatagaaagg aaagaagaa ctaggtccaa ggaagaacct   1620
ctgcctaatg gaagcttaa aaccaagaga aggtcttcgt tctctaattc agaataccct   1680
gagagtggaa ccaagaacac tccagttcca tcaaggaagc caagctatat ggctccaaca   1740
gaatcgttaa aggcgaaatt gcgaggacca cccagattag actctgatct accagtggac   1800
aagaatgcct tcactcgccg tcagtctctt ccttctgctg caaacaatag agcaatcaaa   1860
acagaatgga ggcggtgaag aggctatcaa gcttccaaca ctaggtccaa ttattgtgga   1920
agaaatttca agctgtataa attattgatt agtttatgaa gtttgctgat gtctacctgt   1980
ctctgtcctt gttgttctgt ctacgttata aacatatgtt cttacgccct tttcgaacta   2040
gcttgtggta atatgtttgg tgctatttt tcctcgagtt atcttatagt tccttggtcc    2100
gtgtattaaa tgtaaaaaaa aaaaaaaaa                                    2129

SEQ ID NO: 19           moltype = AA  length = 548
FEATURE                 Location/Qualifiers
source                  1..548
                        mol_type = protein
                        organism = Triticum aestivum
REGION                  1..548
                        note = Ceres CLONE ID no.908518
REGION                  1..548
                        note = Score of 1274.3 for HMM of FIGURE 5.
REGION                  1..548
                        note = Functional Homolog Of Ceres CLONE ID no. 1792354 at
                          SEQ ID NO. 2
REGION                  97..117
                        note = Pfam Name: IQ Pfam Description: IQ
                          calmodulin-binding motif
SEQUENCE: 19
MGKSPAKWIK SVLLGKKSTK SNSTKAKDLP AKAANSNGCT AGKEPESSDN SPLISEPVLV   60
SSHNVSEISN LPNGRAIENM VRVGSDTQIS PEKLREELAA VKAQAAFRGY LARRAFRALK   120
GIIRLQALIR GHLVRRQAVS TLRGTWLIVK FQALVRGRNV RFSSAATQLA VKFGQHKYGG   180
DKSSDAWKEK LSSHPYVRKL LSSPILVQAL HVQYDETNPN SALNWLERWT ISCIWKPVSK   240
PKIVTDGKPQ VRRASYAMET HSAKLKRNVR KSSTATVETQ ANTVESEKWK RNPRKLNGSP   300
ADSVPDSQLS ELEKVKRNLK KAANSMAEAS KISTKADVLK VPNSIADELK ILGSMAELSK   360
KSSIPNGISD HQDSECEKAL ESTREAVFPL GTQDSHSGNL LENSNISKLV PDIKYDLEAS   420
FLGDKVNEPT TVAQADEVIQ LQNLDNGYDI IERKEETRSK EEPLPNGSLK TKRRSSFSNS   480
EYPESGTKNT PVPSRKPSYM APTESLKAKL RGPPRLDSDL PVDKNAFTRR QSLPSAANNR   540
AIKTEWRR                                                           548
```

```
SEQ ID NO: 20           moltype = AA  length = 574
FEATURE                 Location/Qualifiers
source                  1..574
                        mol_type = protein
                        note = subspecies = Japonica
                        organism = Oryza sativa
REGION                  1..574
                        note = Public GI ID no.115465121
REGION                  1..574
                        note = Score of 966.7 for HMM of FIGURE 5.
REGION                  1..574
                        note = Functional Homolog Of Ceres CLONE ID no. 1792354 at
                         SEQ ID NO. 2
REGION                  111..131
                        note = Pfam Name: IQ Pfam Description: IQ
                         calmodulin-binding motif
SEQUENCE: 20
MGKSPAKWIK  SVLFGKKSSR  SGSTKAKDLS  KGSNNKGYAA  AGKDAGFESS  PVISEPVLVT   60
PHNNEAVQEV  GRGENSSLQG  EVVVRDVSQD  LEKQNTVVSD  ASNDPERLRE  EQAAVKAQAA  120
FRGYLARRAF  RALKGIIRLQ  ALIRGHLVRR  QAVATLRATW  LIVKFQALVR  GRNVRLSTNT  180
IQVNWKLVQQ  QSGSGKRDAW  KEKLSSNAFA  RKLLASPILV  EALHFQYDER  DPNSAFNWLE  240
RWTIGRVWRP  ISHPKRAAVT  DAKPHTRKAS  YAMETESGKL  KRNSRRSSAA  PVESSQTNIA  300
METEKSRRNP  RKFTSSTADS  VPESQLTELE  KVKRNLRKVT  NSMAEASKVS  TPATEIPERQ  360
EVQCEKPQRT  AEEVPNYPEI  QEPQNGNLLE  NAKTDILVPD  LQPEPEVPSY  QVETEEKVAE  420
LTVADPTVET  MPLQDIHNEE  NALVNDMEQR  SKEEPLSTES  LKSSKRRSSF  STKTEYPENG  480
SKNSPAVPSY  MAATQSAKAK  LRGQNSPRLS  SDSAEKNGFT  RRHSLPSSNG  KLNSHSPRTQ  540
RPTHAGGKEG  VKADKSMLSS  RDASERPAKA  EWKR                                574

SEQ ID NO: 21           moltype = DNA  length = 2529
FEATURE                 Location/Qualifiers
source                  1..2529
                        mol_type = other DNA
                        organism = Panicum virgatum
misc_feature            1..2529
                        note = Ceres CLONE ID no.1791910
misc_feature            1..2529
                        note = Encodes the peptide sequence at SEQ ID NO 22
SEQUENCE: 21
ggattggagg ttggaggcct gaaggggag gtgggtcgcc ggacaggac ggggagacgg      60
cgagagggcg ttccgcagga gccgttcccg tgcttcctcc accgaccggg ccgacgcgcc    120
gcgccgctgt ttcaggttcc cgcccctgca tttttctgct tgtgcttgcg ctagttcga    180
gggtaggttg cggcgttaga gattggttcg cggcttcgtg gcggcgctgt gtttgtttgg    240
ccagatccgc gtgtgtgctg ctgactcttc gtgatttcct cttctgtttg agctttcctt    300
gctcggcttt tgtgctgctgc ctgcctgctg cttcttttc tggccactgc atttgggttg    360
tgtgccgcgc tacttatcct gctctgcttg tgtttaagat tacagctcgt gtttcttca    420
acgatatttt caccttttgtt tcatcacttg ggaagctggt gccgtaaaag agtctgctaa    480
accatgctaa ctttagcgaa attactgtta ctccagctgt ccagcatgtt ccttccttca    540
tcttagtgaa aataaagtat gttgtggcat actggtatgg atctgtgcat tgctgagctc    600
ctctgtttac aggttccaga atttcaagta ttggccgctt aggatacta tgggaaagtc    660
cccgggaag tggatcaagt ctgtgctctt ggggaagaaa tcgactaaat ccggttctac    720
caaggcaaat gagtcggcta caaataacaa tggacactca gctggggagg agcgtgcatt    780
ttctgaaaat tctccagtga tctctgagcc ggtgcttgtt gaagcccaca aaaatggagc    840
tgtttcagtt aatgggaagg ctgaagatgt caatttgcca agtgacaggg ctggccaaca    900
agatctgcag aaccaaagta ttgttgagtc cgaaacatca gttcctgggc aattgggaa    960
agaccaagct gcagtgaagg cacaggcagc atttcgcggt tacctagcac gaaggtcatt   1020
ccgtgcattg aaaggtatca taagactcca ggcactgatt cgagggcatc ttgtaaggag   1080
acaggctgtt tcaaccccttc aaactacttg gttgattgtg aagtttcaat ctctagttcg   1140
tggaagaaat gtcagactct ctggtgctga cattcaactc aatgtgaagc ttggccaaca   1200
taaccttggt ggcactagat catctgatgc atggaaagag aagttatctt caaatgccta   1260
tgttcggaag cttctgtctt caccaatagt gctagaacct cttcacttcc agtatgacaa   1320
gagggatccc aattcaacct ataactggct agagagatgc accataggct gcatctggaa   1380
gcctgttttt caaccaaaaa gagttcctga tgggaaactg ctggtaagga aggctagtta   1440
tgcaatggaa actgaatcag ccaagttaaa gcgcaacatt aggaagggct ctgctgctac   1500
agttgagagt ttccatacaa gagtgactgg tgaatctgag aaacttaaac gtaatccaaa   1560
gaaattctca aacttccctg ctgactcagt accagatagc cagttatctg aacttgagaa   1620
ggttaaaagg aacctgagga aggtaactga ttccatggct gaagcctcaa agatctctag   1680
ttccagggtt gattcctcaa aggtatctga ttctacacct gatgctccaa aagtatctaa   1740
tcctggggcc gaaatctcta agacatctag tctcctgaac gggatctctg accatcaaga   1800
cagccaatgt gaaaaagcac tacagaatac acgtgaggct tcatttcctc ttgaaactca   1860
agattactct ggcaatggtc agctattgga atattcagat atggataact tcgacttggt   1920
acctggtttt aaaagtgatc tggaaactca gcttgattca gtttctatag agaaaatgt   1980
tgatgagccc actgttggtg cttcagcagc tgaaggtatg ccactgcaga acattgataa   2040
gcccaatagt ttagggaaga aagaggaagc aagtcccaag aagagccatc tgtctaatga   2100
aagccttaga actggcaaga gaaagtcttc atccccatac aaatcagaat atgtggaaaa   2160
cgggactcac actactcctg ctcagccaag gaagccaagc tatatggctg caacggagtc   2220
tgcgaaggcg aaattacgag cacagaattc cccagggtg gattctgatt catcagcaga   2280
aaagaatggc ttcactcgac gccactctct tccttccggt acaaacagta gggcgatcaa   2340
agctgaatgg aagcgctgag gaggcattgg cttgaattga atagtgcgat tgtctgaatc   2400
```

```
tctgctgggt gaactctgcc gctgcttgct ccttttatt tatcctgcga tgtaaagaga  2460
agacgttgtc cctgtattga acaatctttg tgatgagtgc gtctggttca aaaaaaaaaa  2520
aaaaaaaaa                                                          2529
```

```
SEQ ID NO: 22           moltype = AA  length = 569
FEATURE                 Location/Qualifiers
source                  1..569
                        mol_type = protein
                        organism = Panicum virgatum
REGION                  1..569
                        note = Ceres CLONE ID no.1791910
REGION                  1..569
                        note = Score of 824.9 for HMM of FIGURE 5.
REGION                  1..569
                        note = Functional Homolog Of Ceres CLONE ID no. 1792354 at
                         SEQ ID NO. 2
REGION                  105..125
                        note = Pfam Name: IQ Pfam Description: IQ
                         calmodulin-binding motif
SEQUENCE: 22
MGKSPGKWIK SVLLGKKSTK SGSTKANESA TNNNGHSAGE ERAFSENSPV ISEPVLVEAH   60
KNGAVSVNGK AEDVNLPSDR AGQQDLQNQS IVESETSVPG QLGEDQAAVK AQAAFRGYLA  120
RRSFRALKGI IRLQALIRGH LVRRQAVSTL QTTWLIVKFQ SLVRGRNVRL SGADIQLNVK  180
LGQHNLGGTR SSDAWKEKLS SNAYVRKLLS SPIVLEPLHF QYDKRDPNST YNWLERCTIG  240
CIWKPVFQPK RVPDGKLLVR KASYAMETES AKLKRNIRKG SAATVESFHT RVTGESEKLK  300
RNPKKFSNFP ADSVPDSQLS ELEKVKRNLR KVTDSMAEAS KISSSRVDSS KVSDSTPDAP  360
KVSNPVAEIS KTSSLLNGIS DHQDSQCEKA LQNTREASFP LETQDYSGNG QLLEYSDMDN  420
FDLVPGLKSD LETQLDSVSI GENVDEPTVG ASAAEGMPLQ NIDKPNSLGK KEEARSKEEH  480
LSNGSLRTGK RKSSSPYKSE YVENGTHTTP AQPRKPSYMA ATESAKAKLR AQNSPRVDSD  540
SSAEKNGFTR RHSLPSGTNS RAIKAEWKR                                    569

SEQ ID NO: 23           moltype = AA  length = 567
FEATURE                 Location/Qualifiers
source                  1..567
                        mol_type = protein
                        note = subspecies = Japonica
                        organism = Oryza sativa
REGION                  1..567
                        note = Public GI ID no.125595019
REGION                  1..567
                        note = Score of 928.2 for HMM of FIGURE 5.
REGION                  1..567
                        note = Functional Homolog Of Ceres CLONE ID no. 1792354 at
                         SEQ ID NO. 2
REGION                  111..131
                        note = Pfam Name: IQ Pfam Description: IQ
                         calmodulin-binding motif
SEQUENCE: 23
MGKSPAKWIK SVLFGKKSSR SGSTKAKDLS KGSNNKGYAA AGKDAGFESS PVISEPVLVT   60
PHNNEAVQEV GRGENSSLQG EVVVRDVSQD LEKQNTVVSD ASNDPERLRE EQAAVKAQAA  120
FRGYLARRAF RALKGIIRLQ ALIRGHLVRR QAVATLRATW LIVKFQALVR GRNVRLSTNT  180
IQVNWKLVQQ QSGSGKRDAW KEKLSSNAFA RKLLASPILV EALHFQYDER DPNSAFNWLE  240
RWTIGRVWRP ISHPKRAAVT DAKPHTRKAS YAMETESGKL KRNSRRSSAA PVESSQTNIA  300
METEKSRRNP RKFTSSTADS VPESQLTELE KVKRNLRKVT NSMAEASKVS TPATEIPERQ  360
EVQCEKPQRT AEEVPNYPEI QEPQNGNLLE NAKTDILVPD VLPEPEVPSY QVETEEKVAE  420
LTVADPTVET MPLQDIHNEE NALVNDMEQR SKEEPLSTES LKSSKRRSSF STKTEYPENG  480
SKNSPAVPSY MAATQSAKAK LRGQNSPRLS SDSAEKNGFT RRHSLPSSNG KLNSHSPRTQ  540
RPTHAGGKEG VKADKSMLSS RDASGKL                                      567

SEQ ID NO: 24           moltype = AA  length = 636
FEATURE                 Location/Qualifiers
source                  1..636
                        mol_type = protein
                        organism = Arabidopsis thaliana
REGION                  1..636
                        note = Public GI ID no.42568886
REGION                  1..636
                        note = Score of 1517.7 for HMM of FIGURE 5.
REGION                  1..636
                        note = Functional Homolog Of Ceres CLONE ID no. 1792354 at
                         SEQ ID NO. 2
REGION                  129..149
                        note = Pfam Name: IQ Pfam Description: IQ
                         calmodulin-binding motif
SEQUENCE: 24
MGKTPSPGKW IKSLLGKKSS KSSLEKGGEK LRSAKKEELV VKVKDNNVSK LPTEPPVVSS   60
QEVAATQTVV VPDVVIAEKQ LSGDIEGDES SNVNLESGND SEEVKLEEAA TKVQAALRAQ  120
QAREESQNLK GITRVQAVIR GHLVRRQAVA TYSCIWGIVK VQALVRGKKA RSSETVAQLQ  180
KTNTETETSE TLQGSTYSWM ENPTKLSMID KLLVSSPTTL PLKIQYSPED PNSAKVWLGR  240
```

```
WTQLQVWAPG PLVVKNLVPK SQTKKRSFQA VEAEKGKLKR GVRKPTGVST TANSSTSRST 300
ADNEKPKRTV RKASTLGKEL SKIENDKSKQ SSRKSTSAIK EGSSVEVKDE KPRISHKKAS 360
LSNGIGKATR KSAEKKKEIA DAVQKELPIE EVSVSLVDAP EDEKMNLIPV TISKESDLDK 420
DEKSLVLDKP EQDELRTAER DDKAEEELKT AERDDSAEEK IQEPDAQISS ENGNVASENT 480
KPSDRRASLP AKIENHHQDD GLTQSGRKIP SYMAPTASAK ARIRGQGSPR IAQEKPEKNG 540
TTRRHSLPPA ANGKLSTMSP RAHRLLIASA KGSMNSDRSF SSSKDIGGKR FKPITIHKPF 600
CQFLLHYLHP FNKFSSCLYQ TSRRKLSGNG ESTKAE                           636

SEQ ID NO: 25           moltype = AA  length = 650
FEATURE                 Location/Qualifiers
source                  1..650
                        mol_type = protein
                        organism = Arabidopsis thaliana
REGION                  1..650
                        note = Public GI ID no.2947062
REGION                  1..650
                        note = Score of 1502.4 for HMM of FIGURE 5.
REGION                  1..650
                        note = Functional Homolog Of Ceres CLONE ID no. 1792354 at
                          SEQ ID NO. 2
REGION                  143..163
                        note = Pfam Name: IQ Pfam Description: IQ
                          calmodulin-binding motif
SEQUENCE: 25
MGKTPSPGKW IKSLLGKKSS KSSLEKGGEK LVRRVNRSAK KEELVVKVKD NNVSKLPTEP  60
PVVSSQEVAA TQTVVVPDVV IAEKQLSGDI EGDESSNVNL ESGNDSEEVK LEEAATKVQA 120
ALRAQQVNVY IFDILAREES QNLKGITRVQ AVIRGHLVRR QAVATYSCIW GIVKVQALVR 180
GKKARSSETV AQLQKTNTET ETSETLQGST YSWMENPTKL SMIDKLLVSS PTTLPLKIQY 240
SPEDPNSAKV WLGRWTQLQV WAPGPLVVKN LVPKSQTKKR SFQAVEAEKG KLKRGVRKPT 300
GVSTTANSST SRSTADNEKP KRTVRKASTL GKELSKIEND KSKQSSRKST SAIKEGSSVE 360
VKDEKPRISH KKASLSNGIG KATRKSAEKK KEIADAVQKE LPIEEVSVSL VDAPEDEKMN 420
LIPVTISKES DLDKDEKSLV LDKPEQDELR TAERDDKAEE ELKTAERDDS AEEKIQEPDA 480
QISSENGNVA SENTKPSDRR ASLPAKIENH HQDDGLTQSG RKIPSYMAPT ASAKARIRGQ 540
GSPRIAQEKP EKNGTTRRHS LPPAANGKLS TMSPRAHRLL IASAKGSMNS DRSFSSSKDI 600
GGKRFKPITI HKPFCQFLLH YLHPFNKFSS CLYQTSRRKL SGNGESTKAE            650

SEQ ID NO: 26           moltype = DNA  length = 1881
FEATURE                 Location/Qualifiers
source                  1..1881
                        mol_type = other DNA
                        organism = Populus balsamifera
                        sub_species = trichocarpa
misc_feature            1..1881
                        note = Ceres ANNOT ID no.1468228
misc_feature            1..1881
                        note = Encodes the peptide sequence at SEQ ID NO 27
SEQUENCE: 26
atggggagaa aatcacctgc gaaatggata aagactgttt tgtttggaaa gaagtcttcc   60
aaatctctta ttgtcaaagg aagggagaga actgtgaatg acaaagagac attggttgct  120
gtcagagccg tggaagctga tgtgacctca gttcctccgg tggtcaagcc gacagccccc  180
actaccacta atatcactga aaggatgtta gagctagaga gcagggaaac tacagaatca  240
tcacgtgatg gaggtatatt gtcaactgga aatcaagatg caaatcattc tcaattatac  300
actcctgatg ctcctccatc tgatgctgac aaaataaggc ttgatgaagc tgcgacaatg  360
gcacaagccg catttagggg ttacttgata ggtgcactac tggggctgtt tcatgtgacc  420
ttgagggttc gactgacttg gtaccaggct cgccgagcat ttgagctct taaaggcata  480
ataaggcttc aggctcttat ccgtggacac ttggttagaa ggcaagctgt tgctactctc  540
tgctgtgtgc tcggagttgt caagttacag gctcttgctc gaggaagaat ggttaggaat  600
tcagagattg gctatgaggt tcataaatta tgcagccaag taaaactgcc ggagggcaag  660
cttgcagatt ctagtggagt tggtatacaa atggccaagc tgtcatcaaa tgcttttgtt  720
cgcaagcttc ttgctccatc acctgctgta atgcctttgc aactccccta tgattccatg  780
gaaccaaact cagttgcaaa ctggttctagag tgctggtcag cgtcctcttt ctggaaacca  840
gttcccccaac caaaaaaaaat tacttgctca aaaactcaga gaaagcagag taatggtcaa  900
atagtggaag ctgaaactgg taggccaaag cgcactgttc ggagggtccc tgctgcaaat  960
gttgacagta cctcagtaca agcagcctct gaatttgaa aacccaagcg caatttgagg 1020
aaagtttcaa gccatccagc tgattcagca gaaaattcac agattgagct gaaaaggta 1080
aagcgcagct taagaaaggt taataacccc gttatagaaa actctgctca ttcagaggtt 1140
gaaaatgaaa agcaaagca aggtctgaaa aaggtatctg gcacttcagg tgataatgtt 1200
ttgggatgga gcgtaagtaa ttcagctgag aagatgaaga aagaagctac cttgacaaca 1260
tccaatgtac ctgatgtggt gaagaatgat ccaaacttga tgtccaagtt gcctgatgca 1320
gagacagctg atgaacctgt agaaatgatc aaggcattgg aatcatcaca tgacgatcaa 1380
gctgtggtag aatctaaagc ttcagtagat actggtgta tagttgagaa tatgcaaata 1440
aatgggaagt ccatacacca ggatgatcca acaagcaatg aaaatcacaa aactgccaag 1500
aaaccttcat tcacaatgaa accagaacgt gccgagaatg gctacagag cagtcccacc 1560
ctccctagct acatggcagc aactgaatct gcaaaggcaa agctgagaat ggaaggctcc 1620
ccaagatta gtgaagatcg agttgagaaa aataacatca cccgtcgtca ttctctgccc 1680
tcttcaacta atagcaaaat cagctccgag tccccgagga cacaaagagc agttcatggt 1740
agtggcaaag ggggaataa gagtgacaag tctttattgt cttcaagaga tggaaatgct 1800
aagggagccc aaccagagtg gaagagatca tggtgtagca gtgaaacatg gtctatagcc 1860
ggaagggagt atgtggatta a                                          1881
```

```
SEQ ID NO: 27           moltype = AA  length = 626
FEATURE                 Location/Qualifiers
source                  1..626
                        mol_type = protein
                        note = subspecies =Trichocarpa
                        organism = Populus balsamifera
REGION                  1..626
                        note = Ceres ANNOT ID no.1468228
REGION                  1..626
                        note = Score of 1490.5 for HMM of FIGURE 5.
REGION                  1..626
                        note = Functional Homolog Of Ceres CLONE ID no. 1792354 at
                          SEQ ID NO. 2
REGION                  157..177
                        note = Pfam Name: IQ Pfam Description: IQ
                          calmodulin-binding motif
SEQUENCE: 27
MGRKSPAKWI KTVLFGKKSS KSLIVKGRER TVNDKETLVA VRAVEADVTS VPPVVKPTAP   60
TTTNITERML ELESRETTES SRDGGILSTG NQDANHSQLY TPDAPPSDAD KIRLDEAATM  120
AQAAFRGYLI GALLGLFSWT LRVRLTWYQA RRAFRALKGI IRLQALIRGH LVRRQAVATL  180
CCVLGVVKLQ ALARGRMVRN SEIGYEVHKL CSQVKLPEGK LADSSGVGIQ MAKLSSNAFV  240
RKLLAPSPAV MPLQLPYDSM EPNSVANWLE CWSSASSFWKP VPQPKKITCS KTQRKQSNGQ  300
IVEAETGRPK RTVRRVPAAN VDSTSVQAAS EFEKPKRNLR KVSSHPADSA ENSQIELEKV  360
KRSLRKVNNP VIENSAHSEV ENEKPKQGLE KVSGTSGDNV LGWSVSNSAE KMKKEATLTT  420
SNVPDVVKND PNLMSKLPDA ETADEPVEMI KALESSHDDQ AVVESKASVD TGGIVENMQI  480
NGKSIHQDDP TSNENHKTAK KPSFTMKPER AENGLQSSPT LPSYMAATES AKAKLRMQGS  540
PRFSEDRVEK NNITRRHSLP SSTNSKISSE SPRTQRAVHG SGKGGNKSDK SLLSSRDGNA  600
KGAQPEWKRS WCSSETWSIA GREYVD                                      626

SEQ ID NO: 28           moltype = DNA  length = 2050
FEATURE                 Location/Qualifiers
source                  1..2050
                        mol_type = other DNA
                        organism = Gossypium hirsutum
misc_feature            1..2050
                        note = Ceres CLONE ID no.1942388
misc_feature            1..2050
                        note = Encodes the peptide sequence at SEQ ID NO 29
SEQUENCE: 28
atttagtttt aaattcacta aaaaaaagcc tgcacgagat tctcttgttc gaggaatcct    60
tcacgatctc tgaatgctca cagttccggt aatggcagct tagtaccgaa caaggacttc   120
atatttgata ctcttttcag atttccagat ttagaaactt gggattttaa ttatttttgg   180
gtttaactga gatggggaaa tctccagcga aatggatcaa gaccttgctt cttgggaaga   240
aatcttcaaa gtccagtttc tcaaaaggaa aagataagct gaattctgca aataaaggtg   300
aggttttggt ttcttccaag gtaactgtgt ctgacctatc agcggattct ccatcgattt   360
cagcaccat tctagtgagc cgtgctagga atgtgatgga ctctgagaag ggtataccgt   420
cccaattgcc gattgatggg gaaaatattc catctctaaa agtggatgga aataatgcca   480
caaccggtaa ttttggtaac ccagaaaatc ctgataggat taggcttgac ccagctgctg   540
tgacagtaca ggctgctttc agaggttatc tggctcgccg ggaatttcga atcctcaagg   600
gcattataag gctgcaggca gttattcgtg tcacttggt tagaagacaa gctgttgcta   660
cttatgctgt tacatgggga attgttaagt tgcaagcact agctcgtggt caaaaggtca   720
gatgttcaga tattgccatg gaaatacagg aaaaacatct aagactgctt cagggtttga   780
aaagctcaaa ttctgtagga gcgagcatat cttctacagt gaagaattta tcaagtaatg   840
tgtttgttca gaagcttttg gcctcgtcac cttctgtatt gcctctacaa cttcagtatg   900
ttccagagga gcctaactca tcctggcaat ggcttcaacg atggacaaga tcacaatttt   960
gggaatacc ctcaaaacca attaggagtg aaagacaaa gctaagtgtt cagaaactat  1020
cctttgcaaa agctgttaat ggatctagtc atttctacatt ggatgatgaa aaaaataaac  1080
gaggtctgag gagaatttct gtcaactcag cagcagatc agttcgggag catccacaaa  1140
atgagctcga gagggttaag cgcaatttaa gaaagctttc caactcttca aaggaggtta  1200
ctgataagtc tgagtttgtt aatgagaaaa caaagaagac tctgaaaaa tattctagtt  1260
ctaatggccc tgatgtttta gaacaggaat ctgctgagaa gataagagat gtgactgcaa  1320
cactatcaga actgtcaatt cttgaggcag atctgaaatt ttcctcagaa catgcttctc  1380
ttggtgagcc tattgtctgt cctgcagttg atttccacc ggcaaaac aatgataaa  1440
ttgagcacat gccactaaca gaggagttaa actctaagga tgagcaggtc ggtgatgaga  1500
gctcaaacac aaaccaaaga agagcttctt tcccagcaaa tattgataat caggcaaatc  1560
ggttaaatca catgccaaaa gtgcccagtt atatggcacc aactgaatct gcgaaagcta  1620
gactttaggg gtcaagggtcc ccaaggttta tcccgaggc tgttgagaaa atgggtaa  1680
acaggcggta ttctttgcca acttcaacca atagtaatac aggttcacaa tccccacata  1740
ctcaaagaca ggttcgagta gctggcaaag tgctatcat cagtgacaaa tctcaatcat  1800
cctctaaaga tgctaatgat aaggtggtca gagccgagtg gaggaggtaa ttcttgcaca  1860
aggaattgtt tcgatgaagt ttccatgggt aaatatttgt agatgttaca gttgtttatt  1920
tggttcgttt ttgtttggac gtaaaattct ttggatcccc tgttcactct tttctaccat  1980
ttaatatcat aggaatagag tgtgcccatc tccatatctg gctttcgtag aaaaaaaaaa  2040
aaaaaaaaa                                                         2050
```

-continued

```
SEQ ID NO: 29          moltype = AA   length = 552
FEATURE                Location/Qualifiers
source                 1..552
                       mol_type = protein
                       organism = Gossypium hirsutum
REGION                 1..552
                       note = Ceres CLONE ID no.1942388
REGION                 1..552
                       note = Score of 1315.8 for HMM of FIGURE 5.
REGION                 1..552
                       note = Functional Homolog Of Ceres CLONE ID no. 1792354 at
                         SEQ ID NO. 2
REGION                 113..133
                       note = Pfam Name: IQ Pfam Description: IQ
                         calmodulin-binding motif
SEQUENCE: 29
MGKSPAKWIK TLLLGKKSSK SSFSKGKDKL NSANKGEVLV SSKVTVSDLS ADSPSISAPI    60
LVSRARNVMD SEKGIPAQLP IDGENIPSLK VDGNNATTGN FGNPENPDRI RLDPAAVTVQ   120
AAFRGYLARR EFRILKGIIR LQAVIRGHLV RRQAVATLCC TWGIVKLQAL ARGQKVRCSD   180
IAMEIQEKHL RLLQGLKSSN SVGASISSTV KNLSSNVFVQ KLLASSPSVL PLQLQYVPEE   240
PNSSWQWLQR WTRSQFWEYP SKPIRSGKTK LSVQKLSFAK AVNGSSHSTL EYEKNKRGLR   300
RISVNSAADS VREHPQNELE RVKRNLRKLS NSSKEVTDKS EFVNEKTKKT LKKYSSSNGP   360
DVLEQESAEK IRDVTATLSE LSILEADLKF SSEHASLGEP IVCPAVDFPP AKNNGKIEHM   420
PLTEELNSKD EQVGDESSNT NQRRASFPAN IDNQANRLNH MPKVPSYMAP TESAKARLRG   480
QGSPRFIPEA VEKNGLNRRY SLPTSTNSNT GSQSPHTQRQ VRVAGKGAII SDKSQSSSKD   540
ANDKVVRAEW RR                                                      552

SEQ ID NO: 30          moltype = AA   length = 570
FEATURE                Location/Qualifiers
source                 1..570
                       mol_type = protein
                       organism = Arabidopsis thaliana
REGION                 1..570
                       note = Public GI ID no.12324824
REGION                 1..570
                       note = Score of 428.7 for HMM of FIGURE 5.
REGION                 1..570
                       note = Functional Homolog Of Ceres CLONE ID no. 1792354 at
                         SEQ ID NO. 2
REGION                 105..124
                       note = Pfam Name: IQ Pfam Description: IQ
                         calmodulin-binding motif
SEQUENCE: 30
MIVFFFFFFC SNYSYNNAQR VVSGKEVLVT SKVEESDVVS DLPSFEVAET NTVDRSGGML    60
ETQNVGPEEI SDDEIELPEG KSTDSQNVAP VQDHSLSDAE RIQREIAATS VQAAFRGYLA   120
RRAFWALKGI IRLQALIRGH LVRRQAVATL FSVMGIVRLQ AFARGREIRK SDIGVQVYRK   180
CRLQLLQGNK LANPTDAYLG IKKLTANAFA QKLLASSPKV LPVHAYDTSN PNSNLIWLEN   240
WSASCFWKPV PQPKKTISRK PQNRLLVEAE SAKPKKSVRK VPASNFESSS VQTSFEFEKP   300
KRSFRKVSSQ SIEPPAVEDP QIELEKVKRS LRKVHNPVVE SSIQPQRSPR KEVEKPKLGV   360
EKTRESSYPL VHETAEEPVN VCDEKKKQEI SEQPEEEVHA LEMEVHTGP  LETNEALDSS   420
LVNQIDSNEK AMVEEKPSME KDTKEEKTPK PNNKENSAGK ENQKSRKKGS ATSKTEREES   480
NGHHETSPSI PSYMQATKSA KAKLRLQGSP KSAEQDGTEK ATVPRRHSLP SPGNGRITSH   540
SPRTTRLANS GDKTGNKKEK PLLSSREGNG                                   570

SEQ ID NO: 31          moltype = AA   length = 570
FEATURE                Location/Qualifiers
source                 1..570
                       mol_type = protein
                       organism = Arabidopsis thaliana
REGION                 1..570
                       note = Public GI ID no.5882749
REGION                 1..570
                       note = Score of 428.1 for HMM of FIGURE 5.
REGION                 1..570
                       note = Functional Homolog Of Ceres CLONE ID no. 1792354 at
                         SEQ ID NO. 2
REGION                 105..124
                       note = Pfam Name: IQ Pfam Description: IQ
                         calmodulin-binding motif
SEQUENCE: 31
MEMLAYFLSE FQICYNNAQR VVSGKEVLVT SKVEESDVVS DLPSFEVAET NTVDRSGGML    60
ETQNVGPEEI SDDEIELPEG KSTDSQNVAP VQDHSLSDAE RIQREIAATS VQAAFRGYLA   120
RRAFWALKGI IRLQALIRGH LVRRQAVATL FSVMGIVRLQ AFARGREIRK SDIGVQVYRK   180
CRLQLLQGNK LANPTDAYLG IKKLTANAFA QKLLASSPKV LPVHAYDTSN PNSNLIWLEN   240
WSASCFWKPV PQPKKTISRK PQNRLLVEAE SAKPKKSVRK VPASNFESSS VQTSFEFEKP   300
KRSFRKVSSQ SIEPPAVEDP QIELEKVKRS LRKVHNPVVE SSIQPQRSPR KEVEKPKLGV   360
EKTRESSYPL VHETAEEPVN VCDEKKKQEI SEQPEEEVHA LEMEVHTGP  LETNEALDSS   420
LVNQIDSNEK AMVEEKPSME KDTKEEKTPK PNNKENSAGK ENQKSRKKGS ATSKTEREES   480
```

```
NGHHETSPSI PSYMQATKSA KAKLRLQGSP KSAEQDGTEK ATVPRRHSLP SPGNGRITSH      540
SPRTTRLANS GDKTGNKKEK PLLSSREGNG                                     570

SEQ ID NO: 32            moltype = DNA  length = 1461
FEATURE                  Location/Qualifiers
source                   1..1461
                         mol_type = other DNA
                         organism = Zea mays
misc_feature             1..1461
                         note = Ceres CLONE ID no.325403
misc_feature             1..1461
                         note = Encodes the peptide sequence at SEQ ID NO 33
SEQUENCE: 32
aaatgcattt gctcgcaagc ttctatcttc atcaattgtg gttgaggctc ttcacttcca      60
gtatgatgag atggacccta attcagcctt caattggtta gagaggtgga cgataagtca     120
tgtctggaaa cccacttccc agccaaggag agttagtgct gatgctaagc cacatacaag     180
gaaggccagc tatgcaatgg aaacagagtc agtgaaatta aagcgtaatg cacggaggag     240
ctctgcagtg ccatttgaac cttctcaaac aaacactgac attgaaattg agagacaag     300
acggaatcca aggaaattaa gtagcactcc tgctgagtca gttcctgatg gccagttaac     360
agaacttgag aaggttaaac gtagccttag gaaggttact aattctgtgg ctgaaacctc     420
gaaggcacct agtccaaaaa ctgagattcc taaccatcaa gaggtccaat gtgagagacc     480
actaagaaga gcaaaacagg ttccaattca tcttgaaat actgaagcctg ataatgttaa     540
tctgttggac aatgcaaaga tggatattct ggtacctgat atccagcctg atgtggaagt     600
tgcttcagat ccagtcacca tcactaatga agaaaatgtt gatgaccac catctgttgt     660
tgctccagtg gccgaaatta tgccctgca agacatcaac aacgatgaaa atgctttggt     720
gaatgatgtg gaagagagat ccaaagaaga acatccttgt actgagagcc tgaaaggcag     780
caagaggagg tcttcattct cagctaagcc tgaatatcca gaaaatggct ccaaaaattc     840
tccagctctg ccaagctaca tggctgctac acaatcagca aaggcgaaac tgcggggaaa     900
tagctcacca aaacttagct ctgattcagc agagaaaaac ggcttcactc gtcgtcactc     960
ccttccatcc tctaacaacg gtaagatggt ttcacattct ccacgtacac aaaggccagc    1020
taatgctggt tgcaaggatg gagcgaaagg tgacaaggct atgctgtcat caagacatgc    1080
aagcgagaga ccactgaaag ctgagtggag acgttgaggc ggcgaatcaa atccaaatcc    1140
tccatttgat tagcgtgacc gtttgggtgg atggatcgcc cttgcagttt gctcggattt    1200
gttttgtttg tgatgtaaaa aaatgatgtc gtcatcgtcg gcgagatgaa tgaaccggct    1260
ttgttgtgat gaatccgctg ggagtcaact tatttattat agggttttcc gtcatgcctt    1320
ttgtgatgta tagctgaagt attttccggg tttgtttgg ttcccagacc ccagacttc     1380
ctcccttctt gttgagagct gctgatgtta gagagaatga aacatgcat ggattgagtt    1440
gaacaatctt acccatttgg t                                             1461

SEQ ID NO: 33            moltype = AA  length = 371
FEATURE                  Location/Qualifiers
source                   1..371
                         mol_type = protein
                         organism = Zea mays
REGION                   1..371
                         note = Ceres CLONE ID no.325403
REGION                   1..371
                         note = Score of 576.4 for HMM of FIGURE 5.
REGION                   1..371
                         note = Functional Homolog Of Ceres CLONE ID no. 1792354 at
                                SEQ ID NO. 2
SEQUENCE: 33
NAFARKLLSS SIVVEALHFQ YDEMDPNSAF NWLERWTISH VWKPTSQPRR VSADAKPHTR      60
KASYAMETES VKLKRNARRS SAVPFEPSQT NTAIEIEKTR RNPRKLSSTP AESVPDGQLT     120
ELEKVKRSLR KVTNSVAETS KAPSPKTEIP NHQEVQCERP LRRAKQVPIH LENQEPDNVN     180
LLDNAKMDIL VPDIQPDVEV ASDPVTITNE ENVDEPPSVV APVAEIMPLQ DINNDENALV     240
NDVEERSKEE HPCTESLKGS KRRSSFSAKP EYPENGSKNS PALPSYMAAT QSAKAKLRGN     300
SSPKLSSDSA EKNGFTRRHS LPSSNNGKMV SHSPRTQRPA NAGCKDGAKG DKAMLSSRDA     360
SERPLKAEWR R                                                         371

SEQ ID NO: 34            moltype = DNA  length = 783
FEATURE                  Location/Qualifiers
source                   1..783
                         mol_type = other DNA
                         organism = Oryza sativa
                         sub_species = Japonica
misc_feature             1..783
                         note = Ceres GI ID no.56784328
misc_feature             1..783
                         note = Encodes the peptide sequence at SEQ ID NO. 35
SEQUENCE: 34
atgcggggtt tccccgttcc ggtgacgagt tggagctccg ccgcgctcct gggccgctcc      60
atctcctcgg ccagggacgc ggccgaggcc tcctccccca tcaccgccgc ggagatggtc     120
cggttggcga aggaggtggc caacgccgcg gacgcctgcg caagaagctg                180
ctggaggctg cggaagcgct gtccaggtcc gacaccgacg cggagccgag gcggcgcgc     240
gccgagcgga ttttcgatgc ggcgtccatg tggccaagg aggccgacgc gtcaggagcg     300
tcgggtctct cagatgcggc ccaaaatctg acctgcgcga cctacgcgtt ctcggtagcc     360
gcctcggat ggggtccctt gccggagtcc agcacgagcg ggagggacgc cggcgacctc     420
ctaaccgagc cccttcttgg gtcatgtcag gacaagaacg agaagatgac cggcgagggc     480
```

```
aaggacttca gcgagatgag gaatagtgca gcggactctg atccacttca gcaatcggag    540
attaaggagt cgtcccttt  tggaaaatgc aaagaactcc tcaattatgg tttcttgga    600
ggtcctgccc tcctaccta tctaggctct ggactgagga aaacagtgtc acctgcagc    660
ccgtctgtct tccactacat cttctcgtcg tggtggattt gcattgttgt cggatcacat    720
gaacaaggag acttgaagat attacatatc gatagaatca cttctcatcc aaatgataag    780
tag                                                                  783
```

| SEQ ID NO: 35 | moltype = AA length = 260 |
|---|---|
| FEATURE | Location/Qualifiers |
| source | 1..260 |
| | mol_type = protein |
| | note = subspecies = Japonica |
| | organism = Oryza sativa |
| REGION | 1..260 |
| | note = Ceres GI ID no.56784328 |
| REGION | 1..260 |
| | note = Score of 660.5 for HMM of FIGURE 6. |

```
SEQUENCE: 35
MRGFPVPVTS WSSAALLGRS ISSARDAAEA SSPITAAEMV RVAKEVANAA DACGVSGKKL    60
LEAAEALSRS DTDAEPRRRA AERIFDAASM VAKEADASGA SGLSDAAQNL TCATYAFSVA   120
ASGWGSLPES STSGRDAGDL LTEPLLGSCQ DKNEKMTGEG KDFSEMRNSA ADSDPLQQSE   180
IKESSLFGKC KELLNYGFLG GPALLPYLGS GLRKTVSPCS PSVFHYIFSS WWICIVVGSH   240
EQGDLKILHI DRITSHPNDK                                               260
```

| SEQ ID NO: 36 | moltype = AA length = 311 |
|---|---|
| FEATURE | Location/Qualifiers |
| source | 1..311 |
| | mol_type = protein |
| | note = subspecies = Japonica |
| | organism = Oryza sativa |
| REGION | 1..311 |
| | note = Public GI ID no.56784330 |
| REGION | 1..311 |
| | note = Score of 826.7 for HMM of FIGURE 6. |
| REGION | 1..311 |
| | note = Functional Homolog Of Ceres GI ID no. 56784328 at SEQ ID NO. 35 |

```
SEQUENCE: 36
MESRLLRSAA LLARAARLAR AAATSTGRAV TAEHLAEVVA SAAGDRGFPS GALRQAALAL    60
ARSSAPEARP RATAEVVRAA AMVFRAAQEA GSPGVAEVAG DLAHAAHDCV RALVESGPAA   120
ERPRCLLRLW RRKNRHNKNA AGEADLEAPL LHPHERPSSS SSPIGASLSE IIELSESERD   180
FINYGMFGAL AIFPYLTRTG GLKSAYSPLS PSTFHIIFCT WWICVGLDVL CGNRGRAMMK   240
NILAFILAFY ARASARLAIL GVSLLVILYS HLELAPNEIY TLYILLGAAT CMHLLVWAMD   300
YMSRAPGDAA D                                                        311
```

| SEQ ID NO: 37 | moltype = AA length = 311 |
|---|---|
| FEATURE | Location/Qualifiers |
| source | 1..311 |
| | mol_type = protein |
| | note = subspecies = Indica |
| | organism = Oryza sativa |
| REGION | 1..311 |
| | note = Public GI ID no.125528718 |
| REGION | 1..311 |
| | note = Score of 812.3 for HMM of FIGURE 6. |
| REGION | 1..311 |
| | note = Functional Homolog Of Ceres GI ID no. 56784328 at SEQ ID NO. 35 |

```
SEQUENCE: 37
MESRLLRSAA LLARAARLAR AAATSTGRAV TAEHLAEVVA SAAGDRGFPS GALRQAALAL    60
ARSSAPEASP RAAAEVVHAA AMVFRAAQEA GSPGVAEVAG DLAHAAHDCV RALVESGPAA   120
ERPRCLLRLW RRKNRHNKNA AGEADLEAPL LHPHERPSSS SSPIGASLSD IIELSQSERD   180
FINYGMFGAL AIFPYLTRTG GLKSAYSPLS PSTFHIIFCT WWICVGLDVL CGNRGRAMMK   240
NILAFILAFY ARASARLAIL GVSLLVILYS HLELAPNEIY TLYILLGAAT CMHLLVWAMD   300
YMSRAPGDAA D                                                        311
```

| SEQ ID NO: 38 | moltype = AA length = 250 |
|---|---|
| FEATURE | Location/Qualifiers |
| source | 1..250 |
| | mol_type = protein |
| | note = subspecies = Japonica |
| | organism = Oryza sativa |
| REGION | 1..250 |
| | note = Public GI ID no.125572975 |
| REGION | 1..250 |
| | note = Score of 571.2 for HMM of FIGURE 6. |
| REGION | 1..250 |
| | note = Functional Homolog Of Ceres GI ID no. 56784328 at SEQ ID NO. 35 |

```
SEQUENCE: 38
MRGFPVPVTS WSSAALLGRS ISSARDAAEA SSPITAAEMV RVAKEVANAA DACGVSGKKL   60
LEAAEALSRS DTDAEPRRRA AERIFDAASM VAKEADASGA SGLSDAAQNL TCATYAFSVA  120
ASGWGSLPES STSGRDAGDL LTEPLLGSCQ DKNEKMTGEG KDFSEMRNSA ADSDPLQQSE  180
IKESSLFGKC KELLNYGFLG GPALLPYLGS GLRKTVSPCS PSVFHYIFSS WWICIVVVDE  240
LFVRIIDCSQ                                                        250

SEQ ID NO: 39           moltype = AA  length = 250
FEATURE                 Location/Qualifiers
source                  1..250
                        mol_type = protein
                        note = subspecies =Indica
                        organism = Oryza sativa
REGION                  1..250
                        note = Public GI ID no.125528716
REGION                  1..250
                        note = Score of 567.3 for HMM of FIGURE 6.
REGION                  1..250
                        note = Functional Homolog Of Ceres GI ID no. 56784328 at
                        SEQ ID NO. 35
SEQUENCE: 39
MRGFPVPVTS WSSAALLGRA ISSARDAAEA SSPITAAEMV RVAKEVANAA DACGVSDKKL   60
LEAAEALSRS DTDAEPRRRA AERIFDAASM VAKEADASGA SGLSDAAQNL TCATYAFSVA  120
ASGWGSLPES STSGRDAGDL LTEPLLGSCQ DKNEKMTGEG KDFSEMRNSA ADSDPLQQSE  180
IKESSLFGKC KELLNYGFLG GPALLPYLGS GLRKTVSPCS PSVFHYIFSS WWICIVVVDE  240
LFVRIIDCSQ                                                        250

SEQ ID NO: 40           moltype = DNA  length = 1443
FEATURE                 Location/Qualifiers
source                  1..1443
                        mol_type = other DNA
                        organism = Arabidopsis thaliana
misc_feature            1..1443
                        note = Ceres SEEDLINE ID no.ME06748
misc_feature            1..1443
                        note = Encodes the peptide sequence at SEQ ID NO. 41
SEQUENCE: 40
aattgtctct tcttttcttt ttgtacttgt caaaaacaaa aagaacaaca aaaaaaatct   60
caaccgtaga aaattccgac aagagttcag ttcatacaat gaactaagta tgggtttctt  120
tggaagactg ttcggaagta agaagcaaga aaaggcaaca ccgaacagac gaagatggag  180
cttcgctact agatcctcac atcccgagaa tgattcgtct tctcatccaa gcaagagacg  240
tggggatgaa gatgtcttaa acgccgacaa gcatgcgata gccgtcgcgg ctgctacagc  300
tgcagtggct gaagccgcac tcgctgctgc tcgtgcgggg gcggaagtcg tgagactcac  360
caatggtggt agaaactcgt cggtaaaaca aatcagtcgg agtaatcgtc ggtggtctca  420
agagtataaa gcagctatcc gcttttcgtg gctacttggc gaggagggcg ttgagagcac  480
tgaaggcatt agtgaagctt caagcgttgg tgaagggaca catagtaagg aaacaaacgg  540
ctgatatgct gcgtcgaatg caaacgctgg ttcggctcca agcacgagct agagcttcgc  600
gttcttctca cgtttctgac tcttcccatc cgccaacact aatgattcca tcttccccac  660
aatctttcca tgcacgatgc gttttcagag ctgagtacag taaagtcatt gccatggatc  720
accaccacaa caaccaccgt tcaccgatgg gttcaagccg ttattagac  caatggagga  780
cagaggaaag tctatggagc gcaccaaagt acaatgacaaa tgatgacaaa atcctagaag  840
tcgacacttg gaagcctcac ttcagagagt caccaaggaa aagaggatct ctagtggttc  900
ctacaagtgt ggagaacagt ccacaattaa ggtctagaac aggaagcagc agtggtggtt  960
caaggagaaa aactcccttc acgcctgcga gaagcgagta cgagtactac tctgggtatc 1020
accctaacta catggctaac actgagtctt acaaagcaaa agtccgatca caaagcgac  1080
caagacagag actacaagat ttaccttcag agagtggtta caagaggtct atacagggac 1140
agtattacta ctacacacct gctgcagagc gatcgtttga tcagcgttcg gataacggga 1200
tcgcgggtta cagaggagtt tctgatgggt tagatcgaaa ccaaagtgac aaatcgaaga 1260
tgtacacttc gttttttcagt tctaatcctc ttttctttca atagtcgaga aaggatgaaa 1320
aaagtgagtg gaatgtgtaa aattagattt cgacacacga gtacagagac agccagtgat 1380
caatctgtgt tttgtactat tttctaattg actgtatcca acaagggtcc attcttgtct 1440
gac                                                              1443

SEQ ID NO: 41           moltype = AA  length = 252
FEATURE                 Location/Qualifiers
source                  1..252
                        mol_type = protein
                        organism = Arabidopsis thaliana
REGION                  1..252
                        note = Ceres SEEDLINE ID no.ME06748
REGION                  1..252
                        note = Score of 176.1 for HMM of FIGURE 2.
SEQUENCE: 41
MLRRMQTLVR LQARARASRS SHVSDSSHPP TLMIPSSPQS FHARCVSEAE YSKVIAMDHH   60
HNNHRSPMGS SRLLDQWRTE ESLWSAPKYN EDDDKILEVD TWKPHFRESP RKRGSLVVPT  120
SVENSPQLRS RTGSSGGSR RKTPFTPARS EYEYYSGYHP NYMANTESYK AKVRSQSAPR  180
QRLQDLPSES GYKRSIQGQY YYYTPAAERS FDQRSDNGIA GYRGVSDGLD RNQSDKSKMY  240
TSFFSSNPLF FQ                                                    252
```

```
SEQ ID NO: 42          moltype = AA  length = 517
FEATURE                Location/Qualifiers
source                 1..517
                       mol_type = protein
                       organism = Arabidopsis thaliana
REGION                 1..517
                       note = Ceres SEEDLINE ID no.ME20711
REGION                 1..517
                       note = Score of 943.4 for HMM of FIGURE 2.
REGION                 1..517
                       note = Functional Homolog Of Ceres SEEDLINE ID no. ME06748
                         at SEQ ID NO.41
REGION                 169..189
                       note = Pfam Name: IQ Pfam Description: IQ
                         calmodulin-binding motif
SEQUENCE: 42
MGKKGSWFSA IKRVFTPHSK EKQLSNNNQE PEIKSENKEK KKKGFGKKLR NGETNSFLPI   60
FRQPSSIEKI LSEAEREHNL VFRPPTPTDR ANSSSTSVAS PLVRPASPKV PSQRYVSSPK  120
PISPRVAYPQ VHYPKPPSPK PPSPRAVSPR IVQRREFVHR PEPSLLVKNA YAIKIQAAFR  180
GYMARRSFRA LKGLVRLQGV VRGHSVKRQT MNAMKYMQLL VRVQTQVQSR RIQMLENRAR  240
NDKDDTKLVS SRMSDDWDDS VLTKEEKDVR LHRKIDAMIK RERSMAYAYS HQLWKNSPKS  300
AQDIRTSGFP LWWNWVDRQK NQNQPFRLTP TRPSLSPQPQ SSNQNHFRLN NSFDTSTPNS  360
SKSTFVTPSR PIHTPQPYSS SVSRYSRGGG RATQDSPFKD DDSLTSCPPF SAPSYMAPTV  420
SAKAKLRANS NPKERMDRTP VSTNEKRRSS FPLGSFKWNK GSLFMSNNSN NKGPGSSSSG  480
AVVLEKHKTL KSVGNLSIDS TVSMPATIGR RAFNRFA                          517

SEQ ID NO: 43          moltype = AA  length = 383
FEATURE                Location/Qualifiers
source                 1..383
                       mol_type = protein
                       organism = Arabidopsis thaliana
REGION                 1..383
                       note = Ceres SEEDLINE ID no.ME18973
REGION                 1..383
                       note = Score of 543.8 for HMM of FIGURE 2.
REGION                 1..383
                       note = Functional Homolog Of Ceres SEEDLINE ID no. ME06748
                         at SEQ ID NO.41
REGION                 115..135
                       note = Pfam Name: IQ Pfam Description: IQ
                         calmodulin-binding motif
SEQUENCE: 43
MGRATRWFKG LFGIKPSSCS GTDSGTISNR LDRSLCDSYE TIPPNISEKE AAWLRSFYAA   60
GEEEKERRTH AIAVAAATAA AADAAVAAAK AAAAVVRLQG QGKSGPLGGG KSREHRAAMQ  120
IQCAFRGYLA RKALRALRGV VKIQALVRGF LVRNQAAATL RSMEALVRAQ KTVKIQRALR  180
RNGNAAPARK STERFSGSLE NRNNGEETAK IVEVDTGTRP GTYRIRAPVL SGSDFLDNPF  240
RRTLSSPLSG RVPPRLSMPK PEWEECSSKF PTAQSTPRFS GGSPARSVCC SGGGVEAEVD  300
TEADANRFCF LSGEFNSGYM ADTTSFRAKL RSHSAPRQRP ESNASAGGWR RSIGGGGVRM  360
QRQSCSGVRE AVVGNIERRR MRW                                         383

SEQ ID NO: 44          moltype = AA  length = 460
FEATURE                Location/Qualifiers
source                 1..460
                       mol_type = protein
                       organism = Arabidopsis thaliana
REGION                 1..460
                       note = Ceres SEEDLINE ID no.ME08732
REGION                 1..460
                       note = Score of 822.2 for HMM of FIGURE 2.
REGION                 1..460
                       note = Functional Homolog Of Ceres SEEDLINE ID no. ME06748
                         at SEQ ID NO.41
REGION                 128..148
                       note = Pfam Name: IQ Pfam Description: IQ
                         calmodulin-binding motif
SEQUENCE: 44
MAKKKSWFSL VKRLFIWDTH STQDKKEKRR KWIFGRLKSK RLPSIKAPLP SKGTTLSEAE   60
QEQSKHALTV AIASAAAAEA AVTAAHAAAE VVRLTGQRNE NSEESQPVKT RNGAPQSTYQ  120
CQREIKESAA AIKIQTAFRG YLARKALRAL KGIVKLQAII RGRAVRRQAM SSLKCLQSIV  180
SIQSQVCARR LQMVEGRCDY SENEEMQDFK DKIIRMDSNS ERKWDESTVL KEEVDTSCTS  240
KRERTKEYSF NHRRSAESER SKVNGRWRYW LEQWVDTQLS KSKELEDLDS VFSSHSRAGE  300
EYGGRQLKLR SNIQRQNPVE GLDSPILGSR RSFPHRRQCS VGEDHSFLSS PATPAYMAAT  360
ESAKAKARST SSPKIRTGGN VDMNSDSYSP CKKKLSIASS INSEMLSNGR VGKLSVNQQQ  420
RSPSFKGLSV PIKSSRTTIK DLSINSDCSL PNWDRQAFFK                        460
```

```
SEQ ID NO: 45            moltype = AA   length = 403
FEATURE                  Location/Qualifiers
source                   1..403
                         mol_type = protein
                         organism = Arabidopsis thaliana
REGION                   1..403
                         note = Ceres SEEDLINE ID no.ME19657
REGION                   1..403
                         note = Score of 695.5 for HMM of FIGURE 2.
REGION                   1..403
                         note = Functional Homolog Of Ceres SEEDLINE ID no. ME06748
                          at SEQ ID NO.41
REGION                   117..137
                         note = Pfam Name: IQ Pfam Description: IQ
                          calmodulin-binding motif
SEQUENCE: 45
MGFFGRLFGS KKKSDKAASS RDKRRWSFTT RSSNSSKRAP AVTSASVVEQ NGLDADKHAI    60
AVAAAATAAVA EAALTAAHAA AEVVRLTSGN GGRNVGGGGN SSVFQIGRSN RRWAQENIAA   120
MKIQSAFRGY LARRALRALK ALVKLQALVR GHIVRKQTAD MLRRMQTLVR LQSQARARAS   180
RSSHSSASFH SSTALLFPSS SSSPRSLHTR CVSNAEVSSL DHRGGSKRLD WQAEESENGD   240
KILEVDTWKP HYHPKPLRSE RNNESPRKRQ QSLLGPRSTE NSPQVGSSGS RRRTPFTPTS   300
RSEYSWGCNN YYYSGYHPNY MANTESYKAK VRSQSAPKQR VEVSNETSGY KRSVQGQYYY   360
YTAVEEESLD VGSAGYYGGG GGDSDRLNRN QSAKSRMHSS FLV                     403

SEQ ID NO: 46            moltype = DNA   length = 1711
FEATURE                  Location/Qualifiers
source                   1..1711
                         mol_type = other DNA
                         organism = Triticum aestivum
misc_feature             1..1711
                         note = Ceres CLONE ID no.835818
misc_feature             1..1711
                         note = Encodes the peptide sequence at SEQ ID NO 47
SEQUENCE: 46
ccaaatccaa tgctctacat ttcttccttc tcgtgccctt tcttgatttg cgcatggaca    60
gtgacttgcg ttgccagcaa agagccatcc tgctaggccc tttgccaaca tctccgtaga   120
tcacattcca gagcagatag acagaagaat ggagaggaag aagaagggg gttcgagcg    180
catcaagagg ctcttcatct ccgaacccaa gcagaaaccc aaaccagaca agaaggtgaa   240
gagcaagaga tggctggtag ggaagctcaa gacccagcac tcgtttgccc tgccagctcc   300
ggagccggag ccggcgacgg gtcagattca gataaggcag gcggaggagg agcagagcaa   360
gcacgcagtg gcggtcgcgc tcgcctccgc agccggccgca gaggcagccg tcgcggccgc   420
ccacgcggcc gcggaggtgg tccgcctcac aggaccgccc tcgccggcgc cggcgccggc   480
gcgtgaggac gccgcgtctt ccggccacga actgttcgcc gccgtcgcga tccagtcagc   540
ctaccgcgga tacctcgcgc ggagggcact gcgcgcgctc aagggcctgg tgaggctgca   600
ggcggtgatc cgcgggcagg cggtgcggcg gaagacgcg gcgctgc gggggcctcga   660
gtcgctggtc aagatccagg cccggcagcg cgccaggggcc gacgtcgacc acgagcacga   720
cggcgacggc atggacgccc tgctgaggag aggccgggag ctgtacgccc ccgcgctgca   780
agagcagcag cagagcagcc ggggggtggg acggcagcac cctctccaag gaagagatgg   840
gcgccgtgat gaggagcagg gaggaagccg ccatcaagcg cgtgcgcgcg ctgcagtacg   900
cctccatcca gaacgagaag atcggcatca ggaggcagcc catgtccagg gacgagatgg   960
agacgctcaa ccagcgctgg agctggctgg aggagtgggt cggctcgcag cccttcgaca  1020
aggacgtggc cgtcgacgtg gtcacccacc cccaccgc gccgcctcgc tccagggact  1080
ccctcgcctg cctcgaggac gacgacgacc atgatgacga cggctatggc aggcggctcg  1140
gctactcgtc caggcggtcc ttcggccgcg ccaggcgcac gccagggagg gggagcgtcg  1200
acgacgggct gcaggcctgc tcgccggcgg tggctttccc ggggtacatg gcgtccacgg  1260
cgtccgccaa ggccaagttc cggtccatga gcacgcccaa ggagcgcttc gccgtgccat  1320
ccgacgcata tcggagcag tgcttcgccg accgcctcat gtcacccatc cgtccatgt  1380
cgccgatgcc gtccatcgcc agcgacatgg gttttgctcg ctccagcagg ccgccggttg  1440
cgcagcggtc gccgcgtgtc aagggggggc cgatgacgcc gtcgaggatc cgctccagga  1500
ggtcccccag ccgccacagc ttcggctctg aagccgcgct gcaccagatg cagatggagc  1560
actacacccc tattcgctag acacaaacaa acttctttgt aatgtgacca atgctgcctt  1620
gtttggcggg cttgctctct ctgggtctga ccatggaaac cttctcaaac tgaccgtgct  1680
gtgcgaatgc aatatggatc tgcaaacttt c                                 1711

SEQ ID NO: 47            moltype = AA   length = 476
FEATURE                  Location/Qualifiers
source                   1..476
                         mol_type = protein
                         organism = Triticum aestivum
REGION                   1..476
                         note = Ceres CLONE ID no.835818
REGION                   1..476
                         note = Score of 855.1 for HMM of FIGURE 2.
REGION                   1..476
                         note = Functional Homolog Of Ceres SEEDLINE ID no. ME06748
                          at SEQ ID NO.41
```

```
REGION                     122..142
                           note = Pfam Name: IQ Pfam Description: IQ
                           calmodulin-binding motif
SEQUENCE: 47
MERKKKGWFE RIKRLFISEP KQKPKPDKKV KSKRWLVGKL KTQHSFALPA PEPEPATGQI   60
QIRQAEEEQS KHAVAVALAS AAAAEAAVAA AHAAAEVVRL TGPPSPAPAP AREDAASSGH  120
ELFAAVAIQS AYRGYLARRA LRALKGLVRL QAVIRGQAVR RKTAATLRGL ESLVKIQARQ  180
RARADVDHEH DGDGMDALLR RGRELYAAAL QEQQQSSRGW DGSTLSKEEM GAVMRSREEA  240
AIKRVRALQY ASIQNEKIGI RRQPMSRDEM ETLNQRWSWL EEWVGSQPFD KDVAVDVVTH  300
PHPPPPRSRD SLACLEDDDD HDDDGYGRRL GYSSRRSFGR ARRTPGRGSV DDGLQACSPA  360
VAFPGYMAST ASAKAKFRSM STPKERFAVP SDAYSEQCFA DRLMSPIPSM SPMPSIASDM  420
GFARSSRPPV AQRSPRVKGG PMTPSRIRSR RSPSRHSFGS EAALHQMQME HYTPIR     476

SEQ ID NO: 48              moltype = DNA  length = 1651
FEATURE                    Location/Qualifiers
source                     1..1651
                           mol_type = other DNA
                           organism = Panicum virgatum
misc_feature               1..1651
                           note = Ceres CLONE ID no.1796745
misc_feature               1..1651
                           note = Encodes the peptide sequence at SEQ ID NO 49
SEQUENCE: 48
gtagcactag ccactctcac tcccccggc ggcatggaga aggagaagag gcggaggagc    60
tggttcgagc gcatcaggcg gctcttcacc tcctccgagc ccaaggagaa acccaaacct  120
gacaagaagg cgaagagcaa gcggtggcta ccggggacgc tgaggcagca gcagtcgttc  180
gctctgccgg cgccggcatc gcggccgcg gacctgcaga tcaggcaggc ggaggacgag  240
cagagcaagc acgccgtgac cgtcgctctc gccaccgcgg cggccgccga ggccgcggtc  300
gccgccgcgc acgccgccgc cgaggtcgtc cgcctcaccg gccagcaggc cgcggccccg  360
ccggccggca gggagcggga gctggaggag gaggagcatg ccgccgtctt gatccaatcg  420
gcgtaccgcg ggtacctggc tcggcggggc ctgcgcgcgc tcaagggtct ggtgcggctg  480
caggcgctga tccgggggca ggcggtgcgg caccagacgg cggccacgct gcgcggcctc  540
gagtccctga tgaggatcca ggcccagcac cgctcccggg ccggcggccc cgaccacccg  600
gcggcgctcg acggcaacga cgacgccttc tgctccggc gcggccggga gctctacgcc  660
gccgcggtcc accagcagca gcaggcgggc agcaaagggt gggacagcag catcctcgcg  720
aaggaggaga tgcgcgccgt gatgcgcagc cgggaggagg ccgccctcaa gcgcgtcgcg  780
gcgctgcagt acgcgtccct gcagagcgag cggctgggcg tccggcggcc gccgctgccc  840
agggacgagg aggcggacgc gctccaccgc cgctggagct ggctcgagga gtgggtcggc  900
gcgcagccgc ccttcgacaa ggacgtcccc gtggcgcacc agtcgcccta cagcagggac  960
gacgccgccg ccgcaggggc cgccagacg ccgggccggg ccgtcgaccc gctcgccggc 1020
ctcggcggca gcgacgccga ccggctcggt tgctcggcgc ggcggtcctt cgtgcggccg 1080
aggcgcgcgc cggcgcgggc gggcgactac ttctacgagg acgccgcgcc gtgctcgccg 1140
gcgacgttcc cggggtacat ggcgtccacg gcctccgcca aggccaagtt ccggtccatg 1200
agcacgccca aggagcgctt cgccggagcc gacgccttct ccgagcactg cttcccgttc 1260
gccgaccgca tgctctcgcc gatcccgtcc atgtcgccca tcccctccat cgccagcgac 1320
atgggcttcg ccaggtccac caggccgccc gccgcgcaa gatccgccgg ggtggcggcc 1380
aagggcccca tgacgccggc gcggtcgcgc tcacggaggt cgccgagcca ccacagcttc 1440
ggctccgagg ccgcgctgca ccaactgcag atggagcact acacccccagt ccggtgaaca 1500
agactacaga gagtgccttg cttcgttaca ctctttttgtg aagatacaat tccctgctcc 1560
cattctttttg tttgttcacc tttcttgaca gaagggttca actgttcaag tattcagtaa 1620
tggaatgcaa caacgtaaaa aaaaaaaaa a                                  1651

SEQ ID NO: 49              moltype = AA  length = 487
FEATURE                    Location/Qualifiers
source                     1..487
                           mol_type = protein
                           organism = Panicum virgatum
REGION                     1..487
                           note = Ceres CLONE ID no.1796745
REGION                     1..487
                           note = Score of 472.4 for HMM of FIGURE 2.
REGION                     1..487
                           note = Functional Homolog Of Ceres SEEDLINE ID no. ME06748
                           at SEQ ID NO.41
REGION                     121..141
                           note = Pfam Name: IQ Pfam Description: IQ
                           calmodulin-binding motif
SEQUENCE: 49
MEKEKRRRSW FERIRRLFTS SEPKEKPKPD KKAKSKRWLP GKLRTQQSFA LPAPASAAAD   60
LQIRQAEDEQ SKHAVTVALA TAAAAEAAVA AAHAAAEVVR LTGQQAAAPP AGRERELEEE  120
EHAAVLIQSA YRGYLARRAL RALKGLVRLQ ALIRGQAVRH QTAATLRGLE SLMRIQAQHR  180
SRAGGPDHPA ALDGNDDAFL LRRGRELYAA AVHQQQQAGS KGWDSSILAK EEMRAVMRSR  240
EEEAALKRVRA LQYASLQSER LGVRRPPLPR DEEADALHRR WSWLEEWVGA QPPFDKDVPV  300
AHQSPYSRDD AAAARGRQTP GRAVDPLAGL GGGDADRLGC SARRSFVRPR RAPARAGDYF  360
YEDAAPCSPA TFPGYMASTA SAKAKFRSMS TPKERFAGAD AFSEHCFPFA DRMLSPIPSM  420
SPIPSIASDM GFARSTRPPA AQRSPRVAAK GPMTPARSRS RRSPSHHSFG SEAALHQLQM  480
EHYTPVR                                                            487
```

```
SEQ ID NO: 50              moltype = AA  length = 501
FEATURE                    Location/Qualifiers
source                     1..501
                           mol_type = protein
                           note = subspecies = Indica
                           organism = Oryza sativa
REGION                     1..501
                           note = Public GI ID no.125543896
REGION                     1..501
                           note = Score of 538.7 for HMM of FIGURE 2.
REGION                     1..501
                           note = Functional Homolog Of Ceres SEEDLINE ID no. ME06748
                            at SEQ ID NO.41
REGION                     122..142
                           note = Pfam Name: IQ Pfam Description: IQ
                            calmodulin-binding motif
SEQUENCE: 50
MERKRRGWLE RIKRLFVSEP KQKPKPDKKV KSKRWMFAGK LKTQHSFALP APAPAVEEEQ    60
IRQAEDEQSK HAMAVALATA AAAEAAVAAA HAAAEVVRLT GKTAALAPAP ATTTTPTPYG   120
HEHAALMIQS VYRGYLARRA LRALKGLVRL QALIRGQAVR RQTAATLRGL ESLMKIQARQ   180
RARASSAAAA GGDHNAANSP APDGMDALLR RGRELYYAAA AAVHEQQLSK GWDSSTLSKE   240
EMSAMSRSRE EAALKRVRAL QYASLHQSEK VRVRRQPMSR EEMETLNQRW SWLEEWVGSQ   300
PPFDKDIPVA HQSPSRDAAG AAMNDDERPP PPPVLRSRSR ADRLACVGGD DDDADRQLGY   360
SARRSFTRAG RRTPARDDDG GGAAAFPGYM ASTASAKAKF RSMSTPKERS GAGAADAYSE   420
QCFPFADRLL SPIPSMSPIP SIASDIVFAR SSRPAAAQRS PRVKGPMTPT RSRSRRSPGR   480
HSFSSEAALH QLQMEQYTPI R                                            501

SEQ ID NO: 51              moltype = DNA  length = 1494
FEATURE                    Location/Qualifiers
source                     1..1494
                           mol_type = other DNA
                           organism = Populus balsamifera
                           sub_species = trichocarpa
misc_feature               1..1494
                           note = Ceres ANNOT ID no.1483984
misc_feature               1..1494
                           note = Encodes the peptide sequence at SEQ ID NO 52
SEQUENCE: 51
atgtcaggtc tatcagagtt gagaaatatg aaagttggaa aaaagatggg aggtcccatg     60
agtcttgaga aggatgttta tatgagttgt ggtgcttcaa tggctaagaa gagaagctgg   120
ttctatcgag tgaaaggtt atttacttct gacacacagt caagacaaga aaaggaaagg   180
agaagaaaat ggatgttttt tggaaagttt aaggtcagaa atagattggc ctccattgca   240
gctccatcat caccactaag agaagaagca gagaaggagc agagcaagca tgctctaagt   300
gttgctcttg ccactgctgc tgctgctgag gcagctgttg tagctgctca ggctgcggcc   360
gaggtggttt tgctcactgg tgttcctcat tctatcaatg aatatgagaa agaaaccgac   420
catttagcct tcgaagttca aggtgatgcc cctcattcca ctcatcaaca tcgcaggggg   480
atcaaagaac tggctgccat caaaattcaa gctacctta ggggttacct tgcaaggaaa   540
gctttgcggg cgctgaaggg gatagtgaag cttcaagcaa ttatccgagg cggaacgtg   600
agacgccaag ccatgactac tctaaaatgc ttgcaatcca ttgtaaatat ccagtcacaa   660
gtctgtgcaa aaaggatcca aatggtggaa ggtgcttgga cctgtagtga aaataaacag   720
ttagaaaatt tgagtgacaa gataataaag atggatatga atagtgaaag aagatgggat   780
agcagccttc tgcacaaagga agaggcagtt gcctcgtttc taagcaagaa agaggccgcg   840
attaagagag aacggataag agaatactgg ttcaaccgcc ggaattcagc tgaatcgag   900
cgaagcaagc caagtggaag gtggaggtac tggttagatc aatgggtgag tactcaactt   960
gttaagagta aagagcttga agatttggac tcagttttaa cctcaaatcc aaagcctgga  1020
gtggaatata gaggaaagca gattaaactg agaggtttgc agagactgta tcaccttgac  1080
agtgtagatt ctcccatttc agctccaaga aaatccttcc atagaaagca atgctcgttg  1140
ggagaagaca attcctttc tagatctcct gtggttccaa cttacatgga aacaactgaa  1200
tctgccaagg caaaaacaag atcaatgagc tcaccaaagc taaggccagg gagttttgat  1260
gcttactctg acagctattc tccatgtaag aataagcttt tctgatatc atctacaact  1320
actgaagtgc cgagcagtgc taggtacgga aggcctagtg cttatcagca aaggtctcca  1380
agcttgaagg gccttccggg tccgataaaa tgtaaccggc caacgtcgaa agttcttagc  1440
tttgattcag attgctcatt aaagacttgg gataaacaaa gttccttag atga          1494

SEQ ID NO: 52              moltype = AA  length = 464
FEATURE                    Location/Qualifiers
source                     1..464
                           mol_type = protein
                           note = subspecies = trichocarpa
                           organism = Populus balsamifera
REGION                     1..464
                           note = Ceres ANNOT ID no.1483984
REGION                     1..464
                           note = Score of 498.0 for HMM of FIGURE 2.
REGION                     1..464
                           note = Functional Homolog Of Ceres SEEDLINE ID no. ME06748
                            at SEQ ID NO.41
REGION                     130..150
```

```
                          note = Pfam Name: IQ Pfam Description: IQ
                                 calmodulin-binding motif
SEQUENCE: 52
MAKKRSWFYR VRRLFTSDTQ SRQEKERRRK WMFFGKFKVK NRLASIAAPS SPLREEAEKE   60
QSKHALSVAL ATAAAAEAAV VAAQAAAEVV LLTGVPHSIN EYEKETDHLA FEVQGDAPHS  120
THQHARGIKE LAAIKIQATF RGYLARKALR ALKGIVKLQA IIRGRNVRRQ AMTTLKCLQS  180
IVNIQSQVCA KRIQMVEGAW TCSENKQLEN LSDKIIKMDM NSERRWDSSL LTKEEAVASF  240
LSKKEAAIKR ERIREYWFNR RNSAESERSK PSGRWRYWLD QWVDTQLVKS KELEDLDSVL  300
TSNPKPGVEY RGKQIKLRGL QRLYHLDSVD SPISAPRKSF HRKQCSLGED NSFSRSPVVP  360
TYMATTESAK AKTRSMSSPK LRPGSFDAYS DSYSPCKNKL SLISSTTTEV PSSARYGRPS  420
AYQQRSPSLK GLPGPIKCNR PTSKVLSFDS DCSLKTWDKQ SSFR                  464

SEQ ID NO: 53          moltype = DNA   length = 1579
FEATURE                Location/Qualifiers
source                 1..1579
                       mol_type = other DNA
                       organism = Gossypium hirsutum
misc_feature           1..1579
                       note = Ceres CLONE ID no.1924654
misc_feature           1..1579
                       note = Encodes the peptide sequence at SEQ ID NO 54
SEQUENCE: 53
aaggaaaaaa aactatagct ttcttcgttt atgtaatgga attcctcgcc aattctctct   60
caatctaagc tatccaagtt ccaaagacta aagcttttt gaagcggtga ttcctgtttg  120
attctcccaa aatatttaag tattcagtgc acctttata cacaatccat atggaattta  180
ccactatact atattatata agatgatgtt aggatgcaga aatgtaaaaa ttcagaatag  240
tagtacctga agaagtgaga gttctttaat ggcgaagaag aagagctagt tcaatctagt  300
gaagaggttc tttctctttg agacacttat aaatgcacaa aaggataaca gaaggaaatg  360
gatgtttgga aggtttagga ccaaaaggtt agcatccatt aaagctccat caccaccaag  420
agacagcata aatatgaaa cagaggagga ccagaagaaa catgccttaa cagtggcaat  480
tgccgcagtg gctgctgctg aagcagctgt tgcagctgct caggttgcag ccgaggttgt  540
tcgcctcaca ggcaatgacg cccctaaagc taaagaagaa caaaccaatg atgttaaacc  600
tgactgttct tcatctagtg agcttggcaa caagttccaa caacttgctg ctataaaaat  660
ccaggcttct tttcggggtt accttgcaag gaaagctttg agagcattga aagggatagt  720
gaagcttcaa gcaattattc gaggccgagt tgtgagacga caagcattga ctgctttaaa  780
atgcttgcaa tcgattgtaa acattcagtc tcaagtttgt gcaaggagat tccaaattgt  840
agaaggcact tggcaacaac atgatgagaa caaagagttg ataactttga aagataagat  900
tcttaaggtg gataccaaca gtcaaacaag atgggacaat tgtaatggag gattgaagta  960
ctggttagac caatgggtgg atactaaaag taaagatgtt gaagtcgaag acatagactc 1020
ggtttggact tcgaaccgca agcctacgag gctcaagact tttcgagac agtatcattg 1080
tgatgcagaa ggggtagatt ctccggtacg ggttcaagga cgacgatcat ttcatggaaa 1140
gcagagttct ttaggagaag atagttcttt tattacatct cctgtagttc caacttacat 1200
ggcagcaaca caatctacta aagcaaaggt aaggtcaatg agttcaccaa agctaaggcc 1260
aggaacttgt gatactcaat ccgaaagcta ttcaccatat aagaacaagt cgtgtctcct 1320
atcttcagtt acaagcaagc ctaacgctta tgagcagaga tccccaacac taaagggtgt 1380
aaagtcaaag aaaaccttga aggatcttag ctttaactct taatgttcat tgcctaattg 1440
ggtgcaaaaa agcaccttca aatgactcga ccattgtgat gttttaggtc ccttggaagc 1500
aagtctttgt tattgtgttt gtgtgagatt gctgatgctg ttttgtgctt aaacaattga 1560
atgaatcaag ttttgtgtg                                             1579

SEQ ID NO: 54          moltype = AA   length = 384
FEATURE                Location/Qualifiers
source                 1..384
                       mol_type = protein
                       organism = Gossypium hirsutum
REGION                 1..384
                       note = Ceres CLONE ID no.1924654
REGION                 1..384
                       note = Score of 679.6 for HMM of FIGURE 2.
REGION                 1..384
                       note = Functional Homolog Of Ceres SEEDLINE ID no. ME06748
                              at SEQ ID NO.41
REGION                 125..145
                       note = Pfam Name: IQ Pfam Description: IQ
                              calmodulin-binding motif
SEQUENCE: 54
MAKKKSWFNL VKRFFLFETL INAQKDNRRK WMFGRFRTKR LASIKAPSPP RDSIKYETEE   60
DQKKHALTVA IAAVAAAEAA VAAAQVAAEV VRLTGNDAPK AKEEQTNDVK PDCSSSSELG  120
NKFQQLAAIK IQASFRGYLA RKALRALKGI VKLQAIIRGR VVRRQALTAL KCLQSIVNIQ  180
SQVCARRFQI VEGTWQQHDE NKELITLKDK ILKVDTNSQT RWDNCNGGLK YWLDQWVDTK  240
SKDVEVEDID SVWTSNRKPT RLKTFSRQYH CDAEGVDSPV RVQGRRSFHG KQSSLGEDSS  300
FITSPVVPTY MAATQSTKAK VRSMSSPKLR PGTCDTQSES YSPYKNKSCL LSSVTSKPNA  360
YEQRSPTLKG VKSKKTLKDL SFNS                                        384
```

| SEQ ID NO: 55 | moltype = DNA length = 1032 |
|---|---|
| FEATURE | Location/Qualifiers |
| source | 1..1032 |
| | mol_type = other DNA |
| | organism = Populus balsamifera |
| | sub_species = trichocarpa |
| misc_feature | 1..1032 |
| | note = Ceres ANNOT ID no.1468861 |
| misc_feature | 1..1032 |
| | note = Encodes the peptide sequence at SEQ ID NO 56 |

SEQUENCE: 55

```
atgaaggcaa ggagagcact aagggcacta aaagctttgg tgaagcttca agccttagtg    60
agaggccaca ttgtgagaaa gcaaacagca gacatgctta ggcgtatgca agacattagtg  120
agactgcagg ctcgagcccg tgctagtcgc agttatgtgt cggactcatc gcacactact   180
ggcaagtcct ctcattctcg ttatgctgtc cctgcaagtc cttcaaagga tcacctgttt   240
cgtgtttcta gtaccaaatt tgatgggccc tcgattctca agagatgtgg ttcaaatgca   300
aacttagggg agagcattga cttgacaaa gtaaaatggt gttcgaactg gctagaccgt    360
tggatggaag aaagttttt gaatgaccat ggcagcaatc caccgagaag tcgaaatgct    420
gatgatgaga gagtgacaa gattcttgaa gtggacactt ggaagcccca tgtgaaatcc    480
caacaaagta atagaacatt tcagacttca cagcatgctt tggcttcaga tcataacaat   540
cagagcttta tgactttga ctctatgtca aaactatcaa aaaaagaacc gaatccaatg    600
ccgagcatct cttcaggaga aattttgcag tctcttaaat tacctctagg aaatgatgaa   660
gcagtttata ggaccgctga aatagccctc gaatgttct ctgcaacatc tagacctgga    720
agtagtggtc ggagaggagg cccttttaca ccaacaagga gtgagtgctc gtgggcttc    780
tttaatggat actcgggtta ccccaactac atggctaatc tgaatcatc tcgagccaag    840
gtcaggtcac aaagtgcccc aaggcagagg ctagagtttg agaaatatgg ttcaagcaga    900
agatctgttc agggtattc tgattcagaa actcgttcag aaaggggttt tgctcaaaat   960
actgaacttc aaaacaaagc ttacgtagca tctggctact gaatagact agggacttcc  1020
gacttgaggt ga                                                      1032
```

| SEQ ID NO: 56 | moltype = AA length = 343 |
|---|---|
| FEATURE | Location/Qualifiers |
| source | 1..343 |
| | mol_type = protein |
| | note = subspecies = trichocarpa |
| | organism = Populus balsamifera |
| REGION | 1..343 |
| | note = Ceres ANNOT ID no.1468861 |
| REGION | 1..343 |
| | note = Score of 100.0 for HMM of FIGURE 2. |
| REGION | 1..343 |
| | note = Functional Homolog Of Ceres SEEDLINE ID no. ME06748 at SEQ ID NO.41 |
| REGION | 10..30 |
| | note = Pfam Name: IQ Pfam Description: IQ calmodulin-binding motif |

SEQUENCE: 56

```
MKARRALRAL KALVKLQALV RGHIVRKQTA DMLRRMQTLV RLQARARASR SYVSDSSHTT    60
GKSSHSRYAV PASPSKDHLF RVSSTKFDGP SILKRCGSNA NFRESIDFDK VKWGSNWLDR   120
WMEESFLNDH GSNPPRSRNA DDEKSDKILE VDTWKPHVKS QQSNRTFQTS QHALASDHNN   180
QSFMTFDSMS KLSKKEPNPM PSISSGEILQ SLKLPLGNDE AVYRTAENSP RMFSATSRPG   240
SSGRRGGPFT PTRSECSWGF FNGYSGYPNY MANTESSRAK VRSQSAPRQR LEFEKYGSSR   300
RSVQGYSDSE TRSERGFAQN TELQNKAYVA SGYLNRLGTS DLR                     343
```

| SEQ ID NO: 57 | moltype = DNA length = 1646 |
|---|---|
| FEATURE | Location/Qualifiers |
| source | 1..1646 |
| | mol_type = other DNA |
| | organism = Glycine max |
| misc_feature | 1..1646 |
| | note = Ceres CLONE ID no.1641776 |
| misc_feature | 1..1646 |
| | note = Encodes the peptide sequence at SEQ ID NO 58 |

SEQUENCE: 57

```
ctctctctca aacccaaaa ctattcccTt gtgagaactg aggagacata taatgggta     60
aggcgtcgaa gtggtttcgc gggcttcttg gtctcaaaaa aacagagtat gccacctcac   120
ccgccaagcc tccaaagag aaacgccggt ggagcttcgt taaatcatca tacacagaaa   180
aagacaacac cactgccgcc acgtgtccac cactaagaaa caacaacaac cacgcaatgt   240
cagtagcagc agccaccgct gcggtggccg aagcggcggt ggctgccgcc gaagcagccg   300
ccgtcgtggt gagactaact agtaacgcg caggtgcgc cgacggcgga cccacccgga    360
ttcgccaaca ttgggctgct gttaagattc aagccgcttt tcgtggctgt ttggcaagga   420
gagcactgcg agcattaaag ggattggtga agttgcaagc attggtgaga ggccacattg   480
agagaaaacg gacggcagag tggctgaaaa gattgcaaga actcttacat gcacagaccc   540
aagtttctgc agggttgacc ctgcatgcct caccttcgag ttcaaagtta tcaagcacc    600
tccaaggtcc agaacaccc gaaaaatttg aagcccccat tagatctaag agcatgaaac   660
atgagcactc acctatactc aagagaaatg gctccaaatc ctgtgccctg atcaatggct   720
atcaagagat atgtgggagt agatcagaga gtcaaggaa tgaacaatta tggaactcag   780
gaagatcaat gaatagagca cacggctcca atgatgaaag aaatgcaag gttcttgaag   840
```

-continued

```
ttgattctgg aaaaccgcac ttcacactaa agcgtcgaaa cctctcttac tccacaggct  900
ctgatcttta tagtaagagt ttgaacagca caaaggaatc aacatctctt caatctgctc  960
aaagtccatg ttgtgaggtt cagtctcaca gttacagctc gcaaaaagtg aacaatgagg 1020
ttgaggagag tccattctgc actgctgaca atagtccaca atacttatct gcctcttcta 1080
aagatgatgg cttcaaaaga agccctttta ctcctactag aagtgatggc tctagaagct 1140
acattcgcgg ttaccctgat tatcctagtt acatggcatg cactgaatct tcaaaggcaa 1200
aggccagatc tctgagtgca ccaaaacaaa ggcctcaaag tgagaggtct ggttcatcgg 1260
atagatactc actcaatgga tttgatatgt caagattggc cactcaaagg gcaatgcaag 1320
caagcttcac caacaaagca tatccaggtt ctggtcgttt ggacaagctt ggtatgcctg 1380
tggggtacag attctgattg agttatgttt atggtaagag ggttattttg tatctttat 1440
ttttcatagt cttaaagtct taatatctga tcttgctaac caaccggctg tactttgagc 1500
ttccattgcg atttttgtgtc agcattagaa atctacaacc aaattaagtg catactgcta 1560
agtctcaact ttcaagtcat tttattactt ggataaactg tgtaaaagaa ttattatctt 1620
tgcctttcaa aaaaaaaaaa aaaaaa                                     1646
```

| SEQ ID NO: 58 | moltype = AA length = 447 |
|---|---|
| FEATURE | Location/Qualifiers |
| source | 1..447 |
| | mol_type = protein |
| | organism = Glycine max |
| REGION | 1..447 |
| | note = Ceres CLONE ID no.1641776 |
| REGION | 1..447 |
| | note = Score of 433.6 for HMM of FIGURE 2. |
| REGION | 1..447 |
| | note = Functional Homolog Of Ceres SEEDLINE ID no. ME06748 at SEQ ID NO.41 |
| REGION | 106..126 |
| | note = Pfam Name: IQ Pfam Description: IQ calmodulin-binding motif |

SEQUENCE: 58
```
MGKASKWFRG LLGLKKTEYA TSPAKPPKEK RRWSFVKSSY TEKDNTTAAT CPPLRNNNNH  60
AMAVAAATAA VAEAAVAAAE AAAVVVRLTS NSGRCADGGP TRIRQHWAAV KIQAAFRGCL 120
ARRALRALKG LVKLQALVRG HIERKRTAEW LKRLQALLHA QTQVSAGLTL HASPSSSKLS 180
SHLQGPETPE KFESPIRSKS MKHEHSPILK RNGSKSCALI NGYQEICGSR SESQGNEQLW 240
NSGRSMNRAH GSNDERNGKV LEVDSGKPHF TLKRRNLSYS TGSDLYSKSL NSTKESTSLQ 300
SAQSPCCEVQ SHSYSSQKVN NEVEESPFCT ADNSPQYLSA SSKDDGFKRS PFTPTRSDGS 360
RSYIRGYPDY PSYMACTESS KAKARSLSAP KQRPQSERSG SSDRYSLNGF DMSRLATQRA 420
MQASFTNKAY PGSGRLDKLG MPVGYRF                                    447
```

| SEQ ID NO: 59 | moltype = DNA length = 1434 |
|---|---|
| FEATURE | Location/Qualifiers |
| source | 1..1434 |
| | mol_type = other DNA |
| | organism = Populus balsamifera |
| | sub_species = trichocarpa |
| misc_feature | 1..1434 |
| | note = Ceres ANNOT ID no.1438750 |
| misc_feature | 1..1434 |
| | note = Encodes the peptide sequence at SEQ ID NO 60 |

SEQUENCE: 59
```
atgggcaaag cttccaaatg gttccgtgcc gttctcggat taaaaaaacc cgacccacca   60
ctagaccacc cccaaaccac tcgttctaaa gacaaacgga gatggagttt tgttaagtcc  120
cgccgtgaaa aagaccacga ccaccaacag cgacaacaag atattgaagc cagtaaaact  180
ggtgttctgt acgggcagga gtttgaggag gaccccaaca agcatgcggt cgctgtgtgt  240
gctgctaccg ctgcagtcgc ggaggctgct gttgcagcgg ctcaggcagc tgccgaggtt  300
gtgagactta cgagtagtgg gaggtgtgtt aataacagtg tcgcgaacgt tagcgggagt  360
cttggattac gtgaagacct cgctgctgtt aagattcaag ctgcttttccg tggctacctg  420
gctaggagag cattacgggc gttaaaggca ttggtgagac ttcaagctct ggtaagaggt  480
cacattgaga ggaagcgaac tgcagagtgg cttcatcgaa tgcaagcttt gctgcgagcg  540
cagtctcgag cacgttctgg acgtgcccaa atttctgaat cttctcattc aagtagcaag  600
tcctctcgct ttcaacaccc tggtccgcca acccctgaaa aattcgagca tgccattcgt  660
gccaggagtg gaaaatatga acaatcatca atacttaaga gaactgggtc aaaatgtaaa  720
ggcagagcaa ttggtatctt agacgttgca cacttatcct taaattgcta gagcgtcgtg  780
atggatgatc aaacatggga tcaccaagtc cctttggcag gaactggcac tattgatgat  840
gataagagtc acaagatcct tgagattgat actggaaaac cccacattac tcccaagcgt  900
agaaatctct tcactcttc tcaccttttcc ctgtcagatc agtatagcca agtttttcaca  960
actacaaaag actcgacagc ccatcaaact gttccaagtc cctcatcctg tgaagttcaa 1020
tctttaagtc cattgaagtt ttctcatgtt gtcgaagaag cattatgcac tgctgaaaat 1080
agcccacagt tctactctgc atcatcaagg ggtggtagta gtaagagaag tcccttcact 1140
cccagtagga gtgatggctc aagaaaacttc ctaatcggtt attatgccta cccaaattat 1200
atgtgtaaca ctgaatcttc gagggctaag gcgagatctc ttagcgctcc aaaacaaaga 1260
ccccaatatg agagatccag ttcaaccagg agatactcgg ttctcgggtg tggtgagcca 1320
agatcgagta gtgcacagca tgcttctgcc ttgcgtgcaa gttttttcaag caaagcttac 1380
cctggatctg gtcgcttgga caagctggga atgcctattg gcagggata ctaa         1434
```

| SEQ ID NO: 60 | moltype = AA length = 477 |
|---|---|
| FEATURE | Location/Qualifiers |
| source | 1..477 |

```
                        mol_type = protein
                        note = subspecies = trichocarpa
                        organism = Populus balsamifera
REGION                  1..477
                        note = Ceres ANNOT ID no.1438750
REGION                  1..477
                        note = Score of 852.9 for HMM of FIGURE 2.
REGION                  1..477
                        note = Functional Homolog Of Ceres SEEDLINE ID no. ME06748
                         at SEQ ID NO.41
REGION                  126..146
                        note = Pfam Name: IQ Pfam Description: IQ
                         calmodulin-binding motif
SEQUENCE: 60
MGKASKWFRA  VLGLKKPDPP  LDHPQTTRSK  DKRRWSFVKS  RREKDHDHQQ  RQQDIEASKT    60
GVLYGQEFEE  DPNKHAVAVA  AATAAVAEAA  VAAAQAAAEV  VRLTSSGRCV  NNSVANVSGS   120
LGLREDLAAV  KIQAAFRGYL  ARRALRALKA  LVRLQALVRG  HIERKRTAEW  LHRMQALLRA   180
QSRARSGRAQ  ISESSHSSSK  SSRFQHPGPP  TPEKFEHAIR  ARSGKYEQSS  ILKRTGSKCK   240
GRAIGDLDVA  HLSLNWSERR  MDDQTWDHQV  PLAGTGTIDD  DKSDKILEID  TGKPHITPKR   300
RNLFHSSHLS  LSDQYSHSFT  TTKDSTAHQT  VPSPSSCEVQ  SLSPLKFSHV  VEEALCTAEN   360
SPQFYSASSR  GGSSKRSPFT  PSRSDGSRNF  LIGYYGYPNY  MCNTESSRAK  ARSLSAPKQR   420
PQYERSSSTR  RYSVLGCGEP  RSSSAQHASA  LRASFSSKAY  PGSGRLDKLG  MPIGQGY      477

SEQ ID NO: 61           moltype = DNA  length = 1431
FEATURE                 Location/Qualifiers
source                  1..1431
                        mol_type = other DNA
                        organism = Populus balsamifera
                        sub_species = trichocarpa
misc_feature            1..1431
                        note = Ceres ANNOT ID no.1447395
misc_feature            1..1431
                        note = Encodes the peptide sequence at SEQ ID NO 62
SEQUENCE: 61
atgggtaaag cttccaaatg gttccgtgcc gttctcggcc tcaaaaaacc cgacccacca    60
ccagaccgcc ccgttacaac tcgttctaaa gaaaaaagga gatggagttt tgtcaagtcc   120
caccgtgaaa aagaccaaca ccatcaccaa cagcaacaac aagagacgga agccgttaaa   180
gcaggcgttt tgtacgggca ggagtttgag gaggacccaa acaagcatgc gatcgctgtg   240
gctgctgcta ctgctgcagt tgcggaggct gcagttgctg ccgcgcaggc agctgcaag    300
gtggtgcggt taacaagcag tgggaggtgt gttgataaca gtgttgcgta cgttagcggg   360
agtcctggct tacgtgaaga cttcgctgct gttaagatcg aagctgcttt tcgtggctac   420
ctggcaagga gagcgttaag agcattaaaa gcgttggtga ggcttcaggc actggtaaga   480
ggtcaccttg agaggaagcg aacagcagag tggcttcatc gaatgcaagc attgctgaga   540
gcgcaggctc gagcacgtgc aggacgtgcc caaattctg aatcctccca ctcaagcagc   600
aagtcttctc gctatcacct ccctggtctg ccaacccatg aaaaatccga gcatgccatt   660
cgtgctacga gtggaaaata tgaacaatca tcaatgctta agaactgg gtcaaaaact   720
aaaggcagag aaattgccga tcaagatgtt gcacacttat ccttcaattg gtcagaacat   780
ggaatggata gtagaacatg ggatcatcaa gcccctccgc caggaactgg ccccattgat   840
gatgacaaga tcccttgagat tgattctgga aaaccacata ttactcctaa acgcagaaat   900
ctctttcacc cttctcacct ttcccttgtct gcggatcagt atagccatag tttcacaaca   960
tcaaaaggct ccacagtccg tcaagcagtt ccaagccctc catctggcga agttcaatct  1020
ttcagtccat tgaaattctc tcatgaggtt gaggaagcat tttgcaccgc tgataatagc  1080
ccgcaattct gctctgcatc atcaaggggg ggcagtggta agaagaagtcc cttcactccc  1140
agtaggagtg gtggctctag aagcttcatg agtggatact ctgactaccc aaattatatg  1200
tgtaacactg aatcttcaag ggctaaggtg agatctcaa gcgctccaaa acaaagaccc  1260
cagtatgaga gatccagctc aaccaagaga tactccggttc tcggctttgg tgaacaaaga  1320
tcgagtagtg cacagagtgc ttctgccttg cgtgcaagtt ttacaagtaa agcttaccct  1380
ggatctggtc gtttggacag gctgggaatg cctgttgggc agaaatacta a           1431

SEQ ID NO: 62           moltype = AA  length = 476
FEATURE                 Location/Qualifiers
source                  1..476
                        mol_type = protein
                        note = subspecies = trichocarpa
                        organism = Populus balsamifera
REGION                  1..476
                        note = Ceres ANNOT ID no.1447395
REGION                  1..476
                        note = Score of 696.6 for HMM of FIGURE 2.
REGION                  1..476
                        note = Functional Homolog Of Ceres SEEDLINE ID no. ME06748
                         at SEQ ID NO.41
REGION                  149..169
                        note = Pfam Name: IQ Pfam Description: IQ
                         calmodulin-binding motif
SEQUENCE: 62
MGKASKWFRA  VLGLKKPDPP  PDRPVTTRSK  EKRRWSFVKS  HREKDQHHHQ  QQQQETEAVK    60
AGVLYGQEFE  EDPNKHAIAV  AAATAAVAEA  AVAAAQAAAE  VVRLTSSGRC  VDNSVAYVSG   120
SPGLREDFAA  VKIEAAFRGY  LARRALRALK  ALVRLQALVR  GHLERKRTAE  WLHRMQALLR   180
```

```
AQARARAGRA QISESSHSSS KSSRYHLPGL PTHEKSEHAI RATSGKYEQS SMLKRTGSKT    240
KGREIADQDV AHLSFNWSEH GMDSRTWDHQ APSPGTGPID DDKILEIDSG KPHITPKRRN    300
LFHPSHLSLS ADQYSHSFTT SKGSTVRQAV PSPSSGEVQS FSPLKFSHEV EEAFCTADNS    360
PQFCSASSRG GSGKRSPFTP SRSGGSRSFM SGYSDYPNYM CNTESSRAKV RSLSAPKQRP    420
QYERSSSTKR YSVLGFGEQR SSSAQSASAL RASFTSKAYP GSGRLDRLGM PVGQKY        476

SEQ ID NO: 63           moltype = AA  length = 484
FEATURE                 Location/Qualifiers
source                  1..484
                        mol_type = protein
                        organism = Arabidopsis thaliana
REGION                  1..484
                        note = Public GI ID no.79482785
REGION                  1..484
                        note = Score of 311.2 for HMM of FIGURE 2.
REGION                  1..484
                        note = Functional Homolog Of Ceres SEEDLINE ID no. ME06748
                         at SEQ ID NO.41
REGION                  167..187
                        note = Pfam Name: IQ Pfam Description: IQ
                         calmodulin-binding motif
SEQUENCE: 63
MGKASRWFRS LFGVKKPDPG YPDLSVETPS RSTSSNLKRR WSFVKSKREK ESTPINQVPH     60
TPSLPNSTPP PPSHHQSSPR RRRKQKPMWE DEGSEDSDKH AIAVAAATAA VAEAAVAAAN    120
AAAAVVRLTS TSGRSTRSPV KARFSDGFDD VVAHGSKFYG HGRDSCELAV IKIQSIFRGY    180
LAKRALRALK GLVRLQAIVR GHIERKRMSV HLRRMHALVR AQARVRATRV IVTPESSSSQ    240
SNNTKSSHFQ NPGPPTPEKL EHSISSRSSK LAHSHLFKRN GSKASDNNRL YPAHRETFSA    300
TDEEEKILQI DRKHISSYTR RNRPDMFYSS HLILDNAGLS EPVFATPFSP SSSHEEITSQ    360
FCTAENSPQL YSATSRSKRS AFTASSIAPS DCTKSCCDGD HPSYMACTES SRAKARSASA    420
PKSRPQLFYE RPSSKRFGFV DLPYCGDTKS GPQKGSALHT SFMNKAYPGS GRLDRLGMPI    480
GYRY                                                                 484

SEQ ID NO: 64           moltype = AA  length = 543
FEATURE                 Location/Qualifiers
source                  1..543
                        mol_type = protein
                        organism = Arabidopsis thaliana
REGION                  1..543
                        note = Public GI ID no.3292832
REGION                  1..543
                        note = Score of 277.0 for HMM of FIGURE 2.
REGION                  1..543
                        note = Functional Homolog Of Ceres SEEDLINE ID no. ME06748
                         at SEQ ID NO.41
REGION                  167..187
                        note = Pfam Name: IQ Pfam Description: IQ
                         calmodulin-binding motif
SEQUENCE: 64
MGKASRWFRS LFGVKKPDPG YPDLSVETPS RSTSSNLKRR WSFVKSKREK ESTPINQVPH     60
TPSLPNSTPP PPSHHQSSPR RRRKQKPMWE DEGSEDSDKH AIAVAAATAA VAEAAVAAAN    120
AAAAVVRLTS TSGRSTRSPV KARFSDGFDD VVAHGSKFYG HGRDSCELAV IKIQSIFRGY    180
LAKRALRALK GLVRLQAIVR GHIERKRMSV HLRRMHALVR AQARVRATRV IVTPESSSSQ    240
SNNTKSSHFQ NPVSLVKFPM IVPFNLKHGP PTPEKLEHSI SSRSSKLAHS HLFKVLHFQL    300
LFVSSVFVAC GPISSKFQRL YKLLTLLYVQ NKSNLKNWNG SKASDNNRLY PAHRETFSAT    360
DEEEKILQID RKHISSYTRR NRPDMFYSSH LILDNAGLSE PVFATPFSPS SSHEEITSQF    420
CTAENSPQLY SATSRSKRSA FTASSIAPSD CTKSCCDGDH PSYMACTESS RAKARSASAP    480
KSRPQLFYER PSSKRFGFVD LPYCGDTKSG PQKGSALHTS FMNKAYPGSG RLDRLGMPIG    540
YRY                                                                  543

SEQ ID NO: 65           moltype = DNA  length = 1799
FEATURE                 Location/Qualifiers
source                  1..1799
                        mol_type = other DNA
                        organism = Zea mays
misc_feature            1..1799
                        note = Ceres CLONE ID no.1559074
misc_feature            1..1799
                        note = Encodes the peptide sequence at SEQ ID NO 66
SEQUENCE: 65
aagactctcc cagtcccttc ctctcctgct gcctttctct cttctcggtg aagcgtgtgt     60
tcatttcact gttttggttt catctcccgc tctttcttta cccgtgctc cggccaagtg    120
ctggaaccaa gaaagcctca tggggcggcc ggccgacggg cggtagagag cggagatgg    180
gctgggcgcc taggtggctg cgcggggctgc tcggcggcgg caggaaggcc gccgtgacga    240
agccggcgaa ggagaagaag ctctgggat tcgggaagtc cttccggaa aggaccccg    300
cgccagcgcc ggaacggcct cggacgcctt cggtgcagcc cacggcgacg cctcgccggg    360
ggtttcggc ggcgccggat gaggcggacg acgagcagag caagcgtgct atcgctgtgg    420
ccgcggcgac ggcggcggtg gcagaggccg cgtcgctgc tgcccaggcg gccgccgccg    480
tggtgcggtt gacgagctcc ggccggtgcc caccgccggc cgccgcgaag cgggaggagt    540
gggcggctgt tcggatccag gccgctttcc gtggctacct ggcgaggcgg gcgctgaagg    600
```

-continued

```
cgttgagggg gctggtgaag ctgcaggcgc tggtccgggg caacattgtg cggcggcagg    660
cggcggagac gctgcgatgc atgcacgcgc tcgtccgcgt ccaggcgcgc gcgcgcgcgt    720
gtcgcgcaat tcgctcgcag catgtcgcgg ctcatccgga tccgccaacg ccggagaagt    780
acgatcaggc gggtgccccc aggcacgccc gttccggctc tctgaaggca aactcttcca    840
agacgccggc cggcgagggg ctgggtaggg agaggtcgga atcttgcggg aggaactggc    900
tggaccgctg ggtggaggag aggtacacgg acgacgagaa gaacgccaag attctcgaag    960
tggacaacgg caagccaggg cggcacggtt ccaagcggcg cggcggcaac catcaccagt   1020
cgccgtgctc gacgatgacc tccgagcaga acagccggag ctacgcgacc atgccggagt   1080
cgccgtccaa ggactcgacg accgcgcagc agtccgtgcc gagcccgtcg tccgtgggca   1140
tggctgccga ggccctgagc ccgctgcgcg tgccagcgga catcgccgag ctctgcgaca   1200
gcccccagtt cttctcggcg acgtcgcggc ccgggagctc caggaggggg ggcgcgttca   1260
cgccggcggc caagagcgag tgctcgcgca gcctcttcgg cggctactcc gactgcccca   1320
actacatggc gaacacggag tcgttccgcg ccaaggcgcg ttcccagagc gcgcccaagc   1380
agaggccgca gcagtactac gagaagtcgg gctccctccg cagggcgtcg cgcacgccc    1440
tcgcggcggg gccggcagcg gcacagaggc cggtggcctc gttgcacgcc atgaaggcgt   1500
atccgggctc cggcagattg gaccgacttg gcatgccggt caggtactga tccggatcct   1560
acctagctcg cttcaggata atgtggtgct gcgcctgaac tgattgatac ccagtgtctc   1620
aactcaagcg atgaggatga agtgaattct actagtggtc gttattagat cttgttcctt   1680
cggtggtgcc tattaccgtc aacagttttc tgtttgttgc tttgtgtagc gaagtgtaag   1740
ttgctggtac gtagctggta atactatgcg tgcttaaccg cgaaaaaaaa aaaaaaaaa    1799

SEQ ID NO: 66          moltype = AA  length = 457
FEATURE                Location/Qualifiers
source                 1..457
                       mol_type = protein
                       organism = Zea mays
REGION                 1..457
                       note = Ceres CLONE ID no.1559074
REGION                 1..457
                       note = Score of 855.0 for HMM of FIGURE 2.
REGION                 1..457
                       note = Functional Homolog Of Ceres SEEDLINE ID no. ME06748
                         at SEQ ID NO.41
REGION                 121..141
                       note = Pfam Name: IQ Pfam Description: IQ
                         calmodulin-binding motif
SEQUENCE: 66
MGWAPRWLRG LLGGGRKAAV TKPAKEKKLW GFGKSFREKD PAPAPERPRT PSVQPTATPR    60
RGFAAAPDEA DDEQSKRAIA VAAATAAVAE AAVAAAQAAA AVVRLTSSGR CPPPAAAKRE   120
EWAAVRIQAA FRGYLARRAL KALRGLVKLQ ALVRGNIVRR QAAETLRCMH ALVRVQARAR   180
ACRAIRSQHV AAHPDPPTPE KYDQAGAPRH ARSGSLKANS SKTPGGERLG RERSESCGRN   240
WLDRWVEERY TDDEKNAKIL EVDNGKPGRH GSKRRGGNHH QSPCSTMTSE QNSRSYATMP   300
ESPSKDSTTA QQSVPSPSSV GMAAEALSPL RVPADIAELC DSPQFFSATS RPGSSRRGGA   360
FTPAAKSECS RSLFGGYSDC PNYMANTESF RAKARSQSAP KQRPQQQYEK SGSLRRASAH   420
ALAAGPAAAQ RSVASLHAMK AYPGSGRLDR LGMPVRY                            457

SEQ ID NO: 67          moltype = DNA  length = 1821
FEATURE                Location/Qualifiers
source                 1..1821
                       mol_type = other DNA
                       organism = Panicum virgatum
misc_feature           1..1821
                       note = Ceres CLONE ID no.1726548
misc_feature           1..1821
                       note = Encodes the peptide sequence at SEQ ID NO 68
SEQUENCE: 67
gtctagaccc ttcctttctc tcctgctgtc ccttttgctc ttctcggtgt aagcgtgtgc     60
gcgtttcact gctttggttt catctcccgc tctttctttc ctccccactg ctcctccggc    120
caagtgctgg aacgaggaag cctcatgcgg ccgccggccg gggagcggta gagcgccgga    180
gatgggcggg gcgcccaggt ggctgcgcgg gctgctcggc ggcggcaaca aggccgccga    240
gacgaagccc gtgaaggaaa agaggcgctg ggggttcggg aagtccttca gggagaaggc    300
gccggcgccg gtgcggcgc ggcctccgac gccgccgtg cagcccacgg cgacgcctcg     360
ccggggctac gcgccggcgc cggacgaggc ggacgacgag cagagcaagc gcgccatcgc    420
ggtggcgcg gccactcgg cggttgcgga ggccgccgta gccgcggcgc aggccgccgc     480
cgccgtggtg cggctgacga gcagcgggcg gtgcgcgccg gccgccgcca agcgggagga    540
gtgggcgct gttcggatcc aggccgcttt ccgtggatac ctggcgaggc gggcgctcaa     600
ggcgctgcgg gggctggtga agctgcaggc gctggttcgg ggcaacatcg tgcggcggca    660
ggcggcggag acgctgcgcg tgcatgcacg cgctcgtccg cgtccaggcg cgcgccgcgc    720
ctgccgcaca attcgctcgc agcaggtccc ggctcaccca gatccgccga cgccggagaa    780
gtacgatcag gcgggtgccc caggcacgg cgcgttccgg ctctctaaagg ggagctcgtc    840
gaagacaccg gcagcgagg ggctgggcag ggagaggtcg gaatcttgcg ggaggaactg     900
gctgaccgg tgggtggagg agaggtacat ggacgacgag aagaacgcca agatcctgga    960
ggtggacaac ggcaagccag gcggtatgc ttccaagagg cgcggcggcg gcggcaacca    1020
gcaccatcg ccgtgctcga cgatgacgtc cgaccagaac agccggagca tcgaccgat    1080
gccggagtcg acgaccgcgc agcggtccgt gccgagcccg ccgtcggtgg catgggcga    1140
ggccctgagc ccgctccgcc tgccgtggag cattgccgag ctctgcgaca gcccacagtt   1200
cttctcggcg tcgtctcggc cggggagctc cggcggggg cccttcaccc cgagcaagag    1260
cgagtgctcc cgcagcctct cgggggcta ctccgactac cccaactaca tggccaacac    1320
ggagtcgttc cgcgccaagg cgcgctccca gagcgcgccc aagcagaggc cgcactacga    1380
```

```
caagtccagc tccctccgca aggcgtcggc ggcgcaggcc tacttgacgg ggccgtgcgc  1440
gccgacggcg cagcagaggt cggcggcctc gctgcacgcc aagttccacca acaaggcgta  1500
cccgggctct ggcaggctgg atcgactcgg catgcccgtc aagtactgat cctgttatgt  1560
tatcctacca aagttgcttt ctggagtggt gttgcttctt gagcgatcag tgtctcagct  1620
ctcgagcaag gtcgatgaag taaaatctag tagtggtcgt taggcttttg tgtgccttcc  1680
tggtgctgtt accctcgaca gttttctgtt tcttgctttt taatagcgaa gtgtaagttg  1740
gtagtagctg cactgtaata ctatctgtgc tttaacagtt taactgctaa gtgctaactc  1800
caaaaaaaaa aaaaaaaaaa a                                           1821

SEQ ID NO: 68           moltype = AA  length = 455
FEATURE                 Location/Qualifiers
source                  1..455
                        mol_type = protein
                        organism = Panicum virgatum
REGION                  1..455
                        note = Ceres CLONE ID no.1726548
REGION                  1..455
                        note = Score of 892.2 for HMM of FIGURE 2.
REGION                  1..455
                        note = Functional Homolog Of Ceres SEEDLINE ID no. ME06748
                         at SEQ ID NO.41
REGION                  120..140
                        note = Pfam Name: IQ Pfam Description: IQ
                         calmodulin-binding motif
SEQUENCE: 68
MGWAPRWLRG LLGGGNKAAE TKPVKEKRRW GFGKSFREKA PAPVAARPPT PPVQPTATPR   60
RGYAPAPDEA DDEQSKRAIA VAAATAAVAE AAVAAAQAAA AVVRLTSSGR CAPAAAKREE  120
WAAVRIQAAF RGYLARRALK ALRGLVKLQA LVRGNIVRRQ AAETLRCMHA LVRVQARARA  180
CRAIRSQQVP AHPDPPTPEK YDQAGAPRHG RSGSLKGSSS KTPGSERLGR ERSESCGRNW  240
LDRWVEERYM DDEKNAKILE VDNGKPGRYA SKRRGGGGNQ HQSPCSTMTS DQNSRSYATM  300
PESTTAQRSV PSPPSVGMGE ALSPLRLPVD IAELCDSPQF FSASSRPGSS RRGPFTPSKS  360
ECSRSLFGGY SDYPNYMANT ESFRAKARSQ SAPKQRPHYD KSSSLRKASA AQAYLTGPCA  420
PTAQQRSAAS LHAKFTNKAY PGSGRLDRLG MPVKY                             455

SEQ ID NO: 69           moltype = AA  length = 464
FEATURE                 Location/Qualifiers
source                  1..464
                        mol_type = protein
                        note = subspecies = japonica
                        organism = Oryza sativa
REGION                  1..464
                        note = Public GI ID no.115459996
REGION                  1..464
                        note = Score of 886.1 for HMM of FIGURE 2.
REGION                  1..464
                        note = Functional Homolog Of Ceres SEEDLINE ID no. ME06748
                         at SEQ ID NO.41
REGION                  124..144
                        note = Pfam Name: IQ Pfam Description: IQ
                         calmodulin-binding motif
SEQUENCE: 69
MGWASRWLRG LLGGGKKPNS GSGDPKPARE KKRWGFGKSF REKSPAHPPP PPPPSAAVQR   60
AVTPRRAYTA SDEGDDEQSK RAIAVAAATA AVAEAAVAAA QAAAAVVRLT SSGRCAPAAA  120
KREEYAAVRI QAAFRGYLAR RALKALRGLV KLQALVRGNI VRRQAAETLR CMHALVRVQR  180
RARACRAIRS QHVSAHPGPP TPEKYDQATH EGVPKHGRSG CLKGSSSKTP GSERLTRERS  240
ESCGRNWLDK WVEERYLDDE KNAKILEVDT GKPGRHASRR RSGSHHHHSS CSSMTSEQKS  300
RSYATMPESP SKDSTTAQQS VPSPPSVGMA EALSPLLMAV DIAELCDSPQ FFSATSRPGS  360
SRSRAFTPTK SECSRSLFGG YSDYPNYMAN TESFRAKARS QSAPKQRPQY EKSSSLRKAS  420
AHAFGPGSCA PVAQRTTASL HSKFTNKAYP GSGRLDRLGM PVKY                   464

SEQ ID NO: 70           moltype = DNA  length = 1736
FEATURE                 Location/Qualifiers
source                  1..1736
                        mol_type = other DNA
                        organism = Triticum aestivum
misc_feature            1..1736
                        note = Ceres CLONE ID no.697034
misc_feature            1..1736
                        note = Encodes the peptide sequence at SEQ ID NO 71
SEQUENCE: 70
gcctagactc ttcgtctccg tcctgcacct ttttcttctc tggcaagcct gtgcctgtgc   60
gcgtcgcgcc gttttgggtt tcatctcccg ctctttcttc ctcctccctg ctccggccaa  120
gtgctggaac aagagaaagg cgatgggggc ggcggcggag gagcagtagc cggagggagg  180
ggatggggtg ggcttcaagg tggctccgga ggctgcttgg cggcggcaag aaggccggtc  240
ccgcctccgg cgagcacaag ccggagaggg agaagaagcg ctggggcttc ggcaagtcct  300
tccgggagaa ggaccccggtg cgtccaccga cgctcctgt gcagcgggcg gcgacgcccc  360
gccgcaccta cgcgacgtcg gatgacggcg gcgacgagca gaacaaacgc gctatcgccc  420
tggcggcggc gacggcggct gtggccgagg ccgccgttgc cgcggcgcag gcgccggccg  480
ccgtggtgcg gctgacgagc agcgggcggt gcccgccggc cggggcgaag catgaggagt  540
```

```
gggcggccgt ccggatccag gccgctttcc gtggctacct ggcgaggcgc gcactgaagg    600
cgctccgcgg gctggtgaag ctgcaggcgc tggtccgcgg caacatcgtc cggcggcagg    660
cggccgagac gctccggtgc atgcaggcgc tcgtcagcgt gcagtcccgc gcgcgcgcca    720
gccgcgcaac ccgatcccgc caggccgcgg cacacccggg cgcgacgacg ccggagaagt    780
acgagcgggg ggcatacgat ggcgcgctca ggcacggccg ttcaggctca ctcaagggag    840
gctcgtcaaa gacaccgggg agcgagagga tgagcaggga gaggtcagaa tcttgcggga    900
ggaactggct ggatcggtgg gtggaggaga ggtacatgga tgacgagaag aacgccaaga    960
ttctcgaggt ggaccccggc aagcccggcc ggcacgcttc caagaggcga agcagcggcg   1020
gcggccacca ccagtcgtcg tgctcaacca ggacatcaga gcagaacagc cggagctacg   1080
cgacgatgcc ggactcgccg tccagggact cgacgacggc gcagcagtcc gtgcccagcc   1140
cgtcgtcggt gggcatgggc gcgggcgagg ccctcagccc gctgcacatg ccggcagacc   1200
tcgcggcgga gctgtacgag agcccgcagt cttctcggc gacgtcgcgg ccggggagct   1260
cgaagcgggg cgccttcttc acgccgacca agagcgagtg cgcgcgcagc ctcttcggcg   1320
gctactccga ctaccccaac tacatgtcca acacggagtc gttccgggcc aaggcgcgct   1380
cgcagagcgc gcccaagcag cggccgctgt acgagaagtc cgggtccctc cggaaggcgt   1440
cggcacacgc cttcgcgccg gggcagaggt cgtcggcgtc ggcgtccctg cacgccaggt   1500
tcaccaataa ggcgtaccct ggctccggca ggctggaccg gctgggcatg cctgtcaagt   1560
actgaaccct gccgccatgt gaccagtgtt aggtttgagc ttttgtgatg ctattaccgt   1620
cagaaagtac tttcctgtta ttgactgtga cttgttaagt gtaagttgct actgtactgt   1680
tgttcccgca aaaaaagtg taagttgcta gtaatcaccc aaaaaaaaaa aaaaaa         1736

SEQ ID NO: 71          moltype = AA  length = 460
FEATURE                Location/Qualifiers
source                 1..460
                       mol_type = protein
                       organism = Triticum aestivum
REGION                 1..460
                       note = Ceres CLONE ID no.697034
REGION                 1..460
                       note = Score of 750.1 for HMM of FIGURE 2.
REGION                 1..460
                       note = Functional Homolog Of Ceres SEEDLINE ID no. ME06748
                        at SEQ ID NO.41
REGION                 119..139
                       note = Pfam Name: IQ Pfam Description: IQ
                        calmodulin-binding motif
SEQUENCE: 71
MGWASRWLRG LLGGGKKAGP ASGEHKPERE KKRWGFGKSF REKDPVRPPT PPVQRAATPR     60
RTYATSDDGG DEQNKRAIAV AAATAAVAEA AVAAAQAAAA VVRLTSSGRC PPAGAKHEEW    120
AAVRIQAAFR GYLARRALKA LRGLVKLQAL VRGNIVRRQA AETLRCMQAL VSVQSRARAS    180
RATRSRQAAA HPGATTPEKY EQAAYDGALR HGRSGSLKGG SSKTPGSERM SRERSESCGR    240
NWLDRWVEER YMDDEKNAKI LEVDPGKPGR HASKRRSSGG GHHQSSCSTR TSEQNSRSYA    300
TMPDSPSRDS TTAQQSVPSP SSVGMGAGEA LSPLHMPADL AAELYESPQF SATSRPGSS     360
KRGAFFTPTK SECARSLFGG YSDYPNYMSN TESFRAKARS QSAPKQRPLY EKSGSLRKAS    420
AHAFAPGQRS SASASLHARF TNKAYPGSGR LDRLGMPVKY                          460

SEQ ID NO: 72          moltype = DNA  length = 1433
FEATURE                Location/Qualifiers
source                 1..1433
                       mol_type = other DNA
                       organism = Zea mays
misc_feature           1..1433
                       note = Ceres CLONE ID no.353438
misc_feature           1..1433
                       note = Encodes the peptide sequence at SEQ ID NO 73
SEQUENCE: 72
atgatgtgta acctacgagc tgctctggta accgcttccc ctccagcaag gagaacgcca     60
ccttgtggcg tcagctctgc cgtcgtcttt actgcctgcg ccttccaggc ttcttcgttt    120
caggaagcaa ggcgaggcgg gcgctgaagg cgttgcgggg gctggtgaag ctgcaggcgc    180
tggtccgggg caacatcgtg cggcggcagg cggcggagac gctgcgatgc atgcacgcgc    240
tcgtccgcgt ccaggcgcgc gcgcgcgcct ccgcgcaaat tcgctcgacg catgtcacgg    300
cgcatccgga cccgccgacg ccggagaagt acgagcaggc gggtgcggcc aggcacggcc    360
gttccggctc tctgaaggcg aactcttcga ggacaccggg cggcgagagg ctgggcaggg    420
agaggtcgga atcctgcggg aggaactggc tggaccgctg gtggaggag aggtacatgg    480
acgacgagaa gaacgccaag attctcgagg tggacaacgg caagccaggg cgccggtatg    540
cttccaagag gcgcggcggc ggcggcgtcg gcggaaacca ccaccaccag caccaccagt    600
cgccgtgctc gacgacgatg ggctccgagc agaacaccg gagctacgcg accatgccga    660
agtcgccgtc caaggactcg acgaccgcgc agcagtcggt gccgagcccg ccgtcggtgg    720
gcatggccga ggaggaggcc ctgagcccgc tgcgcgtgcc cgtgcccgcg gacgtggccg    780
agctctgcga cagccccag ttcttctcgg ccacgtcgtc gcggcccggg agtcgaggc    840
ggggcccgtt cacgccgacg gccaagagcg agtgctcgcg cagcctcttc ggcggctact    900
ccgactaccc gaactacatg gccaacacgg agtcgttccg caaggccgtt cgtcggcaga    960
gcgcgccgaa gcagaggccg cagtacgagc ggtccagctc cctacgcagg cgtcggcgg   1020
cgcagaggtc ggcggcggcg gcggcctcct ccctgcacgc caagttcacc aacaaggcgt   1080
acccgggctc tggcaggctg atcggcttg gcttgccggc caggtactga tactgagcct   1140
gcctaattcg cgtcaggatg atgtgctgcc gctgtgtctc gagcgaggag gacgacgacg   1200
aagaagtgca atcgactagt ggtagttagg ttccgccgtg ccttggttgt gctattacca   1260
```

```
tcaacagttt tttctgtttc ttgctttgtg tagctagcca tgtctaaagt tgctggtagc   1320
tgtaatgatg ctataatgcg tgcttaactg ctgacgaacc ttttttcctct acatttccgt   1380
ggtatatata tatgtgccgt caaatcatgc atgggaattg aatgtgttgt tgc          1433

SEQ ID NO: 73              moltype = AA    length = 299
FEATURE                    Location/Qualifiers
source                     1..299
                           mol_type = protein
                           organism = Zea mays
REGION                     1..299
                           note = Ceres CLONE ID no.353438
REGION                     1..299
                           note = Score of 204.3 for HMM of FIGURE 2.
REGION                     1..299
                           note = Functional Homolog Of Ceres SEEDLINE ID no. ME06748
                            at SEQ ID NO.41
SEQUENCE: 73
MHALVRVQAR ARACRAIRSQ HVTAHPDPPT PEKYEQAGAA RHGRSGSLKA NSSRTPGGER    60
LGRERSESCG RNWLDRWVEE RYMDDEKNAK ILEVDNGKPG RRYASKRRGG GGVGGNHHHQ   120
HHQSPCSTTM GSEQNSRSYA TMPESPSKDS TTAQQSVPSP PSVGMAEEEA LSPLRVPVPA   180
DVAELCDSPQ FFSATSSRPG SSRRGPFTPT AKSECSRSLF GGYSDYPNYM ANTESFRAKA   240
RSQSAPKQRP QYERSSSLRR ASAAQRSAAA AASSLHAKFT NKAYPGSGRL DRLGLPARY    299

SEQ ID NO: 74              moltype = AA    length = 499
FEATURE                    Location/Qualifiers
source                     1..499
                           mol_type = protein
                           note = subspecies = japonica
                           organism = Oryza sativa
REGION                     1..499
                           note = Public GI ID no.125593074
REGION                     1..499
                           note = Score of 112.2 for HMM of FIGURE 2.
REGION                     1..499
                           note = Functional Homolog Of Ceres SEEDLINE ID no. ME06748
                            at SEQ ID NO.41
REGION                     134..154
                           note = Pfam Name: IQ Pfam Description: IQ
                            calmodulin-binding motif
SEQUENCE: 74
MGKAARWFRN MWGGGRKEQK GEAPASGGKR WSFGKSSRDS AEAAAAAAAA AAEASGGNAA    60
IARAAEAAWL RSVYADTERE QSKHAIAVAA ATAAAADAAL AAAQAAVAVV RLTSKGRSAP   120
VLAATVAGDT RSLAAAAVRI QTAFRGFLAK KALRALKALV KLQALVRGYL VRRQAAATLQ   180
SMQALVRAQA TVRAHRSGAG AAANLPHLHH APFWPRRSLV RRWLNLADDI AMYMFDVDVV   240
CWRWMQQERC AGDDTRSEHG VAAYSRRLSA SIESSSYGYD RRPQDRGGGH RGGPSRGRRR   300
RGGRAPPLLL DARWVRERRR GLVRQLHVVA APVLPPRRRA AAPHRRPDVA PLPRLRLVRA   360
GEGPAGDGAE HAAVRARAAD ADQERVRRRR RRRHPLVAAQ LPELHVQHAV VRGRRCRSQS   420
APKQRPETGG AGAGGGRKRV PLSEVVVVES RASLSGVGMQ RSCNRVQEAF NFKTAVVGRL   480
DRSSESGEND RHAFLQRRW                                                499

SEQ ID NO: 75              moltype = DNA    length = 1807
FEATURE                    Location/Qualifiers
source                     1..1807
                           mol_type = other DNA
                           organism = Gossypium hirsutum
misc_feature               1..1807
                           note = Ceres CLONE ID no.1920115
misc_feature               1..1807
                           note = Encodes the peptide sequence at SEQ ID NO 76
SEQUENCE: 75
ctcctttcct cagtaagctt acgaaacttc ttcttcgctt cttctctgca aatgaatccc     60
gagaaacctc ccaaaccctt atcttattac ccttttttcac cttcttctcc atcaccaaac  120
taacgtttcc gtacacaacg aacaaaatca aagcaatggg taaagcttcc aagtggttcc   180
gcagcatcct cggcttcaaa aatccgaccc ccataaccaa ccttctcctt cttcttcaaa   240
accaacttcc cataaagaca aacggcgttg gagtttcgtc aaatcgtacc gtgaaaagga   300
ctcctccacg aacaatagta atgcgaagtt gccgtcgtct tcgcagcaac agaaagactc   360
tgtttccttc gttgaaagga aaggtgacaa tgaagtaacg gatcctagca agcacgccat   420
cgctgttgct gccgctactg ccgccgttgc cgaagcagcc gttgcggctg ctcaagctgc   480
cgctgcggtg gttaggctca ctagtaacag tggtaggtgc gcgcgtaggt ccggcagcggt  540
ttacgtttgc aacaacaata gctatatagc acacgatgag tcatccgcca ttaagataca   600
atctgcattt cgtggatacc tggcaagaag agcattgcga gcactaaaag gattagtgag   660
actccaagca ttggttagag gtcatataga aaggaagaga actgcagaat ggttaagaag   720
gatgcaagca ttattgagag cacaagcacg tgctcgtgct ggccgggccc aaatttccga   780
gtcttcccaa tcaagctgca aatcgtctca cccgatccag caaccccatg                 840
aaaatttgaa catgttattc gatccaaggg tacaaaatat gaacaatcat caatgttgaa   900
gagaaatgga tcaaagtcaa gtgcaaggac tgttgataat caagagaaat tacactcagg   960
ttggtatcgc cgtgttgatg agcaaacatg ggagcattca acaagaattg gtcctaatga  1020
tgatgaaaag aatgacaaaa tccttgaagt tgacactggg aaaccaaatt tcatctctaa  1080
acggagaaac ctctttcatt caacacatct ttctctgaat tctgatttat atagctgtag  1140
```

```
tttcactaat tcgagagact cacaccaaac agctcctagt ccttcatctg gtgaagttca  1200
gtctttaact ccattgatgc tgtctcactc tgaagcaata caggaaagcc ctttctgcgg  1260
tgctgttgat gataatagtc cacaattcta ttctgcatca tcaaaaggag ctagttccaa  1320
gagaagcccc ttcactcctg ctaagagtga tggcactaga agctacctaa gtggttactc  1380
agaccatcca aattacatgt cttacactga atcgtcaaaa gctaaggtaa ggtctttcag  1440
tgctccaaaa caaaggcctc attatgaaag atctagttca acaaagaggt actccattca  1500
tggttttggt gaattgaaat caactacaca aaggtctgcc atgcatgcaa acttcgccag  1560
caaagcttac cccggttcgg gtaggttgga caggctagga atgccccttg gtatagata   1620
ctaaataatg gttttaccat ttggctaagg aatgttatgt agtttatgtt tagatgttaa  1680
cgatgatgac tctcacctac cctaatgtat ccatcctta atgttttagt gcatgtgagt  1740
tcccaagtta aaaagaatag tagctgcttt acaagaagtt aaattagaaa aaaaaaaaa   1800
aaaaaaa                                                            1807

SEQ ID NO: 76           moltype = AA   length = 300
FEATURE                 Location/Qualifiers
source                  1..300
                        mol_type = protein
                        organism = Gossypium hirsutum
REGION                  1..300
                        note = Ceres CLONE ID no.1920115
REGION                  1..300
                        note = Score of 34.2 for HMM of FIGURE 2.
REGION                  1..300
                        note = Functional Homolog Of Ceres SEEDLINE ID no. ME06748
                        at SEQ ID NO.41
SEQUENCE: 76
MQALLRAQAR ARAGRAQISE SSQSSCKSSH FHHPDPATPE KFEHVIRSKG TKYEQSSMLK   60
RNGSKSSGRT VDNQEKLHSG WYRRVDEQTW EHSTRIGPND DEKNDKILEV DTGKPNFISK   120
RRNLFHSTHL SLNSDLYSCS FTNSRDSHQT APSPSSGEVQ SLTPLMLSHS EAIQESPFCG   180
AVDDNSPQFY SASSKGASSK RSPFTPAKSD GTRSYLSGYS DHPNYMSYTE SSKAKVRSFS   240
APKQRPHYER SSSTKRYSIH GFGELKSTTQ RSAMHANFAS KAYPGSGRLD RLGMPLGYRY   300

SEQ ID NO: 77           moltype = DNA   length = 1614
FEATURE                 Location/Qualifiers
source                  1..1614
                        mol_type = other DNA
                        organism = Arabidopsis thaliana
misc_feature            1..1614
                        note = Ceres CLONE ID no.21821
misc_feature            1..1614
                        note = Encodes the peptide sequence at SEQ ID NO 78
SEQUENCE: 77
ataatttgat gaacagtctt cttctctgat gcagaaaccc tctccctgaa tcttgattct   60
ctcacaatca agatttgaag caaacgtttt gagaaaaatc ttttgacacc atcaaatttg   120
gttggcggat tgtgggagga attccagagc aatatagcag tgatggttg tacaacaatg   180
gctaagaaga agggcttgtt cactgtattg aaaaggattt ttatttcaga agttaattca   240
gaaaagaaag agaagagaag aaaatggaca ttttggaagg ttaggattaa gaaaagatta   300
ccttccatta cagcacctcc agagcacagg acaagtcatg aatcgcatga ggaacagaag   360
gaggaaattg tgtcagatgt gggtgagatc agccaagtgt cttgtagtcg acagttagat   420
tccatagaag agtcaaaagg ttcaacatca ccagaaactg ctgatctggt agtccagtat   480
caaatgtttc ttaatagaca ggaagaagtt cttgctgcta ctcgcattca gaccgccatt   540
cggggtcatc ttgcaaggaa agctctacgt gccttgaagg gaatagtgaa gctccaagca   600
tatatcagag tcgtgctgt gagacgccaa gcaatgacta cactaaaatg cctgcaatct   660
gttgtgaaca ttcagtcaca agtctgtggt aagagaacac agattcccgg aggtgttcac   720
agagattaga aagagagcaa tatattcaat gataacattc tcaaggtgga cacaaacggt   780
caaaagagat gggacgatag tctttttaaca aaggaagaaa aggaagcagt ggtaatgagc   840
aagaaagaag cttcactaag aagagaaagg ataaaggaat atgcagtcac ccaccggaaa   900
tctgcggagt cataccagaa acgaagtaac actaaatgga agtactggtt agacgaatgg   960
gtagatacac aactaaccaa gagcaaggag ctcgaagatc tcgacttctc ttcgaaaaca  1020
aaaccgaaag acgaaacttt gaacgaagag cagcttaaaa ctccaaggaa ctcatccacca  1080
agaagattag tgaataatca tagaagacaa gtttcaatag gtgaagatga acaaagccct  1140
gccgcggtca ctatcactac accaacttat atggttgcaa cagagtcagc aaaggcaaag  1200
tcaagatcat taagctcccc aaggataaga ccgagaagtt tgacacaca gtcagagagt  1260
tactcgccat ataagaacaa gctatgcctg acgacataca tgatggtga agcaccaagc  1320
aaagtaagga ttgccaacaa tggcagtaac actagaccaa gtgcatacca gcaacgtgtc  1380
ccagggttaa ggggatttaa cataggccct ttgaaatcat gcaataataa taatactcta  1440
ttgaacgatc tcagcattaa ttcagaaaga tctctaccta gctggaacaa gcagagcagc  1500
ttgagatgag tggatattga accctgtata tatacatact acatacgttc caatgtttct  1560
tttgactttt gagggtcaca ctcacatatg tgtatcatca aatattgttt cgtt         1614

SEQ ID NO: 78           moltype = AA   length = 443
FEATURE                 Location/Qualifiers
source                  1..443
                        mol_type = protein
                        organism = Arabidopsis thaliana
REGION                  1..443
                        note = Ceres CLONE ID no.21821
REGION                  1..443
                        note = Score of 237.2 for HMM of FIGURE 2.
```

| | | |
|---|---|---|
| REGION | 1..443<br>note = Functional Homolog Of Ceres SEEDLINE ID no. ME06748 at SEQ ID NO.41 | |
| REGION | 111..131<br>note = Pfam Name: IQ Pfam Description: IQ calmodulin-binding motif | |

SEQUENCE: 78

```
MAKKKGLFTV LKRIFISEVN SEKKEKRRKW TFWKLRIKKR LPSITAPPEH RTSHESHEEQ  60
KEEIVSDVGE ISQVSCSRQL DSIEESKGST SPETADLVVQ YQMFLNRQEE VLAATRIQTA 120
FRGHLARKAL RALKGIVKLQ AYIRGRAVRR QAMTTLKCLQ SVVNIQSQVC GKRTQIPGGV 180
HRDYEESNIF NDNILKVDTN GQKRWDDSLL TKEEKEAVVM SKKEASLRRE RIKEYAVTHR 240
KSAESYQKRS NTKWKYWLDE WVDTQLTKSK ELEDLDFSSK TKPKDETLNE KQLKTPRNSS 300
PRRLVNNHRR QVSIGEDEQS PAAVTITTPT YMVATESAKA KSRSLSSPRI RPRSFDTQSE 360
SYSPYKNKLC LTTSMMSEAP SKVRIANNGS NTRPSAYQQR SPGLRGFNIG PLKSCNNNNT 420
LLNDLSINSE RSLPSWNKQS SLR                                        443
```

| | | |
|---|---|---|
| SEQ ID NO: 79 | moltype = DNA length = 1689 | |
| FEATURE | Location/Qualifiers | |
| source | 1..1689<br>mol_type = other DNA<br>organism = Glycine max | |
| misc_feature | 1..1689<br>note = Ceres CLONE ID no.560066 | |
| misc_feature | 1..1689<br>note = Encodes the peptide sequence at SEQ ID NO 80 | |

SEQUENCE: 79

```
tttttatgg gatttgaaaa aatggatcac agacattgaa gttgacctat gtgttgatat   60
tcttaaatgg ccaaaaagaa gagctggttt agtctggtga agaggctctt tatatgggac  120
acacattcca cacaagataa gaaggagaaa agaaggaaat ggatatttgg aaggctaaag  180
agcaagagat tgccttcaat taaagctcca ctaccctcaa aaggaacaac actaagtgaa  240
gcagagcaag aacagagcaa gcatgcttta acagtggcca ttgcctcagc agcagctgct  300
gaagctgctg ttactgctgc tcatgctgct gctgaggttg ttcgcctcac tgggcaacgc  360
aacgaaaact cagaagaatc tcaacctgtt aaaactagga atggtgctcc acaatccaca  420
taccagtgcc agagggagat taagaatctg ctgcagcca tcaaaattca aactgcattt  480
cggggttacc tggcaaggaa ggctttgagg gcgttgaagg gaatagtgaa gcttcaagct  540
atcattcgtg gcagagccgt aagacgccaa gctatgagta gtcttaagtg cttacagtcc  600
attgtgagca tccagtcaca ggtctgtgca aggaggctcc aaatggttga agggagatgt  660
gattactctg aaaatgaaga gatgcaagat tttaaagaca aaataattag gatggactca  720
aacagtgaaa gaaagtggga tgaaagcact gtattgaagg aagaggtaga cacctcttgc  780
acaagcaaga gagaaagaac aaaagaatac tcatttaacc acagaaggtc agcagagtca  840
gaaagaagta aagtaaatgg aagatggagg tactggctag agcagtgggt agatacacaa  900
cttttcaaaga gtaaagagct tgaagattta gactcagttt ttagctcaca ttctagagct  960
ggggaggaat atggaggaag gcaacttaag ctgagaagta atattcagag acaaaatcca 1020
gttgaaggat tggattctcc aatacttggt tcaagaagat cttttcctca taggaggcag 1080
tgttcagtgg gagaggacca ctcattttta agctctcctg caactccagc atacatggct 1140
gcaacagaat cagcaaaagc aaaagcaaga tcaacaagct ccccaaaaat aaggactggg 1200
gggaatgtgg acatgaactc tgatagctat tcaccatgca agaaaaagct atccattgca 1260
tcttctatta acagtgaaat gcttagtaat ggtagggtgg gcaagctcag tgttaaccag 1320
cagcaaagat caccaagctt taagggactt tcagtgccta aaaatcaag ccgaacaact  1380
atcaaggatc tcagtattaa ttcagattgc tcactcccta attgggatcg acaggctttc 1440
ttcaaatgaa tctatgaatg ctgatgttac tcttttcttgc attaacacaa ttccttgtat 1500
catgtgaagg cttggaaaca ataactgttt ataaatatgt atgatatact atatgctatt 1560
ggatgttatt ttggttggga attgaacatt aatgtgacag aaaatagtta ttctggagat 1620
ataagatgaa ttgtatgatt aagaaagaag agatataaga tggattgtat gattaagaaa 1680
gaaggaaag                                                       1689
```

| | | |
|---|---|---|
| SEQ ID NO: 80 | moltype = AA length = 460 | |
| FEATURE | Location/Qualifiers | |
| source | 1..460<br>mol_type = protein<br>organism = Glycine max | |
| REGION | 1..460<br>note = Ceres CLONE ID no.560066 | |
| REGION | 1..460<br>note = Score of 822.2 for HMM of FIGURE 2. | |
| REGION | 1..460<br>note = Functional Homolog Of Ceres SEEDLINE ID no. ME06748 at SEQ ID NO.41 | |
| REGION | 128..148<br>note = Pfam Name: IQ Pfam Description: IQ calmodulin-binding motif | |

SEQUENCE: 80

```
MAKKKSWFSL VKRLFIWDTH STQDKKEKRR KWIFGRLKSK RLPSIKAPLP SKGTTLSEAE  60
QEQSKHALTV AIASAAAEA AVTAAHAAAE VVRLTGQRNE NSEESQPVKT RNGAPQSTYQ  120
CQREIKESAA AIKIQTAFRG YLARKALRAL KGIVKLQAII RGRAVRRQAM SSLKCLQSIV 180
SIQSQVCARR LQMVEGRCDY SENEEMQDFK DKIIRMDSNS ERKWDESTVL KEEVDTSCTS 240
KRERTKEYSF NHRRSAESER SKVNGRWRYW LEQWVDTQLS KSKELEDLDS VFSSHSRAGE 300
```

```
EYGGRQLKLR SNIQRQNPVE GLDSPILGSR RSFPHRRQCS VGEDHSFLSS PATPAYMAAT   360
ESAKAKARST SSPKIRTGGN VDMNSDSYSP CKKKLSIASS INSEMLSNGR VGKLSVNQQQ   420
RSPSFKGLSV PIKSSRTTIK DLSINSDCSL PNWDRQAFFK                        460

SEQ ID NO: 81            moltype = AA  length = 501
FEATURE                  Location/Qualifiers
source                   1..501
                         mol_type = protein
                         note = subspecies = japonica
                         organism = Oryza sativa
REGION                   1..501
                         note = Public GI ID no.115453071
REGION                   1..501
                         note = Score of 546.0 for HMM of FIGURE 2.
REGION                   1..501
                         note = Functional Homolog Of Ceres SEEDLINE ID no. ME06748
                          at SEQ ID NO.41
REGION                   122..142
                         note = Pfam Name: IQ Pfam Description: IQ
                          calmodulin-binding motif
SEQUENCE: 81
MERKRRGWLE RIKRLFVSEP KQKPKPDKKV KSKRWMFAGK LKTQHSFALP APAPAVEEEQ    60
IRQAEDEQSK HAMAVALATA AAAEAAVAAA HAAAEVVRLT GKTAALAPAP ATTTTPTPYG   120
HEHAALMIQS VYRGYLARRA LRALKGLVRL QALIRGQAVR RQTAATLRGL ESLMKIQARQ   180
RARASSAAAA GGDHNAANSP APDGMDALLR RGRELYYAAA AAVHEQQLSK GWDSSTLSKE   240
EMSAMSRSRE EAALKRVRAL QYASLHQSEK VGVRRQPMSR EEMETLNQRW SWLEEWVGSQ   300
PPFDKDIPVA HQSPSRDAAG AAMNDDERPP PPPVLRSRSR ADRLACVGGD DDDADRQLGY   360
SARRSFTRAG RRTPARDDDG GGAAAFPGYM ASTASAKAKF RSMSTPKERS GAGAADAYSE   420
QCFPFADRLL SPIPSMSPIP SIASDIVFAR SSRPAAAQRS PRVKGPMTPT RSRSRRSPGR   480
HSFGSEAALH QLQMEQYTPI R                                            501

SEQ ID NO: 82            moltype = DNA  length = 1814
FEATURE                  Location/Qualifiers
source                   1..1814
                         mol_type = other DNA
                         organism = Gossypium hirsutum
misc_feature             1..1814
                         note = Ceres CLONE ID no.1968211
misc_feature             1..1814
                         note = Encodes the peptide sequence at SEQ ID NO 83
SEQUENCE: 82
aatttccccc ttcctctctc cctcctttcc tcagtaagct tacgaaactt cttcttcgct    60
tcttctctgc aaatgaatcc cgagaaacct cccaaaccct tatcttttta cccttttttca  120
ccttcttctc catcaccaaa ctaacgtttc cgtacacaac gaacaaaatc aaagcaatgg   180
gtaaagcttc caagtggttc cgcagcatcc tcggcttcaa aaaatccgac ccccataacc   240
aaccttctcc ttcttcttca aaaccaactt cccataaaga caaacggcgt tggagtttcg   300
tcaaatcgta ccgtgaaaaa gactcctcca cgaacaatag taatgcgaag ttgccgtcgt   360
cttcgcagca acagaaagac tctgtttcct tcgttgaaag gaaaggtgac aatgaagtaa   420
cggatcctag caagcacgcc atcgctgttg ctgccgctac tgccgccgtt gccgaagcag   480
ccgttgcggc tgctcaagct gccgctgcgg tggttaggct cactagtaac agtggtaggt   540
gcgcgcgtga atcggcagcg gtttacgttt gcaacaacaa tagctatata gcacacgatg   600
agtcatccgc cattaagata caatctgcat ttcgtggata cctggcaaga agagcattgc   660
gagcactaaa aggattagtg agactccaag cattggttag aggtcatata gaaggaaga   720
gaactgcaga atggttaaga aggatgcaag cattattgag agcacaagca cgtgctcgtg   780
ctggccgggc ccaaatttcc gagtcttccc aatcaagctg caaatcgtct cacttccatc   840
atccggatcc agcaacccct gaaaaatttg aacatgttat tcgatccaag ggtacaaaat   900
atgaacaatc atcaatgttg aagagaaatg gatcaaagtc aagtggaagg actgttgata   960
atcaagagaa attacactca ggttggtatc gccgtgttga tgagcaaaca tgggagcatt  1020
caacaagaat tggtcctaat gatgatgaaa agaatgacaa aatccttgaa gttgacactg  1080
ggaaaccaaa tttcatctct aaacggagaa acctctttca ttcaacacat ctttctctga  1140
attctgattt atatagctgt agtttcacta attcgagaga ctcacaccaa acagctccta  1200
gtccttcatc tggtgaagtt cagtctttaa tccattgat gctgtctcac tctgaagcaa  1260
tacaggaaag ccctttctgc ggtgctgttg atgataatag tccacaattc tattctgcat  1320
catcaaaagg agctagttcc aagagaagcc ccttcactcc tgctaagagt gatggcacta  1380
gaagctacct aagtggttac tcagaccatc caaattacat gtcttacact gaatcgtcaa  1440
aagctaaggt aaggtctttc agtgctccaa acaaaggcc tcattatgaa agatctagtt  1500
caacaaagag gtactccatt catggttttg gtgaattgaa atcaactaca caaaggtctg  1560
ccatgcatgc aaacttcgcc agcaaagctt accccgggtc gggtaggttg gacaggctgg  1620
gaatgcccct tgggtataga tactaaataa tggttttacc atttggctaa ggaatggtat  1680
gtagttttatg tttagatgtt aacgatgatg actctcaccct acccctaatgt atccatcctt  1740
taatgttta gtgcatgtga gttcccaagt taaaagaat agtagctgct ttacaaaaaa   1800
aaaaaaaaaa aaaa                                                   1814

SEQ ID NO: 83            moltype = AA  length = 489
FEATURE                  Location/Qualifiers
source                   1..489
                         mol_type = protein
                         organism = Gossypium hirsutum
```

-continued

```
REGION                  1..489
                        note = Ceres CLONE ID no.1968211
REGION                  1..489
                        note = Score of 555.8 for HMM of FIGURE 2.
REGION                  1..489
                        note = Functional Homolog Of Ceres SEEDLINE ID no. ME06748
                         at SEQ ID NO.41
REGION                  142..162
                        note = Pfam Name: IQ Pfam Description: IQ
                         calmodulin-binding motif
SEQUENCE: 83
MGKASKWFRS ILGFKKSDPH NQPSPSSSKP TSHKDKRRWS FVKSYREKDS STNNSNAKLP      60
SSSQQQKDSV SFVERKGDNE VTDPSKHAIA VAAATAAVAE AAVAAAQAAA AVVRLTSNSG     120
RCARESAAVY VCNNNSYIAH DESSAIKIQS AFRGYLARRA LRALKGLVRL QALVRGHIER     180
KRTAEWLRRM QALLRAQARA RAGRAQISES SQSSCKSSHF HHPDPATPEK FEHVIRSKGT     240
KYEQSSMLKR NGSKSSGRTV DNQEKLHSGW YRRVDEQTWE HSTRIGPNDD EKNDKILEVD     300
TGKPNFISKR RNLFHSTHLS LNSDLYSCSF TNSRDSHQTA PSPSSGEVQS LTPLMLSHSE     360
AIQESPFCGA VDDNSPQFYS ASSKGASSKR SPFTPAKSDG TRSYLSGYSD HPNYMSYTES     420
SKAKVRSFSA PKQRPHYERS SSTKRYSIHG FGELKSTTQR SAMHANFASK AYPGSGRLDR     480
LGMPLGYRY                                                             489

SEQ ID NO: 84           moltype = AA   length = 464
FEATURE                 Location/Qualifiers
source                  1..464
                        mol_type = protein
                        note = subspecies = indica
                        organism = Oryza sativa
REGION                  1..464
                        note = Public GI ID no.116310011
REGION                  1..464
                        note = Score of 886.7 for HMM of FIGURE 2.
REGION                  1..464
                        note = Functional Homolog Of Ceres SEEDLINE ID no. ME06748
                         at SEQ ID NO.41
REGION                  124..144
                        note = Pfam Name: IQ Pfam Description: IQ
                         calmodulin-binding motif
SEQUENCE: 84
MGWASRWLRG LLGGGKKPNS GSGDPKPARE KKRWGFGKSF REKSPAHPPP PPPPSAAVQR      60
AVTPRRAYTA SDEGDDEQSK RAIAVAAATA AVAEAAVAAA QAAAAVVRLT SSGRCAPAAA     120
KREEYAAVRI QAAFRGYLAR RALKALRGLV KLQALVRGNI VRRQAAETLR CMHALVRVQR     180
RARACRAIRS QHVSAHPGPP TPEKYDQATH EGVPKHGRSG SLKGSSSKTP GSERLTRERS     240
ESCGRNWLDK WVEERYLDDE KNAKILEVDT GKPGRHASRR RSGSHHHHSS CSSMTSEQKS     300
RSYATMPESP SKDSTTAQQS VPSPPSVGMA EALSPLRMAV DIAELCDSPQ FFSATSRPGS     360
SRSRAFTPTK SECSRSLFGG YSDYPNYMAN TESFRAKARS QSAPKQRPQY EKSSSLRKAS     420
AHAFGPGSCA PVAQRTTASL HSKFTNKAYP GSGRLDRLGM PVKY                      464

SEQ ID NO: 85           moltype = DNA   length = 1019
FEATURE                 Location/Qualifiers
source                  1..1019
                        mol_type = other DNA
                        organism = Arabidopsis thaliana
misc_feature            1..1019
                        note = Ceres SEEDLINE ID no.ME08768
misc_feature            1..1019
                        note = Encodes the peptide sequence at SEQ ID NO. 86
SEQUENCE: 85
gttactaatc tcacgcacat tctttctctc tctaaattct gcaccacaat ccgcaaaatg      60
accaaatact tcttgctgtg aatgtcgaaa atgcctgcag gcacaacatg tgaagtgatg     120
caaaacggca acacttgttt caccagatcc tttcgtcatt gatggggaag aaaggaggca     180
gctggttctc atctgtgaag aaagttttca agtcatcttc taaagattcg ccccagcctg     240
agaagaagaa ggacaacaca cagaaattac agcatgaagt ggcagaggtg gtgtcctttg     300
agcattttcc tgcagagagt tctccagata atgtgagcaa tgcagagatg agtacgacat     360
caacgccagt gaccaacgaa gatagaagcc atgcgattgc cgttcagca gcaactgccg      420
cagctgcaga agctgctgtg gtggctgctc aagcagctgc aagagttgta agattggcag     480
gaagttacgg gcggcagtcc aaggaagaaa gagcagcaac actcattcaa tcatactata     540
gaggctacct ggctcgacgt gcactacgag cattgaaggg attagtgagg ctgcaagcac     600
tggtgagggg acacaatgtg cggaagcaag cgcagatgac gatgcggtgc atgcaagcac     660
tggtgagggt gcaggcacga gtacgggctc gccgattcca attgagtcac gcggatcagg     720
aaagagagaa gaaagaagag cccaagccca taccgtgcc cgtgcccatg agcccctga       780
gaagaataga cgacattaat gactgggaca ataggcgtca agtagctac aaaattaagg      840
aaaacgattt gcgaaacat gaagctgtaa tgaagagaga gagctctt gcatacgctt        900
tcaactatca acaggttagt taatttgtca tgattaaatg gaatatagt ggataaaata      960
gcttagtcta atattctttc aaaacggtac gtgcaattta atttatctat atcttctttt    1019
```

```
SEQ ID NO: 86            moltype = AA  length = 253
FEATURE                  Location/Qualifiers
source                   1..253
                         mol_type = protein
                         organism = Arabidopsis thaliana
REGION                   1..253
                         note = Ceres SEEDLINE ID no.ME08768
REGION                   1..253
                         note = Score of 467.7 for HMM of FIGURE 1.
REGION                   116..136
                         note = Pfam Name: IQ Pfam Description: IQ
                             calmodulin-binding motif
SEQUENCE: 86
MGKKGGSWFS SVKKVFKSSS KDSPQPEKKK DNTQKLQHEV AEVVSFEHFP AESSPDNVSN  60
AEMSTTSTPV TNEDRSHAIA VAAATAAAAE AAVVAAQAAA RVVRLAGSYG RQSKEERAAT 120
LIQSYYRGYL ARRALRALKG LVRLQALVRG HNVRKQAQMT MRCMQALVRV QARVRARRFQ 180
LSHADQEREK KEEPKPIPVP VPMSPLRRID DINDWDNRRQ SSYKIKENDL RKHEAVMKRE 240
RALAYAFNYQ QVS                                                   253

SEQ ID NO: 87            moltype = DNA  length = 1906
FEATURE                  Location/Qualifiers
source                   1..1906
                         mol_type = other DNA
                         organism = Gossypium hirsutum
misc_feature             1..1906
                         note = Ceres CLONE ID no.1943807
misc_feature             1..1906
                         note = Encodes the peptide sequence at SEQ ID NO 88
SEQUENCE: 87
atctttttta tcttcacagt gttggtgtct tggctccttc ttcaaagctt cttttagctg   60
taaatgtagc ttggtttaac cctatccttt gaatgggga tgaaggagg gacttcatgg  120
ttgactgctg tgaaagggc ttttagatct cctactaaag atacccatga agatgaaaag  180
gtaagtgttt caatctattt taatggctgt ttatgaatct aaaaagaaaa ccctttgatt  240
tttttttata tagaagagag ataaacggag gtggatcttt aggaaacaaa atacaagtcc  300
tgtgaagagt gtaggtaata atggtggtgg tggtgcaagt acggcagcag cggagcaaag  360
acatgctatt gctgtggcgg tggctaaagc agctgaagct gaagctgcgg tggcgacggc  420
acaagcagct ttacaagctg ctcggttgac taaacctagt tatggcagga aacatcactt  480
tgctgctatt gttattcaga cagcttttag aggctacctg gccaggagag ctctacgtgc  540
gttaaaaggg ctagtgaagt tacaagcttt agtgagaggt cacaacgtga gaaagcaagc  600
caagatgacg cttcgttgca tgcaagcact ggttaaagtt cagtctcgtg ttttagacca  660
aagaatgagg ctctcgcacg atggttgcag ccggaaatca gcatttagcg acaccaacag  720
tgtatgggaa tcacggtatc ttcaagatat atcggataga agatcattat cgagagaagg  780
aagtagcata gcagatgatt gggacgaaag gccacacaca gttgaagaag tgaaagctat  840
gttacaacat aggaaagaag ctgctttgaa acgtgaaaag agcttgtcac aagcactgtc  900
acaacagatg aggagagctc gaaggagtcc atcaatgggg ggacaagatg agtggcttga  960
tcgttggatg cctgctaaac catgggataa cagaggagga gcttcaatgg atcaaagaga 1020
taatgtcaaa actgttgaaa tggacacttc acagccttat tcatatttag caccaaatta 1080
tagaagaaca aattcaaacc attatcacca aaggcctagt tcacctctcc ataggctca  1140
acacaatgca caacctttcc acccttctcc aattacaccc tctccatcga aaacacgtcc 1200
ggttcaagta cggtccgcga gccctcgttg cgttagggaa gaccgaacat cgttttcatc 1260
atcacaaaca ccaagtttaa ggtccaatta ttattacaca ggaagggtta gtactcaagc 1320
tagtactagc ataaacaatg ctactacatt gcctaattac atggcagcaa cagagtctgc 1380
aaaggctagg attaggtctc aaagtgcacc aagacagagg ccatcgacac cagagaggga 1440
ccgatcggt tcagcaagga aaaggctatc gtttcccgtc ccggaaccat atggtatcgg 1500
gatggggtac ggaggttatg gtcatagctt gaggagcccg agttttaaaa gtgtaagcgg 1560
gtcgcaattc ggattggaac gacagtctaa ctattcatct tgttgtactg agagccttgg 1620
tggtgaaatg tcaccatctt caactagtga tctaagaagg tggttgaggt gatcccatca 1680
atgtagctgt tggttttac tagttttata gtgtgttttcc attgttgatt ttaccaattc 1740
ttggttgaaa ttcaagcttt ataagtgagg caactgcgat gaacccttcc ttactgggat 1800
ctttcatgag attcataacc aaattgagtg tgtaatacta taaagtaact ctgtaattct 1860
gttttgtcat aacttttttaa tatattaaag cttatcatct tttccg              1906

SEQ ID NO: 88            moltype = AA  length = 355
FEATURE                  Location/Qualifiers
source                   1..355
                         mol_type = protein
                         organism = Gossypium hirsutum
REGION                   1..355
                         note = Ceres CLONE ID no.1943807
REGION                   1..355
                         note = Score of 667.2 for HMM of FIGURE 1.
REGION                   1..355
                         note = Functional Homolog Of Ceres SEEDLINE ID no. ME08768
                             at SEQ ID NO.86
SEQUENCE: 88
MTLRCMQALV KVQSRVLDQR MRLSHDGCSR KSAFSDTNSV WESRYLQDIS DRRSLSREGS  60
SIADDWDERP HTVEEVKAML QHRKEAALKR EKSLSQALSQ QMRRARRSPS MGGQDEWLDR 120
WMPAKPWDNR GRASMDQRDN VKTVEMDTSQ PYSYLAPNYR RTNSNHYHQR PSSPLHRAQH 180
```

```
NAQPFHPSPI TPSPSKTRPV QVRSASPRCV REDRTSFSSS QTPSLRSNYY YTGRVSTQAS  240
TSINNATTLP NYMAATESAK ARIRSQSAPR QRPSTPERDR IGSARKRLSF PVPEPYGIGM  300
GYGGYGHSLR SPSFKSVSGS QFGLERQSNY SSCCTESLGG EMSPSSTSDL RRWLR       355

SEQ ID NO: 89           moltype = DNA  length = 1677
FEATURE                 Location/Qualifiers
source                  1..1677
                        mol_type = other DNA
                        organism = Populus balsamifera
                        sub_species = trichocarpa
misc_feature            1..1677
                        note = Ceres ANNOT ID no.1471392
misc_feature            1..1677
                        note = Encodes the peptide sequence at SEQ ID NO 90
SEQUENCE: 89
atggggaaga agggaggtag ctcatggttg accgttgtga aaagggcttt tagatctcct   60
aataaagaaa atgacaagag aactgctggg actacaggcc atgaccaaga agaagatgaa  120
gaaaagaaga gagagaagag gaggtggctg tttaggaaac ctacgaatca agaaacagtg  180
acacaacaga tcctatcaaa ggcaggaaat gtcaaggcct ccacgggtgg tggtggaggt  240
gcaccgacag accatgtgtc ggcagctgca gcagctgagc aaaggcatgc aattgctgta  300
gctgttgcca ctgcagctgc agctgaaact gcattagcca ctgcccaggc ggccgtggag  360
gtggctaggc tcactaggcc ttcttatcac cctagagaac gttccgctgc cattgtcatt  420
caaaccgctt ttagaggata cctggcaagg cgggctcttc gcgcgcttaa agggctagtg  480
aagttgcaag ctttagtgag gggacacaat gtgagaaagc aggccaagat gaccctgaga  540
tgcatgcaag ctctggttcg agtgcaggct cgagtacttg accaacgcat gaggctttca  600
catgaaggca gcagggaatc tgcattcagt gacaccaata gcgtgtttga atcgcgatat  660
cttcaagaaa tttcagaaag aaagtcgatg tcaagagacg gcagcagcat tgcagatgat  720
tgggatgatc ggccacgcac aattgaggaa gtcaaggcca tgttgcaacg caggaaagaa  780
gttgcattca agcgtgagaa ggccttatct caaggtttct ctcaacagat atggagaaac  840
cgtaggagcc catcaatggg caatgaaggt gagctccaag aaagatccaa atggcttgan  900
cattggatgc ctgcaaagcc gtgggacaat agcagcagag cacgagcctc aactgatcaa  960
agaaacccca tcaaaactgt agaaattgaa acctcccaac cttgctcata tttagctcct 1020
aattttggaa gaacgaacca aaaccaatat caccaacacc agagatccaa ttcaataaac 1080
aatggtgtta catgctcggc tcctcctcca ctcccatagg ctcatcaaaa tgcttctctc 1140
cgcaactctc ctattacacc ctccccgtca agaactaggc ctcttcaggt tcgttcagcg 1200
agtccccgat gtgctagaga agatagaagc tgtaattcct ctcgaacacc gagtttaagg 1260
tccaattacc tctataatgg caatctgaaa caacatggaa tcaggggtgg tgctgctagt 1320
gttagtggaa atgctaatgc tacattgcca aattacatgg ctacaactga gtccgccaag 1380
gctagattga gatcacagag tgcgccaagg caaagaccat caacaccaga gcgagacagg 1440
gttgggtctg caagaaaacg gcttttgtat cctgtccccg acccttacgg tgtcgggatg 1500
ggttatggtg gtgttggtta cgggcatggt ttcaggagtc ccagctttaa aagtgtaagt 1560
ggttcacatt ttggtggatt agaacaacaa tctaactatt cttcttgctg cactgatacc 1620
ttcggtgctg agatttcccc ttcttcaacg agcgaccaga gaaggtggtt gagataa    1677

SEQ ID NO: 90           moltype = AA  length = 382
FEATURE                 Location/Qualifiers
source                  1..382
                        mol_type = protein
                        note = subspecies = trichocarpa
                        organism = Populus balsamifera
REGION                  1..382
                        note = Ceres ANNOT ID no.1471392
REGION                  1..382
                        note = Score of 422.0 for HMM of FIGURE 1.
REGION                  1..382
                        note = Functional Homolog Of Ceres SEEDLINE ID no. ME08768
                          at SEQ ID NO.86
SEQUENCE: 90
MTLRCMQALV RVQARVLDQR MRLSHEGSRE SAFSDTNSVF ESRYLQEISE RKSMSRDGSS   60
IADDWDDRPR TIEEVKAMLQ RRKEVAFKRE KALSQGFSQQ IWRNRRSPSM GNEGELQERS  120
QWLDHWMPAK PWDNSSRARA STDQRNPIKT VEIETSQPCS YLAPNFGRTN QNQYHQHQRS  180
NSINNGVTCS APPPLHRAHQ NASLRNSPIT PSPSRTRPLQ VRSASPRCAR EDRSCNSSRT  240
PSLRSNYLYN GNLKQHGIRG GAASVSGNAN ATLPNYMATT ESAKARLRSQ SAPRQRPSTP  300
ERDRVGSARK RLLYPVPDPY GVGMGYGGVG YGHGFRSPSF KSVSGSHFGG LEQQSNYSSC  360
CTDTFGAEIS PSSTSDQRRW LR                                          382

SEQ ID NO: 91           moltype = AA  length = 527
FEATURE                 Location/Qualifiers
source                  1..527
                        mol_type = protein
                        organism = Arabidopsis thaliana
REGION                  1..527
                        note = Public GI ID no.6715635
REGION                  1..527
                        note = Score of 916.5 for HMM of FIGURE 1.
REGION                  1..527
                        note = Functional Homolog Of Ceres SEEDLINE ID no. ME08768
                          at SEQ ID NO.86
```

| REGION | 121..141 |
| --- | --- |
| | note = Pfam Name: IQ Pfam Description: IQ calmodulin-binding motif |

SEQUENCE: 91

```
MGKKNGSSSW LTAVKRAFRS PTKKDHSNDV EEDEEKKREK RRWFRKPATQ ESPVKSSGIS  60
PPAPQEDSLN VNSKPSPETA PSYATTTPPS NAGKPPSAVV PIATSASKTL APRRIYYARE 120
NYAAVVIQTS FRGYLARRAL RALKGLVKLQ ALVRGHNVRK QAKMTLRCMQ ALVRVQSRVL 180
DQRKRLSHDG SRKSAFSDSH AVFESRYLQD LSDRQSMSRE GSSAAEDWDD RPHTIDAVKV 240
MLQRRRDTAL RHDKTNLSQA FSQKMWRTVG NQSTEGHHEV ELEEERPKWL DRWMATRPWD 300
KRASSRASVD QRVSVKTVEI DTSQPYSRTG AGSPSRGQRP SSPSRTSHHY QSRNNFSATP 360
SPAKSRPILI RSASPRCQRD PREDRDRAAY SYTSNTPSLR SNYSFTARSG CSISTTMVNN 420
ASLLPNYMAS TESAKARIRS HSAPRQRPST PERDRAGLVK KRLSYPVPPP AEYEDNNSLR 480
SPSFKSVAGS HFGGMLEQQS NYSSCCTESN GVEISPASTS DFRNWLR            527
```

| SEQ ID NO: 92 | moltype = DNA  length = 1946 |
| --- | --- |
| FEATURE | Location/Qualifiers |
| source | 1..1946 |
| | mol_type = other DNA |
| | organism = Triticum aestivum |
| misc_feature | 1..1946 |
| | note = Ceres CLONE ID no.910109 |
| misc_feature | 1..1946 |
| | note = Encodes the peptide sequence at SEQ ID NO 93 |

SEQUENCE: 92

```
atcaaacccc ccactgcccg cgccagccag ccgcggcaat aataataact ccgccgcctc   60
ctgccatgcc gcacgctagt agtagcacgc taggatcgag tagctcgtag cgtagccgtg  120
cgagggaggg aggtgggtcg atgcccgcgg ccgtgcaacc acagcaaccg cgagccggtg  180
gtgttggcca tggggaataa gaagggcggg tcgtcgtggc tcaccgccgt caagcgggcc  240
ttccgctcgc cgtccaagga ggacagcccc aagaagtctg cacgcctccg cgaggaccct  300
gacgccgacg aggacaagac caagagggag aggaggaagg ggctcttcag gagatcctcg  360
tccccgtctc cgtctccggc gtctgccccc gcgccgccgg agcagcagca gtcggcgtcg  420
aggtcggcac ctgcacccgc tgtgacggac gagcagcgtc acgccatcgc gctggccgtg  480
gcgaccgcgg cgacggccga ggctgccgtg ccacgcgcgc aggcggcggc cgaggtcgtc  540
cgcctgaccc gcccctcctc cagcttcgtg cgggagcact acgtcgccat cgtcgtacag  600
accgccttcc gaggctacct ggcgaggcgt gctctgcgcg cgctcaaggg gctggtgaag  660
ctgcaagcgc tagtcgcgcg gcacaacgtg cggaagcagg ccaacatgac gctgcggtgc  720
atgcaggcgc tggtgcgcgt ccaggcgcgg gtgcgcgacc agcggctgcg actctcccag  780
gagtccttgt ccgccgccgg tgcggctgcg tgcggcagca gcaaatcctc gtacagcgtt  840
gacacctccg cttctcggga ctccaagtac acccaagaat acgtcgaacg ccgctctgtg  900
gagcggtcgc gagacggcag cagcttcgcc gccgaagact gggacgaccg gccgcggacg  960
atagaggaga ttcaggcgat gctgcagacg aggaaagacg ctgctctcaa agcgtgagaga 1020
gcgctctcat acgcctttc tcaccaaatt tggaggaacg ccgctccgtc agtcgaggag 1080
gagatgaacg tcgacgggca gccgcgctgg gcggagaagt ggatggcgtc gcgcgcgtcg 1140
tttgatacaa acaggagcag cgcccgaact gccgcgcgg cggctgctgc ggcaccaggg 1200
cgcgcgtcca ggaccaccg cgaccaggtc aagacgttgg agatcgacac cgcacggcca 1260
ttctcctact ccacgcctcg ccggcatgcc ccaccgtcgc agcacgggaa cggctcgccg 1320
atgcaccgtg cgcaccacca ggcttcggtc acgccgtcgc cggggaaggc gaggccaccg 1380
attcaggtgc gctccgcgag cccgcgagtg gagcgcggca caagtggtgg aggaggaagc 1440
tacacaccga gcttgcactc ccagcgccac cgctcctccg gctcggcggt gccgaactac 1500
atggcggcca cggaatctgc aaaggcacgt atccgctccc agagcgcgcc acggcaacgc 1560
cctgcaaccc cggagcgcga cccgccacag accgcctata accccgccgg aggggagcgcc 1620
aagaagcggc tgtcgttccc cgtcccgcag gacccgtacg gcgttgggta cgcgcagagc 1680
ctgcggagcc cgagcttcaa gagcgcgacg gggcggttca cctccgagca gcgttcgacc 1740
gtctcgtctc tgtcgtgcgc agagagcgtc ggcggggaac cagtctcccc gtcgtccacc 1800
actgacctcc gccgctggct ccgttgagtt gagccccgg cgaggtgttc gttgtaatac 1860
ctgcgttgct aattttctcg taatctcctc ggagaaaaat gaccttctcg taatctattt 1920
ttttgctgct aaaaaaaaaa aaaaaa                                     1946
```

| SEQ ID NO: 93 | moltype = AA  length = 543 |
| --- | --- |
| FEATURE | Location/Qualifiers |
| source | 1..543 |
| | mol_type = protein |
| | organism = Triticum aestivum |
| REGION | 1..543 |
| | note = Ceres CLONE ID no.910109 |
| REGION | 1..543 |
| | note = Score of 1259.0 for HMM of FIGURE 1. |
| REGION | 1..543 |
| | note = Functional Homolog Of Ceres SEEDLINE ID no. ME08768 at SEQ ID NO.86 |
| REGION | 130..150 |
| | note = Pfam Name: IQ Pfam Description: IQ calmodulin-binding motif |

SEQUENCE: 93

```
MGKKAGTTSS WLTAVKRAFR SPSKDDSPNK AARLRDDTDD DKGKRERRRW LFRKSSSPSP  60
APPTPPPPQQ QQQQSRAAAV TEEQRHAIAL AVATAATAEA AVATAQAAAE VVRLTRPSSS 120
FVREHYAAIV VQTAFRGYLA RRALRALKGL VKLQALVRGH NVRKQANMTL RCMQALVRVQ 180
ARVRDQRMRL SQDSISLSAA AASAAPCGSS KSSYSVDTST FWDSKYTHDF AAADRRSIER 240
SRDGSSFAAG DDWDDRPRTI EEIQAMLQTR KDAALKRERA LSYAFSHQIW RNPAPSVEEM 300
```

```
DVDGQPRWAE  RWMASRASFD  TSRSTVRASA  AAAPGRASTD  HRDQVKTLEI  DTARPFSYST  360
PRRHGNASYH  ASSSPMHRAH  HHSPVTPSPS  KARPPIQVRS  ASPRVERGGG  GGGSYTPSLH  420
SHRHHASSGG  AAAVPNYMAA  TESAKARVRS  QSAPRQRPAT  PERDRMSFGG  GGGGGGAKKR  480
LSFPVPIDPY  GAYAQSLRSP  SFKSAAGRFS  SEQRSNVSSS  CAESLGGDVV  SPSSTTDLRR  540
WLR                                                                   543

SEQ ID NO: 94          moltype = AA   length = 543
FEATURE                Location/Qualifiers
source                 1..543
                       mol_type = protein
                       note = subspecies = japonica
                       organism = Oryza sativa
REGION                 1..543
                       note = Public GI ID no.115474509
REGION                 1..543
                       note = Score of 1167.6 for HMM of FIGURE 1.
REGION                 1..543
                       note = Functional Homolog Of Ceres SEEDLINE ID no. ME08768
                        at SEQ ID NO.86
REGION                 125..145
                       note = Pfam Name: IQ Pfam Description: IQ
                        calmodulin-binding motif
SEQUENCE: 94
MGKKAGTTSS  WLTAVKRAFR  SPSKDDSPNK  AARLRDDTDD  DKGKRERRRW  LFRKSSSPSP   60
APPTPPPPQQ  QQQQSRAAAV  TEEQRHAIAL  AVATAATAEA  AVATAQAAAE  VVRLTRPSSS  120
FVREHYAAIV  VQTAFRGYLA  RRALRALKGL  VKLQALVRGH  NVRKQANMTL  RCMQALVRVQ  180
ARVRDQRMRL  SQDSISLSAA  AASAAPCGSS  KSSYSVDTST  FWDSKYTHDF  AAADRRSIER  240
SRDGSSFAAG  DDWDDRPRTI  EEIQAMLQTR  KDAALKRERA  LSYAFSHQIW  RNPAPSVEEM  300
DVDGQPRWAE  RWMASRASFD  TSRSTVRASA  AAAPGRASTD  HRDQVKTLEI  DTARPFSYST  360
PRRHGNASYH  ASSSPMHRAH  HHSPVTPSPS  KARPPIQVRS  ASPRVERGGG  GGGSYTPSLH  420
SHRHHASSGG  AAAVPNYMAA  TESAKARVRS  QSAPRQRPAT  PERDRMSFGG  GGGGGGAKKR  480
LSFPVPIDPY  GAYAQSLRSP  SFKSAAGRFS  SEQRSNVSSS  CAESLGGDVV  SPSSTTDLRR  540
WLR                                                                   543

SEQ ID NO: 95          moltype = DNA   length = 1812
FEATURE                Location/Qualifiers
source                 1..1812
                       mol_type = other DNA
                       organism = Panicum virgatum
misc_feature           1..1812
                       note = Ceres CLONE ID no.1780908
misc_feature           1..1812
                       note = Encodes the peptide sequence at SEQ ID NO 96
SEQUENCE: 95
gtgaccagcc agccatggag cgcgccaac gcccccgcg ccagcaataa tacaaccccc      60
ccaccacccg gccgcgcct gcccgtcgcc ggacatgggc aagaagggcg gcgccacgtc    120
ctgactcacc gccgtcaagc gggccttccg ctcgccctcc aaggacgacg ccgcctcgcc    180
cgcaaggaag gcctcgcgcc tccgcgaccg cgacgacgaa cccgccgacg gcgaccaaga    240
caagcagggg aagcgggagc agcgccggcg atggctgttc cggaggtcct cctcccgtc    300
cccgtcccct gccccgccg cgccggagca cccggccgtc acggaggagc agcgccacgc    360
catcgcgctg cgcctggcga ccgccgccac ggccgaggcc gccgtggcca cggcgcaggc    420
ggcggcggag gtggtccgcc tcaccctccc cggcggcctc gccgcccgcg agcactacgc    480
cgccgtcctc atccagaccg ccttccgggg ctacctgcgg cgcgccgcgc tgcgggcgct    540
caggggcctc gtcaagctgc aaacgctcgt gcgcggccaa aacgtccgca agcaggccaa    600
catgacgctc cgctgcatgc aggcgctggt gcgcgtccag gcgcgcgtcc gggaccagcg    660
gatgcgcctc tcccaggact ccatgtccct gtccatgccg ctgtccgccg ccggcgccgc    720
cgcggcgccg tgcggcagca gcaagtcgtc gtacagcgtc gacacatcca cgttctggga    780
ctccaagtac acccacgact acgccgaccg ccgctccgtc gagcggtcgc gcgacggcag    840
cagcttcgcc gccgacgact gggacgaccg gccgcgaacg atagaggaga tccaggccat    900
gctgcagacg aggaaggacg cggcgctcaa gcgtgagagg cgctgtcct acgccttctc    960
gcatcaactt tggaggaacc cggcgccggc ggcggatgag atggacgtgg acggcggcgg   1020
gcagcagccg cggtggatga cgtcgcgcgc gtccttcgac acgaaccgga gcagcagcat   1080
ccgcggcgcg gcggtgcccg ggcgcgcgtc catggaccac cgcgagcccg tgaagacgct   1140
ggggatggac acggcggcg cccttctcgta ctcgcgaccg cagcagcagg cgccgtcgtc   1200
ctcgccgatg caccaccgcg ggcactcgcc ggtgaccgcg tcgccggga aggcgcggcc   1260
cccgatccag gtccggtcgg cgagcccgcg cgtggaccgc ggcgcgggcg cgggagcta   1320
cacgccgagc ctgctgcact cccagcggca ccaccaccac caggcggggg cggcggtgcc   1380
caactacatg gcgcgacgg agtcggccaa ggcccgggtg cggtcccaga gcgcgccgcg   1440
gcagcggccc gcgacgccg agcgcgaccg cgctctccggg gcgggggaga gcgcgaagaa   1500
gcggctgtcg ttcccggcgg cggcagaggc gtacgcgcag tccctgcgga gcccgagctt   1560
caagagcgcg gcggggcggt tctcgtcgga gcagcggtcg acggtgtcgt cgtcgtcgc   1620
ggagagcctc ggcggagagc cggcgtcgcc gtcgtccacc accgaccttc gccgctggct   1680
ccgctgaggg ccggccggcc gtccgttctc cgttgtagca gtaacgccgc ttttggctc   1740
ggcagacacg accacgtgcc cctgtagcat catcttctct ctcggtgtaa ttcatggcag   1800
cttttttcga gc                                                      1812
```

```
SEQ ID NO: 96            moltype = AA  length = 361
FEATURE                  Location/Qualifiers
source                   1..361
                         mol_type = protein
                         organism = Panicum virgatum
REGION                   1..361
                         note = Ceres CLONE ID no.1780908
REGION                   1..361
                         note = Score of 598.0 for HMM of FIGURE 1.
REGION                   1..361
                         note = Functional Homolog Of Ceres SEEDLINE ID no. ME08768
                            at SEQ ID NO.86
SEQUENCE: 96
MTLRCMQALV RVQARVRDQR MRLSQDSMSL SMPLSAAGAA AAPCGSSKSS YSVDTSTFWD    60
SKYTHDYADR RSVERSRDGS SFAADDWDDR PRTIEEIQAM LQTRKDAALK RERALSYAFS   120
HQLWRNPAPA ADEMDVDGGG QQPRWMTSRA SFDTNRSSSI RGAAVPGRAS MDHREPVKTL   180
GMDTARPFSY STPRQQAPSS SPMHHRGHSP VTPSPGKARP PIQVRSASPR VDRGAGGGSY   240
TPSLLHSQRH HHHQAGAAVP NYMAATESAK ARVRSQSAPR QRPATPERDR LSGGGGSAKK   300
RLSFPAAAEA YAQSLRSPSF KSAAGRFSSE QRSTVSSSCA ESLGGEPASP SSTTDLRRWL   360
R                                                                  361

SEQ ID NO: 97            moltype = DNA  length = 1398
FEATURE                  Location/Qualifiers
source                   1..1398
                         mol_type = other DNA
                         organism = Populus balsamifera
                         sub_species = trichocarpa
misc_feature             1..1398
                         note = Ceres ANNOT ID no.1520883
misc_feature             1..1398
                         note = Encodes the peptide sequence at SEQ ID NO 98
SEQUENCE: 97
atggggaaga aaggaaaagg atggtttaca tctgtgaaga gagtgttcaa atcatcatct    60
cctaaggaat taccagtagg gaaaaagaaa gacaacgcag agaaatggca acatgaggct   120
ccagaagttg tgtcattaga gcattttcct actggaagtt ctcctgatgt tacaaatgat   180
gagagcaatg tatcaactcc agtaactgaa gatagaaatc atgccattgc tgtggcagta   240
gcgactgctg ccgcagcaga agctgcggtt gcagctgctc aagcggcggc taaagttgtt   300
cgcttagctg gttatggacg acaatcaaag gaagaaagag ctgccatcct catacaatca   360
ttctatagg gctaccttgc tcggcgtgcc ttacgcgcat tgaagggatt ggtgaggctc   420
caagcattag tgagaggcca caatgtaaga aagcaagcac aaatgacaat gagaagcatg   480
caagctcttg ttcgtgtgca agcaagagta agagcaagaa gacttgaatt agctcacgag   540
aagcttcaaa ggaagacaga ggaagaagat gaacagtgga taccagtgga cgaagactgt   600
atgaatccaa agaatccatt gaagagttat aaatgggata ggaggaatca aagttcagat   660
aatttcaaag aaaatgcttc aaagaagcat gatgctgtca tgaaaagaga gagagccctt   720
gcttatgctt atgccttcca gcagcagcag cagcaacaat tactctcaca aaatagtcct   780
aatggtaaag aaacaggaca tttttgtgaac gaacacgaaa agatgcaatg gggatggaat   840
tggcttgaga gatggatgtc agcacaatca tataacgtgc gtcaatcggg tccaaatgaa   900
gggtcttacg tgacagtaaa cacaactaca accacgacca ccacagagga catgtccgag   960
aagacagtag agatggacat ggtgacccca acaggcacta gcaatccaa catgggcatg  1020
ctagacacca atccatattc gaatcgaccc caatggcaat caagttcaag tgtcgtacgt  1080
agctacatgg ctccgaccca gtccgcaaag gcgaaagtgc gttctcaaag tttgatcaag  1140
caacgtgccc cagcgacacc tctgtggaat ccatccacca agaaagattc aagcattgtt  1200
ggtccaggtt gtgattcttc cagttcaggt ggtggaacaa caacttatca cgctccaaga  1260
agtccctagcc caaacataa cgggatgcgc ctgcattcga gaagacatgc tggtggatat  1320
agccctgatt tcaatggcgg tgatgattgg aggttgcctc tcttgatgg tcatggatgg  1380
aggaatgatt ttggttga                                                1398

SEQ ID NO: 98            moltype = AA  length = 309
FEATURE                  Location/Qualifiers
source                   1..309
                         mol_type = protein
                         note = subspecies = trichocarpa
                         organism = Populus balsamifera
REGION                   1..309
                         note = Ceres ANNOT ID no.1520883
REGION                   1..309
                         note = Score of 495.7 for HMM of FIGURE 1.
REGION                   1..309
                         note = Functional Homolog Of Ceres SEEDLINE ID no. ME08768
                            at SEQ ID NO.86
SEQUENCE: 98
MRSMQALVRV QARVRARRLE LAHEKLQRKT EEEDERRLPV DEDFMNPKNP LKSYKWDRRN    60
QSSDNFKENA SKKHDAVMKR ERALAYAYAF QQQQQQQLLS QNSPNGKETG HFVNEHEKMQ   120
WGWNWLERWM SAQSYNVRQS GPNEGSYVTV NTTTTTTTTE DMSEKTVEMD MVTPTGTSNP   180
NMGMLDTNPY SNRPQWQSSS SNVRSYMAPT QSAKAKVRSQ SLIKQRAPAT PLWNPSTKKD   240
SSIVGPGCDS SSSGGGTTTY HAPRSPSPKH NGMRLHSRRH AGGYSPDFNG GDDWRLPPLD   300
GHGWRNDFG                                                          309
```

```
SEQ ID NO: 99              moltype = DNA  length = 1445
FEATURE                    Location/Qualifiers
source                     1..1445
                           mol_type = other DNA
                           organism = Arabidopsis thaliana
misc_feature               1..1445
                           note = Ceres CLONE ID no.148018
misc_feature               1..1445
                           note = Encodes the peptide sequence at SEQ ID NO 100
SEQUENCE: 99
attgggattt catttagata atttttttt gggtcttgat ctaagttttg ttctttctaa    60
tttggtaagg caagaagagc attaagagca ttaaaagggt tagtgaagct acaagcattg   120
gtgaggggac ataatgtgag aaagcaagct aaaatgacat taaggtgtat gcaagctctg   180
gttcgagtcc agtctcgtgt gcttgaccaa cgcaaacgct tgtctcatga cggtagtcgc   240
aaatccgcgt tcagtgactc tcacgctgtt tttgaatctc gctatcttca agatttgtca   300
gatcgacaat ccatgtcaag agaaggaagc agcgccgcgg aagattggga tgaccgacca   360
cacacgatag acgcagtgaa agtgatgcta aacggagac gggacacagc attgagacat   420
gacaagacta atttgtcaca agcttttctct caaaagatgt ggaggacggt tggtaaccaa   480
tccacggaag gacaccacga ggtagaactt gaagaggaaa ggccaaaatg cttgaccgg   540
tggatggcta ctagaccgtg ggataaacga gctagtagta gagcttcggt tgaccaaagg   600
gtttcagtta aaaccgttga aatcgacact tctcagcctt actcaagaac aggagcagga   660
agcccgagtc gtggccaaag acctagttcc ccatcaagaa ctagccacca ttaccaatcc   720
cgcaataatt tctcagccac tccatctccg gctaagtcta gaccaatact tattcggtca   780
gctagtccac ggtgccagag agacccgagg gaagaccgtg accgagcagc ttatagttat   840
acatcaaaca caccaagctt gagatccaat tatagtttca cagctaggag tggatgtaca   900
ttagtaccac aatggttaat aatgcatcat tgttgcctaa ttacatggcg agtacagagt   960
cagctaaagc gaggatccgg tctcatagtg caccgaggca acggccctca actcccgaga  1020
gggaccgtgc ggstttrgct acaagaaacg rytctsgtat ccggtaccac cgccagcgga  1080
gtatgaggac aataatagct taaggagtcc aagctttaag agtgtggctg ttcacatttt  1140
tggtggaatg ttagagcagc aatcgaatta ctcttcatgt tgcactgagt ctaacggtgt  1200
tgagatctct ccagcttcta ctagtgactt taggaattgg cttagatgat tggtggtgat  1260
gccaaatcaa ctgtcaagat ctttcatcat cctccaggaa aagaacgttt taaaatttta  1320
tattccagaa gaaaacaaac actttatat tgtgtcgttg aggttgattt gtgtttggaa  1380
gataagttta ttgaccatt gatctgtaac ttcataagat tttgaaacgt tagaagattc  1440
aaaag                                                              1445

SEQ ID NO: 100             moltype = AA  length = 310
FEATURE                    Location/Qualifiers
source                     1..310
                           mol_type = protein
                           organism = Arabidopsis thaliana
REGION                     1..310
                           note = Ceres CLONE ID no.148018
REGION                     1..310
                           note = Score of 458.7 for HMM of FIGURE 1.
REGION                     1..310
                           note = Functional Homolog Of Ceres SEEDLINE ID no. ME08768
                             at SEQ ID NO.86
SITE                       294
                           note = Xaa is any aa, unknown, or other
SITE                       295
                           note = Xaa is any aa, unknown, or other
SITE                       300
                           note = Xaa is any aa, unknown, or other
SITE                       301
                           note = Xaa is any aa, unknown, or other
SEQUENCE: 100
MTLRCMQALV RVQSRVLDQR KRLSHDGSRK SAFSDSHAVF ESRYLQDLSD RQSMSREGSS    60
AAEDWDDRPH TIDAVKVMLQ RRRDTALRHD KTNLSQAFSQ KMWRTVGNQS TEGHHEVELE   120
EERPKWLDRW MATRPWDKRA SSRASVDQRV SVKTVEIDTS QPYSRTGAGS PSRGQRPSSP   180
SRTSHHYQSR NNFSATPSPA KSRPILIRSA SPRCQRDPRE DRDRAAYSYT SNTPSLRSNY   240
SFTARSGCTL VPQWLIMHHC CLITWRVQSQ LKRGSGLIVH RGNGPQLPRG TVRXXLQETX   300
XVSGTTASGV                                                          310

SEQ ID NO: 101             moltype = AA  length = 364
FEATURE                    Location/Qualifiers
source                     1..364
                           mol_type = protein
                           organism = Arabidopsis thaliana
REGION                     1..364
                           note = Public GI ID no.18378797
REGION                     1..364
                           note = Score of 546.8 for HMM of FIGURE 1.
REGION                     1..364
                           note = Functional Homolog Of Ceres SEEDLINE ID no. ME08768
                             at SEQ ID NO.86
SEQUENCE: 101
MTLRCMQALV RVQSRVLDQR KRLSHDGSRK SAFSDSHAVF ESRYLQDLSD RQSMSREGSS    60
AAEDWDDRPH TIDAVKVMLQ RRRDTALRHD KTNLSQAFSQ KMWRTVGNQS TEGHHEVELE   120
```

```
EERPKWLDRW MATRPWDKRA SSRASVDQRV SVKTVEIDTS QPYSRTGAGS PSRGQRPSSP    180
SRTSHHYQSR NNFSATPSPA KSRPILIRSA SPRCQRDPRE DRDRAAYSYT SNTPSLRSNY    240
SFTARSGCSI STTMVNNASL LPNYMASTES AKARIRSHSA PRQRPSTPER DRAGLVKKRL    300
SYPVPPPAEY EDNNSLRSPS FKSVAGSHFG GMLEQQSNYS SCCTESNGVE ISPASTSDFR    360
NWLR                                                                 364

SEQ ID NO: 102         moltype = AA   length = 364
FEATURE                Location/Qualifiers
source                 1..364
                       mol_type = protein
                       organism = Arabidopsis thaliana
REGION                 1..364
                       note = Public GI ID no.21553500
REGION                 1..364
                       note = Score of 524.9 for HMM of FIGURE 1.
REGION                 1..364
                       note = Functional Homolog Of Ceres SEEDLINE ID no. ME08768
                        at SEQ ID NO.86
SITE                   288
                       note = Xaa is any aa, unknown, or other
SITE                   294
                       note = Xaa is any aa, unknown, or other
SITE                   296
                       note = Xaa is any aa, unknown, or other
SITE                   300
                       note = Xaa is any aa, unknown, or other
SITE                   301
                       note = Xaa is any aa, unknown, or other
SEQUENCE: 102
MTLRCMQALV RVQSRVLDQR KRLSHDGSRK SAFSDSHAVF ESRYLQDLSD RQSMSREGSS     60
AAEDWDDRPH TIDAVKVMLQ RRRDTALRHD KTNLSQAFSQ KMWRTVGNQS TEGHHEVELE    120
EERPKWLDRW MATRPWDKRA SSRASVDQRV SVKTVEIDTS QPYSRTGAGS PSRGQRPSSP    180
SRTSHHYQSR NNFSATPSPA KSRPILIRSA SPRCQRDPRE DRDRAAYSYT SNTPSLRSNY    240
SFTARSGCSI STTMVNNASL LPNYMASTES AKARIRSHSA PRQRPSTXER DRAXLXKKRX    300
XYPVPPPAEY EDNNSLRSPS FKSVAGSHFG GMLEQQSNYS SCCTESNGVE ISPASTSDFR    360
NWLR                                                                 364

SEQ ID NO: 103         moltype = DNA   length = 1713
FEATURE                Location/Qualifiers
source                 1..1713
                       mol_type = other DNA
                       organism = Populus balsamifera
                       sub_species = trichocarpa
misc_feature           1..1713
                       note = Ceres ANNOT ID no.1444522
misc_feature           1..1713
                       note = Encodes the peptide sequence at SEQ ID NO 104
SEQUENCE: 103
atggggaaga agggaggtag ctcatggttg actgctgtga aaagggcgtt tagatctcca     60
actaaagaaa gtgacaagag ggctactggg gttggccatg accaagaaga agatgaagaa    120
aagaagagag ggaagagaag atggttattt aggaaaccta caaatcaaga aacggcgaca    180
caacagaacc tgtcaaaggc aggaaatgtt aaggcatccc caggtggtgg tggaggtgct    240
ccagcagacc atgtgtcggc agctgcagca gctgagcaaa gcatgcaat tgcagtagca     300
gttgctactg cagctgcagc tgaagctgct gtagccactg cccaggcggc ggcggaggtt    360
gctcggctca ctaggccttc atatcatcct agagaacatt atgctgccat tgtcattcaa    420
acagctttta gaggatactt ggcaaggcgg gctcttcgtg cacttaaagg gctagtgaag    480
ttgcaagctt tagtaagggg acacaatgtg agaaaacagg ccaagatgac cctgcgatgc    540
atgcaagctc tggctcgagt gcaggctcga gtgcttgatc aacgcgtgag actttcacat    600
gaaggcagca ggaaatctgc atttagtgac accaatagcg tgcttgaatc gcgatatctt    660
caagacattt cagatagaaa atccatgtca agagaaagca gtagcattgc agatgattgg    720
gatgatcggc cacactccat tgaggaagtc aaggccatgt tgcaacgcag gaaagaagct    780
gcgttcaagc gtgaaaagac cttatctcaa gctttctctc agcagctcat ggctaattga    840
ttcaatttt tcaaacccat gtccaagata tggagaaatg gcagaagccc atcaaatggc     900
aatgaagatg agctccaaga aagaccacaa tggcttgatc aatggatgcc tgcaaagcca    960
tgggacaata gcagcagagc aagagcttca actgatcaaa gagaccccat caaaactgta   1020
gaaattgaca cctcccaacc ttattcatat ttagttccta attttagaag aacaaaccaa   1080
aaccaacatc accaaccacca gagatccaat tcatcaaaca atggtgtggc acactctgct   1140
ccttctccac tccatagagc tcatcaaaact gctccactcc accactctcc tatcacaccc   1200
tccccatcaa aaactaggcc tcttcaggtt cgttcagcta gtccacgatg tgcaagagaa   1260
gatagaagtt gtaattcctc tcaaaccaca agtttaaggt ccaattattt ttacaatgga   1320
agtttgaatc aacatggaat cagggtggt gctagtgtta gtagtaatgg taatgctaca     1380
ttgccaaatt acatgcctgc aaccgagtct gccaaggcta gattgagatc acagagtgca   1440
ccaaggcaaa gaccatcaac accagaacga gaccggattg gtctgcaag aaaacgcgtt    1500
tcgtatccag ccccgaccc ttgtgatgtc ggtatagttt atggcggtgc tggttacggc     1560
catggtttaa ggagtccaag ctttaagagc gtgagcggtt cacgtttggg tggactagaa   1620
caacagtcta ctattcttc ttgctgtacg gatagctttg gtggtgagct ttccccttct     1680
tcaactaacg atcttaggag gtggttgaga tga                                1713
```

```
SEQ ID NO: 104          moltype = AA   length = 395
FEATURE                 Location/Qualifiers
source                  1..395
                        mol_type = protein
                        note = subspecies = trichocarpa
                        organism = Populus balsamifera
REGION                  1..395
                        note = Ceres ANNOT ID no.1444522
REGION                  1..395
                        note = Score of 439.2 for HMM of FIGURE 1.
REGION                  1..395
                        note = Functional Homolog Of Ceres SEEDLINE ID no. ME08768
                        at SEQ ID NO.86
SEQUENCE: 104
MTLRCMQALA RVQARVLDQR VRLSHEGSRK SAFSDTNSVL ESRYLQDISD RKSMSRESSS    60
IADDWDDRPH SIEEVKAMLQ RRKEAAFKRE KTLSQAFSQQ LMANWFNFFK PMSKIWRNGR   120
SPSNGNEDEL QERPQWLDQW MPAKPWDNSS RARASTDQRD PIKTVEIDTS QPYSYLVPNF   180
RRTNQNQHHQ HQRSNSSNNG VAHSAPSPLH RAHQTAPLHH SPITPSPSKT RPLQVRSASP   240
RCAREDRSCN SSQTPSLRSN YFYNGSLNQH GIRGGASVSS NGNATLPNYM AATESAKARL   300
RSQSAPRQRP STPERDRIGS ARKRLSYPAP DPCDVGIVYG GAGYGHGLRS PSFKSVSGSR   360
LGGLEQQSNY SSCCTDSFGG ELSPSSTNDL RRWLR                              395

SEQ ID NO: 105          moltype = DNA   length = 1443
FEATURE                 Location/Qualifiers
source                  1..1443
                        mol_type = other DNA
                        organism = Populus balsamifera
                        sub_species = trichocarpa
misc_feature            1..1443
                        note = Ceres ANNOT ID no.1467519
misc_feature            1..1443
                        note = Encodes the peptide sequence at SEQ ID NO 106
SEQUENCE: 105
atgggaaga aaggaaaagg atggtttaca tctgtgaaga gagtgttcaa atcatcatct     60
cctaaggaat taccagtagg gaaaaagaaa gacaacgcag agaaatggca acatgaggct   120
ccagaagttg tgtcattaga gcattttcct actggaagtt ctcctgatgt tacaaatgat   180
gagagcaatg tatccaactcc agtaactgaa gatagaaatc atgccattgc ctgtggcagta 240
gcgactgctg ccgcagcaga agctgcggtt gcagctgctc aagcggcggc taaagttgtt   300
cgcttagctg gttatggacg acaatcaaag gaagaaagag ctgccatcct catacaatca   360
ttctataggg gctaccttgt aatcccttc ttcatttcac tttattttga tcaatataat    420
ctggctcggc gtgccttacg cgcattgaag ggattggtga ggctccaagc attagtgaga   480
ggccacaatg taagaaagca agcacaaatg acaatgagaa gcatgcaagc tcttgttcgt   540
gtgcaagcaa gagtaagagc aagaagactt gaattagctc acgagaagct tcaaaggaag   600
acagaggaag aagatgaacg aagactacca gtggacgaag actttatgaa tccaaagaat   660
ccattgaaga gttataaatg ggataggagg aatcaaagtt cagataattt caaagaaaat   720
gcttcaaaga agcatgatgc tgtcatgaaa agagagagag cccttgctta tgcttatgcc   780
ttccagcagc agcagcagca acaattactc tcacaaaata gtcctaatgg taaagaaaca   840
ggacattttg tgaacgaaca cgagaagatg caatggggat ggaattggct tgagagatgg   900
atgtcagcac aatcatataa cgtgcgtcaa tcgggtccaa atgaagggtc ttacgtgaca   960
gtaaacacaa ctacaaccac gaccaccaca gaggacatgt ccgagaagac agtagagatg  1020
gacatggtga ccccaacagg cactagcaat cccaacatgg gcatgctaga caccaatcca  1080
tattcgaatc gaccccaatg gcaatcaagt tcaagcaatg tacgtagcta catggctccg  1140
acccagtccg caaaggcgaa agtgcgttct caaagtttga tcaagcaacg tgccccagcg  1200
acacctctgt ggaatccatc caccaagaaa gattcaagca ttgttggtcc aggttgtgat  1260
tcttccagtt caggtggtgg aacaacaact tatcacgctc caagaagtcc tagccccaaa  1320
cataacggga tgcgcctgca ttcgagaaga catgctggtg gatatagccc tgatttcaat  1380
ggcggtgatg attggaggtt gcctcctctt gatggtcatg gatggaggaa tgattttggt  1440
tga                                                                1443

SEQ ID NO: 106          moltype = AA   length = 309
FEATURE                 Location/Qualifiers
source                  1..309
                        mol_type = protein
                        note = subspecies = trichocarpa
                        organism = Populus balsamifera
REGION                  1..309
                        note = Ceres ANNOT ID no.1467519
REGION                  1..309
                        note = Score of 495.7 for HMM of FIGURE 1.
REGION                  1..309
                        note = Functional Homolog Of Ceres SEEDLINE ID no. ME08768
                        at SEQ ID NO.86
SEQUENCE: 106
MRSMQALVRV QARVRARRLE LAHEKLQRKT EEEDERRLPV DEDFMNPKNP LKSYKWDRRN    60
QSSDNFKENA SKKHDAVMKR ERALAYAYAF QQQQQQQLLS QNSPNGKETG HFVNEHEKMQ   120
WGWNWLERWM SAQSYNVRQS GPNEGSYVTV NTTTTTTTTE DMSEKTVEMD MVTPTGTSNP   180
```

```
NMGMLDTNPY SNRPQWQSSS SNVRSYMAPT QSAKAKVRSQ SLIKQRAPAT PLWNPSTKKD    240
SSIVGPGCDS SSSGGGTTTY HAPRSPSPKH NGMRLHSRRH AGGYSPDFNG GDDWRLPPLD    300
GHGWRNDFG                                                            309

SEQ ID NO: 107            moltype = AA  length = 291
FEATURE                   Location/Qualifiers
source                    1..291
                          mol_type = protein
                          note = subspecies = indica
                          organism = Oryza sativa
REGION                    1..291
                          note = Public GI ID no.125559938
REGION                    1..291
                          note = Score of 403.9 for HMM of FIGURE 1.
REGION                    1..291
                          note = Functional Homolog Of Ceres SEEDLINE ID no. ME08768
                          at SEQ ID NO.86
SEQUENCE: 107
MQRLQERSRD GSSFAAGDDW DDRPRTIEEI QAMLQTRKDA ALKRERALSY AFSHQIWRNP     60
APSVEEMDVD GQPRWAERWM ASRASFDTSR STVRASAAAA PGRASTDHRD QVKTLEIDTA    120
RPFSYSTPRR HGNASYHASS SPMHRAHHHS PVTPSPSKAR PPIQVRSASP RVERGGGGGG    180
SYTPSLHSHR HHASSGGAAA VPNYMAATES AKARDVIRGA ARRGAKKRLS FPVPIDPYGA    240
YAQSLRSPSF KSAAGRFSSE QRSNVSSSCA ESLGGDVVSP SSTTDLRRWL R             291

SEQ ID NO: 108            moltype = DNA  length = 1509
FEATURE                   Location/Qualifiers
source                    1..1509
                          mol_type = other DNA
                          organism = Arabidopsis thaliana
misc_feature              1..1509
                          note = Ceres SEEDLINE ID no.ME19173
misc_feature              1..1509
                          note = Encodes the peptide sequence at SEQ ID NO. 109
SEQUENCE: 108
acattctccg atattctctc tctctctatc aatctctcac tctcaaactt tctacatacc     60
tgaagaaaaa aataatctac gaattcgagc caaaaagatc gaaacttttt aatctatggg    120
tgcttcaggg aaatgggtca agtccattat cggtctcaag aagctagaga aggatgaaat    180
cgaaaagggt aatgggaaaa acaagaaatg gaagctatgg aggactactg cagtagattc    240
atggaagggt tttcgaggaa aacatccggtc tgattcagac ggtgttgatt cttctactgt    300
ttactctgct gctgttgcta ctgttcttag agctcctcct aaagatttca agctgttag    360
agaagaatgg gctgctatta gaatccaaac cgcttttcgt ggattcttgg cgagaagagc    420
gttgagggca ttgaaaggga tagtgaggtt acaagcttta gtgagaggaa gacaagttag    480
gaaacaagca gctgttacat tgagatgcat gcaagctttg gtgagagtac aagctcgtgt    540
tagagctcgt cgtgtgagga tgactgttga aggacaagct gttcaaaagc ttttagatga    600
acatagaacc aaatctgatc tcttgaaaga agtcgaggaa gggtggtgtg ataggaaagg    660
tactgtggat gatattaagt caaagttgca gcagagacaa gaaggtgctt ttaagaggga    720
acgtgctttg gcttatgctc ttgctcaaaa gcaatgagtg tcaactacta gctcaaacct    780
taagacgaat agttcgattt cgtatcttaa aagtcaagag tttgataaga atagttgggg    840
atggagttgg ttggagcgtt ggatggctgc taggccatgg gagactagac ttatggacac    900
tgttgatacc gctgccacgc ctcctcctct gcctcataaa catttgaaat caccggaaac    960
tgccgatgtt gttcaagtta gaagaaacaa tgtgaccact agagtatctg caaaacctcc   1020
tcctcatatg ctgtcttcaa gtcctggtta tgagtttaac gagagctcag gttcatcctc   1080
gatttgtact tcaactacgc ctgttttctgg aaaaactgga cttgtttcag ataactctag   1140
cagtcaagca aaaagcaca agccaagtta catgagcttg actgaatcga caaaggctaa   1200
gcgaagaact aaccgcggtc tcaggcaatc tatggatgag tttcagttta tgaagaactc   1260
tggaatgttt acaggggaat tgaagactag tccttcctca gatccttttg ttagttttctc   1320
caaaccactc ggtgttccta ctcgattcga gaagccgaga ggttaaatgt gaccttgtta   1380
gattggagtt tcaacagctt gttgttgtct tgtgtgttgt gagatatctg tgtatgttgt   1440
taattgttct tttttccttg gaactacatt ggagttttga atttaaatat aaatttcagt   1500
cttgctttt                                                          1509

SEQ ID NO: 109            moltype = AA  length = 416
FEATURE                   Location/Qualifiers
source                    1..416
                          mol_type = protein
                          organism = Arabidopsis thaliana
REGION                    1..416
                          note = Ceres SEEDLINE ID no.ME19173
REGION                    1..416
                          note = Score of 954.4 for HMM of FIGURE 3.
REGION                    84..104
                          note = Pfam Name: IQ Pfam Description: IQ
                          calmodulin-binding motif
SEQUENCE: 109
MGASGKWVKS IIGLKKLEKD EIEKGNGKNK KWKLWRTTSV DSWKGFRGKH RSDSDGVDSS     60
TVYSAAVATV LRAPPKDFKA VREEWAAIRI QTAFRGFLAR RALRALKGIV RLQAVRGRQ     120
VRKQAAVTLR CMQALVRVQA RVRARRVRMT VEGQAVQKLL DEHRTKSDLL KEVEEGWCDR    180
KGTVDDIKSK LQQRQEGAFK RERALAYALA QKQWRSTTSS NLKTNSSISY LKSQEFDKNS    240
WGWSWLERWM AARPWETRLM DTVDTAATPP PLPHKHLKSP ETADVVQVRR NNVTTRVSAK    300
```

```
PPPHMLSSSP GYEFNESSGS SSICTSTTPV SGKTGLVSDN SSSQAKKHKP SYMSLTESTK    360
AKRRTNRGLR QSMDEFQFMK NSGMFTGELK TSPSSDPFVS FSKPLGVPTR FEKPRG        416

SEQ ID NO: 110          moltype = AA  length = 442
FEATURE                 Location/Qualifiers
source                  1..442
                        mol_type = protein
                        note = subspecies = japonica
                        organism = Oryza sativa
REGION                  1..442
                        note = Public GI ID no.115435054
REGION                  1..442
                        note = Score of 949.2 for HMM of FIGURE 3.
REGION                  1..442
                        note = Functional Homolog Of Ceres SEEDLINE ID no. ME19173
                         at SEQ ID NO.109
REGION                  109..129
                        note = Pfam Name: IQ Pfam Description: IQ
                         calmodulin-binding motif
SEQUENCE: 110
MGGSGKWVKS LIGLKKPDRE DCKEKLQVPS VNGRGGGKGR KWKLWRSSSG DHGSLWRGSR     60
GGGGGGHHR SASSDASDDA SSAAADPFTA AVATVARAPA KDFMAVRQEW AAIRVQTAFR    120
GFLARRALRA LKGLVRLQAI VRGRQVRKQA AVTLRCMQAL VRVQARIRAR RVRMSTEGQA   180
VQKLLEARRT KLDILREAEE GWCDSQGTLE DVRVKLQKRQ EGAIKRERAI AYAYSQQIEG   240
ATKCNQQPKP TSYGRLNQSG MLLKHQHFDK SNGNWSWLER WMAARPWENR LMEEHNQTNS   300
SSPDLLSSKN CEDSFGILGD FSEPNSVKVR KNNVSKRVCA KPPVVSHHQR IKAQSISSLS   360
TELHNDESSA SSSSCFASTP ISFSTFVTTE KTEDSIRARP NYMNMTESIK AKRKACNAQR   420
TTAGKLMEDR KASGVELKVA QV                                           442

SEQ ID NO: 111          moltype = DNA  length = 1661
FEATURE                 Location/Qualifiers
source                  1..1661
                        mol_type = other DNA
                        organism = Gossypium hirsutum
misc_feature            1..1661
                        note = Ceres CLONE ID no.1847857
misc_feature            1..1661
                        note = Encodes the peptide sequence at SEQ ID NO 112
SEQUENCE: 111
attttttttc tctttgagtc ttgttgaaga cttgaggttc tctcccccc ccccaccttt     60
ttttggtgca aaaagatttc cttttgtca ctcatactct gttatcaatt gtttccatcg    120
tagcccattt cctttttctt ttcttaaata acagttgttt gtatctctga gaaaaatata   180
tactttgaaa ctaccatggg tgcttcagcg aaatgggtga aatctcttat tggtctcaag   240
aaaactgtaa aagatgacca agaaagatg ggtggcaaga gcaagaaatg gaagctatgg    300
aggagttctt caggggatgg aataggttcc tcatggaagg gttttaaagg aaagtttaaa   360
gcagattacg aaggatctga ttcttcacca aggtctgaaa tctttctgc tgccatggct    420
gctgtggttc gagctcctcc taaagatttc agggttgtaa ggcaagaatg gctgctatc    480
cgcattcaaa ctgcttttcg aggcttcttg gcaagaaggg ctttaagggc tttaaaggga   540
gtcgttagga tccaagccttt tgttcgcggt cgacaggtga ggaaacaggc tgctgtgaca   600
ctccggtgca tgcaagctct cgttcgtgtc caagctcgtg ttagagctcg tcgtgtccga   660
atgtccatcg agggccaggc agttcaaaag atactcgatg aacaccgcag caaggccgaa   720
ctcttgaaac aagccgagga gggctggtgt gatagtaaag gaacattgga tgatgttaca   780
ataaagctac aactgagaca agaaggtgct tcaagagag aacgagcact tgcttattct    840
cttgcacaaa agcaatggag attgaacatg gattcaaata ctcgaacaaa tagttcggtt   900
tcagttccat atctcaaaaa ccaagtgttt gataagaata gttggggatg gagttggctt   960
gaacgttgga tggcagcccg gccgtgggaa actcgattga tggagcaatc acaggccgaa  1020
ccttccgaac caactccacc atcgaaaact tgttcagagt ctagaaagat tactagaccg   1080
accgaaccat gttcagtgaa ggtacgaaag aacaatgtca caactaggat ttcagcaaag  1140
cctccccata ttggtcaagg tactagatca tcatcgagtc caagttccga attccggttc   1200
gaagagagct ccgcatcatc atcgatatgc acatctacaa cacgggtctc gtggaataca   1260
atgccgactt cagagagaac ggagaagacg gggaatagta ggccaaacta tatgaacttg  1320
acagagtcta ccaaggccaa acaaagagct gcaaatcatg ccttacgaag aatccaaatg   1380
cagtccatgg atgagttcca gttaaagaaa acagctggtt tgtatgatgg ggattcaaag   1440
agtagtgtgg ggtcggatcc tacggtccat atgtctcggc cactgtatcc accaacaaga   1500
ttaggttaaa agtggttgtg tctgtgatta agtagatcgt cagttttatt atgttttcca   1560
acatcttgtt tagtttttagt gtgatgtagc aaacaagttt tgagtgttt ttgtatctaa    1620
ttcgacggca attcattctg caaaaaaaaa aaaaaaaaa a                        1661

SEQ ID NO: 112          moltype = AA  length = 437
FEATURE                 Location/Qualifiers
source                  1..437
                        mol_type = protein
                        organism = Gossypium hirsutum
REGION                  1..437
                        note = Ceres CLONE ID no.1847857
REGION                  1..437
                        note = Score of 1019.5 for HMM of FIGURE 3.
```

```
REGION                   1..437
                         note = Functional Homolog Of Ceres SEEDLINE ID no. ME19173
                           at SEQ ID NO.109
REGION                   91..111
                         note = Pfam Name: IQ Pfam Description: IQ
                           calmodulin-binding motif
SEQUENCE: 112
MGASAKWVKS LIGLKKTVKD DQEKMGGKSK KWKLWRSSSG DGIGSSWKGF KGKFKADYEG   60
SDSSPRSEAF SAAMAAVVRA PPKDFRVVRQ EWAAIRIQTA FRGFLARRAL RALKGVVRIQ  120
AFVRGRQVRK QAAVTLRCMQ ALVRVQARVR ARRVRMSIEG QAVQKILDEH RSKAELLKQA  180
EEGWCDSKGT LDDVTIKLQL RQEGAFKRER ALAYSLAQKQ WRLNMDSNTR TNSSVSVPYL  240
KNQVFDKNSW GWSWLERWMA ARPWETRLME QSQADPSEPT PPSKTCSESR KITRPTEPCS  300
VKVRKNNVTT RISAKPPHIG QGTRSSSSPS SEFRFEESSA SSSICTSTTR VSWNTMPTSE  360
RTEKTGNSRP NYMNLTESTK AKQRAANHAL RRIQMQSMDE FQLKKTAGLY DGDSKSSVGS  420
DPTVHMSRPL YPPTRLG                                                437

SEQ ID NO: 113           moltype = DNA  length = 1353
FEATURE                  Location/Qualifiers
source                   1..1353
                         mol_type = other DNA
                         organism = Populus balsamifera
                         sub_species = trichocarpa
misc_feature             1..1353
                         note = Ceres ANNOT ID no.1455219
misc_feature             1..1353
                         note = Encodes the peptide sequence at SEQ ID NO 114
SEQUENCE: 113
atgggtgcat caggaaaatg ggtgaaatcc attataggtc taaaaaagtc tgataaagat    60
caagaccaat atgagaaggt gagtggaaag agcaagaaat ggaagctatg gaggagttca   120
tcaggagatt tggggtcttc atggaagggt ttcaaaggga accacagagc agcatccagg   180
gcatcgggtt cttcaccact ggctgatcca tttactgctg caatggctac tgtggttaga   240
gctcctccta aggatttcag ggttgtcagg caagaatggg ctgctatcag gattcaaact   300
gcttttcgtg gattcttggc aagaagggct ctgagggcct tgaaggagt ggtgagactc    360
caagctctag ttcgaggtcg acaagtgagg aagcaggctg cagtgacact taagtgcatg   420
caagctcttg ttcgtgttca agctcatgtt agggctcgtc gtgtgcgaat gtccttagaa   480
gggcaggcag tgcagaatat gctgaatgag cgacgtagca aggctgacct cttgaaacat   540
gctgaggaag ggtggtgtga taaaagggg acattagaag acgtgaagtc aaaactgcaa    600
atgaggcaag aaggagcctt caagagagaa agagctattg cttactccct tgctcaaaaa   660
caatgggagat caaaccccag ctcaaacact cgacccaata actcggtata ttctttcaag   720
aatgaggagt ttgataagaa tagctgggga tggagttggc ttgaacgttg gatggcagcc   780
aagccatggg agactagatt gatggaacaa acccatactg atccctcagt gactccacca   840
cccaagtcct gtgtagatgc aagcacacat tcgaaatcct tgaacaaag ttcagtgaaa    900
gtgagaagaa acaatgtaac cactagaatt tcagcgagac ctccaatcgg gcatgttact   960
cgctcatctt caagtccaag ttctgaagtc cgctttgatg agagctcagc ttcttcatca  1020
atttgtactt ctacaacacc aatatcagga aacactggct tggcctcaga taaaacagag  1080
gagagtggta acagcaggcc aaactacatg aacctgaccg agtcaaccaa ggcaaagcaa  1140
aacacatcca gtcatttatt tcataggatt caaaggcagt ccatggatga gtttcagttt  1200
ttcaaaaagt cagcggcgtt ctcaaatgga gattcaaaaa gcagtgctgg ttctgatcct  1260
tcagttaatt tatccaagcc actttgcttg ccgacaagat tgataagaa ctcgatgaaa    1320
caaataagag gaacggatca tttgtatgcc tag                              1353

SEQ ID NO: 114           moltype = AA  length = 450
FEATURE                  Location/Qualifiers
source                   1..450
                         mol_type = protein
                         note = subspecies = trichocarpa
                         organism = Populus balsamifera
REGION                   1..450
                         note = Ceres ANNOT ID no.1455219
REGION                   1..450
                         note = Score of 1091.4 for HMM of FIGURE 3.
REGION                   1..450
                         note = Functional Homolog Of Ceres SEEDLINE ID no. ME19173
                           at SEQ ID NO.109
REGION                   92..112
                         note = Pfam Name: IQ Pfam Description: IQ
                           calmodulin-binding motif
SEQUENCE: 114
MGASGKWVKS IIGLKKSDKD QDQYEKVSGK SKKWKLWRSS SGDLGSSWKG FKGNHRAASE   60
ASGSSPLADP FTAAMATVVR APPKDFRVVR QEWAAIRIQT AFRGFLARRA LRALKGVVRL  120
QALVRGRQVR KQAAVTLKCM QALVRVQAHV RARRVRMSLE GQAVQNMLNE RRSKADLLKH  180
AEEGWCDRKG TLEDVKSKLQ MRQEGAFKRE RAIAYSLAQK QWRSNPSSNT RPNNSVYSFK  240
NEEFDKNSWG WSWLERWMAA KPWETRLMEQ THTDPSVTPP PKSCVDASTH SKSFEQSSVK  300
VRKNNVTTRI SARPPIGHVT RSSSSPSSEV RFDESSASSS ICTSTTPISG NTGLASDKTE  360
ESGNSRPNYM NLTESTKAKQ NTSSHLFHRI QRQSMDEFQF FKKSAAFSNG DSKSSAGSDP  420
SVNLSKPLCL PTRFDKNSMK QIRGTDHLYA                                   450

SEQ ID NO: 115           moltype = DNA  length = 1433
FEATURE                  Location/Qualifiers
```

```
source                    1..1433
                          mol_type = other DNA
                          organism = Zea mays
misc_feature              1..1433
                          note = Ceres CLONE ID no.352452
misc_feature              1..1433
                          note = Encodes the peptide sequence at SEQ ID NO 116
SEQUENCE: 115
cccacacggc agcaggcagg gcgccatctc ctagcagctc ctcccatggc gtcctctgcc   60
cttcttctcc tccatggccg ccgaagcccc tcccatggcc gacgctctct gctccagccc  120
ctccagcagc tatggcgtcc cccctcctcc ccttcttctt cctcaagcca gcaggcacct  180
ccctctactc cctgcgcgca gcagcagcca tggcgctgcc tctcttctcc atggcgagta  240
gcagctcatt cacctctctc tcccatggcg tgctgctcca gtcggcctcc cttctccccc  300
tcggctccct cctccaggcc gggccgtgca gaagctgctc gaggcgcgcc gcacccagat  360
ggatatcctc agggaagccg aggaaggatg gtgtgacagc cagggaacac ttgaacaagt  420
gagggtcaag ctgcagaagc ggcaggaggg cgcaatcaag cgtgagcggg ctatcgccta  480
tgcatattcg cagcaggccg acggtgctgc caaatgcaat ccaccgaagc ttacttccaa  540
tggactggtg aaccactccg gcatgctgct caagcaccag aacttagaca agggcaacgg  600
caactggagc tggctggaga ggtggatggc agcgcggcca tgggagaaca ggctgatgga  660
ggagcacaac tccagctccc cggacttccg gtcctccaag aactgcgagg actcctttgg  720
tgtgctcggc gacttctctg aaccgaactc agtgaaggtg cgcaagaaca atgtcagcaa  780
gcgggtctgc gcaaaacctc cagggccaac acacgccggc ggacatcatc agcgcctcaa  840
ggcccagtcg atctcgtctc tgagcactga gctgcacaac gacgagagct ccgcgtcctc  900
ctcgtcttgc tttgcgtcta cccctatatc attcacactt gtggcttcgg agaagaccga  960
ggacagcgtc aggacgagac ccaactacat gagcatgacg gagtcgatca aggctaagca 1020
gaaggcatgc agcgcccaga ggacggtggc gctgaagcaa tgtgatgata ggaaagccat 1080
gagcgccgag ttgaaggtcg ctcaggtgtg actgtttcgt ggaactccat gcagagatgg 1140
agccgacttc gacatcctct ctatgcccta ggatgtgttg cttggtgtct tgccacattc 1200
ttgagtggct cggtgctgca ttcctgagtt gtcctcctgt tgctgggtgt ctgattattc 1260
aacttcttgt tgtcagattg catctttgtt cagtcattgt ggctgcatct ttgttcagcc 1320
gttgtggctt tgtcagtggt agagtctctg taagatagtt ctttgagtag acagcattgt 1380
ggatttcttt cctgggtgtt gatttcaggt caaaaagac aggataattt act           1433

SEQ ID NO: 116           moltype = AA    length = 250
FEATURE                  Location/Qualifiers
source                   1..250
                         mol_type = protein
                         organism = Zea mays
REGION                   1..250
                         note = Ceres CLONE ID no.352452
REGION                   1..250
                         note = Score of 121.9 for HMM of FIGURE 3.
REGION                   1..250
                         note = Functional Homolog Of Ceres SEEDLINE ID no. ME19173
                           at SEQ ID NO.109
SEQUENCE: 116
MDILREAEEG WCDSQGTLEQ VRVKLQKRQE GAIKRERAIA YAYSQQADGA AKCNPPKLTS   60
NGLVNHSGML LKHQNLDKGN GNWSWLERWM AARPWENRLM EEHNSSSPDF RSSKNCEDSF  120
GVLGDFSEPN SVKVRKNNVS KRVCAKPPGP THAHGHHQRL KAQSISSLST ELHNDESSAS  180
SSSCFASTPI SFTLVASEKT EDSVRTRPNY MSMTESIKAK QKACSAQRTV ALKQCDDRKA  240
MSAELKVAQV                                                        250

SEQ ID NO: 117           moltype = DNA   length = 1949
FEATURE                  Location/Qualifiers
source                   1..1949
                         mol_type = other DNA
                         organism = Triticum aestivum
misc_feature             1..1949
                         note = Ceres CLONE ID no.787908
misc_feature             1..1949
                         note = Encodes the peptide sequence at SEQ ID NO 118
SEQUENCE: 117
acacaggcag gcagccgagc cgagcgagca ataattcgca ccggcacaca ggagcggcag   60
taatggccgc gtggtgccgg tgccagtagc aggcaggcag ggtcaggagt agcgccagtt  120
cactgggcac tgctgacgct tcgagcccac gctcttccct ccacccttgc ccctccctcc  180
cgaaactccc tccctccctt ggcctcctca ggcctcccaa tctcgcagag cggcggccgt  240
cattggccgg cggcggtgcg cggccccggt tgtttcctcc ggcgtcaggt gcccgtgatc  300
tggttgttgc agaggcggcg aggtgaggtg acgcggcggc gcgatgaggt ggctcaagtc  360
gttggttgtg ctgaggaagg tggaggagca gcagcagcgc gcaaggagg atggcgacgc  420
cggcccaaca aaaacagatg ccgtcgatca gttccacttc caggatcagc actcccagga  480
tcacgctagc cttgtcggac cagaagagtt ccctgatgaa aatggtccgt cagaagatga  540
gtgcgataca ccttcatgct caggacctgg tttcagtatg cttagtgtgc cactgcctca  600
aacagaagag gagctcaaag agatctgggc tgccacaatt attcagactg catatagagc  660
cctactggct aggagagccc gccgagcttt aaaaggacctg gttagccttc aagcccttgt  720
aagggggtcat atagtgagaa agcaagctgc tataacactt cggtgtatgc aagctttggt  780
cagggtacaa gcccgtgtta gagcaagcg gttcgtgtg gccttggaaa tcagatgga  840
tgagcaacaa aataatgtag aagagcaaac ggacgaggca catgttcgag aagttgagga  900
tgggtggtgc gatagtatag ggtctgtgga agacatccaa gcaaaattgt tgaagaggca  960
ggaagcagca gccaagcgtg agagagccat ggcctatgcc ctttctcacc agtggcaagc 1020
```

```
aggttcaagg caacaggcag ccattacagc ttctgaacta gacaggaaca gctggagctg  1080
gaattggctg gagagatgga tggccgtccg cccgtgggag agtcggttcc ttggcatgta  1140
cgcagcagat ggaattgcca ttgataccgg agcgcacaat gctgagggaa atgcaaccaa  1200
ggctccatac aggaaacctg tgaaaaagca ggtttcagct cttcattcaa gtgtgttgat  1260
ccagaaggcc cgccccctcga actcggaggg tggtggctca ttgtcgaacc cgtctgccgg  1320
ttcggcgtca gctaaaccga aacggaagct gccaccaaag gaaggttctg atgaagtctc  1380
gtctcgtctt tcgggacttg gtgcccgag cagtagtaat cctaaggaga ggcctgggca  1440
gttacaacct cgggccaaca agaggttctc cttgcctggc actggcacag aagttggcaa  1500
acggcaagtg aataaacctg cggtgaaccg atccccaag gctaccgaag actccccag  1560
gctggaaggg aagcatcgcc gtgccggttc cgttggtctg ctgctcaaga gagttgagct  1620
gcaggcttga caagccatct gaagcccat ctaccgtcgt caaggttcga agtcagcatg  1680
ctgcgctctg atacatgggc ggccttagat tctggaaggt ccattggagc aatgtgcatt  1740
tatttcttag ccatattata ggtatgcagt caaaatgctc atctcaggag atgagatcta  1800
gctagtgctt ggatatgtat gtgctggtca gctggtgcct ctagtcctgg aggttaccat  1860
agcttgtact gttgtatttg tagctaagag caagtatggg ctcacatttt ctggaactat  1920
tttttgtaca atgaaaaaaa aaaaaaaaa                                   1949

SEQ ID NO: 118          moltype = AA   length = 428
FEATURE                 Location/Qualifiers
source                  1..428
                        mol_type = protein
                        organism = Triticum aestivum
REGION                  1..428
                        note = Ceres CLONE ID no.787908
REGION                  1..428
                        note = Score of 891.9 for HMM of FIGURE 3.
REGION                  1..428
                        note = Functional Homolog Of Ceres SEEDLINE ID no. ME19173
                         at SEQ ID NO.109
REGION                  94..112
                        note = Pfam Name: IQ Pfam Description: IQ
                         calmodulin-binding motif
SEQUENCE: 118
MRWLKSLVGL RKVERQQQRR KEDGDAGPTK TDAVDQFHFQ DQHSQDHASL VGPEEFPDEN   60
GPSEDECDTP SCSGPGFSML SVPLPQTEEE LKEIWAATII QTAYRALLAR RARRALKGLV  120
RLQALVRGHI VRKQAAITLR CMQALVRVQA RVRARRVRVA LENQMDEQQN NVEEQTDEAH  180
VREVEDGWCD SIGSVEDIQA KLLKRQEAAA KRERAMAYAL SHQWQAGSRQ QAAITASELD  240
RNSWSWNWLE RWMAVRPWES RFLGMYAADG IAIDTGAHNA EGNATKAPYR KPVKKQVSAL  300
HSSVLIQKAR PSNSEGGGSL SNPSAGSASA KPKRKLPPKE GSDEVSSRLS GLGARSSSNP  360
KERPGQLQPR ANKRFSLPGT GTEVGKRQVN KPAVNRSPKA TEDSPALEGK HRRAGSVGLL  420
LKRVELQA                                                          428

SEQ ID NO: 119          moltype = AA   length = 442
FEATURE                 Location/Qualifiers
source                  1..442
                        mol_type = protein
                        organism = unidentified
REGION                  1..442
                        note = Plant derived amino acid sequence
REGION                  1..442
                        note = Ceres LOCUS ID no. Os01m00929_AP002743
REGION                  1..442
                        note = Score of 949.2 for HMM of FIGURE 3.
REGION                  1..442
                        note = Functional Homolog Of Ceres SEEDLINE ID no. ME19173
                         at SEQ ID NO.109
REGION                  109..129
                        note = Pfam Name: IQ Pfam Description: IQ
                         calmodulin-binding motif
SEQUENCE: 119
MGGSGKWVKS LIGLKKPDRE DCKEKLQVPS VNGRGGGKGR KWKLWRSSSG DHGSLWRGSR   60
GGGGGGHHR SASSDASDDA SSAAADPFTA AVATVARAPA KDFMAVRQEW AAIRVQTAFR  120
GFLARRALRA LKGLVRLQAI VRGRQVRKQA AVTLRCMQAL VRVQARIRAR RVRMSTEGQA  180
VQKLLEARRT KLDILREAEE GWCDSQGTLE DVRVKLQKRQ EGAIKRERAI AYAYSQQIEG  240
ATKCNQQPKP TSYGRLNQSG MLLKHQHFDK SNGNWSWLER WMAARPWENR LMEEHNQTNS  300
SSPDLLSSKN CEDSFGILGD FSEPNSVKVR KNNVSKRVCA KPPVVSHHQR IKAQSISSLS  360
TELHNDESSA SSSSCFASTP ISFSTFVTTE KTEDSIRARP NYMNMTESIK AKRKACNAQR  420
TTAGKLMEDR KASGVELKVA QV                                          442

SEQ ID NO: 120          moltype = DNA   length = 1801
FEATURE                 Location/Qualifiers
source                  1..1801
                        mol_type = other DNA
                        organism = Zea mays
misc_feature            1..1801
                        note = Ceres CLONE ID no.246398
misc_feature            1..1801
                        note = Encodes the peptide sequence at SEQ ID NO 121
```

```
-continued

SEQUENCE: 120
gtctcgtctc tacgcccgct ctccactctt cctcccaaag cctgcgccg cgtgggggt      60
tgcttgctgg ctgcccgctc ctctccctgc tcctcctgtg tctgccgccc accgcttccg   120
ggaacaagtc cggttgccgc cgccgccgtc gctgctctgt ccgagaggag ggaggaacag   180
agcgggatgg gagggtccgg gaagtgggtc aagtcgctga tagggctcaa gaagcagccc   240
gagaaggaag actgcaagga caagctgcag ctcccatcag tccacggcgg aggattgcga   300
ggcaagggcc gcaggtggaa gctgtggcgg acctcctccg gcgaccaggg ctccatgtgg   360
cgcggctcca gaggcggcag ccagcgctcg gcggcgtcgg aggcctcgga cgacgcgtcc   420
tcggtggccg ccgtccccgc cgacccgttc acggccgccg tcgccaccgt cgcccgcgcc   480
ccggccaggg acttcatggc cgtccgccag gagtgggccg ccatccgcgt ccagaccgcc   540
ttccgcgggt tcttggctcg gcgggcgctc cgggcgctca aggggctggt gcggctccag   600
gcgatcgtgc gcgggcggca ggtcggaag caggcggccg tgacgctgcg gtgcatgcag   660
gcgctggtgc gggtgcaggc gcgcatccgg gcgcgccgtg tgcgcatgtc caccgaggg    720
caggccgtcg agaagctgct cgaggcgcgc cgcacccaga tggatatcct caggaagcc   780
gaggaaggat ggtgtgacag ccagggaaca cttgaacaag tgagggtcaa gctgcagaag   840
cggcaggagg gcgcaatcaa gcgtgagcgg ggctatcgcc tatgcatatt cgcagcaggc   900
cgacggtgct gccaaatgca atccaccgaa gcttacttcc aatggactgg tgaaccactc   960
cggcatgctg ctcaagcacc agaacttaga caagggcaac tggcaactgg gctggctgga  1020
gaggtggatg gcagcgcggc catgggagaa caggctgatg gaggagcaca actccagctc  1080
cccggacttc cggtcctcca agaactgcga ggactccttt ggtgtgctcg gcgacttctc  1140
tgaaccgaac tcagtgaaga tgcgcaagaa caatgtcagc aagcgggtct cgcaaaaacc  1200
tccaggccga acacacgccc acggacatca tcagcgcgca aaggcccagt cgatctcgtc  1260
tctgagcact gagctgcaca acgacgagag ctccgcgtcc tcctcgtctt gctttgcgtc  1320
tacccctata tcattcacac ttgtggcttc ggagaagacc gaggacagcg tcaggacgag  1380
acccaactac atgagcatga cggagtcgat caaggctaag cagaaggcat gcagcgccca  1440
gaggacggtg gcgctgargc aatgtgatga taggaaagcc atgagcgcg agttgaaggt  1500
cgctcaggtg tgactgtttc gtggaactcc atgcagagat ggagccgact tcgacatcct  1560
ctctatgccc taggatgtgt tgcttggtgt cttgccacat tcttgagtgg ctcggtgctg  1620
cattcctgag ttgtcctcct gttgctgggt gtctgattat tcaacttctt gttgtcgat   1680
tgcatctttg ttcagtcatt gtggctgcat cttgttcag ccgttgtgcc tttgtcagtg  1740
gtagagtctc tgtaagatag ttctttgagt akryagtwtt gkggatktct ktcctrkgtk  1800
t                                                                   1801

SEQ ID NO: 121          moltype = AA    length = 318
FEATURE                 Location/Qualifiers
source                  1..318
                        mol_type = protein
                        organism = Zea mays
REGION                  1..318
                        note = Ceres CLONE ID no.246398
REGION                  1..318
                        note = Score of 291.2 for HMM of FIGURE 3.
REGION                  1..318
                        note = Functional Homolog Of Ceres SEEDLINE ID no. ME19173
                        at SEQ ID NO.109
REGION                  109..129
                        note = Pfam Name: IQ Pfam Description: IQ
                        calmodulin-binding motif
SEQUENCE: 121
MGGSGKWVKS LIGLKKQPEK EDCKDKLQLP SVHGGGLRGK GRRWKLWRTS SGDQGSMWRG    60
SRGGSQRSAA SEASDDASSV AAVPADPFTA AVATVARAPA RDFMAVRQEW AAIRVQTAFR   120
GFLARRALRA LKGLVRLQAI VRGRQVRKQA AVTLRCMQAL VRVQARIRAR RVRMSTEGQA   180
VQKLLEARRT QMDILREAEE GWCDSQGTLE QVRVKLQKRQ EGAIKRERGY RLCIFAAGRR   240
CCQMQSTEAY FQWTGEPLRH AAQAPELRQG QRQLELAGEV DGSAAMGEQA DGGAQLQLPG   300
LPVLQELRGL LWCARRLL                                                 318

SEQ ID NO: 122          moltype = AA    length = 440
FEATURE                 Location/Qualifiers
source                  1..440
                        mol_type = protein
                        note = subspecies = indica
                        organism = Oryza sativa
REGION                  1..440
                        note = Public GI ID no.125527441
REGION                  1..440
                        note = Score of 619.5 for HMM of FIGURE 3.
REGION                  1..440
                        note = Functional Homolog Of Ceres SEEDLINE ID no. ME19173
                        at SEQ ID NO.109
REGION                  87..107
                        note = Pfam Name: IQ Pfam Description: IQ
                        calmodulin-binding motif
SEQUENCE: 122
MGASGKWIRT LVGLRPAAER EKERGGGGGK GRKWSRLWRS SSSQRGGGNA SASEVYSETS    60
SSADALSSVV AAVVRAPPRD FRLIRQEWAA VRIQTAFRAF LARRALRALR GIVRLQALVR   120
GRRVRKQLAV TLKCMQALVR VQARARDRRA RISADGLDSQ DMLDERGGRV DPVKEAEAGW   180
CDSQGTADDV RSKIHMRHEG AIKRERALTY AQSHQRCSNH GGRPSSPAVS LKHHGNGATR   240
SNHSWSYLEG WMATKPWESR LMEQTHTENS TNSRCSESVE EVSVGGPKLS DASSVKIRRN   300
NVTKRVAAKP PSMISATSSD FVCDESSPST SSVTPLSANN SLATERRSDC GQVGGPSYMS   360
```

```
LTKSAKARLS GYGSHKPPLQ RQRSGDLLHH NRMAFSSIDV QSTAGSEVSV TSKRLNSLAL    420
KGRATRSLDK ENERRPSSLL                                                440

SEQ ID NO: 123          moltype = AA  length = 420
FEATURE                 Location/Qualifiers
source                  1..420
                        mol_type = protein
                        note = subspecies = japonica
                        organism = Oryza sativa
REGION                  1..420
                        note = Public GI ID no.125595056
REGION                  1..420
                        note = Score of 536.3 for HMM of FIGURE 3.
REGION                  1..420
                        note = Functional Homolog Of Ceres SEEDLINE ID no. ME19173
                         at SEQ ID NO.109
REGION                  79..99
                        note = Pfam Name: IQ Pfam Description: IQ
                          calmodulin-binding motif
SEQUENCE: 123
MGASGKWIKS LVSLKAAPEG TTKGRRWTRL WRSSSSASAS ASTAGDASES ASSEADAFSS     60
VVAAVVRAPP RDFRVIRQEW AAVRVQAAFR AFLARRALKA LRGIVRLQAL VRGRLVRRQL    120
AVTLKCMNAL LRVQERARER RARCSADGRD SQDAVGERDG RADPIKQAEA LILQLLPPFH    180
NEQWCDSQGS VSEVRSKIHM RHDAVAKRER AIAYALSHQP RSSKQSARPS SPARSLRNHF    240
SNRCNHDWSY IEGWMATKPW ESRLMEQSHA ELKCSKNSGE LNLAGAQLSN ASSVKMRGNR    300
VAAKPPSVLS ASSSDFPCDV SSASTSSATP ARSDGGHGEG PSYMSLTKSA KARQSCNSPF    360
QIQRQRSGGM SSYKRVALSP LDVQSNACSE FSVTSRKLNS LSLKGRSMTR SLDKENDNLF    420

SEQ ID NO: 124          moltype = DNA  length = 1682
FEATURE                 Location/Qualifiers
source                  1..1682
                        mol_type = other DNA
                        organism = Zea mays
misc_feature            1..1682
                        note = Ceres CLONE ID no.236071
misc_feature            1..1682
                        note = Encodes the peptide sequence at SEQ ID NO 125
SEQUENCE: 124
acatcccagt gccgagtgtc cccacacaac caagcggaag cttcggtcga acagagggag     60
taagcagttg cgtttcgcat tgcgcggcgc cgatgggggc gtcggggaag tggatcaagt    120
cgctggtggc cctgaaggcg cccgagaagg cggcggggca caaggcggt cgcaaatgcg     180
gtctctggcg gagctcgtcg gccacgtcca gggccagcgc cggcgagggc agtgcgctgg    240
cgtccgagtc ttcttcggcg tcggccgact cgttcaactc ggtcctcgcc gccgtggtcc    300
gcgcgccgcc cagggatttc ctgctcatca ggcaggaatg ggccgccgtc cgcatcccata   360
ccgccttccg cggattcttg gcgagacggg cgttgaaggc gctgagggc atcgtccggc     420
tgcaggcgct ggtgcggcc cggcgcgtgc gcaagcaact ggccgtcacg ctcaagtgca    480
tgcacgcact gctgcgggtg caggaacgcg cccgggagcg ccgggcgcgc tcctccgctc    540
atggccacgg ctcacaggc caggacgcgc tcaacggctg tgccagttct accaaagacg    600
ctatggaaca atggtgtgac cgccacggat ctgttgctga agtaagatca aattacaca    660
tgaagcatga aggtgcagca aagagagaaa gggcaattgc ctatgctgtg tctcaccagc    720
ctcggggttc aagacagaag gggagaccaa gctctcctgc taactgcgtt agaagccatg    780
atcctaatgg gtgcgatcag gacttcagtt acttagacgg atggatggca acgaagccat    840
gggagaccag atctacggag cgaaaccata cgcgactcgca gctcgcgaag cacgaggagc    900
tgaacttgcc cgcctccaag ctttccgatg ccagctcagt taagatcaga agaaacaatg     960
tcacaactag ggtatctgca gcaaagcgtc tcctccatc ttcagtgctg tcagctgctt    1020
cttccgactc cgcgtgcggc ggcgagagct ctcggtcgga accatcggtg accctgacgt    1080
ctgctaccac caacactgtc ttagcgtcag aagcaagatc agacagtggc gacaccggag    1140
gcccgaacta catgagcttg accaagtctg ccaaggcgag gctgagtgga tgcagcggca    1200
gcagccatca caggtcgttc cagcgaccac ggtccgggga catgtcgagg gtgacactgt    1260
cttcgatcga cacccagagc aacgcgggct cggagattc agtcacctcg aagagactga    1320
acagcatgtc cctgaacctg aaaggccgga gcttggacaa ggagaacgag gaggattgaa    1380
ccatccacca acggacaaag cagctgtcgt aggtctggtg cagtactacc acgcgttcaa    1440
agcagcatct ctgtatttac ggaatttacg gaggaagacg cggttatctc ttttcataaa    1500
ctccacacat gtcacatgtg agagagctct ggcactaggt caccgcttct atcatcatta    1560
tcatccttag tttagtttag tgcgtaagtt ttgtacacat ccaatcgatg tccagttcct    1620
aatttccttg tctctagttt gtacccataa attagtaata taagtactta tatcagcacg    1680
cg                                                                   1682

SEQ ID NO: 125          moltype = AA  length = 428
FEATURE                 Location/Qualifiers
source                  1..428
                        mol_type = protein
                        organism = Zea mays
REGION                  1..428
                        note = Ceres CLONE ID no.236071
REGION                  1..428
                        note = Score of 873.4 for HMM of FIGURE 3.
```

| | | |
|---|---|---|
| REGION | 1..428 | |
| | note = Functional Homolog Of Ceres SEEDLINE ID no. ME19173 at SEQ ID NO.109 | |
| REGION | 82..102 | |
| | note = Pfam Name: IQ Pfam Description: IQ calmodulin-binding motif | |

SEQUENCE: 125
```
MGASGKWIKS LVALKAPEKA AGHKGGRKWR LWRSSSATSR ASAGEGSALA SESSSASADS   60
FNSVLAAVVR APPRDFLLIR QEWAAVRIHT AFRGFLARRA LKALRGIVRL QALVRGRRVR  120
KQLAVTLKCM HALLRVQERA RERRARSSAD GHGSQGQDAL NGCASSTKDA MEQWCDRHGS  180
VAEVRSNLHM KHEGAAKRER AIAYAVSHQP RGSRQKGRPS SPANCVRSHD PNGCDQDFSY  240
LDGWMATKPW ETRSTERNHS DSQLAKHEEL NLPASKLSDA SSVKIRRNNV TTRVSAAKRP  300
PPSSVLSAAS SDSACGGESS RSRPSVTLTS ATTNTVLASE ARSDSGDTGG PNYMSLTKSA  360
KARLSGCSGS SHHRSFQRPR SGDMSRVTLS SIDTQSNAGS EISVTSKRLN SMSLNLKGRS  420
LDKENEED                                                          428
```

| | | |
|---|---|---|
| SEQ ID NO: 126 | moltype = AA  length = 455 | |
| FEATURE | Location/Qualifiers | |
| source | 1..455 | |
| | mol_type = protein | |
| | note = subspecies = indica | |
| | organism = Oryza sativa | |
| REGION | 1..455 | |
| | note = Public GI ID no.125524760 | |
| REGION | 1..455 | |
| | note = Score of 926.5 for HMM of FIGURE 3. | |
| REGION | 1..455 | |
| | note = Functional Homolog Of Ceres SEEDLINE ID no. ME19173 at SEQ ID NO.109 | |
| REGION | 109..129 | |
| | note = Pfam Name: IQ Pfam Description: IQ calmodulin-binding motif | |

SEQUENCE: 126
```
MGGSGKWVKS LIGLKKPDRE DCKEKLQVPS VNGGGGKGR KWKLWRSSSG DHGSLWRGSR   60
GGGGGGGHHR SASSDASDDA SSAAGDPFTA AVATVARAPA KDFMAVRQEW AAIRVQTAFR  120
GFLARRALRA LKGLVRLQAI VRGRQVRKQA AVTLRCMQAL VRVQARIRAR RVRMSTEGQA  180
VQKLLEARRT KLDILREAEE GWCDSQGTLE DVRVKLQKRQ EGAIKRERAI AYAYSQQIEG  240
ATKCNFWTKC VIFLVFAQQQ PKPTSYGRLN QSGMLLKHQH FDKSNGNWSW LERWMAARPW  300
ENRLMEEHNQ TNSSSPDLLS SKNCEDSFGI LGDFSEPNSV KVRKNNVSKR VCAKPPVVSH  360
HQRIKAQSIS SLSTELHNDE SSASSSSCFA STPISFSTFV TTEKTEDSIR ARPNYMNMTE  420
SIKAKRKACN AQRTTAGKLM EDRKASGVEL KVAQV                            455
```

| | | |
|---|---|---|
| SEQ ID NO: 127 | moltype = AA  length = 455 | |
| FEATURE | Location/Qualifiers | |
| source | 1..455 | |
| | mol_type = protein | |
| | note = subspecies = japonica | |
| | organism = Oryza sativa | |
| REGION | 1..455 | |
| | note = Public GI ID no.125569365 | |
| REGION | 1..455 | |
| | note = Score of 926.7 for HMM of FIGURE 3. | |
| REGION | 1..455 | |
| | note = Functional Homolog Of Ceres SEEDLINE ID no. ME19173 at SEQ ID NO.109 | |
| REGION | 109..129 | |
| | note = Pfam Name: IQ Pfam Description: IQ calmodulin-binding motif | |

SEQUENCE: 127
```
MGGSGKWVKS LIGLKKPDRE DCKEKLQVPS VNGRGGGKGR KWKLWRSSSG DHGSLWRGSR   60
GGGCCGGHHR SASSDASDDA SSAAADPFTA AVATVARAPA KDFMAVRQEW AAIRVQTAFR  120
GFLARRALRA LKGLVRLQAI VRGRQVRKQA AVTLRCMQAL VRVQARIRAR RVRMSTEGQA  180
VQKLLEARRT KLDILREAEE GWCDSQGTLE DVRVKLQKRQ EGAIKRERAI AYAYSQQIEG  240
ATKCNFWTEC VIFLVFAQQQ PKPTSYGRLN QSGMLLKHQH FDKSNGNWSW LERWMAARPW  300
ENRLMEEHNQ TNSSSPDLLS SKNCEDSFGI LGDFSEPNSV KVRKNNVSKR VCAKPPVVSH  360
HQRIKAQSIS SLSTELHNDE SSASSSSCFA STPISFSTFV TTEKTEDSIR ARPNYMNMTE  420
SIKAKRKACN AQRTTAGKLM EDRKASGVEL KVAQV                            455
```

| | | |
|---|---|---|
| SEQ ID NO: 128 | moltype = AA  length = 441 | |
| FEATURE | Location/Qualifiers | |
| source | 1..441 | |
| | mol_type = protein | |
| | note = subspecies = japonica | |
| | organism = Oryza sativa | |
| REGION | 1..441 | |
| | note = Public GI ID no.115439499 | |
| REGION | 1..441 | |
| | note = Score of 617.2 for HMM of FIGURE 3. | |
| REGION | 1..441 | |

```
                         note = Functional Homolog Of Ceres SEEDLINE ID no. ME19173
                           at SEQ ID NO.109
REGION                   87..107
                         note = Pfam Name: IQ Pfam Description: IQ
                           calmodulin-binding motif
SEQUENCE: 128
MGASGKWIRT LVGLRPAAER EKERGGGGGK GRKWSRLWRS SSSQRGGGNA SASEVYSETS     60
SSADALSSVV AAVVRAPPRD FRLIRQEWAA VRIQTAFRAF LARRALRALR GIVRLQALVR    120
GRRVRKQLAV TLKCMQALVR VQARARDRRA RISADGLDSQ DMLDERGGRV DHVKEAEAGW    180
CDSQGTADDV RSKIHMRHEG AIKRERARTY AQSHQRCSNH GGRPSSPAVS LKHHGNGATR    240
SNHSWSYLEG WMATKPWESR LMEQTHTENS TNSRCSESVE EVSVGGPKLS DASSVKIRRN    300
NVTTRVAAKP PSMISATSSD FVCDESSPST SSVTPLSANN SLATERRSDC GQVGGPSYMS    360
LTKSAKARLS GYGSHKPPLQ RQRSGDLLHH NNRMAFSSID VQSTAGSEVS VTSKRLNSLA    420
LKGRATRSLD KENERRPSSL L                                              441

SEQ ID NO: 129           moltype = AA  length = 416
FEATURE                  Location/Qualifiers
source                   1..416
                         mol_type = protein
                         organism = Arabidopsis thaliana
REGION                   1..416
                         note = Public GI ID no.15225258
REGION                   1..416
                         note = Score of 954.4 for HMM of FIGURE 3.
REGION                   1..416
                         note = Functional Homolog Of Ceres SEEDLINE ID no. ME19173
                           at SEQ ID NO.109
REGION                   84..104
                         note = Pfam Name: IQ Pfam Description: IQ
                           calmodulin-binding motif
SEQUENCE: 129
MGASGKWVKS IIGLKKLEKD EIEKGNGKNK KWKLWRTTSV DSWKGFRGKH RSDSDGVDSS     60
TVYSAAVATV LRAPPKDFKA VREEWAAIRI QTAFRGFLAR RALRALKGIV RLQALVRGRQ    120
VRKQAAVTLR CMQALVRVQA RVRARRVRMT VEGQAVQKLL DEHRTKSDLL KEVEEGWCDR    180
KGTVDDIKSK LQQRQEGAPK RERALAYALA QKQWRSTTSS NLKTNSSISY LKSQEFDKNS    240
WGWSWLERWM AARPWETRLM DTVDTAATPP PLPHKHLKSP ETADVVQVRR NNVTTRVSAK    300
PPPHMLSSSP GYEFNESSGS SSICTSTTPV SGKTGLVSDN SSSQAKKHKP SYMSLTESTK    360
AKRRTNRGLR QSMDEFQFMK NSGMFTGELK TSPSSDPFVS FSKPLGVPTR FEKPRG        416

SEQ ID NO: 130           moltype = AA  length = 408
FEATURE                  Location/Qualifiers
source                   1..408
                         mol_type = protein
                         organism = Oryza sativa
REGION                   79..99
                         note = Pfam Name: IQ Pfam Description: IQ
                           calmodulin-binding motif
REGION                   1..408
                         note = Functional Homolog Of Ceres SEEDLINE ID no. ME19173
                           at SEQ ID NO.109
REGION                   1..408
                         note = Score of 554.2 for HMM of FIGURE 3.
REGION                   1..408
                         note = Public GI ID no.115465173
SEQUENCE: 130
MGASGKWIKS LVSLKAAPEG TTKGRRWTRL WRSSSSASAS ASTAGDASES ASSEADAFSS     60
VVAAVVRAPP RDFRVIRQEW AAVRVQAAFR AFLARRALKA LRGIVRLQAL VRGRLVRRQL    120
AVTLKCMNAL LRVQERARER RARCSADGRD SQDAVGERDG RADPIKQAEE QWCDSQGSVS    180
EVRSKIHMRH DAVAKRERAI AYALSHQPRS SKQSARPSSP SKQSARPSSP RCNHDWSYIE    240
GWMATKPWES RLMEQSHAEL KCSKNSGELN LAGAQLSNAS SVKMRGNRVA AKPPSVLSAS    300
SSDFPCDVSS ASTSSATPAR SDGGHGEGPS YMSLTKSAKA RQSCNSPPQI QRQRSGGMSS    360
YKRVALSPLD VQSNACSEFS VTSRKLNSLS LKGRSMTRSL DKENDNLF                 408

SEQ ID NO: 131           moltype = DNA  length = 1164
FEATURE                  Location/Qualifiers
source                   1..1164
                         mol_type = other DNA
                         organism = Populus balsamifera
                         sub_species = trichocarpa
misc_feature             1..1164
                         note = Ceres ANNOT ID no.1477059
misc_feature             1..1164
                         note = Encodes the peptide sequence at SEQ ID NO 132
SEQUENCE: 131
atgggtgcat caggaaaatg ggtgaaatcc cttataggtt ttaaaagtc tgataaagat      60
caagaccatg taaatggcaa gagcaagaaa tggaagctat ggaggagctc atctggtgac   120
ttggggtctt catggaagga ttttaaaggg aacatagaa cagcgtcaga ggcatcgggt    180
tcttcaccat taactgatcc atttactacc gcaatggcta ctgtggttag agctcctcct   240
aagggttta gggttgtcag gcaagagtgg ctgctatca ggattcaaac tgcttttcgt    300
```

```
ggattcttgg caagaagggc tctgagggct ttgaaagcag tggtgagact ccaagctata    360
gttcgaggtc gacaagtgag aaagcaggct gctgtgatgc tttggtgtat gcaggctctt    420
gttcgagttc aagctcgagt cagggctcat cctgtgcgaa tgtccataga agggcaggca    480
gtgcagaata tgctaaatga gcgacatagc aaggctgatc tcttgaaaca tgctgaggaa    540
gggtggtgcg atggcaaggg gacattggaa gatgtgaagt caaaactgca aatgaggcaa    600
gaaggagcct tcaagagaga aagagcaatt gcatactccc ttgctcagaa acaatggaga    660
tcaaaccccca gctcaaatac tcgaaccaat agctcagtat actcattcaa gaatcaggag    720
tttgataaga atagctgggg atggactagg cctccaattg gcatattac tcgctcatct     780
tccagtccaa gttctgaatt ccgctttgat gagagttcag cttcttcatc aatttgtaca    840
tctacaacac caatatcagg aaacactggc ttggcctctg ataaaacaga ggagagtggt    900
aacagtaggc caaattacat gaacctgacc gagtcaacca aggcaaagca aaaaacatcc    960
ggtcattttat ctcataggat ccaaaggcag tctatggatg agtttcagtt tctcaaaaag   1020
tcaggagcat tctcaaatgg agattcgaaa acagtactg gttctgatcc gtcagttaat    1080
ttatctaagc cactttgctt gccaacaaga tttgataaga actcgacgaa acaactaaga   1140
ggaatggatc atttgtatga ttag                                         1164

SEQ ID NO: 132         moltype = AA  length = 387
FEATURE                Location/Qualifiers
source                 1..387
                       mol_type = protein
                       note = subspecies = trichocarpa
                       organism = Populus balsamifera
REGION                 1..387
                       note = Ceres ANNOT ID no.1477059
REGION                 1..387
                       note = Score of 765.3 for HMM of FIGURE 3.
REGION                 1..387
                       note = Functional Homolog Of Ceres SEEDLINE ID no. ME19173
                        at SEQ ID NO.109
REGION                 89..109
                       note = Pfam Name: IQ Pfam Description: IQ
                        calmodulin-binding motif
SEQUENCE: 132
MGASGKWVKS LIGFKKSDKD QDHVNGKSKK WKLWRSSSGD LGSSWKDFKG KHRTASEASG     60
SSPLTDPFTT AMATVVRAPP KGFRVVRQEW AAIRIQTAFR GFLARRALRA LKAVVRLQAI    120
VRGRQVRKQA AVMLWCMQAL VRVQARVRAH PVRMSIEGQA VQNMLNERHS KADLLKHAEE    180
GWCDGKGTLE DVKSKLQMRQ EGAFKRERAI AYSLAQKQWR SNPSSNTRTN SSVYSFKNQE    240
FDKNSWGWTR PPIGHITRSS SSPSSEFRFD ESSASSSICT STTPISGNTG LASDKTEESG    300
NSRPNYMNLT ESTKAKQKTS GHLSHRIQRQ SMDEFQFLKK SGAFSNGDSK NSTGSDPSVN    360
LSKPLCLPTR FDKNSTKQLR GMDHLYD                                       387

SEQ ID NO: 133         moltype = DNA  length = 1059
FEATURE                Location/Qualifiers
source                 1..1059
                       mol_type = other DNA
                       organism = Populus balsamifera
                       sub_species = trichocarpa
misc_feature           1..1059
                       note = Ceres ANNOT ID no.1530547
misc_feature           1..1059
                       note = Encodes the peptide sequence at SEQ ID NO 134
SEQUENCE: 133
atgggtgcat caggaaaatg ggtgaaatcc cttataggtt ttaaaaagtc tgataaagat     60
caagaccatg taaatggcaa gagcaagaaa tggaagctat ggaggagctc atctggtgac    120
ttggggtctt catggaagga ttttaaaggg aaacatagaa cagcgtcaga ggcatcgggt    180
tcttcaccat taactgatcc atttactacc gcaatggcta ctgtggttag agctcctcct    240
aagggtttta gggttgtcag gcaagagtgg gctgctatca ggattcaaac tgctttccgt    300
ggattcttgg ctcttgttcg agttcaagct cgagtcaggg ctcatcctgt gcgaatgtcc    360
atagaagggc aggcagtgca gaatatgcta aatgagcgac atagcaaggc tgatctcttg    420
aaacatgctg aggaagggtg gtgcgatggc aaggggacat tggaagatgt gaagtcaaaa    480
ctgcaaatga ggcaagaagg agccttcaag agagaaagag caattgcata ctcccttgct    540
cagaaacaat ggagatcaaa ccccagctca aatactcgaa ccaatagctc agtatactca    600
ttcaagaatc aggagtttga taagaatagc tggggatgga ctaggcctcc aattgggcat    660
attactcgct catcttccag tccaagttct gaattccgct ttgatgagag ttcagcttct    720
tcatcaattt gtacatctac aacaccaata tcaggaaaca ctggcttggc ctctgataaa    780
acagaggaga gtggtaacag taggccaaat tacatgaacc tgaccgagtc aaccaaggctt   840
aagcaaaaaa catccggtca tttatctcat aggatccaaa ggcagtctat ggatgagttt    900
cagtttctca aaaagtcagg agcattctca aatggagatt cgaaaacag tactggttct    960
gatccgtcag ttaatttatc taagccactt tgcttgccaa caagatttga taagaactcg   1020
acgaaacaac taagaggaat ggatcatttg tatgattag                          1059

SEQ ID NO: 134         moltype = AA  length = 352
FEATURE                Location/Qualifiers
source                 1..352
                       mol_type = protein
                       note = subspecies = trichocarpa
                       organism = Populus balsamifera
```

```
REGION              1..352
                    note = Ceres ANNOT ID no.1530547
REGION              1..352
                    note = Score of 607.6 for HMM of FIGURE 3.
REGION              1..352
                    note = Functional Homolog Of Ceres SEEDLINE ID no. ME19173
                     at SEQ ID NO.109
REGION              89..109
                    note = Pfam Name: IQ Pfam Description: IQ
                     calmodulin-binding motif
SEQUENCE: 134
MGASGKWVKS LIGFKKSDKD QDHVNGKSKK WKLWRSSSGD LGSSWKDFKG KHRTASEASG  60
SSPLTDPFTT AMATVVRAPP KGFRVVRQEW AAIRIQTAFR GFLALVRVQA RVRAHPVRMS 120
IEGQAVQNML NERHSKADLL KHAEEGWCDG KGTLEDVKSK LQMRQEGAFK RERAIAYSLA 180
QKQWRSNPSS NTRTNSSVYS FKNQEFDKNS WGWTRPPIGH ITRSSSSPSS EFRFDESSAS 240
SSICTSTTPI SGNTGLASDK TEESGNSRPN YMNLTESTKA KQKTSGHLSH RIQRQSMDEF 300
QFLKKSGAFS NGDSKNSTGS DPSVNLSKPL CLPTRFDKNS TKQLRGMDHL YD         352

SEQ ID NO: 135      moltype = DNA  length = 1923
FEATURE             Location/Qualifiers
source              1..1923
                    mol_type = other DNA
                    organism = Arabidopsis thaliana
misc_feature        1..1923
                    note = Ceres SEEDLINE ID no.ME24091
misc_feature        1..1923
                    note = Encodes the peptide sequence at SEQ ID NO. 136
SEQUENCE: 135
acaaatactc ttcttcacac agctttgaat ccatctgtct tctcctctct ctctcttctc   60
catttgcaat tacgataatg tgaaagcaat aagaagagga aaagttatct tcgcacctca  120
gcaaagatcc aatcgattcg attcttaagc ttttcgtct tctccgataa ggtcactact   180
tagaagccgc gttgtggttt agttgactcc tccaggtttt atcttcaagc tttttcgtct  240
atcagatctg gtgtcactgt cttctcatag gattacatag agatgggaa aaaagctaaa   300
tggttttcaa gtgttaagaa agcattcagc ccagattcaa agaagtcgaa gcaaaaattg  360
gctgagggac aaaatggtgt tatctctaat cctcctgttg tggataatgt tagacaatct  420
tcttcttctc ctcctcctgc tcttgctcct cgtgaagtga gagtagctga agtgattgtt  480
gaacggaaca gggatctttc acctccttct acagcagatg ctgtgaatgt tacagctact  540
gatgtycctg tagttccatc ttcatctgct cctggtgttg ttcgtcgcgc tacacctact  600
cgatttgctg gaaagtcaaa cgaagaagcc gctgctatct tgatccagac tatatttaga  660
ggttatttgg caaggagagc gttgcgggca atgagggggt tggtcagact taagttattg  720
atggaaggat ctgttgttaa gcggcaagct gcaaatactc taaaatgtat gcagactctc  780
tctcgtgtac agtcgcagat ccgagctagg agaatcaggr tgtcagaaga gaatcaggct  840
cgccagaaac aactccttca gaaacatgct aaagagctag ctggcttgaa gaacggggat  900
aactggaatg atagcattca atcaaaggag aaagttgaag cgaatttgct aagcaagtac  960
gaggcaacaa tgagaaggga aagggcattg gcttattcat actctcatca scaaaactgg 1020
aagaacaact ctaaatctgg aaacccgatg ttcatggatc caagcaaccc gacatggggt 1080
tggagctggt tggagagatg gatggctggt aggccactag agagttccga gaaagaacaa 1140
agcaacagca acaatgacaa tgctgcctcg gtcaagggct ctattaaccg caacgaagct 1200
gcaaaatctc taacccgcaa tggctcaact caaccaaaca caccatcatc cgcaagaggg 1260
accccaagaa acaaaaaacag tttcttctca cctccaactc cctcaaggct aaaccaatcc 1320
tcgaggaaat ccaatgacga cgactccaaa agcacaatcc cggtcctgtc cgagaggaac 1380
cgcagacaca scattgctgg ttcatcagtc asagacgatg agagcctcgc tggctcacca 1440
gctctcccga gctacatggt tccaactaaa tcagctcgag ccaggctcaa gccccaaagc 1500
ccattaggtg gtaccacaca ggaaaacgaa gggttcacag acaaggcatc agctaagaaa 1560
cggctctcgt atccaacttc gcctgcattg cctaaaccac gcggttctc agctcccccct 1620
aaggtggaga gtggcggcgt taccgtgacc aacggagcag gcagctgagg tatttttattt 1680
aatataatta ttttcccact tatgaatgtg tccgagattg ttgtctctta tgtgttccct 1740
tcatttcgta attcatttgt gcagtgtaag cgccagtcat ttattttttt actataataa 1800
atttttataac cttttaaaat tcatgttctt ttgtttcttt gaatatttaa gttattttta 1860
ttaatgttgg atgaattgga atatgatgat gttatttgta ttgtaatgca gatcctttaa 1920
agc                                                               1923

SEQ ID NO: 136      moltype = AA  length = 461
FEATURE             Location/Qualifiers
source              1..461
                    mol_type = protein
                    organism = Arabidopsis thaliana
REGION              1..461
                    note = Ceres SEEDLINE ID no.ME24091
REGION              1..461
                    note = Score of 1104.8 for HMM of FIGURE 4.
SITE                88
                    note = Xaa is any aa, unknown, or other
REGION              115..135
                    note = Pfam Name: IQ Pfam Description: IQ
                     calmodulin-binding motif
```

```
SITE                    180
                        note = Xaa is any aa, unknown, or other
SITE                    243
                        note = Xaa is any aa, unknown, or other
SITE                    370
                        note = Xaa is any aa, unknown, or other
SITE                    377
                        note = Xaa is any aa, unknown, or other
SEQUENCE: 136
MGKKAKWFSS VKKAFSPDSK KSKQKLAEGQ NGVISNPPVV DNVRQSSSSP PPALAPREVR   60
VAEVIVERNR DLSPPSTADA VNVTATDXPV VPSSSAPGVV RRATPTRFAG KSNEEAAAIL  120
IQTIFRGYLA RRALRAMRGL VRLKLLMEGS VVKRQAANTL KCMQTLSRVQ SQIRARRIRX  180
SEENQARQKQ LLQKHAKELA GLKNGDNWND SIQSKEKVEA NLLSKYEATM RRERALAYSY  240
SHXQNWKNNS KSGNPMFMDP SNPTWGWSWL ERWMAGRPLE SSEKEQSNSN NDNAASVKGS  300
INRNEAAKSL TRNGSTQPNT PSSARGTPRN KNSFFSPPTP SRLNQSSRKS NDDDSKSTIS  360
VLSERNRRHX IAGSSVXDDE SLAGSPALPS YMVPTKSARA RLKPQSPLGG TTQENEGFTD  420
KASAKKRLSY PTSPALPKPR RFSAPPKVES GGVTVTNGAG S                     461

SEQ ID NO: 137          moltype = DNA  length = 1930
FEATURE                 Location/Qualifiers
source                  1..1930
                        mol_type = other DNA
                        organism = Zea mays
misc_feature            1..1930
                        note = Ceres CLONE ID no.375578
exon                    223..1716
                        note = Encodes the peptide sequence at SEQ ID NO 138
SEQUENCE: 137
aattcgagtg agcttattgg agactgacat cctaatcgaa aacccggttt atttttcctt   60
cgtcctggat gcgtcggtcg cgtgtttgat ctgactaagc cgcggaggag ggtgctagat  120
gtccgtgcgg tgggcggtgg ctcccgaggg cgaccggagt taggtccttg ccgccttcag  180
tgcggtgggg aagcgagaca ttgaaggcgc agaacccaaa gaatgggtaa gagaggaaag  240
tggtttagtg cggtgaagaa agtcttcagc tcctccgatc cagatggaaa ggaagccaag  300
gcccagaagg cagacaaatc gaaatccaag gatggaaagg aagccaaggc ccagaaggca  360
gacaaatcga aatccaagac ggtgccaggc actgctccag cagtagctcc gttgccatca  420
ccaccagcaa ctcagcccca ctctctggag atcaaagatg tcaatccagt tgaaacagac  480
agtgagcaga acaagcatgc ctactccgtt gcgcttgcgt ctgctgtcgc tgctgaagct  540
gcagcagttg ctgcccaggc tgctgcggaa gttgtccgcc tcacagcagt taccacggct  600
gcaccaagat gcctgttag ttcgagggaa gaacttgccg ccaccaagat tcagactgcc  660
ttcaggggtt atctggcaag gagagcattg cgtgcactaa gagggctagt tagaggttat  720
ctggcaagga gagcattgcg tgcactaaga gggctagtta aggtatct gtcaaggaga  780
gcattgcgtg cactaagagg gctagttaga tctagaaggg tgaagttgga ggaggagaaa  840
caggctcttc aaagacaact ccaattgaaa catcaaaggg aacttgagaa aatgaagatt  900
gatgaagatt gggatcacag ccatcaatcc aaagagcaaa ttgaggccaa cctaatgatg  960
aaacaggaag ctgcactgag gcgagagaga gcacttgcat atgcattttc tcaccagtgg 1020
aggaattctg gtcgaactat aaccccctact tttacggaac ctggaaccc caactggggc 1080
tggagctgga tggagcgctg gatgacagca agaccatggg agagtcggtt ggcggcggca 1140
tcggacaagg accctaaaga acgtgctgtg acaaagaatg cgagcaccag tgctgttcga 1200
gtacctgtat cccgtgccat ctcgattcag agaccagcaa caccaaacaa gtcgagccgc 1260
ccaccaagcc ggcagtcact ttcaaccccg ccatcgaaga cccgtcagc ctcaggaaag 1320
gccaggccgg caagtccaag gaacagttgg ctgtacaagg aggatgacct gaggagcatc 1380
acgagcatcc gctccgagcg cccaaggagg cagagcacgg tggaggctc ggtccgggac 1440
gataccagcc tgaccagcac accacctctc cccagctaca tgcagtcgac cgagtctgca 1500
cgggccaagt ctcggtaccg cagtctacta ctgactgaga agcttgaggt tcctgagaga 1560
gcgcctctgg cccactccgt tgtcaagaag cgcctgtcgt tccccgtcgt cgagaagcca 1620
agcgttgtgc cgacagagaa gcccagggaa agagtgaggc gccattccga ccctccggaa 1680
gtcgatcctg cgacgctcaa ggatgcccct gctgcctgac cagtgaccag gccttatgtg 1740
attgttaggt ttcgtgctct tttaacaccg tgatgtatta tctgagttag ttgctttgt 1800
tcgtgtcatc gtatgatctg tccgggttga ttttgagaca gttctaactg tgtttacaga 1860
caatgcgtga tgctaaatgt atgtgtggtt ggttggcttt aaatgtactg atatgatagt 1920
atttgatttc                                                       1930

SEQ ID NO: 138          moltype = AA  length = 498
FEATURE                 Location/Qualifiers
source                  1..498
                        mol_type = protein
                        organism = Zea mays
REGION                  1..498
                        note = Ceres CLONE ID no.375578
REGION                  1..498
                        note = Score of 1275.4 for HMM of FIGURE 4.
REGION                  1..498
                        note = Functional Homolog Of Ceres SEEDLINE ID no. ME24091
                         at SEQ ID NO.136
REGION                  137..157
                        note = Pfam Name: IQ Pfam Description: IQ
                         calmodulin-binding motif
```

```
SEQUENCE: 138
MGKRGKWFSA VKKVFSSSDP DGKEAKAQKA DKSKSKRRWP FGKSKHSEPS ISTVPGTAPA    60
VAPLPSPPAT QPHSLEIKDV NPVETDSEQN KHAYSVALAS AVAAEAAAVA AQAAAEVVRL   120
TAVTTAAPKM PVSSREELAA TKIQTAFRGY LARRALRALR GLVRLKSLVD GNAVKRQTAH   180
TLQCTQAMTR VQTQIYSRRV KLEEEKQALQ RQLQLKHQRE LEKMKIDEDW DHSHQSKEQI   240
EANLMMKQEA ALRRERALAY AFSHQWRNSG RTITPTFTEP GNPNWGWSWM ERWMTARPWE   300
SRLAAASDKD PKERAVTKNA STSAVRVPVS RAISIQRPAT PNKSSRPPSR QSLSTPPSKT   360
PSASGKARPA SPRNSWLYKE DDLRSITSIR SERPRRQSTG GGSVRDDTSL TSTPPLPSYM   420
QSTESARAKS RYRSLLLTEK LEVPERAPLA HSVVKKRLSF PVVEKPSVVP TEKPRERVRR   480
HSDPPKVDPA TLKDAPAA                                                498

SEQ ID NO: 139          moltype = DNA   length = 1930
FEATURE                 Location/Qualifiers
source                  1..1930
                        mol_type = other DNA
                        organism = Zea mays
misc_feature            1..1930
                        note = Ceres CLONE ID no.375578
SEQUENCE: 139
aattcgagtg agcttattgg agactgacat cctaatcgaa aacccggttt atttttctt    60
cgtcctggat gcgtcggtcg cgtgtttgat ctgactaagc cgcggaggag ggtgctagat   120
gtccgtgcgg tgggcggtgg ctcccgaggg cgaccggagt taggtccttg ccgccttcag   180
tgcggtgggg aagcgagaca ttgaaggcgc agaacccaaa gaatgggtaa gagaggaaag   240
tggtttagtg cggtgaagaa agtcttcagc tcctccgatc cagatggaaa ggaagccaag   300
gcccagaagg cagacaaatc gaaatccaag aggagatggc catttggaaa gtccaagcac   360
tcggagcctt ccatatcgac ggtgccaggc actgctccag cagtagctcc gttgccatca   420
ccaccagcaa ctcagcccca ctctctggag atcaaagatg tcaatccagt gaaacagac    480
agtgagcaga acaagcatgc ctactccgtt gcgcttgcgt ctgctgtcgc tgctgaagct   540
gcagcagttg ctgcccaggc tgctgcgaaa gttgtccgcc tcacagcagt taccacggct   600
gcaccaaaga tgcctgttag ttcgagggaa taacttgccg ccaccaagat tcagactgcc   660
ttcaggggtt atctggcaag gagagcattg cgtgcactaa gagggctagt tagattgaag   720
tcgcttgttg atggaaatgc tgtcaaacgc caaaccgctc acaccttgca atgcacacaa   780
gcaatgacaa gagttcaaac tcaaatctac tctagaaggg tgaagttgga ggaggagaaa   840
caggctcttc aaagacaact ccaattgaaa catcaaaggg aacttgagaa aatgaagatt   900
gatgaagatt gggatcacag ccatcaatcc aaagagcaaa ttgaggccaa cctaatgatg   960
aaacaggaag ctgcactgag gcgagagaga gcacttgcat atgcattttc tcaccagtgg  1020
aggaattctg gtcgaactat aaccctact tttacgaac ctgggaaccc caactggggc   1080
tggagctgga tggagcgctg gatgacagca agaccatggg agagtcggtt ggcggcggca  1140
tcggacaagg accctaaaga acgtgctgtg acaaagaatg cgagccaccag tgctgttcga  1200
gtacctgtat cccgtgccat ctcgattcag agaccagcaa caccaaacaa gtcgagccgc  1260
ccaccaagcc ggcagtcact ttcaacccg ccatcgaaga ccccgtcagc ctcaggaaag   1320
gccaggccgg caagtccaag gaacagttgg ctgtacaagg aggatgacct gaggagcatc  1380
acgagcatcc gctccgagcg cccaaggagg cagagcagtg ggtgaggctc ggtccgggac  1440
gataccagcc tgaccagcac accacctctc cccagctaca tgcagtcgac cgagtctgca  1500
cgggccaagt ctcggtaccg cagtctacta ctgactgaga agcttgaggt tcctgagaga   1560
gcgcctctgg cccactccgt tgtcaagaag cgcctgtcgt tccccgtcgt cgagaagcca  1620
agcgttgtgc cgacagagaa gcccagggaa agagtgaggc gccattccga cccctccgaag 1680
gtcgatcctg cgacgctcaa ggatgcccct gctgcctgac cagtgaccag gccttatgtg  1740
attgttaggt ttcgtgctct tttaacaccg tgatgtatta tctgagttag ttgctttgt   1800
tcgtgtcatc gtatgatctg tccgggttga ttttgagaca gttctaactg tgtttacaga  1860
caatgcgtga tgctaaatgt atgtgtggtt ggttggcttt aaatgtactg atatgatagt  1920
atttgatttc                                                         1930

SEQ ID NO: 140          moltype = AA   length = 311
FEATURE                 Location/Qualifiers
source                  1..311
                        mol_type = protein
                        organism = Zea mays
REGION                  1..311
                        note = Ceres CLONE ID no.375578
REGION                  1..311
                        note = Score of 653.4 for HMM of FIGURE 4.
REGION                  1..311
                        note = Functional Homolog Of Ceres SEEDLINE ID no. ME24091
                        at SEQ ID NO.136
SEQUENCE: 140
MTRVQTQIYS RRVKLEEEKQ ALQRQLQLKH QRELEKMKID EDWDHSHQSK EQIEANLMMK    60
QEAALRRERA LAYAFSHQWR NSGRTITPTF TEPGNPNWGW SWMERWMTAR PWESRLAAAS   120
DKDPKERAVT KNASTSAVRV PVSRAISIQR PATPNKSSRP PSRQSLSTPP SKTPSASGKA   180
RPASPRNSWL YKEDDLRSIT SIRSERPRRQ STGGGSVRDD TSLTSTPPLP SYMQSTESAR   240
AKSRYRSLLL TEKLEVPERA PLAHSVVKKR LSFPVVEKPS VVPTEKPRER VRRHSDPPKV   300
DPATLKDAPA A                                                       311

SEQ ID NO: 141          moltype = AA   length = 217
FEATURE                 Location/Qualifiers
source                  1..217
                        mol_type = protein
                        organism = Arabidopsis thaliana
```

```
REGION              1..217
                    note = Ceres SEEDLINE ID no.ME10681
REGION              1..217
                    note = Score of 322.9 for HMM of FIGURE 4.
REGION              1..217
                    note = Functional Homolog Of Ceres SEEDLINE ID no. ME24091
                      at SEQ ID NO.136
SEQUENCE: 141
MGKKGKWFGA VKKVFSPESK EKKEESNIDR GSVKSMSLNL GEGEITKAFN RRDSKLEKPS    60
PPTPRPARPT SRHSPLTPSA RVAPIPARRK SVTPKNGLSQ VDDDARSVLS VQSERPRRHS   120
IATSTVRDDE SLTSSPSLPS YMVPTESARA KSRLQGSAMA NGAETPEKGG STGPAKKRLS   180
FQGGTAAASP MRRHSGPPKV EIAPPQPEAL VVNGGSK                            217

SEQ ID NO: 142         moltype = AA  length = 311
FEATURE                Location/Qualifiers
source                 1..311
                       mol_type = protein
                       organism = Arabidopsis thaliana
REGION                 1..311
                       note = Ceres SEEDLINE ID no.ME03140
REGION                 1..311
                       note = Score of 653.4 for HMM of FIGURE 4.
REGION                 1..311
                       note = Functional Homolog Of Ceres SEEDLINE ID no. ME24091
                         at SEQ ID NO.136
SEQUENCE: 142
MTRVQTQIYS RRVKLEEEKQ ALQRQLQLKH QRELEKMKID EDWDHSHQSK EQIEANLMMK    60
QEAALRRERA LAYAFSHQWR NSGRTITPTF TEPGNPNWGW SWMERWMTAR PWESRLAAAS   120
DKDPKERAVT KNASTSAVRV PVSRAISIQR PATPNKSSRP PSRQSLSTPP SKTPSASGKA   180
RPASPRNSWL YKEDDLRSIT SIRSERPRRQ STGGGSVRDD TSLTSTPPLP SYMQSTESAR   240
AKSRYRSLLL TEKLEVPERA PLAHSVVKKR LSFPVVEKPS VVPTEKPRER VRRHSDPPKV   300
DPATLKDAPA A                                                       311

SEQ ID NO: 143         moltype = AA  length = 421
FEATURE                Location/Qualifiers
source                 1..421
                       mol_type = protein
                       organism = Arabidopsis thaliana
REGION                 1..421
                       note = Ceres SEEDLINE ID no.ME24076
REGION                 1..421
                       note = Score of 908.3 for HMM of FIGURE 4.
REGION                 1..421
                       note = Functional Homolog Of Ceres SEEDLINE ID no. ME24091
                         at SEQ ID NO.136
REGION                 60..80
                       note = Pfam Name: IQ Pfam Description: IQ
                         calmodulin-binding motif
SEQUENCE: 143
LEVNLSVPPP PAPPPVLHQA EEVGVPEAEQ EQSKHVAVEE APAAAPAQAS VLPPAVPTQE    60
LAAVKIQTAF RGYLARRALR ALRGLVRLKS LVEGNSVKRQ SASTLRCMQT LSRVQSQISS   120
RRAKMSEENQ ALQRQLLLKQ ELENFRMGEN WDDSTQSKEQ IEASLISRQE AAIRRERALA   180
YAFSHQWKST SRSVNPMFVD PNNLQWGWSW LERWMAAKPW EGRNGADKES NIDRGSVKSM   240
SLNLGEGEIT KAFNRRDSKL EKPSPPTPRP ARPTSRHSPL TPSARVAPIP ARRKSVTPKN   300
GLSQVDDDAR SVLSVQSERP RRHSIATSTV RDDESLTSSP SLPSYMVPTE SARAKSRLQG   360
SAMANGAETP EKGGSTGPAK KRLSFQGGTA AASPMRRHSG PPKVEIAPPQ PEALVVNGGS   420
K                                                                  421

SEQ ID NO: 144         moltype = AA  length = 311
FEATURE                Location/Qualifiers
source                 1..311
                       mol_type = protein
                       note = subspecies = japonica
                       organism = Oryza sativa
REGION                 1..311
                       note = Ceres SEEDLINE ID no.ME24217
REGION                 1..311
                       note = Score of 653.4 for HMM of FIGURE 4.
REGION                 1..311
                       note = Functional Homolog Of Ceres SEEDLINE ID no. ME24091
                         at SEQ ID NO.136
SEQUENCE: 144
MTRVQTQIYS RRVKLEEEKQ ALQRQLQLKH QRELEKMKID EDWDHSHQSK EQIEANLMMK    60
QEAALRRERA LAYAFSHQWR NSGRTITPTF TEPGNPNWGW SWMERWMTAR PWESRLAAAS   120
DKDPKERAVT KNASTSAVRV PVSRAISIQR PATPNKSSRP PSRQSLSTPP SKTPSASGKA   180
RPASPRNSWL YKEDDLRSIT SIRSERPRRQ STGGGSVRDD TSLTSTPPLP SYMQSTESAR   240
AKSRYRSLLL TEKLEVPERA PLAHSVVKKR LSFPVVEKPS VVPTEKPRER VRRHSDPPKV   300
DPATLKDAPA A                                                       311
```

```
SEQ ID NO: 145          moltype = AA   length = 500
FEATURE                 Location/Qualifiers
source                  1..500
                        mol_type = protein
                        note = subspecies = japonica
                        organism = Oryza sativa
REGION                  1..500
                        note = Public GI ID no.115440873
REGION                  1..500
                        note = Score of 1281.0 for HMM of FIGURE 4.
REGION                  1..500
                        note = Functional Homolog Of Ceres SEEDLINE ID no. ME24091
                         at SEQ ID NO.136
REGION                  142..162
                        note = Pfam Name: IQ Pfam Description: IQ
                         calmodulin-binding motif
SEQUENCE: 145
MGKKGNWFSA VKKVFSSSDP DGREAKIEKA DKSRSRRKWP FGKSKKSDPW TSTVAVPTST   60
APPPQPPPPP PTHPIQPQPE EIKDVKAVET DSEQNKHAYS VALASAVAAE AAAVAAQAAA  120
EVVRLTTATT AVPKSPVSSK DELAAIKIQT AFRGYLARRA LRALRGLVRL KSLVDGNAVK  180
RQTAHTLHCT QTMTRVQTQI YSRRVKMEEE KQALQRQLQL KHQRELEKMK IDEDWDHSHQ  240
SKEQVETSLM MKQEAALRRE RALAYAFSHQ WKNSGRTITP TFTDQGNPNW GWSWMERWMT  300
SRPWESRVIS DKDPKDHYST KNPSTSASRT YVPRAISIQR PATPNKSSRP PSRQSPSTPP  360
SRVPSVTGKI RPASPRDSWL YKEDDLRSIT SIRSERPRRQ STGGASVRDD ASLTSTPALP  420
SYMQSTESAR AKSRYRSLLT DRFEVPERVP LVHSSIKKRL SFPVADKPNG EHADKLMERG  480
RRHSDPPKVD PASLKDVPVS                                              500

SEQ ID NO: 146          moltype = DNA   length = 1695
FEATURE                 Location/Qualifiers
source                  1..1695
                        mol_type = other DNA
                        organism = Triticum aestivum
misc_feature            1..1695
                        note = Ceres CLONE ID no.826796
misc_feature            1..1695
                        note = Encodes the peptide sequence at SEQ ID NO 147
SEQUENCE: 146
ataggacttc acagacagac tgactcaatc ctaacccaat ccctcccatg cttccatcta   60
ctctagcaga aattgcagag gaggttggcc gccgccggct ccagcgcagg cgcagcctac  120
ccgcgggatc tgacgccctc cgcctcctac ctcgaggcac gcgcctcagg ctcagctccc  180
ccgcccgccc tccccgcta ccccgacgac ttccaagagg aggagcatga aattgagcat  240
gtcgccgccg cgccagcgcc agcgccagcc acggatgcgc cgctacctgc ccctcctgcc  300
gccgcaccac cacaggttca ggctgccatt gcgccggctt cttcctccttg tgtcatgtcc  360
agggagctcg ccgccaccaa gatccagacc gccttccgag gtcacctggc aagaagggcg  420
ctgcgggcat tgaaaggcct ggtccagact aagtcgctgg tccaaggcca ctccgtcaag  480
cgccaggcca ccagcacgct tcgctgcatg cagactctgt cccgggtcca gtccaagata  540
cggacgagga ggatcaagat ggccgaggag aaccaggccc ttcagcgcca gctcttgttg  600
aaccaggaac tagagactct caggatggga gatcagtgga ataccagcct gcagtccaag  660
gagcaaatcg aggcgagcct cgtgagcagg caagaggccg cggctagaag agaacgggct  720
ctcgcatacg cattctccca ccagtggaag agcacctcaa ggtctgccaa cccgatgttc  780
gtggaccgga gtaacccgca ctggggctgg agctggctgg agcggtggat ggcgtcgagg  840
ccgttcgacg gccgcaacgg ggcgtccgag aaggagggca gcagcgtcga ccgcacgtcg  900
gtgcacagca ccagcctgag catgaacctc ggagaaggtg agacggtcac aaaggcggac  960
aaccaggtgg tggactcttt gaagccgaat gatgataagc cgccgccgct ttcgactccg 1020
aagccgtccg gccctgcccc caggcagtcc ccgtcgacgc cctcccgcgc gctggcgagg 1080
aagaagagcg cgacgcccaa gagtggagac tgcgacggcg acgacgcgag gagcgtggtc 1140
agcactgtcc ggtccgagcg gccccggagg cacagcatcg gcgcgtccag cgtgcgtgac 1200
gacgcgggct cttccccgtc ggtgccgagc tacatggcgg ccaccaagtc ggcgtcggcc 1260
agggccaagt cgcgtgtgca gagcccgacg ctgaccgagg gtgctgctca agctgagacg 1320
ctggagaaag gatggtcttc tgtgggttca gcgaagaagc ggctgtcctt tccggctggg 1380
acgccaccgc cggtgccggc ggcggcggcg aggcggcact ccgggcctcc caaggtgcgg 1440
caggcgggcg tggaaggtgg tacgaggaa cgggactcgt cccttgcgtg acatcatggg 1500
aagcagatta tggtgtggag cagagcagag cggaatttgt tgcatttgtt gagtgaaagg 1560
aacgcagaat gtgtgttgtg tggatccatt ggatttgatt tgatttgtat gatggcagta 1620
ttcctatttg attattcatt gaataatata agtatctgta atgaagataa aaggagggga 1680
cacgaacatt atttc                                                  1695

SEQ ID NO: 147          moltype = AA   length = 378
FEATURE                 Location/Qualifiers
source                  1..378
                        mol_type = protein
                        organism = Triticum aestivum
REGION                  1..378
                        note = Ceres CLONE ID no.826796
REGION                  1..378
                        note = Score of 903.8 for HMM of FIGURE 4.
REGION                  1..378
                        note = Functional Homolog Of Ceres SEEDLINE ID no. ME24091
                         at SEQ ID NO.136
```

| | | |
|---|---|---|
| REGION | 4..24 | |
| | note = Pfam Name: IQ Pfam Description: IQ calmodulin-binding motif | |
| SEQUENCE: 147 | | |

```
MSRELAATKI QTAFRGHLAR RALRALKGLV RLKSLVQGHS VKRQATSTLR CMQTLSRVQS    60
KIRTRRIKMA EENQALQRQL LLNQELETLR MGDQWNTSLQ SKEQIEASLV SRQEAAARRE   120
RALAYAFSHQ WKSTSRSANP MFVDPSNPHW GWSWLERWMA SRPFDGRNGA SEKEGSSVDR   180
TSVHSTSLSM NLGEGETVTK ADNQVVDSLK PNDDKPPPLS TPKPSGPAPR QSPSTPSPAL   240
ARKKSATPKS GDCDGDDARS VVSTVRSERP RRHSIGASSV RDDAGSSPSV PSYMAATKSA   300
SARAKSRVQS PTLTEGAAQA ETLEKGWSSV GSAKKRLSFP AGTPPPVPAA AARRHSGPPK   360
VRQAGVEGGT EERDSSLA                                                378
```

| | | |
|---|---|---|
| SEQ ID NO: 148 | moltype = DNA  length = 1470 | |
| FEATURE | Location/Qualifiers | |
| source | 1..1470 | |
| | mol_type = other DNA | |
| | organism = Populus balsamifera | |
| | sub_species = trichocarpa | |
| misc_feature | 1..1470 | |
| | note = Ceres ANNOT ID no.1465047 | |
| misc_feature | 1..1470 | |
| | note = Encodes the peptide sequence at SEQ ID NO 149 | |
| SEQUENCE: 148 | | |

```
atggggaaaa gagggagttg gttctctgct ttgaagaaag ccctcggttc tctaagaaa      60
tccaaatcaa agaagaaatg gtcagaaaaa gagaagaacc gggatctagg tgtttcttca    120
catgaagaaa ccgttgcacc ctctctttct cctcctcgta caccacctcc tcctacagca    180
gaagatgtga aattaactga agctgagaac gagcagagca agcatgctta ttccgtggcg    240
cttgccactg ctgtggcagc tgaggcagct gttgcagccg cccaggctgc cgctgaggtt    300
gttcggctta ctacagtggc acattactct ggaaaatcga aggaggaaat agctgcaatc    360
aggattcaaa cagcatttag aggatacctg gcgaggaggg cattacgtgc tttgagaggg    420
ctggtgagat tgaagtcatt gatacaaggg caatctgtca aacggcaagc aactgccaca    480
ttacgagcca tgcagactct tgctcgtgtg cagtctcaga ttcgtgcaag aaggatcaga    540
atgtccgagg aaaatgaggc cctccaacgg cagctccagc agaaacatga caagaacttt    600
gagaagttga gaacttctat tggagaacaa tgggatgata gcccacaatc aaaggaagaa    660
gttgaagcca gcctactaca aaagcaagaa agctactcgt tggccatga aagagaaag    720
ggcactggct                                                       
tatgcatact cgcatcagca aatgtggaag caatcttcaa aatcagcaaa tgctacattc    780
atggatccaa acaatcctcg ttggggatgg agttggttag agaggtggat ggcagcccga    840
ccttgggaga gccgaagcac aatagataac aatgatcggt cctctgttaa gagtacaaca    900
agccgtacca tgtctcttgg agaaatcagc agagcttatt ctcgtcgtga tcttaaccat    960
gacaataaag cttctcctgg tgcgcaaaaa tcaagtcggc ctcccagtcg gcaatccct   1020
tctactcccc cctctaaggc accatctaca tcttcagtaa cagggaaagc aaagccacca   1080
agccctagag ggagtgcttg gggaggagac gaggactcca ggagcacatt cagtgtccag   1140
tctgagcgct atcggagaca tagcatagca gggtcatcaa taagagatga tgagagtctt   1200
gcaagttcgc cttcagttcc aagttacatg gcacccacac ggtcacagtc agcaaaggca   1260
aaatcccgct tgtcaagccc gttaggcata gataataatg gacaccaga taaggcatca   1320
gtgggttatg taaagaagcg gctttccttc tctgcttcac cagctggagc aaggagacac   1380
tctggtcctc ctagggtgga tgccagtgct gttaaagaca ttcaaatgca cagagaagag   1440
aaaatgagca atggagcaag cagcaagtag                                   1470
```

| | | |
|---|---|---|
| SEQ ID NO: 149 | moltype = AA  length = 326 | |
| FEATURE | Location/Qualifiers | |
| source | 1..326 | |
| | mol_type = protein | |
| | note = subspecies = trichocarpa | |
| | organism = Populus balsamifera | |
| REGION | 1..326 | |
| | note = Ceres ANNOT ID no.1465047 | |
| REGION | 1..326 | |
| | note = Score of 746.5 for HMM of FIGURE 4. | |
| REGION | 1..326 | |
| | note = Functional Homolog Of Ceres SEEDLINE ID no. ME24091 at SEQ ID NO.136 | |
| SEQUENCE: 149 | | |

```
MQTLARVQSQ IRARRIRMSE ENEALQRQLQ QKHDKELEKL RTSIGEQWDD SPQSKEEVEA    60
SLLQKQEAAM RRERALAYAY SHQQMWKQSS KSANATFMDP NNPRWGWSWL ERWMAARPWE   120
SRSTIDNNDR ASVKSTTSRT MSLGEISRAY SRRDLNHDNK ASPGAQKSSR PPSRQSPSTP   180
PSKAPSTSSV TGKAKPPSPR GSAWGGDEDS RSTFSVQSER YRRHSIAGSS IRDDESLASS   240
PSVPSYMAPT RSQSAKAKSR LSSPLGIDNN GTPDKASVGY VKKRLSFSAS PAGARRHSGP   300
PRVDASAVKD IQMHREEKMS NGASSK                                       326
```

| | | |
|---|---|---|
| SEQ ID NO: 150 | moltype = DNA  length = 1901 | |
| FEATURE | Location/Qualifiers | |
| source | 1..1901 | |
| | mol_type = other DNA | |
| | organism = Gossypium hirsutum | |
| misc_feature | 1..1901 | |
| | note = Ceres CLONE ID no.1919901 | |
| misc_feature | 1..1901 | |
| | note = Encodes the peptide sequence at SEQ ID NO 151 | |

```
SEQUENCE: 150
aactttctt     agttatcctc    tgcaaatgcc    aacctgttct    tttattatta    ttttccgcca      60
ttttgctct     ctttcaagca    ttttttttt     gcctagatcc    acttctctct    ctttgatttt     120
taattactgc    atttttgttt    taatacacaa    taagaacaac    taagagatag    aatgtgactt     180
atcaatcttt    taactgagat    ctgtgagaat    ttttctatgt    accaaggaat    tatttacaga     240
tgggaaaaaa    aggtggctgg    ctttctattg    tgaagaaagc    tttgagccct    gaatccaaga     300
aatctcagca    ccaaactcca    aagccaaaga    aaaaatggtt    cggaaaaagc    aaaaatttga     360
gccctgtgtc    tgtgcctgaa    gaaactgaag    tgataactga    agatgcaaag    ctaaagaag      420
ctgaaaacga    acaaagcaaa    catgcctact    ctgtggctct    tgccaccgct    gtggcggccg     480
aggcagcggt    ggcagctgct    caggcggctg    ctgaagttgt    ccgtctcact    tctcagccgc     540
gccatctggg    gaagtcaaag    gaggaaatag    ctgctatcag    gattcaaaca    gcatttcgtg     600
gatatttggc    taggagggca    ctgcgagctt    tgagagggtt    ggtaaggttg    aaatcgttga     660
tcagagggca    atccgtcaaa    cgccaagcaa    ctacaacgtt    aagatgcatg    cagactctag     720
ctcgtctgca    gtctgagatt    tctgcaagga    ggattagaat    gtcagaagag    aaccaggctc     780
ttcagcgcca    gcttcaacag    aaatgccaga    aagagctcga    gaagttgaga    gctcccatga     840
gagaagactg    gaacgatagt    acacagtcga    aggagcagat    cgaagcaaga    caacaaaata     900
agcaaggagc    tactatgaaa    agggaaagag    cattggctta    tgcatactgt    caccagcgat     960
cgtggaagaa    ctgttctaga    tcagtgaatc    aaacatttat    ggatccgagt    aattcacact    1020
ggggttggag    ttggttagag    cgatggatgg    cagcccgacc    atgggaagtc    aaagcacaa    1080
ctgataacaa    tgaccgtggc    tcagtcaaga    gtatgggtgc    ttgttcgata    tctataagtg    1140
aaatcagcag    agcttattct    cgaagagatc    ttaacaatga    taacaaacca    tctccaacac    1200
ctcagaagtc    aagtcgatct    cctagccgcc    agtctccatc    gactccacct    tcaaaggcac    1260
cttcgatttc    atcggtttct    ggtaaaacaa    gactgccaag    tccgagagga    agtcaatggg    1320
gagggtatga    agactcaagg    agcatactca    gtacccggtc    tgatcgttat    aggagacata    1380
gcattgcagg    gtcctcaatg    agagacgatg    agagccttac    aagctcacct    gcagttccaa    1440
gttatatgcc    accaacacag    tccacaaagg    ccaggtccca    cataccaagc    cccttaggaa    1500
gtggcacacc    agataggaga    gtggcagggt    ctgcaaagaa    acggcttttg    ttcccagcat    1560
ccccagccag    tagtaggaga    cattcagagc    ctcctaaagt    ggacataagt    gaggctagaa    1620
agaatcagca    tgcaccaagc    aatggaaggc    aagtggcttg    tgaagagtg     caacaaaagt    1680
tagattgaat    aaacatggaa    gggttatttc    aacttgaagt    tcttgtagtg    tggttgtgat    1740
tatcttttc     ttcctaggtt    ttatgattat    taattataa     aggggttactt   ttttctgggt    1800
gagatttagt    ttattgtttg    tggttgacaa    acattcttaa    aaatcttcaa    gtttagtttc    1860
aattcatgaa    atttgtaatt    aaaaaaaaaa    aaaaaaaaa     a                           1901

SEQ ID NO: 151         moltype = AA   length = 474
FEATURE                Location/Qualifiers
source                 1..474
                       mol_type = protein
                       organism = Gossypium hirsutum
REGION                 1..474
                       note = Ceres CLONE ID no.1919901
REGION                 1..474
                       note = Score of 1214.2 for HMM of FIGURE 4.
REGION                 1..474
                       note = Functional Homolog Of Ceres SEEDLINE ID no. ME24091
                        at SEQ ID NO.136
REGION                 109..129
                       note = Pfam Name: IQ Pfam Description: IQ
                        calmodulin-binding motif
SEQUENCE: 151
MGKKGGWLSI    VKKALSPESK    KSQHQTPKPK    KWFGKSKNL     SPVSVPEETE    VITEDAKLKE      60
AENEQSKHAY    SVALATAVAA    EAAVAAAQAA    AEVVRLTSQP    RHLGKSKEEI    AAIRIQTAFR     120
GYLARRALRA    LRGLVRLKSL    IRGQSVKRQA    TTTLRCMQTL    ARLQSEISAR    RIRMSEENQA     180
LQRQLQQKCQ    KELEKLRAPM    REDWNDSTQS    KEQIEARQQN    KQGATMKRER    ALAYAYCHQR     240
SWKNCSRSVN    QTFMDPSNSH    WGWSWLERWM    AARPWEVQST    TDNNDRGSVK    SMGACSISIS     300
EISRAYSRRD    LNNDNKPSPT    PQKSSRVPSR    QSPSTPPSKA    PSISSVSGKT    RLPSPRGSQW     360
GGYEDSRSIL    STRSDRYRRH    SIAGSSMRDD    ESLTSSPAVP    SYMAPTQSTK    ARSHIPSPLG     420
SGTPDRRVAG    SAKKRLLFPA    SPASSRRHSE    PPKVDISEAR    KNQHAPSNGR    QVAW           474

SEQ ID NO: 152         moltype = DNA   length = 1362
FEATURE                Location/Qualifiers
source                 1..1362
                       mol_type = other DNA
                       organism = Glycine max
misc_feature           1..1362
                       note = Ceres CLONE ID no.520008
misc_feature           1..1362
                       note = Encodes the peptide sequence at SEQ ID NO 153
SEQUENCE: 152
atgcattcac    tcatcaggtt    ttttttaaaaa   aaaaaattc     tcatcaattt    acacatgcga      60
gaaaatgggt    gaaaaattta    atacgaactg    aaaaatcttt    caaaaatatc    gcatattata     120
aacactaaaa    tgagaaatca    agcatcctta    ttatactata    tggatatact    cttcactgtt     180
tctttatctc    ttgaatctgt    tatactttcc    aactgagact    taggcctgat    tcctgataag     240
tgcacgagtc    ctttcctatc    tgtcactat    cttcagagcc    atatcctctg    cactctcctt     300
tctcactgcc    acgatgatct    tttgcataat    ccaatgatat    gctaatgctt    tgttaagtaa     360
gttgcagcgt    aaattcttcc    tcaatttgt     caatggaagt    attttgttac    tgaaataaag     420
tggcatgcta    tattatgtaa    catatttga     atgaatagca    ttctgcctat    gatatgattt     480
tcaatcataa    gtgtaagttc    cttgatgctg    tcaacaaatt    cagtgtttga    tatttggggg     540
caaaaaatat    ttggcagcaa    aactggaaga    actcgtctag    atctgtaaat    ccaatgttta     600
```

-continued

```
tggatccaac taatccgagc tggggttgga gctggttgga acgatggatg gcagcccgac   660
cttgggagag ccgtagccat atggataaag agttgaatga ccactcctcc ataagaagct   720
caagccgcag cattaccggt ggagaaatca gcaagtcatt tgctcgtttc cagctcaatt   780
cggaaaagca ctctccaaca gccagccaga atcctggctc ccctagcttt cagtccactc   840
cttccaagcc agcttcatca tctgctaaga aaccaaagaa ggtaagtcca agcccaaggg   900
gcagctgggt tatggacgag gactccaaaa gcttggtcag tgtacactct gaccggttcc   960
ggaggcactc cattgccggt tcatcggtga gagatgacga gagccttgct agctctccag  1020
cagttccaag ctacatggtg ccaactcaat ctgcaaaagc caagtccagg acacaaagtc  1080
cattagcctc agaaaatgca aaagcagaga aaggttcctt tgggagtgca aagaagcggc  1140
tttctttccc agcttcacct gccaggccaa ggcgccattc aggtccacca aaggttgaaa  1200
gcagcagctt aaatgcagag ttagctgtgg acaagggtgt ggacagttga tcatacaagt  1260
aaaaggatgg aaaagcatta aagtaggatt gaaaatatat cactgaagaa ataaaacaaa  1320
aagagtttat ttaaaaaaaa aaaaaaaaaa aaaaaaaaa aa                     1362

SEQ ID NO: 153         moltype = AA  length = 218
FEATURE                Location/Qualifiers
source                 1..218
                       mol_type = protein
                       organism = Glycine max
REGION                 1..218
                       note = Ceres CLONE ID no.520008
REGION                 1..218
                       note = Score of 156.2 for HMM of FIGURE 4.
REGION                 1..218
                       note = Functional Homolog Of Ceres SEEDLINE ID no. ME24091
                         at SEQ ID NO.136
SEQUENCE: 153
MFMDPTNPSW GWSWLERWMA ARPWESRSHM DKELNDHSSI RSSSRSITGG EISKSFARFQ   60
LNSEKHSPTA SQNPGSPSFQ STPSKPASSS AKKPKKVSPS PRGSWVMDED SKSLVSVHSD  120
RPFRRHSIAGS SVRDDESLAS SPAVPSYMVP TQSAKAKSRT QSPLASENAK AEKGSFGSAK  180
KRLSFPASPA RPRRHSGPPK VESSSLNAEL AVDKGVDS                          218

SEQ ID NO: 154         moltype = AA  length = 445
FEATURE                Location/Qualifiers
source                 1..445
                       mol_type = protein
                       organism = Arabidopsis thaliana
REGION                 1..445
                       note = Public GI ID no.7413581
REGION                 1..445
                       note = Score of 1020.8 for HMM of FIGURE 4.
REGION                 1..445
                       note = Functional Homolog Of Ceres SEEDLINE ID no. ME24091
                         at SEQ ID NO.136
REGION                 114..134
                       note = Pfam Name: IQ Pfam Description: IQ
                         calmodulin-binding motif
SEQUENCE: 154
MGKKAKWFSS VKKAFSPDSK SKQKLAEGQN GVISNPPVVD NVRQSSSSPP PALAPREVRV   60
AEVIVERNRD LSPPSTADAV NVTATDVPVV PSSSAPGVVR RATPTRFAGK SNEEAAAILI  120
QTIFRGYLAR RALRAMRGLV RLKLLMEGSV VKRQAANTLK CMQTLSRVQS QIRARRIRMS  180
EENQARQKQL LQKHAKELAG LKNGDNWNDS IQSKEKVEAN LLSKYEATMR RERALAYSYS  240
HQQNWKNNSK SGNPMFMDPS NPTWVPRKNK SNSNNDNAAS VKGSINRNEA AKSLTRNGST  300
QPNTPSSARG TPRNKNSFFS PPTPSRLNQS SRKSNDDDSK STISVLSERN RRHSIAGSSV  360
RDDESLAGSP ALPSYMVPTK SARARLKPQS PLGGTTQENE GFTDKASAKK RLSYPTSPAL  420
PKPRRFSAPP KVESGGVTVT NGAGS                                       445

SEQ ID NO: 155         moltype = DNA  length = 1806
FEATURE                Location/Qualifiers
source                 1..1806
                       mol_type = other DNA
                       organism = Zea mays
misc_feature           1..1806
                       note = Ceres CLONE ID no.228069
misc_feature           1..1806
                       note = Encodes the peptide sequence at SEQ ID NO 156
SEQUENCE: 155
gagccgcgga ggagcagcgg cgcatcgcaa cactaaccaa agtcctcctc tccaggtgcc   60
gagccagggt gactgttccg aggagcgtgg cgtggaccca tggggaagaa gggcaagtgg  120
ttcggtgccg tcaagaaggt cttcagcccc gaatccaagg agaagaaaga ggagaggcta  180
aggaggaaat cagcagctag caacccagca ccggtagatc tgaccccatc tacctccctg  240
gaagtcaatg tttcggtgcc accccctccg gctcctcctc cagttcctcg ccagaccgac  300
gaggtcaggg tccccgaagc cgagcaggag cagagcaagc atgtcaccct ggaggaggcc  360
cctgctgctg ctgctgcccc agcacaggcg tcggtgctga cacctggtgc gccaaccgaa  420
gagctcgccg caatcaagat ccagaccgcc ttccgaggtt acctggcaag gagggcacta  480
agagcactac gaggccttgt acgattgaag tcattggttg agggtaattc agttaagcgt  540
caatctgcaa gcactctgcg ctgtatgcaa actctatcgc gggtgcagtc acaaatacga  600
tctaggagag caaagatgtc cgaggagaac caggccctcc aacgccagct cctacttaaa  660
caggaactgg agaatttcag aatggggtgag aactgggacg cagcactca atccaaggag  720
```

```
caaatcgagg caagcctaat aagcaggcaa gaggcagcga taagaagaga aagagctctt   780
gcatatgcat tttcacatca gtggaagagc acatcaagat ctgcgaaccc aatgtttgta   840
gacccaaata acttgcagtg gggctggagc tggttggagc gctggatggc agcaaaacct   900
tgggagggac gcaatgggac cgacaaggag agcaacattg atcgcggctc cgtcaagaat   960
atgagcttga accttggagt tggagagggt gagatcaaca aagcttttcaa ccgccgggac  1020
tcaaagccag agaagccatc accaccgact ccaaaaccgg cccgtccagc ttccaggcaa  1080
tccccttcga cgccctctgc tagagtggcc ccaatacctg cgaggaggaa atccagcacg  1140
ccaaagaatg ggctttcaca ggtggacgat gacgtgagga gcgtgctcag tgtgcagtct  1200
gagcgaccaa ggaggcacag catagccacg acgtcgacca tgcgggacga tgagagcctg  1260
gcgagctccc cgtcgctccc gagctacatg gttcccacag aatctgcgag ggccaaatct  1320
cgcacagcaa cggccaatgg cgcagagacg cctgagaaag gaggctctgc tggaccagtc  1380
aagaagaggt tgtctttcca aggtggagct gcggctgcct caccgatgcg acggcattct  1440
ggccctccca aggtggagag cgctgtgaag gacattgctg cgccaccaca gcctgaggcc  1500
ttggtagcca atggtggtgg aagcaagtga cttgtattga caagttccag gatgggggag  1560
cgggttatgg tcttatggag ggacatgttt catccgtgaa cagaagttaa gagtggtgcc  1620
ggatctacga atggtttgaa ttgtttttccc gttacaacca cattgtttgc tgtataagat  1680
tcactgtacc tgccagttgg ttccatttgt tgttttctgt aaaacaaaca tcaatttgtc  1740
actagaatct gtgatgcttg tatgtaaaca ggtcctctat ttatgtgagc catatatttc  1800
attttc                                                             1806

SEQ ID NO: 156           moltype = AA  length = 476
FEATURE                  Location/Qualifiers
source                   1..476
                         mol_type = protein
                         organism = Zea mays
REGION                   1..476
                         note = Ceres CLONE ID no.228069
REGION                   1..476
                         note = Score of 953.8 for HMM of FIGURE 4.
REGION                   1..476
                         note = Functional Homolog Of Ceres SEEDLINE ID no. ME24091
                          at SEQ ID NO.136
REGION                   108..128
                         note = Pfam Name: IQ Pfam Description: IQ
                          calmodulin-binding motif
SEQUENCE: 156
MGKKGKWFGA VKKVFSPESK EKKEERLRRK SAASNPAPVD LTPSTSLEVN VSVPPPPAPP    60
PVPRQTDEVR VPEAEQEQSK HVTLEEAPAA AAAPAQASVL PPGAPTEELA AIKIQTAFRG   120
YLARRALRAL RGLVRLKSLV EGNSVKRQSA STLRCMQTLS RVQSQIRSRR AKMSEENQAL   180
QRQLLLKQEL ENFRMGENWD DSTQSKEQIE ASLISRQEAA IRRERALAYA FSHQWKSTSR   240
SANPMFVDPN NLQWGWSWLE RWMAAKPWEG RNGTDKESNI DRGSVKNMSL NLGVGEGEIT   300
KAFNRRDSKP EKPSPPTPKP ARPASRQSPS TPSARVAPIP ARRKSSTPKN GLSQVDDDVR   360
SVLSVQSERP RRHSIATTST MRDDESLASS PSLPSYMVPT ESARAKSRTA TANGAETPEK   420
GGSAGPVKKR LSFQGGAAAA SPMRRHSGPP KVESAVKDIA APPQPEALVA NGGGSK       476

SEQ ID NO: 157           moltype = DNA  length = 1703
FEATURE                  Location/Qualifiers
source                   1..1703
                         mol_type = other DNA
                         organism = Glycine max
misc_feature             1..1703
                         note = Ceres CLONE ID no.467508
misc_feature             1..1703
                         note = Encodes the peptide sequence at SEQ ID NO 158
SEQUENCE: 157
aaaccatcct ctcttagcat ttggcaagat ctgatttccc tcttcacaag gagagaaata    60
gaaaggcata tgatcttctt caagttgcaa tcttttttaga gagagagggt tagaagaaca   120
acatacttga gatctgtcac tttgtttgag ttcagatctt caaagtttcc ttccttgttc   180
ttttggtgca aaggatcaaa ttaaggaatg ccaaatgggg aggaagggga attggttttc   240
cagtgtgatg aaagctctca gtcctgactc aaaggagaag aaagaacaga aatcaagtaa   300
atctaagaag aaatggtttg ggaagcaaaa attggagact tcagtctcat actcagaagc   360
tcataaagca ccaccaccac cgcgacctat tcctccacca gaagcgatta aattaactga   420
tattgaaaat gaaatcagtc atgatcacga ctatgttgtt gaagttgcaa ctgccatgga   480
tgccgaggaa cctgttcctt ctgttcagat agaacctgtt aggggttgaag ctgccccaat   540
tgctcattat gctggtaaac caaggatgga gtggcagct atcaaaattc aaacagcttt   600
tcgtggatac ttgcaagaa gagcattgcg ggctttaagg gggctggtca ggttgaaatt   660
attgatggaa gggccagttg ttaaacgcca agccacaagt accctccact ctatgcagac   720
attatctcgc ttgcagtctc agattcgttc aaggaggatc agaatgttag aggagaatca   780
ggctctgcag agacagctct tacagaagca tgcaagagg cttgaagca tgcggatgag   840
agaggaatgg gatgacagcc tacaatcaaa agaacaaatc gaagccagt tacttagcaa   900
gtatgaagct actacgagaa gagaaagagc gctggcttat gcattcactc atcagcaaaa   960
ttggaagaac tcatctagat ctgtaaatcc aatgttcatg gatccaacca atccaagctg  1020
gggttggagc tggttggaac gatggatggc agcccgacct tgggagagcc gtagccatat  1080
agagaagaag ttgaatgacc actcatccgt aagaagctca agaagcagtg ttaccggtgg  1140
agaaatcagc aagtcatttg ctcgtttcca gctcaatttg gaaaagcact tccaacagc   1200
ctgccagaat cctggctcac ctagctttca gtccactcct tccaagccag cttcaatatc  1260
tgctaagaaa ccaagaagg taagtccaag cccaagggc agctgggtta cagacgagga   1320
ctccaaaagc ttggtcagtg tacagtcaga ccggttccgg aggcactcca ttgccggttc  1380
attggtgaga gatgatgaga gccttgctag ctctccagca gttccaagct acatggtgcc  1440
```

```
aactcaatct gcaaaagcca agtccaggac acaaagtcca ttagcccag aaaatggaaa   1500
agcagagaaa ggttcctttg ggagtgcgaa gaagcggctt tctttcccag cttcacctgc   1560
caggccaagg cgccattcag gtccaccaaa ggtagaaagc agcagcttaa atgcagagtt   1620
agctgtggac aagggtgtgg acagttgatc atacaagtaa aaggatggaa aaacattaaa   1680
gtaggattga aaatatatca ctg                                          1703

SEQ ID NO: 158           moltype = AA   length = 477
FEATURE                  Location/Qualifiers
source                   1..477
                         mol_type = protein
                         organism = Glycine max
REGION                   1..477
                         note = Ceres CLONE ID no.467508
REGION                   1..477
                         note = Score of 852.8 for HMM of FIGURE 4.
REGION                   1..477
                         note = Functional Homolog Of Ceres SEEDLINE ID no. ME24091
                             at SEQ ID NO.136
REGION                   119..139
                         note = Pfam Name: IQ Pfam Description: IQ
                             calmodulin-binding motif
SEQUENCE: 158
MGRKGNWFSS VMKALSPDSK EKKEQKSSKS KKKWFGKQKL ETSVSYSEAH KAPPPPRPIP   60
PPEAIKLTDI ENEISHDHDY VVEVATAMDA EEPVPSVQIE PVRVEAAPIA HYAGKPKDEV   120
AAIKIQTAFR GYLARRALRA LRGLVRLKLL MEGPVVKRQA TSTLHSMQTL SRLQSQIRSR   180
RIRMLEENQA LQRQLLQKHA RELESLRMGE EWDDSLQSKE QIEAKLLSKY EATTRRERAL   240
AYAFTHQQNW KNSSRSVNPM FMDPTNPSWG WSWLERWMAA RPWESRSHMD KELNDHSSVR   300
SSSSRSITGGE ISKSFARFQL NLEKHSPTAC QNPGSPSFQS TPSKPASISA KKPKKVSPSP   360
RGSWVTDEDS KSLVSVQSDR FRRHSIAGSL VRDDESLASS PAVPSYMVPT QSAKAKSRTQ   420
SPLAPENGKA EKGSFGSAKK RLSFPASPAR PRRHSGPPKV ESSSLNAELA VDKGVDS      477

SEQ ID NO: 159           moltype = DNA   length = 1495
FEATURE                  Location/Qualifiers
source                   1..1495
                         mol_type = other DNA
                         organism = Gossypium hirsutum
misc_feature             1..1495
                         note = Ceres CLONE ID no.1829581
misc_feature             1..1495
                         note = Encodes the peptide sequence at SEQ ID NO 160
SEQUENCE: 159
attattttca atgcaattta agagttttat ttattttatg ttataaattt tttaacctct   60
aaatatgatt tgaaatgtta attccattgg ttgtttttgg ttttgaagga gaatttattg   120
aggaatgggc aaaaaaggaa gctggtttac tgctgtgaag aaagttctaa gccttgaacc   180
caacaaagaa gagaagattc aaaaatccaa gaaaaatggg gttaaattac ctgagaagat   240
caaaggaagc aaacgtgaca actggttcgc tccggccacc accatggtga ccggcgcgtt   300
ggttcgcctt acttttgtcg cacactactt gggaaaatca atggaggaaa tagctactgt   360
taagattcaa actgtgtttc gaggatacct ggcgaggaag gcattgcgag atttgagagg   420
gttagagagg ttgaaatcat tgatacaagg gcaatccatg aaacgacaag ccactattac   480
gttacgatgc atgcggacac ttgctcgagt gcagtcccaa actcgaacaa ggcaactcag   540
agtgtctgaa caaaaccgag cacttcaaaa gcatctttcaa ataaatacg aaaaacagtt   600
gcaaaattcc aaatcttaca tgggagaaga ttggaatgta agtactaagt ctaaagcaga   660
aatgcaagca aacaacaat atagacaagt agcagccatg cgaagggaga gagctttagc   720
ttactcattt actcatcagc gatcctggaa ggtcacttgt agatcgatga atcacacatc   780
tatggatcca tttaatccta aatggagctg gagttggtta gagcgatgga tgtcaactcg   840
accatgggag attcaaaatg caccggataa caatgatcat ggcccaagta agagtgttga   900
tgctgagata accaaagcta agtctcaaag tgatgttaac aatgatcaca ataaacaatc   960
ttcaacaccg gcaaaaccga ttcgacctcc gaaccgtagg tcctcttcga ctccaccgtc   1020
taaaacgcat tctatttcta gcaagaaggg attggaaagc ccagtccga cacgaattca   1080
gttgcctgat tgttacaaga ggcatagcat cggaggctta tcattggaga gagacgatga   1140
ggtctttgca aactcaccac ctaataataa aataccggca cgttcgtcat caaaggaccg   1200
gtctcgacca ccgagcatta atagaaatcc agttaatact aggagacatt ctggtcctcc   1260
gaaagttgat atttttccca actaaggaag aaatgccaaa caatgacaaa ggcaggtagt   1320
ttatgaagca tagacacttt agtcgcgagt gccggccaca tgtttaatat tgaaatggct   1380
ccgacacaat caaatgtgtg ttggttatat gacgatatat ttttttcaaaa aatcaaatac   1440
tatcagaaaa aaatataaag aaagattaat tggataaaaa aaaaaaaaaa aaaaa         1495

SEQ ID NO: 160           moltype = AA   length = 386
FEATURE                  Location/Qualifiers
source                   1..386
                         mol_type = protein
                         organism = Gossypium hirsutum
REGION                   1..386
                         note = Ceres CLONE ID no.1829581
REGION                   1..386
                         note = Score of 365.8 for HMM of FIGURE 4.
REGION                   1..386
                         note = Functional Homolog Of Ceres SEEDLINE ID no. ME24091
                             at SEQ ID NO.136
```

| REGION | 75..95 |
| --- | --- |
| | note = Pfam Name: IQ Pfam Description: IQ calmodulin-binding motif |

SEQUENCE: 160
```
MGKKGSWFTA VKKVLSLEPN KEEKIQKSKK NGVKLPEKIK GSKRDNWFAP ATTMVTGALV    60
RLTLSPHYLG KSMEEIATVK IQTVFRGYLA RKALRDLRGL ERLKSLIQGQ SMKRQATITL   120
RCMRTLARVQ SQTRTRQLRV SEQNRALQKH LQTKYEKQLQ NSKSYMGEDW NVSTKSKEQM   180
QAKQQYRQVA AMRRERALAY SFTHQRSWKV TCRSMNHTSM DPFNPKWSWS WLERWMSTRP   240
WEIQNAPDNN DHGPSKSVGA EITKAKSQSD VNNDHNKQSS TPAKPIRPPN RRSSSTPPSK   300
THSISSKKGL ESPSPTRIQL PDCYKRHSIG GLSLERDDEV FANSPPNNKI PARSSSKDRS   360
RPPSINRNPV NTRRHSGPPK VDIFSN                                       386
```

| SEQ ID NO: 161 | moltype = DNA length = 1543 |
| --- | --- |
| FEATURE | Location/Qualifiers |
| source | 1..1543 |
| | mol_type = other DNA |
| | organism = Zea mays |
| misc_feature | 1..1543 |
| | note = Ceres CLONE ID no.229668 |
| misc_feature | 1..1543 |
| | note = Encodes the peptide sequence at SEQ ID NO 162 |

SEQUENCE: 161
```
cttggaagtc aatctttcgg tgccaccgcc tccagctcct ccccagttc ttcaccaggc     60
cgaggaggtt ggggtccctg aagccgagca ggagcagagc aagcatgtcg ccgtggagga   120
ggcccctgct gccgcccag cgcaggcgtc ggtgctgcca cctgctgtgc aacccaaga    180
gctcgccgca gtcaagatcc agaccgcctt ccgaggttac ctggcaagga gggcactacg   240
agcactgcga ggccttgttc gattgaagtc attggttgag ggtaattcag taaagcgtca   300
atctgcaagc actctgcgct gcatgcaaac tctatcacgg gtgcagtcac agatatcttc   360
caggagagca aagatgtccg aggagaacca ggctctccaa cgccagctcc tacttaaaca   420
ggaactggag aatttcagaa tgggtgagaa ctgggatgac agcacccaat ccaaggagca   480
aatcgaggca agcctgataa gcaggcaaga ggcggcgata agaagagaaa gagcgcttgc   540
atatgcattt tcacaccagt ggaagagtac atcgagatct gtcaacccaa tgttttgtaga  600
cccaaacaac ctgcagtggg gctgagctg ctggagctg tggatggcag caaaaccatg    660
ggaaggccgc aatggggctg acaaggagag caacattgac cggggatccg ttaagagcat   720
gagcttgaac cttggagagg gtgagatcac aaaagctttc aaccgccggg actcaaagct   780
agaaaagcca tcgccgccaa ctccaagacc ggcccgtcca acttccaggc attccccttt   840
gacgccctct gctagagtgg caccgatacc tgcgaggaga aaatctgtca cgcccaagaa   900
cgggctttca caggtggacg atgacgcgag gagcgtgctc agtgtgcagt ctgagcggcc   960
aaggaggcac agtatagcca cctcgactgt gcgggacgac gagagcctca cgagctcccc  1020
gtcgctccca agctacatgg ttcccacaga atctgcaagg gccaaatctc gcctccaggg  1080
ttcagcaatg gccaatggcg cagagacacc tgagaaagga ggctcaactg gaccagccaa  1140
gaagaggtta tccttccagg gtggaactgc ggctgcctcg ccaatgcgac gcattctgg   1200
tcctcccaag gtggagatcg cgccaccaca accagaggcc ttggtagtca atggtggaag  1260
caagtgacac atatgtgatg agtaccagga tgagaaacgg attatgaaga tattagtttc  1320
attttcatcc atgaatagaa gttaaaagtg gtatcatatc tatgaatggt ttcaattgtt  1380
tttctgttac aaccacatta tttgctatat acgattcaca gtaccgtcca gttgattcca  1440
ttggttgttt ctgtaaaaca aatatcaatt tgtcactaga atctgtgatg tttgtatgta  1500
aacagatcct ctatttatgt gagacatata tttctttttct ttc                    1543
```

| SEQ ID NO: 162 | moltype = AA length = 421 |
| --- | --- |
| FEATURE | Location/Qualifiers |
| source | 1..421 |
| | mol_type = protein |
| | organism = Zea mays |
| REGION | 1..421 |
| | note = Ceres CLONE ID no.229668 |
| REGION | 1..421 |
| | note = Score of 908.3 for HMM of FIGURE 4. |
| REGION | 1..421 |
| | note = Functional Homolog Of Ceres SEEDLINE ID no. ME24091 at SEQ ID NO.136 |
| REGION | 60..80 |
| | note = Pfam Name: IQ Pfam Description: IQ calmodulin-binding motif |

SEQUENCE: 162
```
LEVNLSVPPP PAPPPVLHQA EEVGVPEAEQ EQSKHVAVEE APAAAPAQAS VLPPAVPTQE    60
LAAVKIQTAF RGYLARRALR ALRGLVRLKS LVEGNSVKRQ SASTLRCMQT LSRVQSQISS   120
RRAKMSEENQ ALQRQLLLKQ ELENFRMGEN WDDSTQSKEQ IEASLISRQE AAIRRERALA   180
YAFSHQWKST SRSVNPMFVD PNNLQWGWSW LERWMAAKPW EGRNGADKES NIDRGSVKSM   240
SLNLGEGEIT KAFNRRDSKL EKPSPPTPRP ARPTSRHSPL TPSARVAPIP ARRKSVTPKN   300
GLSQVDDDAR SVLSVQSERP RRHSIATSTV RDDESLTSSP SLPSYMVPTE SARAKSRLQG   360
SAMANGAETP EKGGSTGPAK KRLSFQGGTA AASPMRRHSG PPKVEIAPPQ PEALVVNGGS   420
K                                                                  421
```

```
SEQ ID NO: 163          moltype = AA  length = 500
FEATURE                 Location/Qualifiers
source                  1..500
                        mol_type = protein
                        note = subspecies = indica
                        organism = Oryza sativa
REGION                  1..500
                        note = Public GI ID no.125550655
REGION                  1..500
                        note = Score of 911.0 for HMM of FIGURE 4.
REGION                  1..500
                        note = Functional Homolog Of Ceres SEEDLINE ID no. ME24091
                         at SEQ ID NO.136
REGION                  107..121
                        note = Pfam Name: IQ Pfam Description: IQ
                         calmodulin-binding motif
SEQUENCE: 163
MGKKGKWFGA VKKVFSPESK EKKEERLRRK LAASNPNPPD LTPSASLEVN VSVPPPPPPP  60
PVQQIEEVKV PEVEQEQSKH VTVEAVPEAV PVPAQTSSLP PGVSREEQAA IKIQTAFRGY 120
LLSENSSWLF ISSAAFIYHC VGANITKARR ALRALRGLVR LKSLVEGNSV KRQAASTLRC 180
MQTLARVQSQ IRSRRLKMSE ENQALQRQLL LKQELESLRM GEQWDDSTQS KEQIEASLIS 240
RQEAAVRRER ALAYAFSHQW KSTSRSVNPM FVDPNNPQWG WSWLERWMAA KPWEGRAGTD 300
KESNLDRASA KSASLNLGEG EITKAFNRRG SKPDKSSPTT PKLTRPASRQ SPSTPSAKVS 360
PIFAKKKSAT PKNGLSQVDD DAKSVFSVQS ERPRRHSIAT STVRDDESLA SSPSVPSYMA 420
PTKSARAKLR LQGSAVTDGA ETPPEKVASV GSVKKKLSFQ AGMVPPSPMR RHSGPPKVEV 480
VKDIAEPPQP EALVINGGSK                                            500

SEQ ID NO: 164          moltype = DNA  length = 1923
FEATURE                 Location/Qualifiers
source                  1..1923
                        mol_type = other DNA
                        organism = Arabidopsis thaliana
misc_feature            1..1923
                        note = Ceres CLONE ID no.106263
misc_feature            1..1923
                        note = Encodes the peptide sequence at SEQ ID NO 165
SEQUENCE: 164
acaaatactc ttcttcacac agctttgaat ccatctgtct tctcctctct ctctcttctc   60
catttgcaat tacgataatg tgaaagcaat aagaagagga aaagttatct tcgcacctca  120
gcaaagatcc aatcgattcg attcttaagc ttttcgtct tctccgataa ggtcactact  180
tagaagccgc gttgtggttt agttgactcc tccaggtttt atcttcaagc ttttcgtct  240
atcagatctg gtgtcactgt cttctcatag gattacatag agatgggaa aaaagctaaa  300
tggttttcaa gtgttaagaa agcattcagc ccagattcaa agaagtcgaa gcaaaaattg  360
gctgagggac aaaatggtgt tatctctaat cctcctgttg tggataatgt tagacaatct  420
tcttcttctc ctcctcctgc tcttgctcct cgtgaagtga gagtagctga agtgattgtt  480
gaacggaaca gggatctttc acctccttct acagcagatg ctgtgaatgt tacagctact  540
gatgtyccctg tagttccatc ttcatctgct cctggtgttg ttcgtcgcgc tacacctact  600
cgatttgctg gaaagtcaaa cgaagaagcc gctgctatct tgatccagac tatatttaga  660
ggttatttgg caaggagagc gttgcgggca atgaggggtt tggtcagact taagttattg  720
atggaaggat ctgttgttaa gcggcaagct gcaaatactc taaaatgtat gcagactctc  780
tctcgtgtac agtcgcagat ccgagctagg agaatcaggr tgtcagaaga gaatcaggct  840
cgccagaaac aactccttca gaaacatgct aaagagctag ctggcttgaa gaacggggat  900
aactggaatg atagcattca atcaaaggag aaagttgaag cgaatttgct aagcaagtac  960
gaggcaacaa tgagaaggga aagggcattg gcttattcat actctcatca scaaaactgg 1020
aagaacaact ctaaatctgg aaacccgatg ttcatggatc caagcaaccc gacatggggt 1080
tggagctggt tggagagatg gatggctggt aggccactag agagttccga gaaagaacaa 1140
agcaacagca acaatgacaa tgctgcctcg gtcaagggct ctattaaccg caacgaagct 1200
gcaaaatctc taacccgcaa tggctcaact caaccaaaca caccatcatc cgcaagaggg 1260
accccaagaa acaaaaacag tttcttctca cctccaactc cctcaaggct aaaccaatcc 1320
tcgaggaaat ccaatgacga cgactccaaa agcacaatct cggtcctgtc cgagaggaac 1380
cgcagacaca scattgctgg ttcatcagtc asagacgatg agagcctcgc tggctcacca 1440
gctctcccga gctacatggt tccaactaaa tcagctcgag ccaggctcaa gccccaaagc 1500
ccattaggtg gtaccacaca ggaaaacgaa gggttcacag acaaggcatc agctaagaaa 1560
cggctctcgt atccaacttc gcctgcattg cctaaaccac ggcggttctc agctcccct  1620
aaggtggaga gtgcggcgt taccgtgacc aacggagcag gcagctgagg tatttatttt 1680
aatataatta ttttcccact tatgaatgtg tccgagattg ttgtctctta tgtgttccct 1740
tcatttcgta attcattttgt gcagtgtaag cgccagtcat ttatttttt actataataa 1800
attttataac ctttttaaaat tcatgttctt ttgtttctt gaatatttaa gttatttta  1860
ttaatgttgg atgaattgga atatgatgat gttatttgta ttgtaatgca gatcctttaa 1920
agc                                                               1923

SEQ ID NO: 165          moltype = AA  length = 461
FEATURE                 Location/Qualifiers
source                  1..461
                        mol_type = protein
                        organism = Arabidopsis thaliana
REGION                  1..461
                        note = Ceres CLONE ID no.106263
```

```
REGION                  1..461
                        note = Score of 1104.8 for HMM of FIGURE 4.
REGION                  1..461
                        note = Functional Homolog Of Ceres SEEDLINE ID no. ME24091
                          at SEQ ID NO.136
SITE                    88
                        note = Xaa is any aa, unknown, or other
REGION                  115..135
                        note = Pfam Name: IQ Pfam Description: IQ
                          calmodulin-binding motif
SITE                    180
                        note = Xaa is any aa, unknown, or other
SITE                    243
                        note = Xaa is any aa, unknown, or other
SITE                    370
                        note = Xaa is any aa, unknown, or other
SITE                    377
                        note = Xaa is any aa, unknown, or other
SEQUENCE: 165
MGKKAKWFSS VKKAFSPDSK KSKQKLAEGQ NGVISNPPVV DNVRQSSSSP PPALAPREVR      60
VAEVIVERNR DLSPPSTADA VNVTATDXPV VPSSSAPGVV RRATPTRFAG KSNEEAAAIL     120
IQTIFRGYLA RRALRAMRGL VRLKLLMEGS VVKRQAANTL KCMQTLSRVQ SQIRARRIRX     180
SEENQARQKQ LLQKHAKELA GLKNGDNWND SIQSKEKVEA NLLSKYEATM RRERALAYSY     240
SHXQNWKNNS KSGNPMFMDP SNPTWGWSWL ERWMAGRPLE SSEKEQSNSN NDNAASVKGS     300
INRNEAAKSL TRNGSTQPNT PSSARGTPRN KNSFFSPPTP SRLNQSSRKS NDDDSKSTIS     360
VLSERNRRHX IAGSSVXDDE SLAGSPALPS YMVPTKSARA RLKPQSPLGG TTQENEGFTD     420
KASAKKRLSY PTSPALPKPR RFSAPPKVES GGVTVTNGAG S                        461

SEQ ID NO: 166          moltype = AA  length = 430
FEATURE                 Location/Qualifiers
source                  1..430
                        mol_type = protein
                        organism = Arabidopsis thaliana
REGION                  1..430
                        note = Public GI ID no.15231175
REGION                  1..430
                        note = Score of 592.8 for HMM of FIGURE 4.
REGION                  1..430
                        note = Functional Homolog Of Ceres SEEDLINE ID no. ME24091
                          at SEQ ID NO.136
REGION                  108..128
                        note = Pfam Name: IQ Pfam Description: IQ
                          calmodulin-binding motif
SEQUENCE: 166
MGKSWFSAVK KALSPEPKQK KEQKPHKSKK WFGKSKKLDV TNSGAAYSPR TVKDAKLKEI      60
EEQQSRHAYS VAIATAAAAE AAVAAAQAAA EVVRLSALSR FPGKSMEEIA AIKIQTAFRG     120
YMARRALRAL RGLVRLKSLV QGKCVRRQAT STLQSMQTLA RVQYQIRERR LRLSEDKQAL     180
TRQLQQKHNK DFDKTGENWN DSTLSREKVE ANMLNKQVAT MRREKALAYA FSHQNTWKNS     240
TKMGSQTFMD PNNPHWGWSW LERWMAARPN ENHSLTPDNA EKDSSARSVA SRAMSEMIPR     300
GKNLSPRGKT PNSRRGSSPR VRQVPSEDSN SIVSFQSEQP CNRRHSTCGS IPSTRDDESF     360
TSSFSQSVPG YMAPTQAAKA RARFSNLSPL SSEKTAKKRL SFSGSPKTVR RFSGPPKLES     420
NVTKKDTNLA                                                          430

SEQ ID NO: 167          moltype = AA  length = 461
FEATURE                 Location/Qualifiers
source                  1..461
                        mol_type = protein
                        organism = Arabidopsis thaliana
REGION                  1..461
                        note = Public GI ID no.145357576
REGION                  1..461
                        note = Score of 1118.9 for HMM of FIGURE 4.
REGION                  1..461
                        note = Functional Homolog Of Ceres SEEDLINE ID no. ME24091
                          at SEQ ID NO.136
REGION                  115..135
                        note = Pfam Name: IQ Pfam Description: IQ
                          calmodulin-binding motif
SEQUENCE: 167
MGKKAKWFSS VKKAFSPDSK KSKQKLAEGQ NGVISNPPVV DNVRQSSSSP PPALAPREVR      60
VAEVIVERNR DLSPPSTADA VNVTATDVPV VPSSSAPGVV RRATPTRFAG KSNEEAAAIL     120
IQTIFRGYLA RRALRAMRGL VRLKLLMEGS VVKRQAANTL KCMQTLSRVQ SQIRARRIRM     180
SEENQARQKQ LLQKHAKELA GLKNGDNWND SIQSKEKVEA NLLSKYEATM RRERALAYSY     240
SHQQNWKNNS KSGNPMFMDP SNPTWGWSWL ERWMAGRPLE SSEKEQSNSN NDNAASVKGS     300
INRNEAAKSL TRNGSTQPNT PSSARGTPRN KNSFFSPPTP SRLNQSSRKS NDDDSKSTIS     360
VLSERNRRHS IAGSSVRDDE SLAGSPALPS YMVPTKSARA RLKPQSPLGG TTQENEGFTD     420
KASAKKRLSY PTSPALPKPR RFSAPPKVES GGVTVTNGAG S                        461
```

```
SEQ ID NO: 168        moltype = AA  length = 474
FEATURE               Location/Qualifiers
REGION                1..474
                      note = Public GI ID no.125528277
REGION                1..474
                      note = Score of 1169.9 for HMM of FIGURE 4.
REGION                1..474
                      note = Functional Homolog Of Ceres SEEDLINE ID no. ME24091
                       at SEQ ID NO.136
REGION                142..162
                      note = Pfam Name: IQ Pfam Description: IQ
                       calmodulin-binding motif
source                1..474
                      mol_type = protein
                      note = subspecies = indica
                      organism = Oryza sativa
SEQUENCE: 168
MGKKGNWFSA VKKVFSSSDP DGREAKIEKA DKSRSRRKWP FGKSKKSDPW TSTVAVPTST   60
APPPQPPPPP PTHPIQPQPE EIKDVKAVET DSEQNKHAYS VALASAVAAE AAAVAAQAAA  120
EVVRLTTATT AVPKSPVSSK DELAAIKIQT AFRGYLARRA LRALRGLVRL KSLVDGNAVK  180
RQTAHTLHCT QTMTRVQTQI YSRRVKMEEE KQALQRQLQL KHQRELEKMK IDEDWDHSHQ  240
SKEQWKNSGR TITPTFTDQG NPNWGWSWME RWMTSRPWES RVISDKDPKD HYSTKNPSTS  300
ASRTYVPRAI SIQRPATPNK SSRPPSRQSP STPPSRVPSV TGKIRPASPR DSWLYKEDDL  360
RSITSIRSER PRRQSTGGAS VRDDASLTST PALPSYMQST ESARAKSRYR SLLTDRFEVP  420
ERVPLVHSSI KKRLSFPVAD KPNGEHADKL MERGRRHSDP PKVDPASLKD VPVS        474
```

NUCLEOTIDE SEQUENCES AND CORRESPONDING POLYPEPTIDES CONFERRING MODULATED GROWTH RATE AND BIOMASS IN PLANTS GROWN IN SALINE AND OXIDATIVE CONDITIONS

This application is a Divisional of co-pending application Ser. No. 17/063,395 filed Oct. 5, 2020, which is a Divisional of application Ser. No. 16/694,109 filed on Nov. 25, 2019, now U.S. Pat. No. 11,034,972, which is a Divisional of application Ser. No. 16/265,525, filed on Feb. 1, 2019, now U.S. Pat. No. 10,619,166 which is a Divisional of application Ser. No. 15/962,986, filed on Apr. 25, 2018 now U.S. patent Ser. No. 10/233,461, which is a Divisional of application Ser. No. 15/679,052, filed on Aug. 16, 2017 now U.S. Pat. No. 10,006,043 which is a Divisional of application Ser. No. 13/465,841, filed on May 7, 2012, now issued as U.S. Pat. No. 9,765,355 which is a Divisional of application Ser. No. 11/858,117, filed on Sep. 19, 2007 (abandoned), which is a Continuation in Part of Application No. PCT/US2007/06544, filed on Mar. 14, 2007, which claims priority under 35 U.S.C. § 119 of U.S. Provisional No. 60/782,735, filed on Mar. 14, 2006, the contents of each of which are hereby incorporated by reference in their entirety.

INCORPORATION OF SEQUENCE LISTING

The sequence listing that is contained in the file named "CRES038USD12-revised2", which is 511 KB (as measured in Microsoft Windows®) and was created on Nov. 16, 2022, is filed herewith by electronic submission and is incorporated by reference herein.

TECHNICAL FIELD

The present invention relates to isolated nucleic acid molecules and their corresponding encoded polypeptides able to enhance plant growth under saline and/or oxidative stress conditions. The present invention further relates to using the nucleic acid molecules and polypeptides to make transgenic plants, plant cells, plant materials or seeds of a plant having improved growth rate, vegetative growth, seedling vigor and/or biomass under saline and/or oxidative stress conditions as compared to wild-type plants grown under similar conditions.

BACKGROUND

Plants specifically improved for agriculture, horticulture, biomass conversion, and other industries (e.g. paper industry, plants as production factories for proteins or other compounds) can be obtained using molecular technologies. As an example, great agronomic value can result from enhancing plant growth in saline and/or oxidative stress conditions.

Salinity

A wide variety agriculturally important plant species demonstrate significant sensitivity to saline and/or oxidative stress conditions. Upon salt concentration exceeding a relatively low threshold, many plants suffer from stunted growth, necrosis, and death that results in an overall stunted appearance and reduced yields of plant material, seeds, fruit and other valuable products. Physiologically, plants challenged with salinity experience disruption in ion and water homeostasis, inhibition of metabolism, and damage to cellular membranes that result in developmental arrest and cell death (Huh et al. (2002) *Plant J,* 29(5):649-59).

In many of the world's most productive agricultural regions, agricultural activities themselves lead to increased water and soil salinity, which threatens their sustained productivity. One example is crop irrigation in arid regions that have abundant sunlight. After irrigation water is applied to cropland, it is removed by the processes of evaporation and transpiration. While these processes remove water from the soil, they leave behind dissolved salts carried in irrigation water. Consequently, soil and groundwater salt concentrations build over time, rendering the land and shallow groundwater saline and thus damaging to crops.

In addition to human activities, natural geological processes have created vast tracts of saline land that would be highly productive if not saline. In total, approximately 20% of the irrigated lands are negatively affected by salinity. (Yamaguchi and Blumwald, 2005, *Trends in Plant Science,* 10: 615-620). For these and other reasons, it is of great interest and importance to identify genes that confer improved salt tolerance characteristics to thereby enable one to create transgenic plants (such as crop plants) with enhanced growth and/or productivity characteristics in saline conditions.

Despite this progress, today there continues to be a great need for generally applicable processes that improve forest or agricultural plant growth to suit particular needs depending on specific environmental conditions. To this end, the present invention is directed to advantageously manipulating plant tolerance to salinity in order to maximize the benefits of various crops depending on the benefit sought, and is characterized by expression of recombinant DNA molecules in plants. These molecules may be from the plant itself, and simply expressed at a higher or lower level, or the molecules may be from different plant species.

Oxidative Stress

Plants lead a sessile lifestyle and so are generally destined to reside where their seed germinates. Consequently, they can be exposed to unfavorable environmental conditions arising from weather, pollution and location. Stress conditions, such as extremes in temperature, drought and desiccation, salinity, soil nutrient content, heavy metals, UV radiation, pollutants such as ozone and $SO_2$, mechanical stress, high light and pathogen attack, have a large impact on plant growth and development. These types of stress exposure induce formation of toxic oxygen species, which are generated in all aerobic cells and are associated with oxidative damage at the cellular level. Several recently published reports have characterized toxic oxygen species generation and the subsequent oxidative damage caused by abiotic stresses (see Larkindale and Knight (2002); Borsani et al. (2001); Lee et al (2004); Aroca et al (2005); Luna et al (2005); and Noctor et al (2002)).

The toxic oxygen species are referred to as reactive oxygen species (ROS), reactive oxygen intermediates (ROI) or activated oxygen species (AOS) and are partially reduced or activated derivatives of oxygen. ROS/ROI/AOS include the oxygen-centered superoxide ($O_2$) and hydroxyl (—OH) free radicals as well as hydrogen peroxide ($H_2O_2$), nitric oxide (NO) and $O_2^1$. These oxygen species are generated as byproducts from reactions that occur during photosynthesis, respiration and photorespiration, and are predominantly formed in the chloroplasts, mitochondria, endoplasmic reticulum, microbodies (e.g. peroxisomes and glyoxysomes), plasma membranes and cell walls. While the toxicity of $O_2^-$ and $H_2O_2$ themselves is relatively low, their metal-dependent conversion to highly toxic —OH is thought to be responsible for the majority of the biological damage associated with these molecules.

Oxidative stress damages cell structure and affects cell metabolism and catabolism. Membrane lipids are subject to oxidation by ROS/ROI/AOS, resulting in accumulation of high molecular weight, cross-linked fatty acids and phospholipids. Oxidative attack on proteins results in site-specific amino acid modifications, fragmentation of the peptide chain, aggregation of cross-linked reaction products, altered electrical charge and increased susceptibility to proteolysis, all of which frequently leads to elimination of enzyme activity. ROS/ROI/AOS that generate oxygen free radicals, such as ionizing radiation, also induce numerous lesions in DNA at both the sugar and base moieties which cause deletions, mutation and other lethal genetic effects such as base degradation, single strand breakage and cross-linking to proteins. Morphologically, the adverse effects of high levels of ROS accumulation are manifested as stunted growth and necrotic lesions.

Although capable of producing damage, ROS/ROI/AOS are also key regulators of metabolic and defense pathways, playing roles as signaling or secondary messenger molecules. For example, pathogen-induced ROS/ROI/AOS production is critical in disease resistance where these molecules are involved at three different levels: penetration resistance, hypersensitive response (HR) and systemic acquired resistance (Levine et al. (1994); Lamb and Dixon (1997); Zhou et al. (2000); Aviv et al. (2002)). In penetration resistance, ROS/ROI/AOS function by reinforcing cell walls through polyphenolic cross-linking. With respect to hypersensitive response, $H_2O_2$ is an active signaling molecule whose effect is dose dependent. At high dosages, $H_2O_2$ triggers hypersensitive cell death and thus restricts the pathogen to local infection sites (Lamb and Dixon (1997)) while low dosages block cell cycle progression (Reichheld et al. (1999)) and signal secondary wall differentiation (Potikha et al. (1999)). Lastly, ROS/ROI/AOS molecules play a role in broad-spectrum systemic acquired disease resistance by triggering micro-HR systematically after the first pathogen inoculation.

In the signal cascades leading to oxidative stress, salicylic acid (SA) has been identified as an important signaling molecule to mediate ROS/ROI/AOS accumulation in various stress conditions, such as salt and osmotic stress (Borsani et al. (2001)), drought (Senaratna et al. (2000)), heat (Dat et al. (1998)), cold (Scott et al. (2004)), UV-light (Surplus et al. (1998)), paraquat (Kim et al. (2003)) and disease resistance against different pathogens (Zhou et al. (2004)). High levels of SA induce $H_2O_2$ production as well as cell death.

Several signaling components required for SA-mediated ROS/ROI/AOS accumulation and gene expression have been characterized. For example, NPR1 is required for SA-induced PR gene expression and disease resistance (Cao et al. (1994)). The mutations in eds1 and eds5 block SA-mediated signaling and enhance disease susceptibility (Rusterucci et al. (2001)). Over-expression of NahG in various plant species also suppresses SA-induced responses to both abiotic and biotic stresses (Delaney et al. (1994)). Recently, Scott and colleagues (2004) reported that chilling treatment induced accumulation of SA in *Arabidopsis* and the degradation of SA by overexpression of NahG enhanced cold tolerance in a transgenic plant.

SA, as a phytohormone, also promotes early flowering (Martinez et al. (2004)). SA at various levels may play different roles in plant growth and stress responses. However, most of the time, the increased tolerance to high levels of SA appears to be beneficial, since it reduces the side effects of SA accumulation while stimulating SA-mediated stress responses.

Similarly, NO is capable of generating ROS/ROI/AOS and is a plant signaling molecule involved in the regulation of seed germination, stomatal closure (Mata and Lamattina (2001); Desikan et al (2002)), flowering time (He et al. (2004)), antioxidant reactions to suppress cell death (Beligni et al. (2002)) and tolerance to biotic and abiotic stress conditions (Mata and Lamattina (2001)). While the effects of NO can be mimicked through the application of sodium nitroprusside (SNP), endogenous NO production in plants results from the activity of a nitric oxide synthase that uses L-arginine (Guo et al. (2003)) as well as nitrate reductase-mediated reactions (Desikan et al (2002)). NO can react with redox centers in proteins and membranes, thereby causing cell damage and inducing cell death.

In order to control the two-fold nature of ROS/ROI/AOS molecules, plants have developed a sophisticated regulatory system which involves both production and scavenging of ROS/ROI/AOS in cells. During normal growth and development, this pathway monitors the level of ROS/ROI/AOS produced by metabolism and controls the expression and activity of ROS/ROI/AOS scavenging pathways. The major ROS/ROI/AOS scavenging mechanisms include the action of the superoxide dismutase (SOD), ascorbate peroxidase (APX) and catalase (CAT) enzymes as well as nonenzymatic components such as ascorbic acid, α-tocopherol and glutathione.

The antioxidant enzymes are believed to be critical components in preventing oxidative stress, in part because pretreatment of plants with one form of stress, and which induces expression of these enzymes, can increase tolerance for a different stress (cross-tolerance) Allen (1995)). In addition, plant lines selected for resistance to herbicides that function by inducing ROS/ROI/AOS generally have increased levels of one or more of these antioxidant enzymes and also exhibit cross-tolerance (Gressel and Galun (1994)).

Plant development and yield depend on the ability of the plant to manage oxidative stress, whether it is via the signaling or the scavenging pathways. Consequently, improvements in a plant's ability to withstand oxidative stress, or to obtain a higher degree of cross-tolerance once oxidative stress has been experienced, has significant value in agriculture. The sequences and methods of the invention provide the means by which tolerance to oxidative stress can be improved, either via the signaling or the scavenging pathways.

The availability and sustainability of a stream of food and feed for people and domesticated animals has been a high priority throughout the history of human civilization and lies at the origin of agriculture. Specialists and researchers in the fields of agronomy science, agriculture, crop science, horticulture, and forest science are even today constantly striving to find and produce plants with an increased growth potential to feed an increasing world population and to guarantee a supply of reproducible raw materials. The robust level of research in these fields of science indicates the level of importance leaders in every geographic environment and climate around the world place on providing sustainable sources of food, feed and energy.

Manipulation of crop performance has been accomplished conventionally for centuries through selection and plant breeding. The breeding process is, however, both time-consuming and labor-intensive. Furthermore, appropriate breeding programs must be specially designed for each relevant plant species.

On the other hand, great progress has been made in using molecular genetic approaches to manipulate plants to provide better crops. Through the introduction and expression of recombinant nucleic acid molecules in plants, researchers are now poised to provide the community with plant species tailored to grow more efficiently and yield more product despite suboptimal geographic and/or climatic environments. These new approaches have the additional advantage of not being limited to one plant species, but instead being applicable to multiple different plant species (Zhang et al. (2004) *Plant Physiol.* 135:615; Zhang et al. (2001) *Proc. Natl. Acad. Sci. USA* 98:12832).

SUMMARY

This document provides methods and materials related to plants having modulated levels of tolerance to salinity and/or oxidative stress. For example, this document provides transgenic plants and plant cells having increased levels of tolerance to salinity and/or oxidative stress, nucleic acids used to generate transgenic plants and plant cells having increased levels of tolerance to salinity and/or oxidative stress, and methods for making plants and plant cells having increased levels of tolerance to salinity and/or oxidative stress. Such plants and plant cells provide the opportunity to produce crops or plants under saline and/or oxidative stress conditions without stunted growth and diminished yields. Increased levels of tolerance to salinity and/or oxidative stress may be useful to produce biomass which may be converted to a liquid fuel or other chemicals and/or to produce food and feed on land that is currently marginally productive, resulting in an overall expansion of arable land.

Methods of producing a plant and/or plant tissue are provided herein. In one aspect, a method comprises growing a plant cell comprising an exogenous nucleic acid. The exogenous nucleic acid comprises a regulatory region operably linked to a nucleotide sequence encoding a polypeptide. The Hidden Markov Model (HMM) bit score of the amino acid sequence of the polypeptide is greater than about 30 using an HMM generated from the amino acid sequences depicted in one of FIGS. 1-6. The plant and/or plant tissue has a difference in the level of tolerance to salinity and/or oxidative stress as compared to the corresponding level in tolerance to salinity and/or oxidative stress of a control plant that does not comprise the exogenous nucleic acid. In some embodiments the amino acid sequence of the polypeptide has an HMM bit score greater than about 400 using an HMM generated from the amino acid sequences depicted in FIG. 1. In some embodiments the amino acid sequence of the polypeptide has an HMM bit score greater than about 30 using an HMM generated from the amino acid sequences depicted in FIG. 2. In some embodiments the amino acid sequence of the polypeptide has an HMM bit score greater than about 120 using an HMM generated from the amino acid sequences depicted in FIG. 3. In some embodiments the amino acid sequence of the polypeptide has an HMM bit score greater than about 150 using an HMM generated from the amino acid sequences depicted in FIG. 4. In some embodiments the amino acid sequence of the polypeptide has an HMM bit score greater than about 425 using an HMM generated from the amino acid sequences depicted in FIG. 5. In some embodiments the amino acid sequence of the polypeptide has an HMM bit score greater than about 550 using an HMM generated from the amino acid sequences depicted in FIG. 6.

In another aspect, a method comprises growing a plant cell comprising an exogenous nucleic acid. The exogenous nucleic acid comprises a regulatory region operably linked to a nucleotide sequence encoding a polypeptide having 85 percent or greater sequence identity to an amino acid sequence set forth in SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140. A plant produced from the plant cell has a difference in the level of tolerance to salinity and/or oxidative stress as compared to the corresponding level in a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence having 85 percent or greater sequence identity to at least a fragment of a nucleotide sequence set forth in SEQ ID NOs. 1, 3, 5, 7, 10, 12, 16, 18, 21, 26, 28, 32, 34, 40, 46, 48, 51, 53, 55, 57, 59, 61, 65, 67, 70, 72, 75, 77, 79, 82, 85, 87, 89, 92, 95, 97, 99, 103, 105, 108, 111, 113, 115, 117, 120, 124, 131, 133, 135, 137, 139, 146, 148, 150, 152, 155, 157, 159, 161, and 164 and to a nucleotide sequence encoding any of the amino acid sequences set forth in the sequence listing. A plant and/or plant tissue produced from the plant cell has a difference in the level of salinity and/or oxidative stress tolerance as compared to the corresponding level in a control plant that does not comprise the exogenous nucleic acid.

Methods of modulating the level of salt tolerance and/or oxidative stress tolerance in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than 30, using an HMM generated from the amino acid sequences depicted in one of FIGS. 1-6. A plant and/or plant tissue produced from the plant cell has a difference in the level of tolerance to salinity and/or oxidative stress as compared to the corresponding level in a control plant that does not comprise the exogenous nucleic acid.

In another aspect, a method comprises introducing into a plant cell an exogenous nucleic acid that comprises a regulatory region operably linked to a nucleotide sequence encoding a polypeptide having 85% percent or greater sequence identity to an amino acid sequence set forth in SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140. A plant and/or plant tissue produced from the plant cell has a difference in the level of tolerance to salinity or oxidative stress as compared to the corresponding level in a control plant that does not comprise the exogenous nucleic acid.

In some embodiments, the methods comprise introducing into the plant cell an exogenous nucleic acid encoding polypeptides selected from the group consisting of SEQ ID NOs: 43, 44, 45, 86, 140, 141, 142, 143, 144, and amino acid coordinates 1 to 135 of SEQ ID NO: 140. A plant and/or plant tissue produced from the plant cell has a difference in the level of tolerance to salinity as compared to the corresponding level in a control plant that does not comprise the exogenous nucleic acid. In some embodiments, the methods comprise introducing into the plant cell an exogenous nucleic acid encoding polypeptides selected from the group consisting of SEQ ID NO: 136, and 141, and a plant and/or plant tissue produced from the plant cell has a difference in the level of tolerance to oxidative stress as compared to the corresponding level in a control plant that does not comprise the exogenous nucleic acid.

In another aspect, a method comprises introducing into a plant cell an exogenous nucleic acid, that comprises a regulatory region operably linked to a nucleotide sequence having 85 percent or greater sequence identity to a nucleotide sequence set forth in SEQ ID NOs: 1, 3, 5, 7, 10, 12, 16, 18, 21, 26, 28, 32, 34, 40, 46, 48, 51, 53, 55, 57, 59, 61, 65, 67, 70, 72, 75, 77, 79, 82, 85, 87, 89, 92, 95, 97, 99, 103, 105, 108, 111, 113, 115, 117, 120, 124, 131, 133, 135, 137, 139, 146, 148, 150, 152, 155, 157, 159, 161, and 164 and to a nucleotide sequence encoding any of the amino acid sequences set forth in the sequence listing. A plant and/or plant tissue produced from the plant cell has a difference in the level of tolerance to salinity or oxidative stress as compared to the corresponding level in a control plant that does not comprise the exogenous nucleic acid.

Plant cells comprising an exogenous nucleic acid are provided herein. In one aspect, the exogenous nucleic acid comprises a regulatory region operably linked to a nucleotide sequence encoding a polypeptide. The HMM bit score of the amino acid sequence of the polypeptide is greater than 30, using an HMM based on the amino acid sequences depicted in one of FIGS. 1-6. The plant and/or plant tissue has a difference in the level of tolerance to salinity or oxidative stress as compared to the corresponding level in a control plant that does not comprise the exogenous nucleic acid. In another aspect, the exogenous nucleic acid comprises a regulatory region operably linked to a nucleotide sequence encoding a polypeptide having 85 percent or greater sequence identity to an amino acid sequence selected from the group consisting of SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140 A plant and/or plant tissue produced from the plant cell has a difference in the level of tolerance to salinity or oxidative stress as compared to the corresponding level in a control plant that does not comprise the exogenous nucleic acid. In another aspect, the exogenous nucleic acid comprises a regulatory region operably linked to a nucleotide sequence having 85 percent or greater sequence identity to at least a fragment of a nucleotide sequence selected from the group consisting of SEQ ID Nos. 1, 3, 5, 7, 10, 12, 16, 18, 21, 26, 28, 32, 34, 40, 46, 48, 51, 53, 55, 57, 59, 61, 65, 67, 70, 72, 75, 77, 79, 82, 85, 87, 89, 92, 95, 97, 99, 103, 105, 108, 111, 113, 115, 117, 120, 124, 131, 133, 135, 137, 139, 146, 148, 150, 152, 155, 157, 159, 161, and 164, and to a nucleotide sequence encoding any of the amino acid sequences set forth in the sequence listing. A plant and/or plant tissue produced from the plant cell has a difference in the level of tolerance to salinity or oxidative stress as compared to the corresponding level in a control plant that does not comprise the exogenous nucleic acid. A transgenic plant comprising such a plant cell is also provided. In some embodiments, the transgenic plant is a member of a species selected from the group consisting of *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet). Some embodiments are related to products comprising seed or vegetative tissue from transgenic plants as described above. Some embodiments relate to food or feed products from transgenic plants as described above.

In another aspect, an isolated nucleic acid comprises a nucleotide sequence encoding a polypeptide having 80% or greater sequence identity to the amino acid sequence set forth in SEQ ID Nos. 2, 4, 6, 22, 27, 29, 49, 52, 54, 56, 60, 62, 68, 76, 83, 88, 90, 96, 98, 104, 106, 112, 114, 132, 134, 149, 151, or 160.

In another aspect, methods of identifying a genetic polymorphism associated with variation in the level of salinity and/or oxidative stress tolerance are provided. The methods include providing a population of plants, and determining whether one or more genetic polymorphisms in the population are genetically linked to the locus for a polypeptide selected from the group consisting of the polypeptides depicted in FIGS. 1-6 and functional homologs thereof. The correlation between variation in the level of salinity tolerance and/or oxidative stress tolerance in plants and/or plant tissues of the population and the presence of the one or more polymorphisms in plants of the population is measured, thereby permitting identification of whether or not the one or more polymorphisms are associated with such variation.

In another aspect, methods of making a plant line is provided. The methods include determining whether one or more genetic polymorphisms in a population of plants is associated with the locus for a polypeptide selected from the group consisting of the polypeptides depicted in FIGS. 1-6 and functional homologs thereof, identifying one or more plants in the population in which the presence of at least one allele at the one or more polymorphisms is associated with variation in salt tolerance or oxidative stress tolerance, crossing each of the one or more identified plants with itself or a different plant to produce seed, crossing at least one progeny plant grown from said seed with itself or a different plant, and repeating the crossing steps for an additional 0-5 generations to make the plant line. The at least one allele will be present in the plant line. The method of making a plant line may be applied, for example, to a population of switchgrass plants.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE FIGURES

FIG. 1 and the other alignment Figures provided herein were generated using the program MUSCLE version 3.52

FIG. 2 is an alignment of amino acid sequences of homologues of ME06748 (SEQ ID NO: 41).

FIG. 3 is an alignment of amino acid sequences of homologues of ME19173 (SEQ ID NO: 109).

FIG. 4 is an alignment of amino acid sequences of homologues of ME02064C (SEQ ID NO: 140).

FIG. 5 is an alignment of amino acid sequences of homologues of Ceres Clone ID No. 1792354 (SEQ ID NO:2).

FIG. 6 is an alignment of amino acid sequences of homologues of Ceres Clone ID No. 56784328 (SEQ ID NO: 35).

DETAILED DESCRIPTION

Figure 1:
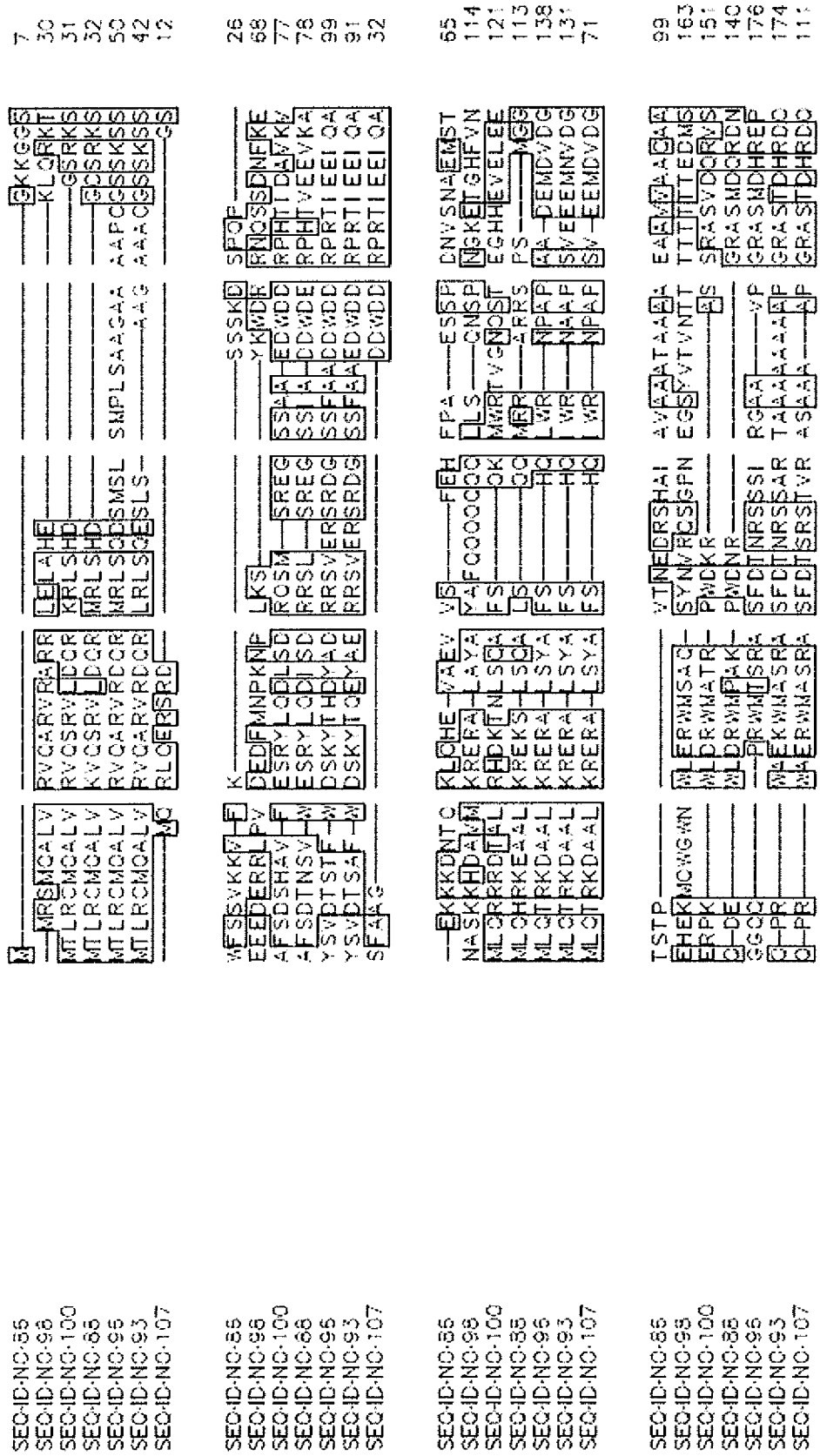
FIG. 1 is an alignment of amino acid sequences of homologues of (ME08768; SEQ ID NO: 86). In all the alignment Figures shown herein, a dash in an aligned sequence represents a gap, i.e., a lack of an amino acid at that position. Identical amino acids or conserved amino acid substitutions among aligned sequences are identified by boxes.

The invention features methods and materials related to modulating salinity tolerance and/or oxidative stress tolerance levels in plants and/or plant tissues. In some embodiments, the plants may also have increased biomass and/or yield. The methods can include transforming a plant cell with a nucleic acid encoding a salinity and/or oxidative stress tolerance-modulating polypeptide, wherein expression of the polypeptide results in a modulated level of salinity tolerance and/or oxidative stress tolerance. Plant cells produced using such methods can be grown to produce plants having an increased salinity tolerance, oxidative stress tolerance, and/or biomass, in comparison to wild type plants grown under the same conditions. Such plants, and the seeds of such plants, may be used to produce, for example, yield and/or biomass utilized for biofuel production, such as, but not limited to, ethanol and butanol.

I. DEFINITIONS

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Modulation" of the level of a compound or constituent refers to the change in the level of the indicated compound or constituent that is observed as a result of expression of, or transcription from, an exogenous nucleic acid in a plant cell. The change in level is measured relative to the corresponding level in control plants.

"Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure.

A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

Oxidative stress: Plant species vary in their capacity to tolerate ROS/ROI/AOS. "Oxidative stress" can be defined as the set of environmental conditions under which a plant will begin to suffer the effects of elevated ROS/ROI/AOS concentration, such as decreases in enzymatic activity, DNA breakage, DNA-protein crosslinking, necrosis and stunted growth.

For these reasons, plants experiencing oxidative stress typically exhibit a significant reduction in biomass and/or yield.

Elevated oxidative stress may be caused by natural, geological processes and by human activities, such as pollution. Since plant species vary in their capacity to tolerate oxidative stress, the precise environmental conditions that cause stress cannot be generalized. However, under oxidative stress conditions, oxidative stress tolerant plants produce higher biomass, yield and survivorship than plants that are not oxidative stress tolerant. Differences in physical appearance, recovery and yield can be quantified Photosynthetic efficiency: photosynthetic efficiency, or electron transport via photosystem II, is estimated by the relationship between Fm, the maximum fluorescence signal and the variable fluorescence, Fv. A reduction in the optimum quantum yield (Fv/Fm) indicates stress and can be used to monitor the performance of transgenic plants compared to non-transgenic plants under salt or oxidative stress conditions.

Salicylic Acid Growth Index (SAGI): Photosynthetic efficiency×seedling area.

Salt growth index (SGI): Photosynthetic efficiency×seedling area (under salinity stress condition).

Salinity: Plant species vary in their capacity to tolerate salinity. "Salinity" can be defined as the set of environmental conditions under which a plant will begin to suffer the effects of elevated salt concentration, such as ion imbalance, decreased stomatal conductance, decreased photosynthesis, decreased growth rate, increased cell death, loss of turgor (wilting), or ovule abortion. For these reasons, plants experiencing salinity stress typically exhibit a significant reduction in biomass and/or yield.

Elevated salinity may be caused by natural, geological processes and by human activities, such as pollution. Since plant species vary in their capacity to tolerate salinity, the precise environmental conditions that cause stress cannot be generalized. However, under saline conditions, salinity tolerant plants produce higher biomass, yield and survivorship than plants that are not saline tolerant. Differences in physical appearance, recovery and yield can be quantified.

Elevated salinity may be caused by natural, geological processes and by human activities, such as irrigation. Since plant species vary in their capacity to tolerate water deficit, the precise environmental salt conditions that cause stress cannot be generalized.

However, under saline conditions, salt tolerant plants produce higher biomass, yield and survivorship than plants that are not salt tolerant. Differences in physical appearance, recovery and yield can be quantified and statistically analyzed using well known measurement and analysis methods.

II. POLYPEPTIDES

Polypeptides described herein include salinity tolerance and/or oxidative stress tolerance-modulating polypeptides. Salinity tolerance and/or oxidative stress tolerance—modulating polypeptides can be effective to modulate salinity tolerance and/or oxidative stress tolerance levels when expressed in a plant or plant cell. Such polypeptides typically contain at least one domain indicative of salinity tolerance and/or oxidative stress tolerance-modulating polypeptides, as described in more detail herein. Salinity tolerance and/or oxidative stress tolerance-modulating polypeptides typically have an HMM bit score that is greater than 30, as described in more detail herein. In some embodiments, salinity tolerance and/or oxidative stress tolerance-modulating polypeptides have greater than 85% identity to SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140 as described in more detail herein.

A. Domains Indicative of Salinity Tolerance and/or Oxidative Stress Tolerance—Modulating Polypeptides A salinity tolerance and/or oxidative stress tolerance-modulating polypeptide can contain an IQ calmodulin-binding motif domain, which is predicted to be characteristic of an salinity tolerance and/or oxidative stress tolerance-modulating polypeptide. Calmodulin (CaM) is recognized as a major calcium sensor and orchestrator of regulatory events through its interaction with a diverse group of cellular proteins. Three classes of recognition motifs exist for many of the known CaM binding proteins; the IQ motif as a consensus for $Ca^{2+}$-independent binding and two related motifs for $Ca^{2+}$-dependent binding, termed 18-14 and 1-5-10 based on the position of conserved hydrophobic residues PUBMED:9141499.

For example, the regulatory domain of scallop myosin is a three-chain protein complex that switches on this motor in response to $Ca2^+$ binding. Side-chain interactions link the two light chains in tandem to adjacent segments of the heavy chain bearing the IQ-sequence motif. The $Ca^{2+}$-binding site is a novel EF-hand motif on the essential light chain and is stabilized by linkages involving the heavy chain and both light chains, accounting for the requirement of all three chains for $Ca2^+$ binding and regulation in the intact myosin molecule PUBMED:8127365.

For example, SEQ ID NO:86 sets forth the amino acid sequence of an *Arabidopsis* clone, identified herein as Ceres SEEDLINE ID no. ME08768, that is predicted to encode a polypeptide containing a IQ calmodulin-binding motif domain from residues 116-136.

In some embodiments, a salinity tolerance and/or oxidative stress tolerance-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5 amino acids shorter or longer typically exhibit the salinity tolerance and/or oxidative stress tolerance-modulating activity of a truncated polypeptide. In some embodiments, a truncated polypeptide is a dominant negative polypeptide. SEQ ID NO: 138 sets forth the amino sequence of a salinity tolerance and/or oxidative stress tolerance-modulating polypeptide that is truncated at the 5' end relative to the naturally occurring polypeptide. Expression in a plant of such a truncated polypeptide confers a difference in the level of salinity tolerance and/or oxidative stress tolerance in a plant and/or plant tissue as compared to the corresponding level a control plant and/or tissue thereof that does not comprise the truncation.

B. Functional Homologs Identified by Reciprocal BLAST

In some embodiments, one or more functional homologs of a reference salinity tolerance and/or oxidative stress tolerance-modulating polypeptide defined by one or more of the pfam descriptions indicated above are suitable for use as salinity tolerance and/or oxidative stress tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs.

Variants of a naturally occurring functional homolog, such as polypeptides encoded by mutants of a wild type coding sequence, may themselves be functional homologs. Functional homologs can also be created via site-directed mutagenesis of the coding sequence for a salinity tolerance and/or oxidative stress tolerance-modulating polypeptide, or by combining domains from the coding sequences for different naturally-occurring salinity tolerance and/or oxidative stress tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of salinity tolerance and/or oxidative stress tolerance-modulating polypeptides. Sequence analysis can involve BLAST, Reciprocal BLAST, or PSI-BLAST analysis of nonredundant databases using a salinity tolerance and/or oxidative stress tolerance-modulating polypeptide amino acid sequence as the reference sequence. Amino acid sequence is, in some instances, deduced from the nucleotide sequence.

Those polypeptides in the database that have greater than 40% sequence identity are candidates for further evaluation for suitability as a salinity tolerance and/or oxidative stress tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in salinity tolerance and/or oxidative stress tolerance-modulating polypeptides, e.g., conserved functional domains.

Conserved regions can be identified by locating a region within the primary amino acid sequence of a salinity tolerance and/or oxidative stress tolerance-modulating polypeptide that is a repeated sequence, forms some secondary structure (e.g., helices and beta sheets), establishes positively or negatively charged domains, or represents a protein motif or domain.

See, e.g., the Pfam web site describing consensus sequences for a variety of protein motifs and domains on the World Wide Web at sanger.ac.uk/Software/Pfam/and pfam.janelia.org/. A description of the information included at the Pfam database is described in Sonnhammer et al., *Nucl. Acids Res.*, 26:320-322 (1998); Sonnhammer et al.,

*Proteins,* 28:405-420 (1997); and Bateman et al., *Nucl. Acids Res.,* 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Amino acid sequences of functional homologs of the polypeptide set forth in SEQ ID NO: 86 are provided in FIG. 1 and in the Sequence Listing. Such functional homologs include (SEQ ID NO: 88, 90, 91, 93, 94, 96, 98, 100, 101, 102, 104, 106, and 107). In some cases, a functional homolog of SEQ ID NO: 86 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 86.

Figure 2:
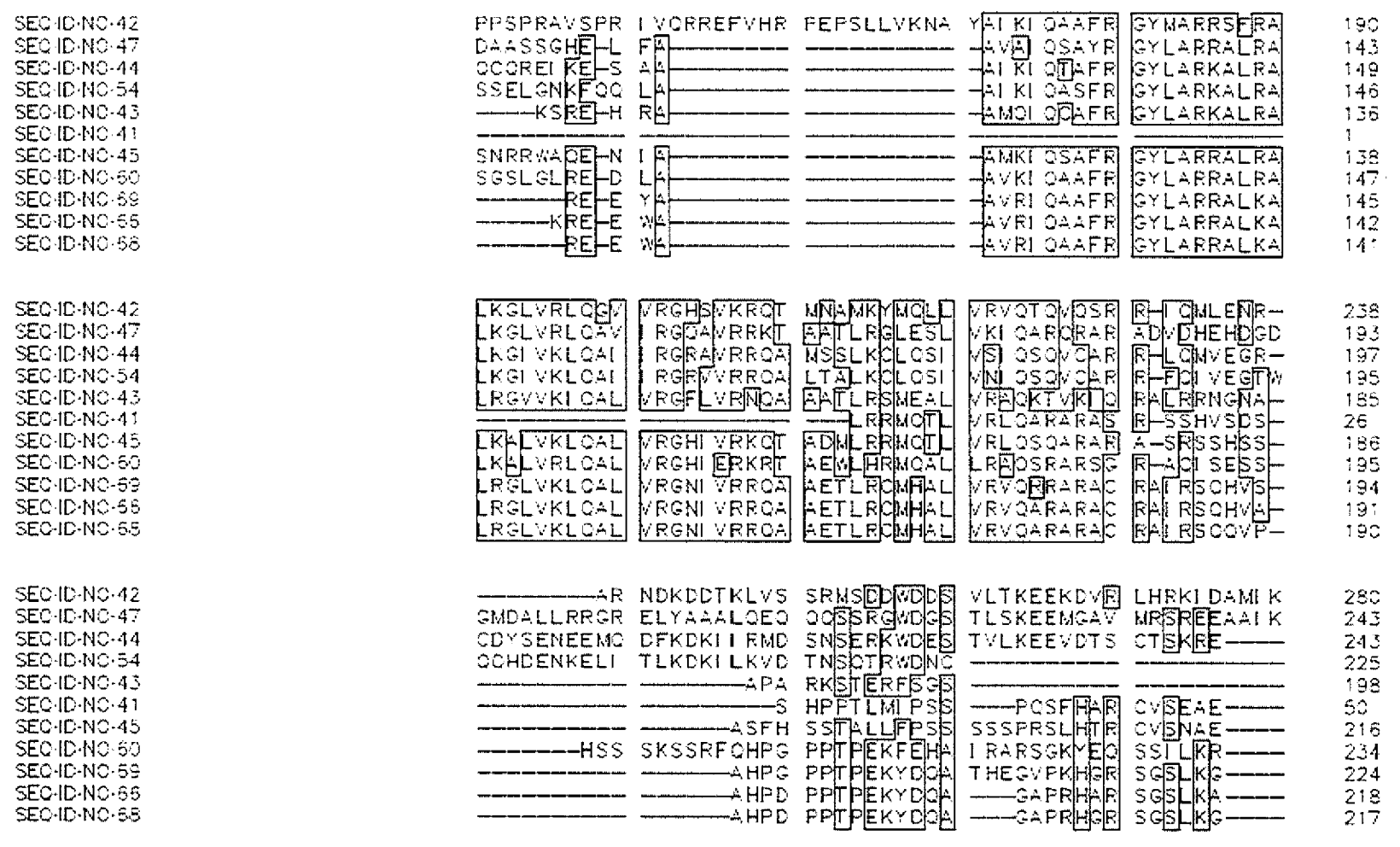
Figure 2:
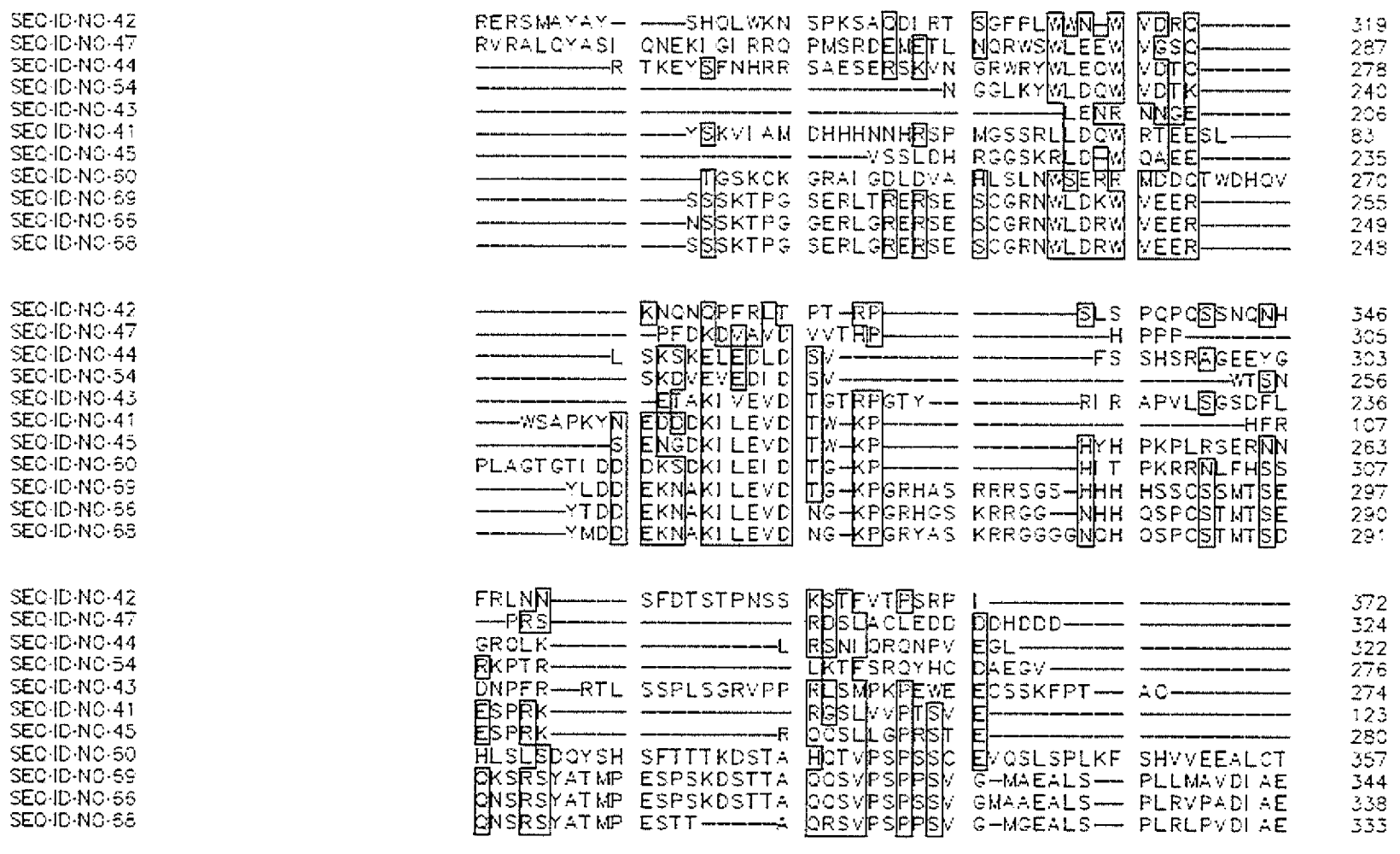
Figure 2:
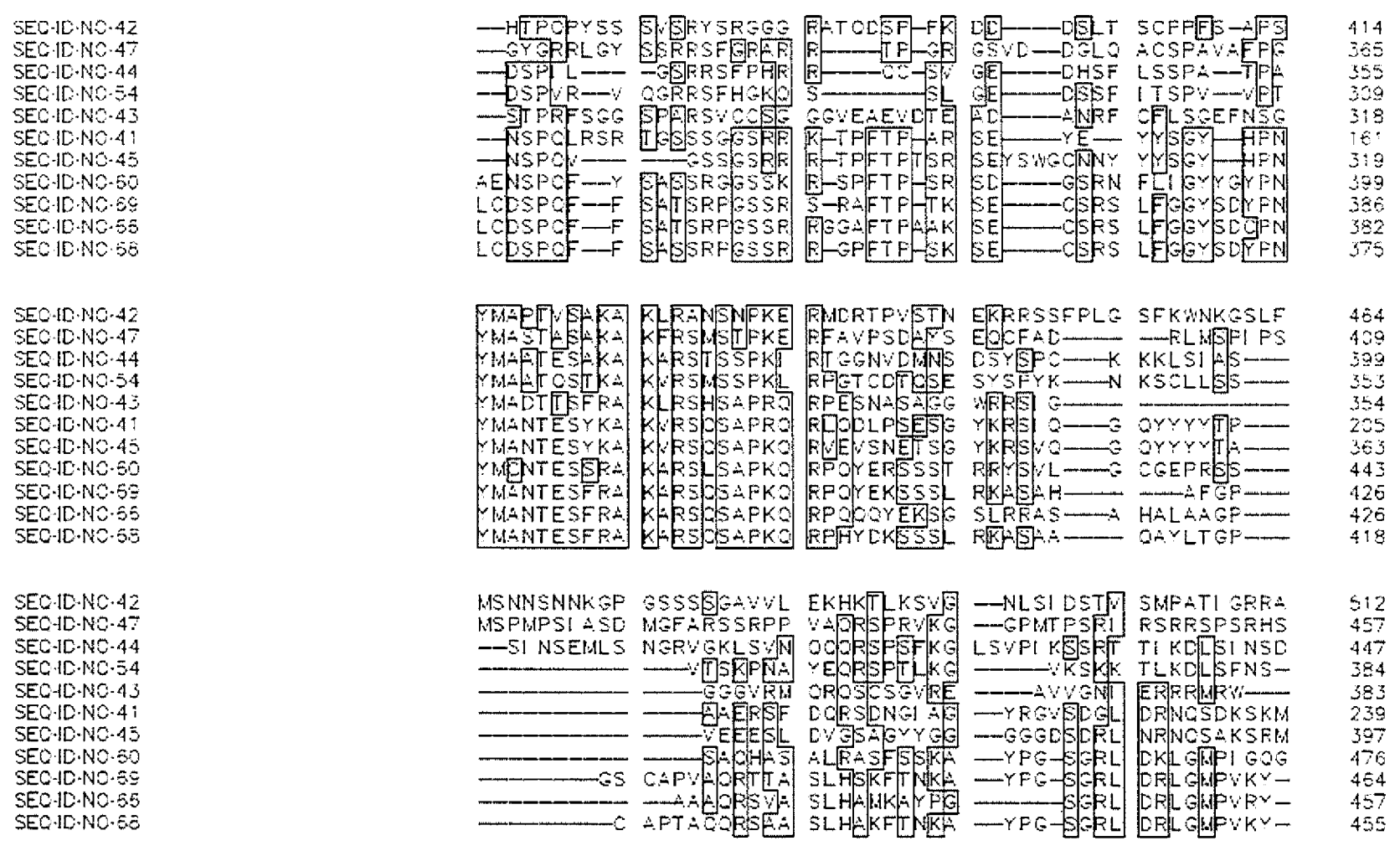

Amino acid sequences of functional homologs of the polypeptide set forth in SEQ ID NO: 41 are provided in FIG. 2. Such functional homologs include (SEQ ID NO: 42, 43, 44, 45, 47, 49, 50, 52, 54, 56, 58, 60, 62, 63, 64, 66, 68, 69, 71, 73, 74, 76, 78, 80, 81, 83, and 84). In some cases, a functional homolog of SEQ ID NO: 41 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 41.

Figure 3:
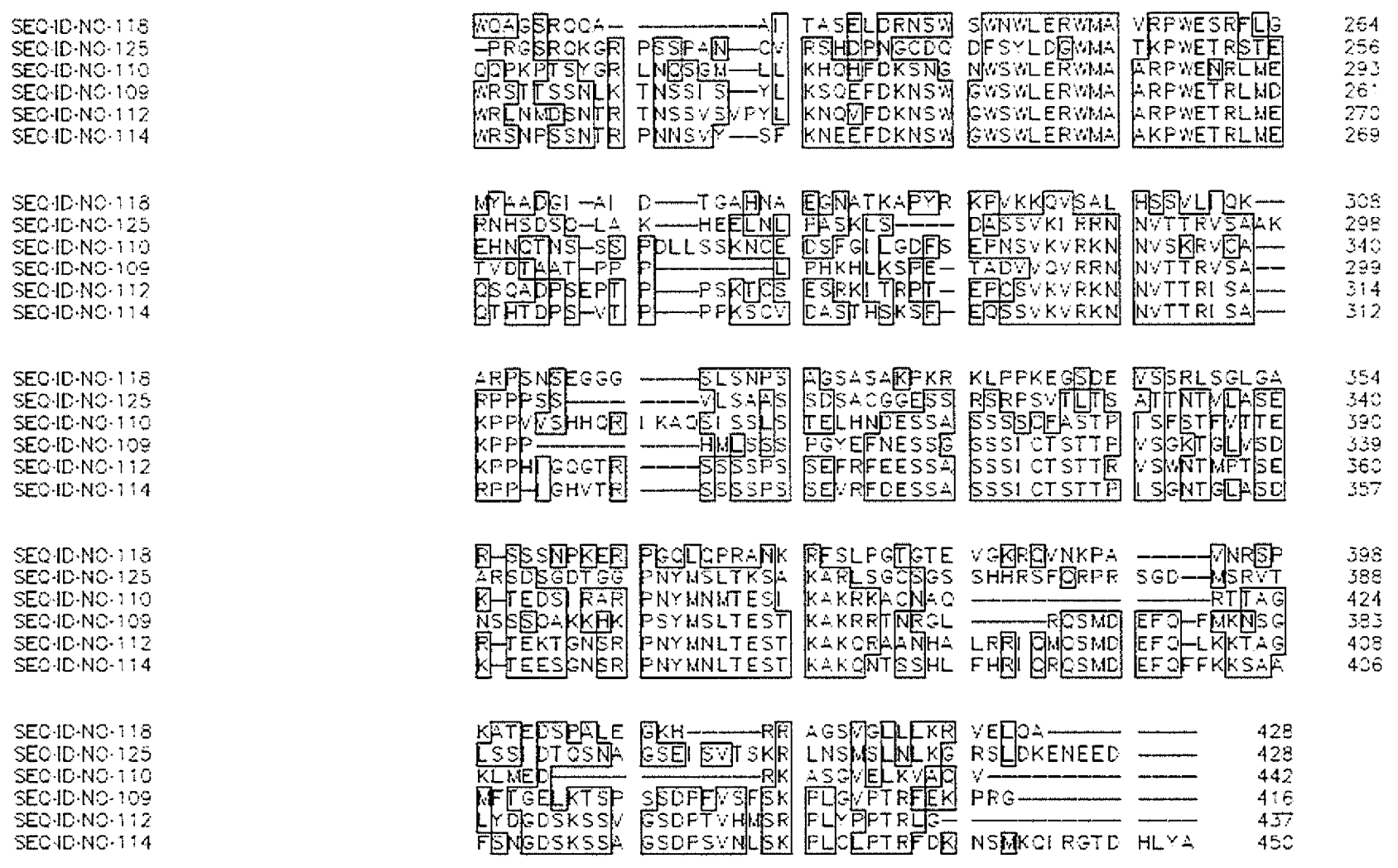

Amino acid sequences of functional homologs of the polypeptide set forth in SEQ ID NO: 109 are provided in FIG. 3. Such functional homologs include (SEQ ID NO: 110, 112, 114, 116, 118, 119, 121, 122, 123, 125, 126, 127, 128, 129, 130, 132, and 134). In some cases, a functional homolog of SEQ ID NO: 109 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 109.

Figure 4:
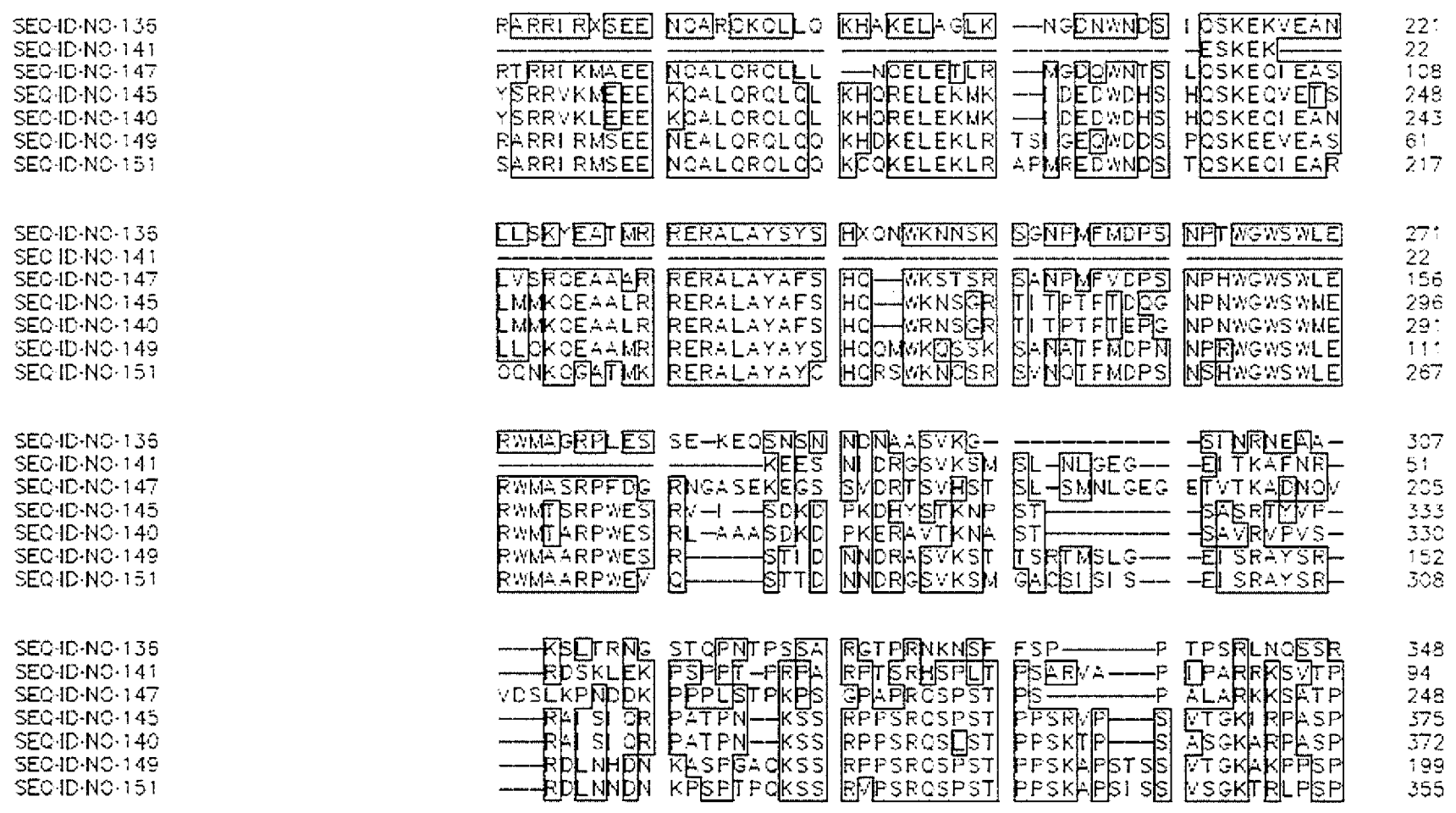
Figure 4:
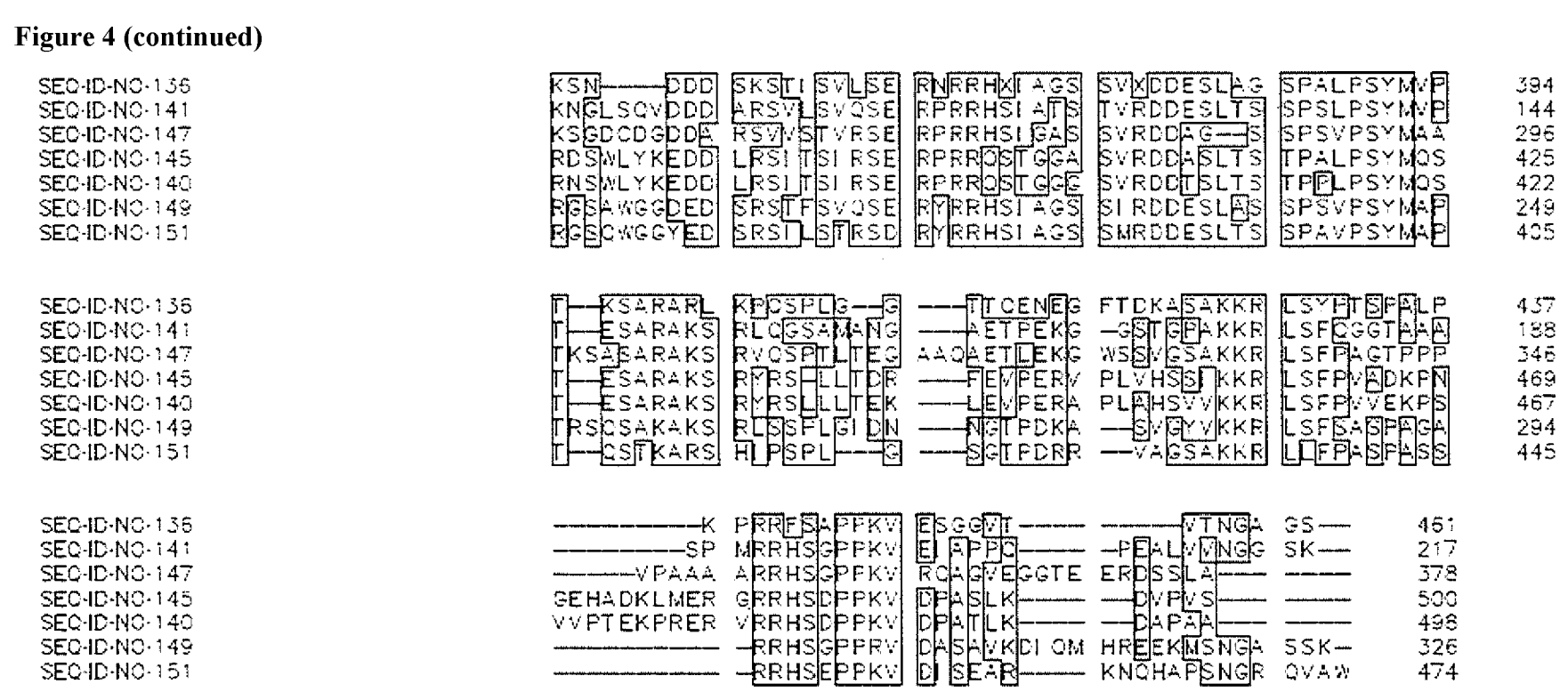

Amino acid sequences of functional homologs of the polypeptide set forth in SEQ ID NO:140 are provided in FIG. 4. Such functional homologs include (SEQ ID NO: 136, 138, 140, 141, 142, 143, 144, 145, 147, 149, 151, 153, 154, 156, 158, 160, 162, 163, 165, 166, 167, and 168). In some cases, a functional homolog of SEQ ID NO: 140 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 140.

Figure 5:
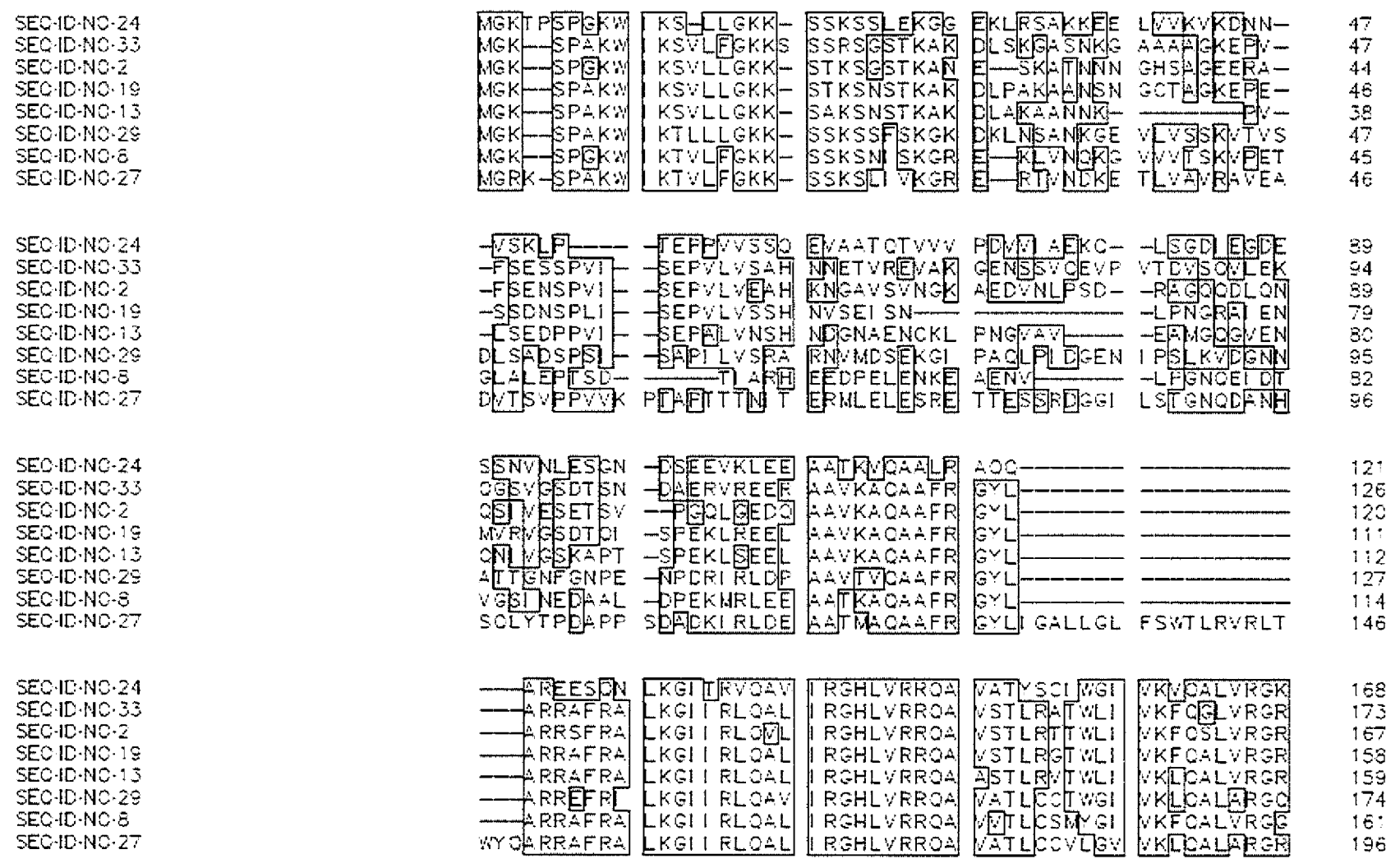
Figure 5:
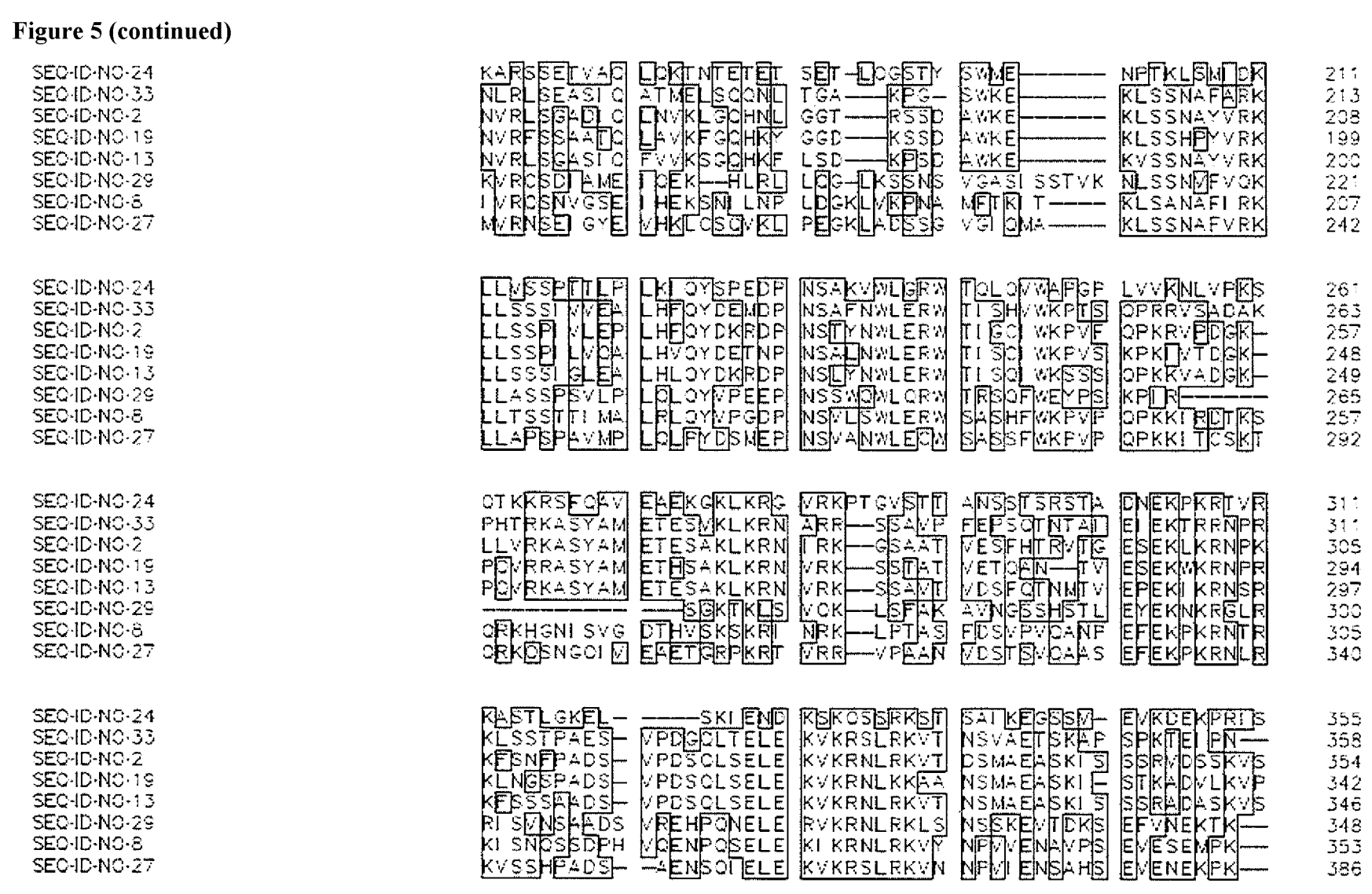
Figure 5:
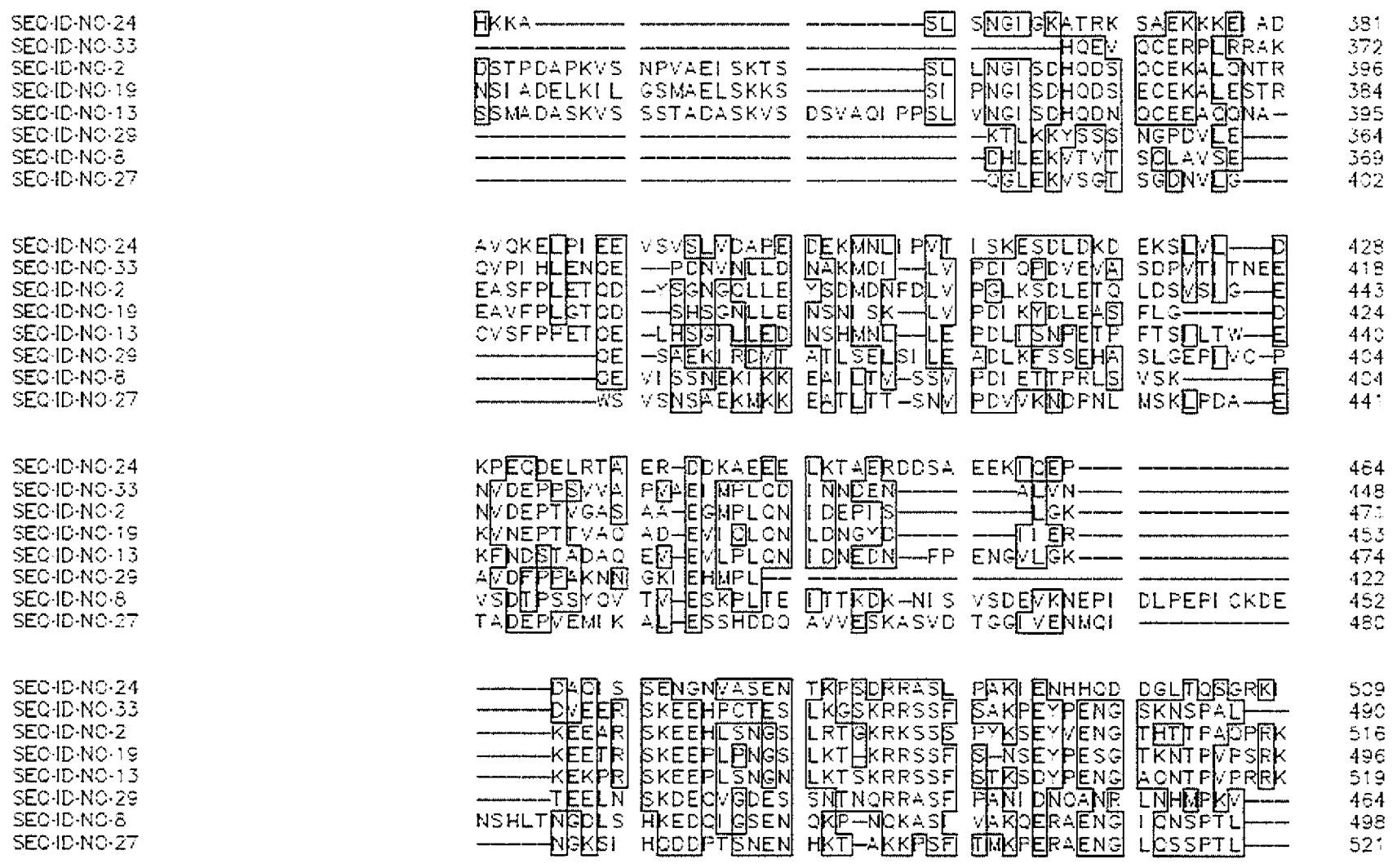
Figure 5:
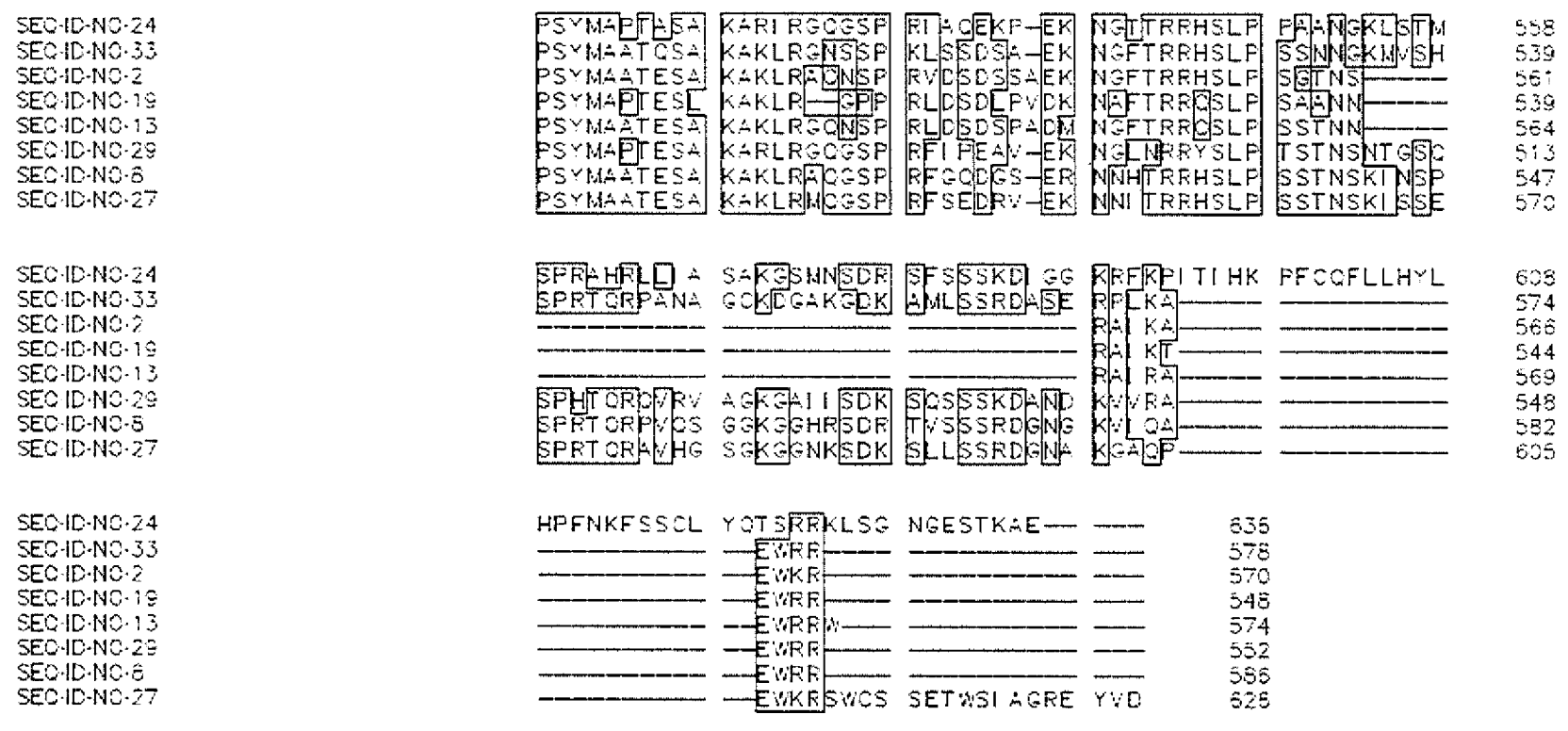

Amino acid sequences of functional homologs of the polypeptide set forth in SEQ ID NO: 2 are provided in FIG. 5. Such functional homologs include (SEQ ID NO: 2, 4, 6, 8, 9, 11, 13, 14, 15, 17, 19, 20, 22, 23, 24, 25, 27, 29, 30, 31, and 33). In some cases, a functional homolog of SEQ ID NO: 2 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2.

Amino acid sequences of functional homologs of the polypeptide set forth in SEQ ID NO: 35 are provided in FIG. 6. Such functional homologs include (SEQ ID NO: 35, 36, 37, 38, and 39). In some cases, a functional homolog of SEQ ID NO: 35 has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 35.

The identification of conserved regions in a salinity tolerance and/or oxidative stress tolerance-modulating polypeptide facilitates production of variants of salinity tolerance and/or oxidative stress tolerance-modulating polypeptides. Variants of salinity tolerance and/or oxidative stress tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIGS. 1 thru 6. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

C. Functional Homologues Identified by HMM

In some embodiments, useful salinity and/or oxidative stress tolerance-modulating polypeptides include those that fit a Hidden Markov Model based on the polypeptides set forth in any one of FIGS. 1-6. A Hidden Markov Model (HMM) is a statistical model of a consensus sequence for a group of functional homologs. See, Durbin et al., *Biological Sequence Analysis: Probabilistic Models of Proteins and Nucleic Acids,* Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, --consistency REPS of 2; -ir, --iterative-refinement REPS of 100; -pre, --pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web. Hmmbuild outputs the model as a text file.

The HMM for a group of functional homologs can be used to determine the likelihood that a candidate salinity tolerance and/or oxidative stress tolerance-modulating polypeptide sequence is a better fit to that particular HMM than to a null HMM generated using a group of sequences that are not structurally or functionally related. The likelihood that a subject polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the subject sequence carries out one or more of the biochemical or physiological function(s) of the polypeptides used to generate the HMM. A high HMM bit score is at least 20, and often is higher.

As those of skill in the art would appreciate, the HMM scores provided in the sequence listing are merely exemplary. Since multiple sequence alignment algorithms, such as ProbCons, can only generate near-optimal results, slight variations of the model can arise due to factors such as the order in which sequences are processed for alignment. Nevertheless, HMM score variability is minor, and so the HMM scores in the sequence listing are representative of models made with the respective sequences.

The salinity and/or oxidative stress-modulating polypeptides discussed below fit the indicated HMM with an HMM bit score greater than 20 (e.g., greater than 20, 30, 40, 50, 60, 70, 80, 90, 100, 200, 300, 400, or 500). In some embodiments, the HMM bit score of a salinity and/or oxidative stress-modulating polypeptide discussed below is about 50%, 60%, 70%, 80%, 90%, or 95% of the HMM bit score of a functional homolog provided in the Sequence Listing. In some embodiments, a salinity and/or oxidative stress-modulating polypeptide discussed below fits the indicated HMM with an HMM bit score greater than 20, and has a domain indicative of an salinity and/or oxidative stress-modulating polypeptide. In some embodiments, a salinity and/or oxidative stress-modulating polypeptide discussed below fits the indicated HMM with an HMM bit score greater than 20, and has 85% or greater sequence identity (e.g., 75%, 80%, 85%, 90%, 95%, or 100% sequence identity) to an amino acid sequence shown in any one of FIGS. 1 thru 6 or to an amino acid sequence correlated in the Sequence Listing to a any one of FIGS. 1 thru 6.

In the Sequence Listing polypeptides are provided that have HMM bit scores greater than 400, 450, 500, 550, 600, 650, 700, 750, 800, 850, 900, 950, 1000, 1050, or 1100, when fitted to an HMM generated from the amino acid sequences set forth in FIG. 1. Such polypeptides include Ceres SEEDLINE ID no. ME08768, Ceres CLONE ID no. 1943807, Ceres ANNOT ID no. 1471392, Public GI ID no. 6715635, Ceres CLONE ID no. 910109, Public GI ID no. 115474509, Ceres CLONE ID no. 1780908, Ceres ANNOT ID no. 1520883, Ceres CLONE ID no. 148018, Public GI ID no. 18378797, Public GI ID no. 21553500, Ceres ANNOT ID no. 1444522, Ceres ANNOT ID no. 146751, and Public GI ID no. 125559938 (SEQ ID NO: 86, 88, 90, 91, 93, 94, 96, 98, 100, 101, 102, 104, 106, and 107)

In the Sequence Listing polypeptides are provided that have HMM bit scores greater than 30, 50, 100, 150, 200, 250, 300, 350, 400, 450, 500, 550, 600, 650, 700, 750, 800, 850, 900, 950, or 1000 when fitted to an HMM generated from the amino acid sequences set forth in FIG. 2. Such polypeptides include Ceres SEEDLINE ID no. ME06748, Ceres SEEDLINE ID no. ME20711, Ceres SEEDLINE ID no. ME18973, Ceres SEEDLINE ID no. ME08732, Ceres SEEDLINE ID no. ME19657, Ceres CLONE ID no. 835818, Ceres CLONE ID no. 1796745, Public GI ID no. 125543896, Ceres ANNOT ID no. 1483984, Ceres CLONE ID no. 1924654, Ceres ANNOT ID no. 1468861, Ceres CLONE ID no. 1641776, Ceres ANNOT ID no. 1438750, Ceres ANNOT ID no. 1447395, Public GI ID no. 79482785, Public GI ID no. 3292832, Ceres CLONE ID no. 1559074, Ceres CLONE ID no. 1726548, Public GI ID no. 115459996, Ceres CLONE ID no. 697034, Ceres CLONE ID no. 353438, Public GI ID no. 125593074, Ceres CLONE ID no. 1920115, Ceres CLONE ID no. 21821, Ceres CLONE ID no. 560066, Public GI ID no. 115453071, Ceres CLONE ID no. 1968211, and Public GI ID no. 116310011_ (SEQ ID NO: 42, 43, 44, 45, 47, 49, 50, 52, 54, 56, 58, 60, 62, 63, 64, 66, 68, 69, 71, 73, 74, 76, 78, 80, 81, 83, and 84).

In the Sequence Listing polypeptides are provided that have HMM bit scores greater than 120, 150, 200, 250, 300, 350, 400, 450, 500, 550, 600, 650, 700, 750, 800, 850, 900, 950, 1000, 1050, 1100, 1150, or 1200 when fitted to an HMM generated from the amino acid sequences set forth in FIG. 3. Such polypeptides include Ceres SEEDLINE ID no. ME19173, Public GI ID no. 115435054, Ceres CLONE ID no. 1847857, Ceres ANNOT ID no. 1455219, Ceres CLONE ID no. 352452, Ceres CLONE ID no. 787908, Ceres LOCUS ID no. Os01m00929_AP002743, Ceres CLONE ID no. 246398, Public GI ID no. 125527441, Public GI ID no. 125595056, Ceres CLONE ID no. 236071, Public GI ID no. 125524760, Public GI ID no. 125569365, Public GI ID no. 115439499, Public GI ID no. 15225258, Public GI ID no. 115465173, Ceres ANNOT ID no. 1477059, and Ceres ANNOT ID no. 1530547 (SEQ ID NO: 110, 112, 114, 116, 118, 119, 121, 122, 123, 125, 126, 127, 128, 129, 130, 132, and 134).

In the Sequence Listing polypeptides are provided that have HMM bit scores greater than 150, 200, 250, 300, 350, 400, 450, 500, 550, 600, 650, 700, 750, 800, 850, 900, 950, 1000, 1050, 1100, 1150, 1200, 1250, 1300, or 1350 when fitted to an HMM generated from the amino acid sequences set forth in FIG. 4. Such polypeptides include Ceres SEEDLINE ID no. ME24091, Ceres CLONE ID no. 375578, Ceres CLONE ID no. 375578, Ceres SEEDLINE ID no. ME10681, Ceres SEEDLINE ID no. ME03140, Ceres SEEDLINE ID no. ME24076, Ceres SEEDLINE ID no. ME24217, Public GI ID no. 115440873, Ceres CLONE ID no. 826796, Ceres ANNOT ID no. 1465047, Ceres CLONE ID no. 1919901, Ceres CLONE ID no. 520008, Public GI ID no. 7413581, Ceres CLONE ID no. 228069, Ceres CLONE ID no. 467508, Ceres CLONE ID no. 1829581, Ceres CLONE ID no. 229668, Public GI ID no. 125550655, Ceres CLONE ID no. 106263, Public GI ID no. 15231175, Public GI ID no. 145357576, and Public GI ID no. 125528277 (SEQ ID NO: 136, 138, 140, 141, 142, 143, 144, 145, 147, 149, 151, 153, 154, 156, 158, 160, 162, 163, 165, 166, 167, and 168).

In the Sequence Listing polypeptides are provided that have HMM bit scores greater than 425, 450, 500, 550, 600, 650, 700, 750, 800, 850, 900, 950, 1000, 1050, 1100, 1150, 1200, 1250, 1300, 1350, 1400, 1450, 1500, or 1550, when fitted to an HMM generated from the amino acid sequences set forth in FIG. 5. Such polypeptides include Ceres CLONE ID no. 1792354, Ceres CLONE ID no. 1925477, Ceres ANNOT ID no. 1521592, Ceres CLONE ID no. 463594, Public GI ID no. 22330633, Ceres CLONE ID no. 345954, Ceres LOCUS ID no. Os01m05025_AP003288, GI ID no. 56784330, Public GI ID no. 125527495, Public GI ID no. 125553119, Ceres CLONE ID no. 236431, Ceres CLONE ID no. 908518, Public GI ID no. 115465121, Ceres CLONE ID no. 1791910, Public GI ID no. 125595019, Public GI ID no. 42568886, Public GI ID no. 2947062, Ceres ANNOT ID no. 1468228, Ceres CLONE ID no. 1942388, Public GI ID no. 12324824, Public GI ID no. 5882749, and Ceres CLONE ID no. 325403 (SEQ ID NO: 2, 4, 6, 8, 9, 11, 13, 14, 15, 17, 19, 20, 22, 23, 24, 25, 27, 29, 30, 31, and 33).

In the Sequence Listing polypeptides are provided that have HMM bit scores greater than 550, 600, 650, or 700 when fitted to an HMM generated from the amino acid sequences set forth in FIG. 6. Such polypeptides include Ceres GI ID no. 56784328, Public GI ID no. 56784330, Public GI ID no. 125528718, Public GI ID no. 125572975, and Public GI ID no. 125528716 (SEQ ID NO: 35, 36, 37, 38, and 39).

D. Percent Identity

In some embodiments, a salinity and/or oxidative stress tolerance-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to one of the amino acid sequences set forth in SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140. Polypeptides having such a percent sequence identity often have a domain indicative of a salinity and/or oxidative stress-modulating polypeptide and/or have an HMM bit score that is greater than 20, as discussed above. Examples of amino acid sequences of salinity and/or oxidative stress tolerance-modulating polypeptides having at least 85% sequence identity to one of the amino acid sequences set forth in SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140 are provided in FIGS. 1-6.

"Percent sequence identity" refers to the degree of sequence identity between any given reference sequence, e.g., SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140, and a candidate salinity and/or oxidative stress-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., Nucleic Acids Res., 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a salinity and/or oxidative stress tolerance-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to one or more of the amino acid sequence set forth in SEQ ID NO: 86 Amino acid sequences of polypeptides having high sequence identity to the polypeptide set forth in SEQ ID NO: 86 are provided in the Sequence Listing. Such polypeptides include SEQ ID NO: 88, 90, 91, 93, 94, 96, 98, 100, 101, 102, 104, 106, and 107.

In some cases, a salinity and/or oxidative stress tolerance-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 41. Amino acid sequences of polypeptides having high sequence identity to the polypeptide set forth in SEQ ID NO: 41 are provided in the Sequence Listing. Such polypeptides include SEQ ID NO: 42, 43, 44, 45, 47, 49, 50, 52, 54, 56, 58, 60, 62, 63, 64, 66, 68, 69, 71, 73, 74, 76, 78, 80, 81, 83, and 84.

In some cases, a salinity and/or oxidative stress-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 109. Amino acid sequences of polypeptides having high sequence identity to the polypeptide set forth in SEQ ID NO: 109 are provided in the Sequence Listing. Such polypeptides include SEQ ID NO: 110, 112, 114, 116, 118, 119, 121, 122, 123, 125, 126, 127, 128, 129, 130, 132, and 134.

In some cases, a salinity and/or oxidative stress-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 140. Amino acid sequences of polypeptides having high sequence identity to the polypeptide set forth in SEQ ID NO: 140 are provided in the Sequence Listing. Such polypeptides include SEQ ID NO: 136, 138, 141, 142, 143, 144, 145, 147, 149, 151, 153, 154, 156, 158, 160, 162, 163, 165, 166, 167, and 168.

In some cases, a salinity and/or oxidative stress-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2. Amino acid sequences of polypeptides having high sequence identity to the polypeptide set forth in SEQ ID NO: 2 are provided in the Sequence Listing. Such polypeptides include SEQ ID NO: 4, 6, 8, 9, 11, 13, 14, 15, 17, 19, 20, 22, 23, 24, 25, 27, 29, 30, 31, and 33.

In some cases, a salinity and/or oxidative stress-modulating polypeptide has an amino acid sequence with at least 50% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 35. Amino acid sequences of polypeptides having high sequence identity to the polypeptide set forth in SEQ ID NO: 35 are provided in the Sequence Listing. Such polypeptides include SEQ ID NO: 36, 37, 38, and 39.

E. Other Sequences

It should be appreciated that a salinity and/or oxidative stress tolerance-modulating polypeptide can include additional amino acids that are not involved in salinity and/or oxidative stress tolerance modulation, and thus such a polypeptide can be longer than would otherwise be the case. For example, a salinity and/or oxidative stress-tolerance modulating polypeptide can include a purification tag, a chloroplast transit peptide, an amyloplast transit peptide, a mitochondrial transit peptide, or a leader sequence added to the amino or carboxy terminus. In some embodiments, a salinity and/or oxidative stress-tolerance modulating polypeptide includes an amino acid sequence that functions as a reporter, e.g., a green fluorescent protein or yellow fluorescent protein.

III. NUCLEIC ACIDS

Nucleic acids described herein include nucleic acids that are effective to modulate salinity and/or oxidative stress tolerance levels when transcribed in a plant or plant cell. Such nucleic acids include, without limitation, those that encode a salinity and/or oxidative stress tolerance-modulating polypeptide and those that can be used to inhibit expression of a salinity tolerance and/or oxidative stress tolerance-modulating polypeptide via a nucleic acid based method.

A. Nucleic Acids Encoding Salinity Tolerance and/or Oxidative Stress Tolerance-Modulating Polypeptides Nucleic acids encoding salinity tolerance and/or oxidative stress tolerance-modulating polypeptides are described herein. Such nucleic acids include SEQ ID NOs: 1, 3, 5, 7, 10, 12, 16, 18, 21, 26, 28, 32, 34, 40, 46, 48, 51, 53, 55, 57, 59, 61, 65, 67, 70, 72, 75, 77, 79, 82, 85, 87, 89, 92, 95, 97, 99, 103, 105, 108, 111, 113, 115, 117, 120, 124, 131, 133, 135, 137, 139, 146, 148, 150, 152, 155, 157, 159, 161, and 164, as described in more detail below.

A salinity tolerance and/or oxidative stress tolerance-modulating nucleic acid can comprise the nucleotide sequence set forth in SEQ ID NO: 85. Alternatively, a salinity tolerance and/or oxidative stress tolerance-modulating nucleic acid can be a variant of the nucleic acid having the nucleotide sequence set forth in SEQ ID NO: 85. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 85, 87, 89, 92, 95, 97, 99, 103, and 105.

A salinity tolerance and/or oxidative stress tolerance-modulating nucleic acid can comprise the nucleotide sequence set forth in SEQ ID NO: 40. Alternatively, a salinity tolerance and/or oxidative stress tolerance-modulating nucleic acid can be a variant of the nucleic acid having the nucleotide sequence set forth in SEQ ID NO: 40. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 40, 46, 48, 51, 53, 55, 57, 59, 61, 65, 67, 70, 72, 75, 77, 79, and 82.

A salinity tolerance and/or oxidative stress tolerance-modulating nucleic acid can comprise the nucleotide sequence set forth in SEQ ID NO: 108. Alternatively, a salinity tolerance and/or oxidative stress tolerance-modulating nucleic acid can be a variant of the nucleic acid having the nucleotide sequence set forth in SEQ ID NO: 108. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 108, 111, 113, 115, 117, 120, 124, 131, and 133.

A salinity tolerance and/or oxidative stress tolerance-modulating nucleic acid can comprise the nucleotide sequence set forth in SEQ ID NO: 139. Alternatively, a salinity tolerance and/or oxidative stress tolerance-modulating nucleic acid can be a variant of the nucleic acid having the nucleotide sequence set forth in SEQ ID NO: 139. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 135, 137, 139, 146, 148, 150, 152, 155, 157, 159, 161, and 164.

A salinity tolerance and/or oxidative stress tolerance-modulating nucleic acid can comprise the nucleotide sequence set forth in SEQ ID NO: 1. Alternatively, a salinity tolerance and/or oxidative stress tolerance-modulating nucleic acid can be a variant of the nucleic acid having the nucleotide sequence set forth in SEQ ID NO: 1. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1, 3, 5, 7, 10, 12, 16, 18, 21, 26, 28, and 32.

A salinity tolerance and/or oxidative stress tolerance-modulating nucleic acid can comprise the nucleotide sequence set forth in SEQ ID NO: 34. Alternatively, a salinity tolerance and/or oxidative stress tolerance-modulating nucleic acid can be a variant of the nucleic acid having the nucleotide sequence set forth in SEQ ID NO: 34. For example, a salinity tolerance and/or oxidative stress tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:34.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Salinity Tolerance and/or Oxidative Stress Tolerance-Modulating Polypeptide A nucleic acid encoding one of the salinity tolerance and/or oxidative stress tolerance-modulating polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular salinity tolerance and/or oxidative stress tolerance-modulating polypeptide; i.e., for many amino acids, there is more than one nucleotide triplet that serves as the codon for the amino acid. Thus, codons in the coding sequence for a given salinity tolerance and/or oxidative stress tolerance-modulating polypeptide can be modified such that optimal expression in a particular plant species is obtained, using appropriate codon bias tables for that species.

In some cases, expression of a salinity tolerance and/or oxidative stress tolerance-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of a Salinity Tolerance and/or Oxidative Stress Tolerance-Modulating Polypeptide Polynucleotides and recombinant constructs described herein can be used to inhibit expression of a salinity tolerance and/or oxidative stress tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); Dorsett and Tuschl, *Nature Reviews Drug Discovery* 3: 318-329 (2004); and *Nature Reviews RNA interference collection*, October 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Antisense technology is one well-known method. In this method, a nucleic acid segment from a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid segment need not be the entire sequence of the gene to be repressed, but typically will be substantially complementary to at least a portion of the sense strand of the gene to be repressed. Generally, higher homology can be used to compensate for the use of a shorter sequence. Typically, a sequence of at least 30 nucleotides is used, e.g., at least 40, 50, 80, 100, 200, 500 nucleotides or more.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254, 678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA,* 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, NJ RNA endoribonucleases which have been described, such as the one that occurs naturally in *Tetrahymena thermophila,* can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence of a salinity tolerance and/or oxidative stress tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand of the coding sequence of the salinity tolerance and/or oxidative stress tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region of an mRNA encoding a salinity tolerance and/or oxidative stress tolerance-modulating polypeptide, and the other strand of the stem portion of the double stranded RNA comprises a sequence that is similar or identical to the sequence that is complementary to the 3' or 5' untranslated region, respectively, of the mRNA encoding the salinity tolerance and/or oxidative stress tolerance-modulating polypeptide. In other embodiments, one strand of the stem portion of a double stranded RNA comprises a sequence that is similar or identical to the sequence of an intron in the pre-mRNA encoding a salinity tolerance and/or oxidative stress tolerance-modulating polypeptide, and the other strand of the stem portion comprises a sequence that is similar or identical to the sequence that is complementary to the sequence of the intron in the pre-mRNA. The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron. A double stranded RNA can have zero, one, two, three, four, five, six, seven, eight, nine, ten, or more stem-loop structures. A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence of a salinity tolerance and/or oxidative stress tolerance-modulating polypeptide. The transcription product can also be unpolyadenylated, lack a 5' cap structure, or contain an unsplicable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a salinity tolerance and/or oxidative stress tolerance-modulating polypeptide. In some embodiments, the sense or antisense sequence is identical or complementary to a sequence of the regulatory region that drives transcription of the gene encoding a salinity tolerance and/or oxidative stress tolerance-modulating polypeptide. In each case, the sense sequence is the sequence that is complementary to the antisense sequence.

The sense and antisense sequences can be any length greater than about 12 nucleotides (e.g., 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence encoding a salinity tolerance and/or oxidative stress tolerance-modulating polypeptide described herein. The sense sequence complementary to the antisense sequence can be a sequence present within the mRNA of the salinity tolerance and/or oxidative stress tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, *Antisense Nucleic Acid Drug Dev.*, 7:187-195; Hyrup et al., *Bioorgan. Med. Chem.*, 4:5-23 (1996). In addition, the deoxyphosphate backbone can be replaced with, for example, a phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate salinity tolerance and/or oxidative stress tolerance levels. A recombinant nucleic acid construct can comprise a nucleic acid encoding a salinity tolerance and/or oxidative stress tolerance-modulating polypeptide as described herein, operably linked to a regulatory region suitable for expressing the salinity tolerance and/or oxidative stress tolerance-modulating polypeptide in the plant or cell. Thus, a nucleic acid can comprise a coding sequence that encodes any of the salinity tolerance and/or oxidative stress tolerance-modulating polypeptides as set forth in SEQ ID NOs: 1, 3, 5, 7, 10, 12, 16, 18, 21, 26, 28, 32, 34, 40, 46, 48, 51, 53, 55, 57, 59, 61, 65, 67, 70, 72, 75, 77, 79, 82, 85, 87, 89, 92, 95, 97, 99, 103, 105, 108, 111, 113, 115, 117, 120, 124, 131, 133, 135, 137, 139, 146, 148, 150, 152, 155, 157, 159, 161, and 164. Examples of nucleic acids encoding salinity tolerance and/or oxidative stress tolerance-modulating polypeptides are set forth in SEQ ID NOs: 2, 4, 6, 8, 9, 11, 13, 14, 15, 17, 19, 20, 22, 23, 24, 25, 27, 29, 30, 31, 33, 35, 36, 37, 38, 39, 41, 42, 43, 44, 45, 47, 49, 50, 52, 54, 56, 58, 60, 62, 63, 64, 66, 68, 69, 71, 73, 74, 76, 78, 80, 81, 83, 84, 86, 88, 90, 91, 93, 94, 96, 98, 100, 101, 102, 104, 106, 107, 109, 110, 112, 114, 116, 118, 119, 121, 122, 123, 125, 126, 127, 128, 129, 130, 132, 134, 136, 138, 140, 141, 142, 143, 144, 145, 147, 149, 151, 153, 154, 156, 158, 160, 162, 163, 165, 166, 167, 168, and amino acid coordinates 1 to 135 of SEQ ID NO: 140. The salinity tolerance and/or oxidative stress tolerance-modulating polypeptide encoded by a recombinant nucleic acid can be a native salinity tolerance and/or oxidative stress tolerance-modulating polypeptide, or can be heterologous to the cell. In some cases, the recombinant construct contains a nucleic acid that inhibits expression of a salinity tolerance and/or oxidative stress tolerance-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen (Madison, WI), Clontech (Palo Alto, CA), Stratagene (La Jolla, CA), and Invitrogen/Life Technologies (Carlsbad, CA).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, 0-glucuronidase (GUS), green fluorescent protein (GFP), glutathione S-transferase (GST), polyhistidine, c-myc, hemagglutinin, or Flag™ tag (Kodak, New Haven, CT) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable promoters initiate transcription only, or predominantly, in certain cell types. The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al., *Plant Cell*, 1:855-866 (1989); Bustos et al., *Plant Cell*, 1:839-854 (1989); Green et al., *EMBO J.*, 7:4035-4044 (1988); Meier et al., *Plant Cell*, 3:309-316 (1991); and Zhang et al., *Plant Physiology*, 110:1069-1079 (1996).

Examples of various classes of regulatory regions are described below. Some of the regulatory regions indicated below as well as additional regulatory regions are described in more detail in U.S. Patent Application Ser. Nos. 60/505, 689; 60/518,075; 60/544,771; 60/558,869; 60/583,691; 60/619,181; 60/637,140; 60/757,544; 60/776,307; 10/957, 569; 11/058,689; 11/172,703; 11/208,308; 11/274,890; 60/583,609; 60/612,891; 11/097,589; 11/233,726; 11/408, 791; 11/414,142; 10/950,321; 11/360,017; PCT/US05/ 011105; PCT/US05/23639; PCT/US05/034308; PCT/US05/ 034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/ US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/ 62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA*, 86:7890-7894 (1989)), root cell specific promoters reported by Conkling et al., *Plant Physiol.*, 93:1203-1211 (1990), and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., *Plant Cell*, 1(9):839-853 (1989)), the soybean trypsin inhibitor promoter (Riggs et al., *Plant Cell*, 1(6):609-621 (1989)), the ACP promoter (Baerson et al., *Plant Mol. Biol.*, 22(2):255-267 (1993)), the stearoyl-ACP desaturase promoter (Slocombe et al., *Plant Physiol.*, 104(4):167-176 (1994)), the soybean α' subunit of β-conglycinin promoter (Chen et al., *Proc. Natl. Acad. Sci. USA*, 83:8560-8564 (1986)), the oleosin promoter (Hong et al., *Plant Mol. Biol.*, 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.*, 13:5829-5842 (1993)), the beta-amylase promoter, and the barley hordein promoter. Other maturing endosperm promoters include the YP0092, PT0676, and PT0708 promoters.

iv. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see, Urao (1996) *Plant Mol. Biol.*, 32:571-57; Conceicao (1994) *Plant*, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics*, 142: 1009-1020); maize Cat3 (see, GenBank No. L05934; Abler (1993) *Plant Mol. Biol.*, 22:10131-1038). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOsFIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104:997-1006 (1994)), the cab1R promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb1*2 promoter (Cerdan et al., *Plant Mol. Biol.*, 33:245-255 (1997)), the *Arabidopsis thaliana* SUC2 sucrose-H+ symporter promoter (Truernit et al., *Planta*, 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, *Plant Cell*, 3(10):1051-1061 (1991)), the *Commelina* yellow mottle virus (CoYMV) promoter (Medberry et al., *Plant Cell*, 4(2):185-192 (1992)), and the rice tungro bacilliform virus (RTBV) promoter (Dai et al., *Proc. Natl. Acad. Sci. USA*, 101(2):687-692 (2004)).

ix. Inducible Promoters

Inducible promoters confer transcription in response to external stimuli such as chemical agents or environmental stimuli. For example, inducible promoters can confer transcription in response to hormones such as gibberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) Nature Biotech 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a salt and/or oxidative stress tolerance modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

Alternatively, misexpression can be accomplished using a two component system, whereby the first component consists of a transgenic plant comprising a transcriptional activator operatively linked to a promoter and the second component consists of a transgenic plant that comprise a nucleic acid molecule of the invention operatively linked to the target-binding sequence/region of the transcriptional activator. The two transgenic plants are crossed and the nucleic acid molecule of the invention is expressed in the progeny of the plant. In another alternative embodiment of the present invention, the misexpression can be accomplished by having the sequences of the two component system transformed in one transgenic plant line.

IV. TRANSGENIC PLANTS AND PLANT CELLS

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant having the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous salinity tolerance and/or oxidative stress tolerance-modulating polypeptide whose expression has not previously been confirmed in particular recipient cells.

Techniques for introducing nucleic acids into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/selection

A population of transgenic plants can be screened and/or selected for those members of the population that have a trait or phenotype conferred by expression of the transgene. For example, a population of progeny of a single transformation event can be screened for those plants having a desired level of expression of a salinity tolerance and/or oxidative stress tolerance-modulating polypeptide or nucleic acid. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of salinity tolerance and/or oxidative stress tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a salinity tolerance and/or oxidative stress tolerance level relative to a control plant that lacks the transgene. Selected or screened transgenic plants have an altered phenotype as compared to a corresponding control plant, as described in the "Transgenic Plant Phenotypes" section herein.

A population of transgenic plants can be screened and/or selected for those members of the population that have a trait or phenotype conferred by expression of the transgene. For example, a population of progeny of a single transformation event can be screened for those plants having a desired level of expression of a saline and/or oxidative stress tolerance-modulating polypeptide and/or nucleic acid. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of saline and/or oxidative stress tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a saline and/or oxidative stress tolerance level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

Suitable species include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Medicago sativa* (alfalfa), *Arundo donax* (giant reed), *Secale cereale* (rye), *Salix* spp. (willow), *Eucalyptus* spp. (*eucalyptus*), Triticosecale (*triticum*—wheat X rye) and bamboo.

Suitable species also include *Helianthus annuus* (sunflower), Carthamus tinctorius (safflower), *Jatropha curcas* (jatropha), *Ricinus communis* (castor), *Elaeis guineensis* (palm), *Linum usitatissimum* (flax), and *Brassica juncea*.

Suitable species also include *Beta vulgaris* (sugarbeet), and *Manihot esculenta* (cassava).

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, brusselsprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum* annum (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica., Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (=*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii*, and *Tanacetum parthenium*.

Suitable species also include *Parthenium argentatum* (guayule), *Hevea* spp. (rubber), *Mentha spicata* (mint), *Mentha piperita* (mint), *Bixa orellana*, and Alstroemeria spp.

Suitable species also include Rosa spp. (rose), *Dianthus caryophyllus* (carnation), *Petunia* spp. (*petunia*) and Poinsettia *pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), Acer spp. (maple, *Hordeum vulgare* (barley), *Poa pratensis* (bluegrass), *Lolium* spp. (ryegrass) and *Phleum pratense* (timothy).

Thus, the methods and compositions can be used over a broad range of plant species, including species from the dicot genera *Brassica*, Carthamus, Glycine, *Gossypium, Helianthus, Jatropha, Parthenium, Populus*, and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum*, and *Zea*. In some embodiments, a plant is a member of the species *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledonous plants and plant cell systems, wherein such plants are hybrids of different species or varieties of a species (e.g., *Saccharum* sp. X *Miscanthus* sp.)

D. Transgenic Plant Phenotypes

In some embodiments, a plant in which expression of a salinity and/or oxidative stress modulating polypeptide is modulated can have increased levels of tolerance to salinity and/or oxidative stress. For example, a salinity and/or oxidative stress-modulating polypeptide described herein can be expressed in a transgenic plant, resulting in increased levels of tolerance to salinity and/or oxidative stress. The salinity and/or oxidative stress tolerance levels can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to those levels in a corresponding control plant that does not express the transgene.

The nucleic acid molecules and polypeptides of the present invention are of interest because when the nucleic acid molecules are mis-expressed (i.e., when expressed at a non-natural location or in an increased or decreased amount relative to wild-type) they produce plants that exhibit improved salt tolerance and/or oxidation tolerance as compared to wild-type plants, as evidenced in part by the results of various experiments disclosed below. In particular, plants transformed with the nucleic acid molecules and polypeptides of the present invention can have any of a number of modified characteristics as compared to wild-type plants. Examples of modified characteristics include photosynthetic efficiency, seedling area, and biomass as it may be measured by plant height, leaf or rosette area, or dry mass. The modified characteristics may be observed and measured at different plant developmental stages, e.g. seed, seedling, bolting, senescense, etc. Often, salt or oxidative tolerance can be expressed as ratios or combinations of measurements, such as salt growth index values, or salicylic acid growth index values. For example, plants transformed with the sequences of the present invention can exhibit increases in SGI, seedling area and/or SAGI values of at least 5%, at least 10%, at least 25%, at least 50%, at least 75%, at least 100%, at least 200%, at least 300%, at least 400%, or even at least 500%. These traits can be used to exploit or maximize plant products. For example, the nucleic acid molecules and polypeptides of the present invention are used to increase the expression of genes that cause the plant to have improved biomass, growth rate and/or seedling vigor in saline and/or oxidative conditions, in comparison to wild type plants under the same conditions.

Because the disclosed sequences and methods increase vegetative growth and growth rate in saline and/or oxidative conditions, the disclosed methods can be used to enhance plant growth in plants grown in saline and/or oxidative conditions. For example, plants of the present invention show, under saline and/or oxidative conditions, increased photosynthetic efficiency and increased seedling area as compared to a plant of the same species that is not genetically modified for substantial vegetative growth. Examples of increases in biomass production include increases of at least 5%, at least 20%, or even at least 50%, when compared to an amount of biomass production by a wild-type plant of the same species under identical conditions.

Typically, a difference in the amount of tolerance to salinity and/or oxidative stress in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the amount of tolerance to salinity and/or oxidative stress is statistically significant at $p<0.01$, $p<0.005$, or $p<0.001$.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest.

Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

V. PLANT BREEDING

Genetic polymorphisms are discrete allelic sequence differences in a population. Typically, an allele that is present at 1% or greater is considered to be a genetic polymorphism. The discovery that polypeptides disclosed herein can modulate salinity tolerance and/or oxidative stress tolerance content is useful in plant breeding, because genetic polymorphisms exhibiting a degree of linkage with loci for such polypeptides are more likely to be correlated with variation in a salinity tolerance and/or oxidative stress tolerance trait. For example, genetic polymorphisms linked to the loci for such polypeptides are more likely to be useful in marker-assisted breeding programs to create lines having a desired modulation in the salinity tolerance and/or oxidative stress tolerance traits.

Thus, one aspect of the invention includes methods of identifying whether one or more genetic polymorphisms are associated with variation in a salinity tolerance and/or oxidative stress tolerance trait. Such methods involve determining whether genetic polymorphisms in a given population exhibit linkage with the locus for one of the polypeptides depicted in FIGS. 1 thru 6 and/or a functional homolog thereof, such as, but not limited to, those in the Sequence Listing. The correlation is measured between variation in the salinity tolerance and/or oxidative stress tolerance traits in plants of the population and the presence of the genetic polymorphism(s) in plants of the population, thereby identifying whether or not the genetic polymorphism(s) are associated with variation for the traits. If the presence of a particular allele is statistically significantly correlated with a desired modulation in the salinity tolerance and/or oxidative stress tolerance traits, the allele is associated with variation for one or both of the traits and is useful as a marker for one or more of the traits. If, on the other hand, the presence of a particular allele is not significantly correlated with the desired modulation, the allele is not associated with variation for one or more of the traits and is not useful as a marker.

Such methods are applicable to populations containing the naturally occurring endogenous polypeptide rather than an exogenous nucleic acid encoding the polypeptide, i.e., populations that are not transgenic for the exogenous nucleic acid. It will be appreciated, however, that populations suitable for use in the methods may contain a transgene for another, different trait, e.g., herbicide resistance.

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. If the probes flank an SSR in the population, PCR products of different sizes will be produced. See, e.g., U.S. Pat. No. 5,766,847. Alternatively, SSR polymorphisms can be identified by using PCR product(s) as a probe against Southern blots from different individuals in the population. See, U. H. Refseth et al., (1997) Electrophoresis 18: 1519. The identification of RFLPs is discussed, for example, in Alonso-Blanco et al. (Methods in Molecular Biology, vol. 82, "Arabidopsis Protocols", pp. 137-146, J. M. Martinez-Zapater and J. Salinas, eds., c. 1998 by Humana Press, Totowa, NJ); Burr ("Mapping Genes with Recombinant Inbreds", pp. 249-254, in Freeling, M. and V. Walbot (Ed.), The Maize Handbook, c. 1994 by Springer-Verlag New York, Inc.: New York, NY, USA; Berlin Germany; Burr et al. Genetics (1998) 118: 519; and Gardiner, J. et al., (1993) Genetics 134: 917). The identification of AFLPs is discussed, for example, in EP 0 534 858 and U.S. Pat. No. 5,878,215.

In some embodiments, the methods are directed to breeding a plant line. Such methods use genetic polymorphisms identified as described above in a marker assisted breeding program to facilitate the development of lines that have a desired alteration in the salinity tolerance and/or oxidative stress tolerance trait(s). Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VI. ARTICLES OF MANUFACTURE

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought. In some embodiments, plants described herein have a composition that permits more efficient processing into free sugars, and subsequently ethanol, for energy production. In some embodiments, such plants provide higher yields of ethanol, butanol, other biofuel molecules, and/or sugar-derived co-products per kilogram of plant material, relative to control plants. By providing higher yields at an equivalent or even decreased cost of production relative to controls, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

Enhanced salt and/or oxidative stress tolerance gives the opportunity to grow crops in saline or oxidative stress conditions without stunted growth and diminished yields due to salt-induced ion imbalance, disruption of water homeostasis, inhibition of metabolism, damage to membranes, and/or cell death. The ability to grow plants in saline or oxidative stress conditions would result in an overall expansion of arable land and increased output of land currently marginally productive due to elevated salinity or oxidative stress conditions.

Seed or seedling vigor is an important characteristic that can greatly influence successful growth of a plant, such as crop plants. Adverse environmental conditions, such as saline and/or oxidative conditions, can affect a plant growth cycle, germination of seeds and seedling vigor (i.e. vitality and strength under such conditions can differentiate between successful and failed plant growth). Seedling vigor has often been defined to comprise the seed properties that determine "the potential for rapid, uniform emergence and development of normal seedlings under a wide range of field conditions". Hence, it would be advantageous to develop plant seeds with increased vigor, particularly in elevated salinity and/or in oxidative stress conditions.

For example, increased seedling vigor would be advantageous for cereal plants such as rice, maize, wheat, etc. production. For these crops, germination and growth can often be slowed or stopped by salination and/or oxidation. Genes associated with increased seed vigor under saline and/or oxidative stress conditions have therefore been sought for producing improved plant varieties. (Walia et al. (2005) *Plant Physiology* 139:822-835).

The invention will be further described in the following examples, which do not limit the scope of the invention described in the claims.

VII. EXAMPLES

Example 1: *Agrobacterium*-Mediated Transformation of *Arabidopsis*

Host Plants and Transgenes: Wild-type *Arabidopsis thaliana* Wassilewskija (WS) plants were independently transformed with Ti plasmids containing clones encoding polypeptides at SEQ ID NOs: 43, 44, 45, 86, 136, 138, 140, 141, 142, 143, 144, and amino acid coordinates 1 to 135 of SEQ ID NO: 140. Examples include Ceres CLONE ID no. 1792354, Ceres SEEDLINE ID no. ME06748, Ceres SEEDLINE ID no. ME08768, Ceres SEEDLINE ID no. ME19173, and Ceres CLONE ID no. 375578. Unless otherwise indicated, each Ceres Clone and/or Seedline derived from a Clone is in the sense orientation relative to either the 35S promoter in a Ti plasmid. A Ti plasmid vector useful for these constructs, CRS 338, contains the Ceres-constructed, plant selectable marker gene phosphinothricin acetyltransferase (PAT), which confers herbicide resistance to transformed plants.

Preparation of Soil Mixture: 24 L Sunshine Mix #5 soil (Sun Gro Horticulture, Ltd., Bellevue, WA) is mixed with 16 L Therm-O-Rock vermiculite (Therm-O-Rock West, Inc., Chandler, AZ) in a cement mixer to make a 60:40 soil mixture. To the soil mixture is added 2 Tbsp Marathon 1% granules (Hummert, Earth City, MO), 3 Tbsp OSMOCOTE® 14-14-14 (Hummert, Earth City, MO) and 1 Tbsp Peters fertilizer 20-20-20 (J. R. Peters, Inc., Allentown, PA), which are first added to 3 gallons of water and then added to the soil and mixed thoroughly. Generally, 4-inch diameter pots are filled with soil mixture. Pots are then covered with 8-inch squares of nylon netting.

Planting: Using a 60 mL syringe, 35 mL of the seed mixture is aspirated. 25 drops are added to each pot. Clear propagation domes are placed on top of the pots that are then placed under 55% shade cloth and subirrigated by adding 1 inch of water.

Plant Maintenance: 3 to 4 days after planting, lids and shade cloth are removed. Plants are watered as needed. After 7-10 days, pots are thinned to 20 plants per pot using forceps. After 2 weeks, all plants are subirrigated with Peters fertilizer at a rate of 1 Tsp per gallon of water. When bolts are about 5-10 cm long, they are clipped between the first node and the base of stem to induce secondary bolts. Dipping infiltration is performed 6 to 7 days after clipping.

Preparation of *Agrobacterium*: To 150 mL fresh YEB is added 0.1 mL each of carbenicillin, spectinomycin and rifampicin (each at 100 mg/ml stock concentration). *Agrobacterium* starter blocks are obtained (96-well block with *Agrobacterium* cultures grown to an $OD_{600}$ of approximately 1.0) and inoculated one culture vessel per construct by transferring 1 mL from appropriate well in the starter block. Cultures are then incubated with shaking at 27° C. Cultures are spun down after attaining an $OD_{600}$ of approximately 1.0 (about 24 hours). 200 mL infiltration media is added to resuspend *Agrobacterium* pellets. Infiltration media is prepared by adding 2.2 g MS salts, 50 g sucrose, and 5 µL 2 mg/ml benzylaminopurine to 900 ml water.

Dipping Infiltration: The pots are inverted and submerged for 5 minutes so that the aerial portion of the plant is in the *Agrobacterium* suspension. Plants are allowed to grow normally and seed is collected.

Example 2: Saline Condition Screening

Saline condition screening: Screening is routinely performed by high-salt agar plate assay and also by high-salt soil assay. Traits assessed in high-salt conditions include: seedling area, photosynthesis efficiency, salt growth index and regeneration ability.

Seedling area: the total leaf area of a young plant about 2 weeks old.

Photosynthesis efficiency (Fv/Fm): Seedling photosynthetic efficiency, or electron transport via photosystem II, is estimated by the relationship between Fm, the maximum fluorescence signal and the variable fluorescence, Fv. Here, a reduction in the optimum quantum yield (Fv/Fm) indicates stress, and so can be used to monitor the performance of transgenic plants compared to non-transgenic plants under salt stress conditions.

Salt growth index=seedling area×photosynthesis efficiency (Fv/Fm).

Regeneration ability: the ability of a plant to regenerate shoots in saline soil after stems are cut off and the soil is irrigated with 200 mM NaCl solution.

Transformant identification: PCR was used to amplify the cDNA insert in one randomly chosen $T_2$ plant. This PCR product was then sequenced to confirm the sequence in the plants.

Identification of Tolerant Plant to Salt Stress: A superpool of seeds was screened for transgenic plants that show enhanced tolerance to SA, as detailed below, and high salt. Three independent candidate plants were sequenced and the transgene sequence matched ME02064.

Assessing Tolerance to Salt Stress: Generally, between four and ten independently transformed plant lines are selected and qualitatively evaluated for their tolerance to salt stress in the $T_1$ generation. Two or three of the transformed lines that qualitatively show the strongest tolerance to salt stress in the $T_1$ generation are selected for further evaluation in the $T_2$ and $T_3$ generations. This evaluation involves sowing seeds from the selected transformed plant lines on MS agar plates containing either 100 mM or 150 mM NaCl and incubating the seeds for 5 to 14 days to allow for germination and growth. For example, for ME02064 five T2 events were compared to wild-type Ws for salt stress tolerance on salt plates. Three events, ME02064-01, -03 and -04 were selected based on the measurement of seedling area on 36 plants of each event as compared to the control, Ws. Further evaluation of salt tolerance in ME02064-01, -03 and -04 was performed with $T_2$ and $T_3$ generations.

Calculating SGI: After germination and growth, seedling area and photosynthesis efficiency of transformed lines and a wild-type control are determined. From these measurements, the Salt Growth Index (SGI) is calculated and compared between wild-type and transformed seedlings. The SGI calculation is made by multiplying seedling area with photosynthesis efficiency measurements taken from two replicates of 36 seedlings for each transformed line and a wild-type control and performing a t-test.

Determining Transgene Copy Number: $T_2$ generation transformed plants are tested on BASTA™ plates in order to determine the transgene copy number of each transformed line. A BASTA™ resistant:BASTA™ sensitive segregation ratio of 15:1 generally indicates two copies of the transgene, and such a segregation ratio of 3:1 generally indicates one copy of the transgene.

Example 3: Oxidative Stress Conditions Screening

Under normal growth conditions, Arabidopsis rosette contains about 0.5 μg/g fresh weight of free SA. In response to stress conditions or pathogen attacks, the free SA levels can reach as high as 10 μg/g fresh weight, which is approximately equivalent to 60 μM. The exogenous application of 100-500 μM SA to Arabidopsis leaves by spraying is able to induce strong defense responses without triggering obvious necrotic lesion formation. Once the SA concentration increases to 5 mM or above, the cell death in form of necrotic lesions will appear on the sprayed leaves. If SA is applied through growth media, Arabidopsis is more sensitive to SA-induced oxidative stress, probably because of continuous absorption. The addition of 100-150 μM SA to growth media significant reduces plant growth but does not kills the plants in wild type Arabidopsis Ws. Therefore we use this range of SA to screen for enhanced oxidative stress tolerance.

Salicylic Acid Screening: Screening is routinely performed by agar plate assay using 100 μM or 150 μM exogenous sodium salicylate. Media contains ½×MS (Sigma), 150 μM sodium salicylate (Sigma), 0.5 g MES hydrate (Sigma) and 0.7% phytagar (EM Science), adjusted to pH 5.7 using 1ON KOH.

To screen superpools, seeds are surface sterilized in 30% bleach solution for 5 minutes and then rinsed repeatedly with sterile water. Approximately 2500 seeds are sown on media plates in a monolayer at a density of 850 seeds per plate. Wild-type and positive controls are grown on comparable plates. Plates are wrapped with vent tape and placed at 4° C. in the dark for three days to stratify. At the end of this time, plates are transferred to a Conviron growth chamber set at 22 C, 16:8 hour light:dark cycle, 70% humidity with a combination of incandescent and fluorescent lamps emitting a light intensity of ~100 μEinsteins.

Seedlings are screened daily starting at 6 days. Seedlings that grow larger and stay greener compared to WS control plants are selected as positive candidates and transferred to soil for recovery and seed set.

Candidate plants are re-screened by placing 36 seeds from each candidate together with a WS control on the same sodium salicylate plate. Plates are treated as described above and seedling screening begun after at 4 days after germination. Leaf tissue is harvested from confirmed tolerant candidates for DNA extraction and amplification of the transgene by PCR.

Alternatively, superpool seeds are sown directly on soil and sprayed with 10 mM SA.

Leaf tissue is harvested from tolerant candidate plants to isolate DNA for PCR amplification of the transgene and subsequent sequencing of the PCR product.

Traits assessed under sodium salicylate conditions include: seedling area, photosynthesis efficiency, salicylic acid growth index (SAG) and regeneration ability.

Seedling area: the total leaf area of a young plant about 2 weeks old.

Photosynthesis efficiency (Fv/Fm): Seedling photosynthetic efficiency, or electron transport via photosystem II, is estimated by the relationship between Fm, the maximum fluorescence signal and the variable fluorescence, Fv. Here, a reduction in the optimum quantum yield (Fv/Fm) indicates stress, and so can be used to monitor the performance of transgenic plants compared to non-transgenic plants under oxidative stress conditions.

Salicylic Acid Growth (SAG) Index=seedling area $(cm^2)$×photosynthesis efficiency (Fv/Fm).

PCR was used to amplify the cDNA insert in one randomly chosen $T_2$ plant. This PCR product was then sequenced to confirm the sequence in the plants.

Assessing Tolerance to Oxidative Stress: Initially, All available independently transformed T2 plant lines are qualitatively evaluated for their tolerance to oxidative stress as compared to wild-type controls. The positive transgenic lines that qualitatively show the strongest tolerance to oxidative stress are selected for further evaluation in the $T_2$ and $T_3$ generations using internal non-transgenic segregants as controls. This evaluation involves sowing seeds from the selected transformed plant lines on MS agar plates containing 100 μM or 150 μM sodium salicylate and incubating the seeds for at least 4 days to allow for germination and growth and transgene status analysis.

Calculating SAG: After germination and growth, seedling area and photosynthesis efficiency of transformed lines and a wild-type control are determined. From these measurements, the Salicylic Acid Growth Index (SAG) is calculated and compared between wild-type and transformed seedlings. The SAG calculation is made by multiplying seedling area with photosynthesis efficiency measurements taken from two replicates of 36 seedlings for each transformed line and a wild-type control and performing a t-test.

Determining Transgene Copy Number: $T_2$ generation transformed plants are tested on BASTA™ plates in order to determine the transgene copy number of each transformed line. A BASTA™ resistant:BASTA™ sensitive segregation ratio of 15:1 generally indicates two copies of the transgene, and such a segregation ratio of 3:1 generally indicates one copy of the transgene.

In some cases, validation is performed using media that is further supplemented with 100 uM SNP.

Example 4: ME02064 (Ceres Clone 375578; SEQ ID No. 138)

Wild-type Arabidopsis thaliana Wassilewskija was transformed with a Ti plasmid carrying the 35S promoter and Ceres Clone 375578. Three transformed lines, ME02064-01 and ME02064-03, ME02064-04, showed the strongest qualitative tolerance to salt stress in a prevalidation assay (Table 4-1). Their tolerance to 150 mM NaCl was further evaluated in a validation assay for two generations. Segregation ratios (BASTA™ resistant: BASTA™ sensitive) indicated ME02064-01 and ME02064-03, ME02064-04 transformed lines each carry one copy of the transgene.

TABLE 4-1

Prevalidation assay of ME02064 salt tolerance as compared to wild-type Ws

|  | Ws Wild-type | ME02064-01 | ME02064-02 | ME02064-03 | ME02064-04 | ME02064-05 |
|---|---|---|---|---|---|---|
| Mean* | 0.0359 | 0.0435 | 0.0346 | 0.0441 | 0.0438 | 0.0305 |
| Standard Error | 0.0016 | 0.0048 | 0.004 | 0.0041 | 0.0035 | 0.0019 |

*Average seedling area of 36 plants grown on MS agar plates containing 150 mM NaCl for 14 days When grown on MS agar plates containing 150 mM NaCl, ME02064-01 and ME02064-03, ME02064-04 transgenic plants showed significantly greater seedling area and SGI relative to non-transgenic plants. As shown in Table 4-2, the T2-generation SGI value for ME02064-01 seedlings increased by 110% while ME02064-03 seedlings increased by 131% and ME02064-04 seedlings increased by 72% compared to non-transgenic control seedlings. In the $T_3$ generation, the SGI increase was 43% for ME02064-01, 47% for ME02064-03, and 64% for ME02064-04. The differences between transgenic and non-transgenic seedlings are statistically significant, and clearly demonstrate that the enhanced tolerance to salt stress was a result of the ectopic expression of Ceres Clone 375578 in the ME02064 transformant lines.

TABLE 4-2

Validation assay of ME02064 on salt tolerance in two generations

| ME Events | SGI* of transgenics | | | SGI of pooled non-transgenics | | | t-Test | | % of SGI increase |
|---|---|---|---|---|---|---|---|---|---|
| | Avg | SE | N | Avg | SE | N | t-value | $t_{0.05}$ | |
| ME02064-01-$T_2$ | 2.057 | 0.249 | 12 | 0.977 | 0.205 | 17 | 3.35 | 1.70 | 110.5 |
| ME02064-03-$T_2$ | 2.237 | 0.371 | 5 | 0.968 | 0.140 | 24 | 3.20 | 1.70 | 131.1 |
| ME02064-04-$T_2$ | 1.810 | 0.146 | 14 | 1.055 | 0.135 | 13 | 3.81 | 1.70 | 71.6 |
| ME02064-01-$T_3$ | 2.438 | 0.170 | 21 | 1.708 | 0.289 | 9 | 2.18 | 1.70 | 42.7 |
| ME02064-03-$T_3$ | 2.837 | 0.257 | 20 | 1.927 | 0.271 | 14 | 2.43 | 1.70 | 47.2 |
| ME02064-04-$T_3$ | 2.770 | 0.318 | 16 | 1.688 | 0.188 | 19 | 2.93 | 1.70 | 64.1 |

*SGI (Salt Growth Index) = seedling area × Fv/Fm (photosynthesis efficiency)

Summary of Results:
Ectopic expression of Ceres Clone 375578 under the control of the 35S promoter enhances tolerance to salt stress that causes necrotic lesions and stunted growth in wild-type Ws seedlings.

Example 5: ME03140; Clone 375578; SEQ ID No. 142

Wild-type *Arabidopsis thaliana* Wassilewskija was transformed with a Ti plasmid carrying the 35S promoter operatively linked to Ceres Clone 375578 (SEQ ID NO: 142), and five transgenic lines, ME03140-01, ME03140-02, ME03140-03, ME03140-04 and ME03140-05 were investigated for tolerance to salt stress. When grown on MS agar plates containing 150 mM NaCl, these transgenic lines showed increased tolerance to salt stress in quantitative assays as compared to non-transgenic control seedlings.

When grown on MS agar plates containing 150 mM NaCl, ME03140-01, ME03140-02, ME03140-03, ME03140-04 and ME03140-05 transgenic plants showed significantly greater seedling area and SGI relative to non-transgenic plants. As shown in Table 5, the T2-generation SGI value for ME03140-01 seedlings increased 102.18%, ME03140-02 seedlings increased 60.78%, ME03140-03 seedlings increased 120.32%, ME03140-04 seedlings increased 45.07% and ME03140-05 seedlings increased 90.53% as compared to non-transgenic control seedlings. The differences in SGI values between transgenic and non-transgenic seedlings have statistically significant P values for all transgenic lines, and these quantitative experiments clearly demonstrate that ectopic expression of Ceres Clone 375578 confers enhanced tolerance to salt stress in transgenic seedlings.

TABLE 5

Validation assay of ME03140 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME03140-01-$T_2$ | 4.34 | 0.590403017 | 17 | 2.15 | 0.478695 | 26 | 3.10E−03 | 102.18% |
| ME03140-02-$T_2$ | 4.09 | 0.395692005 | 18 | 2.54 | 0.367281 | 28 | 3.22E−03 | 60.78% |
| ME03140-03-$T_2$ | 4.03 | 0.646365854 | 12 | 1.83 | 0.397508 | 36 | 2.86E−03 | 120.32% |
| ME03140-04-$T_2$ | 4.86 | 0.534320049 | 17 | 3.35 | 0.446161 | 36 | 1.74E−02 | 45.07% |
| ME03140-05-$T_2$ | 4.31 | 0.5237326 | 25 | 2.26 | 0.665646 | 20 | 9.91E−03 | 90.53% |

*SGI (Salt Growth Index) = seedling area × Fv/Fm (photosynthesis efficiency)

Summary of Results:

Ectopic expression of Ceres Clone 375578 under the control of the 35S promoter enhances tolerance to salt stress that causes necrotic lesions and stunted growth in wild-type Ws seedlings.

Example 6: ME08732; Clone 560066; SEQ ID No. 44

Wild-type *Arabidopsis thaliana* Wassilewskija was transformed with a Ti plasmid carrying the 35S promoter operatively linked to Ceres Clone 560066 (SEQ ID NO: 44), and three transgenic lines, ME08732-01, ME08732-02 and ME08732-03, were investigated for tolerance to salt stress. When grown on MS agar plates containing 150 mM NaCl, these transgenic lines showed increased tolerance to salt stress in quantitative assays as compared to non-transgenic control seedlings.

When grown on MS agar plates containing 150 mM NaCl, ME08732-01, ME08732-02 and ME08732-03 transgenic plants showed significantly greater seedling area and SGI relative to non-transgenic plants. As shown in Table 6, the T2-generation SGI value for ME08732-01 seedlings increased 88.35%, ME08732-02 seedlings increased 41.72% and ME08732-03 seedlings increased 26.23%, as compared to non-transgenic control seedlings. The differences in SGI values between transgenic and non-transgenic seedlings have statistically significant P values for ME08732-01 and ME08732-02 transgenic lines, and these quantitative experiments clearly demonstrate that ectopic expression of Ceres Clone 560066 confers enhanced tolerance to salt stress in transgenic seedlings.

TABLE 6

Validation assay of ME08732 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME08732-01-$T_2$ | 4.07 | 0.164301729 | 24 | 2.16 | 0.472565 | 14 | 2.57E−04 | 88.35% |
| ME08732-02-$T_2$ | 3.42 | 0.391450599 | 21 | 2.41 | 0.336042 | 26 | 2.86E−02 | 41.72% |
| ME08732-03-$T_2$ | 4.71 | 0.566761111 | 10 | 3.73 | 0.285925 | 52 | 6.44E−02 | 26.23% |

*SGI (Salt Growth Index) = seedling area × Fv/Fm (photosynthesis efficiency)

Summary of Results:
Ectopic expression of Ceres Clone 560066 under the control of the 35S promoter enhances tolerance to salt stress that causes necrotic lesions and stunted growth in wild-type Ws seedlings.

Example 7: ME08768; Clone 539458; SEQ ID No. 86

Wild-type *Arabidopsis thaliana* Wassilewskija was transformed with a Ti plasmid carrying the 35S promoter operatively linked to Ceres Clone 539458 (SEQ ID NO: 86), and five transgenic lines, ME08768-01, ME08768-02, ME08768-03, ME08768-04 and ME08768-05, were investigated for tolerance to salt stress. When grown on MS agar plates containing 150 mM NaCl, these transgenic lines showed increased tolerance to salt stress in quantitative assays as compared to non-transgenic control seedlings.

When grown on MS agar plates containing 150 mM NaCl, ME08768-01, ME08768-02, ME08768-03, ME08768-04 and ME08768-05 transgenic plants showed significantly greater seedling area and SGI relative to non-transgenic plants. As shown in Table 7, the T2-generation SGI value for ME08768-01 seedlings increased 80.04%, ME008768-02 seedlings increased 111.63%, ME008768-03 seedlings increased 22.62%, ME008768-04 seedlings increased 115.40% and ME008768-05 seedlings increased 74.41% as compared to non-transgenic control seedlings. The differences in SGI values between transgenic and non-transgenic seedlings have statistically significant P values for ME08768-01, ME08768-02, ME08768-04 and ME08768-05 transgenic lines, and these quantitative experiments clearly demonstrate that ectopic expression of Ceres Clone 539458 confers enhanced tolerance to salt stress in transgenic seedlings.

TABLE 7

Validation assay of ME08768 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME08768-01-$T_2$ | 14.48 | 1.254125111 | 20 | 8.04 | 1.321838 | 26 | 4.91E-04 | 80.04% |
| ME08768-02-$T_2$ | 11.09 | 0.822117225 | 20 | 5.24 | 0.751908 | 32 | 1.55E-06 | 111.63% |
| ME08768-03-$T_2$ | 13.72 | 1.676864172 | 21 | 11.19 | 1.57188 | 30 | 0.1380406 | 22.62% |
| ME08768-04-$T_2$ | 14.82 | 1.3958585 | 16 | 6.88 | 0.777162 | 40 | 3.58E-06 | 115.40% |
| ME08768-05-$T_2$ | 10.02 | 1.365308 | 13 | 5.75 | 0.751134 | 38 | 4.23E-03 | 74.41% |

*SGI (Salt Growth Index) = seedling area × Fv/Fm (photosynthesis efficiency)

Summary of Results:
Ectopic expression of Ceres Clone 539458 under the control of the 35S promoter enhances tolerance to salt stress that causes necrotic lesions and stunted growth in wild-type Ws seedlings.

Example 8: ME10681; Clone 335348 SEQ ID No. 141

Wild-type *Arabidopsis thaliana* Wassilewskija was transformed with a Ti plasmid carrying the 35S promoter operatively linked to Ceres Clone 335348 (SEQ ID NO: 141), and six transgenic lines, ME10681-01-$T_2$, ME10681-01-T3, ME10681-02-$T_2$, ME10681-02-T3, ME10681-04-$T_2$ and ME10681-05-$T_2$, were investigated for tolerance to salt stress. When grown on MS agar plates containing 150 mM NaCl, these transgenic lines showed increased tolerance to salt stress in quantitative assays as compared to non-transgenic control seedlings.

When grown on MS agar plates containing 150 mM NaCl, ME10681-01-$T_2$, ME10681-01-$T_3$, ME10681-02-$T_2$, ME10681-02-$T_3$, ME10681-04-$T_2$ and ME10681-05-$T_2$ transgenic plants showed significantly greater seedling area and SGI relative to non-transgenic plants. As shown in Table 8, the T2-generation SGI value for ME010681-01-$T_2$ seedlings increased 39.17%, ME010681-01-$T_3$ seedlings increased 19.77%%, ME10681-02-$T_2$ seedlings increased 119.17%, ME10681-02-$T_3$ seedlings increased 6.21%, ME010681-04-$T_2$ seedlings increased 113.51% and ME010681-05-$T_2$ seedlings increased 103.98%, as compared to non-transgenic control seedlings. The differences in SGI values between transgenic and non-transgenic seedlings have statistically significant P values for ME10681-01-$T_3$, ME10681-02-T$_2$, ME10681-04-T$_2$ and ME10681-05-T$_2$ transgenic lines, and these quantitative experiments clearly demonstrate that ectopic expression of Ceres Clone 335348 confers enhanced tolerance to salt stress in transgenic seedlings.

TABLE 8

Validation assay of ME10681 salt stress tolerance in two generations

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME10681-01-T$_2$ | 3.87 | 0.683711333 | 9 | 2.78 | 0.302501 | 48 | 7.54E−02 | 39.17% |
| ME10681-01-T$_3$ | 4.7 | 0.31544415 | 23 | 3.93 | 0.3015141 | 43 | 3.99E−02 | 19.77% |
| ME10681-02-T$_2$ | 4.13 | 0.3353564 | 25 | 1.89 | 0.3969 | 22 | 4.16E−05 | 119.17% |
| ME10681-02-T$_3$ | 3.65 | 0.258400663 | 31 | 3.44 | 0.3060094 | 34 | 0.2980488 | 6.21% |
| ME10681-04-T$_2$ | 6.22 | 0.478672159 | 12 | 2.91 | 0.39405 | 30 | 2.04E−06 | 113.51% |
| ME10681-05-T$_2$ | 5.25 | 0.391550037 | 20 | 2.57 | 0.4265902 | 30 | 1.44E−05 | 103.98% |

*SGI (Salt Growth Index) = seedling area × Fv/Fm (photosynthesis efficiency)

Summary of results:
Ectopic expression of Ceres Clone 335348 under the control of the 35S promoter enhances tolerance to salt stress that causes necrotic lesions and stunted growth in wild-type Ws seedlings.

Example 9: ME18973; Ceres cDNA ID 23457556; SEQ ID No. 43

Wild-type *Arabidopsis thaliana* Wassilewskija was transformed with a Ti plasmid carrying the 35S promoter operatively linked to Ceres cDNA ID 23457556 (SEQ ID NO: 43), and six transgenic lines, ME18973-01-T$_2$, ME18973-02-T$_2$, ME18973-02-01-T$_3$, ME18973-03-T$_2$, ME18973-05-T$_2$ and ME18973-05-03-T$_3$ were investigated for tolerance to salt stress.

When grown on MS agar plates containing 150 mM NaCl, these transgenic lines showed increased tolerance to salt stress in quantitative assays as compared to non-transgenic control seedlings.

When grown on MS agar plates containing 150 mM NaCl, ME18973-01, ME18973-02-T$_2$, ME18973-02-01-T$_3$, ME18973-03-T$_2$, ME18973-05-T$_2$ and ME18973-05-03-T$_3$ transgenic plants showed significantly greater seedling area and SGI relative to non-transgenic plants. As shown in Table 9, the T2 & T3-generation SGI value for ME018973-01-T$_2$ seedlings increased 230.01%, ME18973-02-T$_2$ seedlings increased 22.44%, ME18973-02-01-T$_3$ seedlings increased 14.96%, ME18973-05-T$_2$ seedlings increased 16.12% and ME18973-05-03-T$_3$ seedlings increased 13.97%, as compared to non-transgenic control seedlings. The differences in SGI values between transgenic and non-transgenic seedlings have statistically significant P values for the ME18973 transgenic lines, and these quantitative experiments clearly demonstrate that ectopic expression of Ceres cDNA ID 23457556 results in enhanced tolerance to salt stress in transgenic seedlings.

TABLE 9

Validation assay of ME18973 salt stress tolerance in two generations

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME18973-01-T$_2$ | 4.41 | 0.253654648 | 26 | 1.34 | 0.367022 | 18 | 1.03E−08 | 230.01% |
| ME18973-02-T$_2$ | 4.47 | 0.373604899 | 27 | 3.65 | 0.526316 | 18 | 0.1058348 | 22.44% |
| ME18973-02-01-T$_3$ | 4.82 | 0.205971746 | 44 | 4.19 | 0.3832982 | 25 | 7.71E−02 | 14.96% |
| ME18973-05-T$_2$ | 4.74 | 0 | 1 | 4.09 | 0.503725 | 26 | 0.160517 | 16.12% |
| ME18973-05-03-T$_3$ | 4.38 | 0.233610226 | 32 | 3.84 | 0.503725 | 37 | 6.89E−02 | 13.97% |

*SGI (Salt Growth Index) = seedling area × Fv/Fm (photosynthesis efficiency)

Summary of results:
Ectopic expression of Ceres cDNA ID 23457556 under the control of the 35S promoter enhances tolerance to salt stress that causes necrotic lesions and stunted growth in wild-type Ws seedlings.

Example 10: ME19657; cDNA ID 23621377; SEQ ID No. 45

Wild-type *Arabidopsis thaliana* Wassilewskija was transformed with a Ti plasmid carrying the 35S promoter operatively linked to Ceres cDNA ID 23621377 (SEQ ID NO: 45), and two transgenic lines, ME19657-01-$T_2$, ME19657-01-05-$T_3$, ME19657-01-08-$T_3$, ME19657-02-$T_2$, ME19657-03-$T_2$, ME19657-04-$T_2$ and ME19657-04-01-$T_3$, were investigated for tolerance to salt stress. When grown on MS agar plates containing 150 mM NaCl, these transgenic lines showed increase tolerance to salt stress in quantitative assays as compared to non-transgenic control seedlings.

When grown on MS agar plates containing 150 mM NaCl, ME19657-01-$T_2$, ME19657-01-05-$T_3$, ME19657-01-08-$T_3$, ME19657-02-$T_2$, ME19657-03-$T_2$, ME19657-04-$T_2$ and ME19657-04-01-$T_3$ transgenic plants showed significantly greater seedling area and SGI relative to non-transgenic plants. As shown in Table 10, the T2 & T3-generation SGI value for ME19657-01-$T_2$ seedlings increased 82.29%, ME19657-01-05-$T_3$ seedlings increased 82.29%, ME19657-01-08-$T_3$ seedlings increased 21.90%, ME19657-02-$T_2$ seedlings increased 39.50%, ME19657-03-$T_2$ seedlings increased 98.28%, and ME19657-04-$T_2$ seedlings increased 4.38% and ME19657-04-01-$T_2$ seedlings increased 7.44%, as compared to non-transgenic control seedlings. The differences in SGI values between transgenic and non-transgenic seedlings have statistically significant P values for ME19657-01-$T_2$, ME19657-01-05-$T_3$, ME19657-01-08-$T_3$, ME19657-02-$T_2$ and ME19657-03-$T_2$ transgenic lines, and these quantitative experiments clearly demonstrate that ectopic expression of Ceres cDNA ID 23621377 results in enhanced tolerance to salt stress in transgenic seedlings.

TABLE 10

Validation assay of ME19657 salt stress tolerance in two generations

| ME Events | SGI* of transgenics | | | SGI of pooled non-transgenics | | | P value | % of SGI increase |
| --- | --- | --- | --- | --- | --- | --- | --- | --- |
| | Avg | SE | N | Avg | SE | N | | |
| ME19657-01-$T_2$ | 4.54 | 0.311964078 | 21 | 2.49 | 0.539972 | 15 | 5.62E−05 | 82.29% |
| ME19657-01-05-$T_3$ | 0.7 | 0.311964078 | 21 | 0.7 | 0.5399721 | 15 | 1.18E−03 | 82.29% |
| ME19657-01-08-$T_3$ | 5.4 | 0.278520121 | 27 | 4.43 | 0.3061552 | 36 | 1.18E−03 | 21.90% |
| ME19657-02-$T_2$ | 3.97 | 0.32089576 | 23 | 2.84 | 0.527849 | 18 | 0.0111868 | 39.50% |
| ME19657-03-$T_2$ | 4.79 | 0.313786256 | 22 | 2.41 | 0.299954 | 22 | 3.83E−02 | 98.28% |
| ME19657-04-$T_2$ | 3.67 | 0.341681304 | 15 | 3.52 | 0.324049 | 40 | 1.15E−06 | 4.38% |
| ME19657-04-01-$T_3$ | 4.56 | 0.495154 | 9 | 4.25 | 0.3487774 | 37 | 0.3723989 | 7.44% |

*SGI (Salt Growth Index) = seedling area × Fv/Fm (photosynthesis efficiency)

Summary of results:
Ectopic expression of Ceres cDNA ID 23621377 under the control of the 35S promoter enhances tolerance to salt stress that causes necrotic lesions and stunted growth in wild-type Ws seedlings.

Example 11: ME24076; Clone 229668; SEQ ID No. 143

Wild-type *Arabidopsis thaliana* Wassilewskija was transformed with a Ti plasmid carrying the 35S promoter operatively linked to Ceres Clone: 229668 (SEQ ID NO: 143), and two transgenic lines, ME24076-01 and ME24076-02, were investigated for tolerance to salt stress. When grown on MS agar plates containing 150 mM NaCl, these transgenic lines showed increase tolerance to salt stress in quantitative assays as compared to non-transgenic control seedlings.

When grown on MS agar plates containing 150 mM NaCl, only ME024076-01-$T_2$ and transgenic plants showed significantly greater seedling area and SGI relative to non-transgenic plants. As shown in Table 11, the T2-generation SGI value for ME24076-01-$T_2$ seedlings increased 65.57% and ME24076-02-$T_2$ seedlings decreased by 1.12%, as compared to non-transgenic control seedlings. The differences in SGI values between transgenic and non-transgenic seedlings have statistically significant P values for transgenic line ME24076-01, and these quantitative experiments clearly demonstrate that ectopic expression of Ceres Clone 229668 results in enhanced tolerance to salt stress in transgenic seedlings.

TABLE 11

Validation assay of ME24076 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME24076-01-$T_2$ | 11.18 | 0.924279499 | 17 | 6.75 | 0.9761984 | 32 | 9.45E−04 | 65.57% |
| ME24076-02-$T_2$ | 0.7 | 0.082529059 | 10 | 0.7 | 0.0506174 | 48 | 0.4675565 | −1.12% |

*SGI (Salt Growth Index) = seedling area × Fv/Fm (photosynthesis efficiency)

Summary of results:

Ectopic expression of Ceres Clone 229668 under the control of the 35S promoter enhances tolerance to salt stress that causes necrotic lesions and stunted growth in wild-type Ws seedlings.

Example 12: ME24217; Clone 375578; SEQ ID No. 144

Wild-type *Arabidopsis thaliana* Wassilewskija was transformed with a Ti plasmid carrying the 35S promoter operatively linked to Ceres Clone 375578 (SEQ ID NO: 144), and two transgenic lines, ME24217-07-$T_2$ and ME24217-09-$T_2$, were investigated for tolerance to salt stress. When grown on MS agar plates containing 150 mM NaCl, these transgenic lines showed increase tolerance to salt stress in quantitative assays as compared to non-transgenic control seedlings.

When grown on MS agar plates containing 150 mM NaCl, ME24217-07-$T_2$ and ME24217-09-$T_2$ transgenic plants showed significantly greater seedling area and SGI relative to non-transgenic plants. As shown in Table 12, the T2-generation SGI value for ME24217-07 seedlings increased 30.41% and ME24217-09 seedlings increased 134.46%, as compared to non-transgenic control seedlings. The differences in SGI values between transgenic and non-transgenic seedlings have statistically significant P values for ME24217-07-$T_2$ and ME24217-09-$T_2$ transgenic lines, and these quantitative experiments clearly demonstrate that ectopic expression of Ceres Clone 375578 results in enhanced tolerance to salt stress in transgenic seedlings.

TABLE 12

Validation assay of ME24217salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME24217-07-$T_2$ | 4.69 | 0.413823734 | 20 | 3.6 | 0.4284669 | 30 | 3.62E−02 | 30.41% |
| ME24217-09-$T_2$ | 4.92 | 0.446345081 | 22 | 2.1 | 0.506974 | 22 | 7.20E−05 | 134.46% |

*SGI (Salt Growth Index) = seedling area × Fv/Fm (photosynthesis efficiency)

Summary of results:
Ectopic expression of Ceres Clone 375578 under the control of the 35S promoter enhances tolerance to salt stress that causes necrotic lesions and stunted growth in wild-type Ws seedlings.

Example 13: ME02064C; Clone 375578C: SEQ ID No. 140

Wild-type *Arabidopsis thaliana* Wassilewskija was transformed with a Ti plasmid carrying the 35S promoter operatively linked to Ceres Clone 375578 (SEQ ID NO: 140), and six transgenic lines, ME02064C-01-$T_2$, ME02064C-02-$T_2$, ME02064C-03-$T_2$, ME02064C-04-$T_2$, ME02064C-05-$T_2$ and ME02064C-06-$T_2$ were investigated for tolerance to salt stress.

When grown on MS agar plates containing 150 mM NaCl, most of these transgenic lines did not show tolerance to salt stress in quantitative assays as compared to non-transgenic control seedlings.

Table 13 shows that, when grown on MS agar plates containing 100 mM NaCl, the T2-generation SGI value for: ME02064C-01-$T_2$ seedlings as compared to non-transgenic control seedlings was 0.55%; ME02064C-02-$T_2$ seedlings as compared to non-transgenic control seedlings was 1.31%; ME02064C-03-$T_2$ seedlings as compared to non-transgenic control seedlings was 9.67%; ME02064C-04-$T_2$ seedlings as compared to non-transgenic control seedlings was −7.78%; ME02064C-05-$T_2$ seedlings as compared to non-transgenic control seedlings was −15.77%; and ME02064C-06-$T_2$ seedlings as compared to non-transgenic control seedlings 17.78%.

TABLE 13

Validation assay of ME02064C salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME02064C-01-$T_2$ | 10.89 | 0.735174679 | 33 | 10.83 | 0.707901 | 34 | 0.4769106 | 0.55% |
| ME02064C-02-$T_2$ | 10.7 | 0.595225094 | 50 | 10.56 | 0.971548 | 21 | 0.4517289 | 1.31% |
| ME02064C-03-$T_2$ | 9.39 | 0.582009053 | 48 | 8.56 | 0.958475 | 23 | 0.2314441 | 9.67% |
| ME02064C-04-$T_2$ | 10.66 | 0.555387069 | 51 | 11.56 | 1.046386 | 21 | 0.2252269 | −7.78% |
| ME02064C-05-$T_2$ | 10.84 | 0.60377588 | 48 | 12.87 | 0.839921 | 24 | 2.68E−02 | −15.77% |
| ME02064C-06-$T_2$ | 12.55 | 0.608556025 | 44 | 10.65 | 0.764179 | 28 | 2.83E−02 | 17.78% |

*SGI (Salt Growth Index) = seedling area × Fv/Fm (photosynthesis efficiency)

Summary of results:
Ectopic expression of Ceres Clone 375578 under the control of the 35S might not promote enhances tolerance to salt stress that causes necrotic lesions and stunted growth in wild-type Ws seedlings.

Example 14: ME02064P1; Clone 375578P1—Amino Acids 1 to 135 of SEQ ID No. 140

Wild-type *Arabidopsis thaliana* Wassilewskija was transformed with a Ti plasmid carrying the 35S promoter operatively linked to a nucleic acid encoding Ceres Clone 375578P1 (amino acids 1 to 135 of SEQ ID NO: 140), a 3' truncation variant of Ceres Clone 375578 described above in Example 1. Five transgenic lines, ME02064P1-03-$T_2$, ME02064P1-07-$T_2$, ME02064P1-09-$T_2$, ME02064P1-10-$T_2$ and ME02064P1-15-$T_2$ were investigated for tolerance to salt stress. All five of these transgenic lines showed tolerance to salt stress in quantitative assays as compared to non-transgenic control seedlings. As shown in Table 10, the T2-generation SGI value for ME02064P1 seedlings increased by 32.57%, 89.52%, 66.84%, 25.43%, 36.95%. compared to non-transgenic control seedlings.

When grown on MS agar plates containing 150 mM NaCl, ME02064P1-03, ME02064P1-07, ME02064P1-09, ME02064P1-10 and ME02064P1-15 transgenic plants showed significantly greater seedling area and SGI relative to non-transgenic plants. As shown in Table 14, the T2-generation SGI value for ME02064P1-03 seedlings increased 32.57%, ME02064P1-07 seedlings increased 89.52%, ME02064P1-09 seedlings increased 66.84%, ME02064P1-10 seedlings increased 25.43% and ME02064P1-15 seedlings increased 36.95% as compared to non-transgenic control seedlings. The differences in SGI values between transgenic and non-transgenic seedlings have statistically significant under P values for transgenic lines ME02064P1-03-$T_2$, ME02064P1-07-$T_2$, ME02064P1-09-$T_2$, ME02064P1-10-$T_2$ and ME02064P1-15-$T_2$, and these quantitative experiments clearly demonstrate that ectopic expression of Ceres Clone 37558P1 results in enhanced tolerance to salt stress in transgenic seedlings.

TABLE 14

Validation assay of ME02064P1 salt stress tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME02064P1-03-$T_2$ | 10.76 | 0.507929031 | 47 | 8.12 | 0.925474 | 25 | 7.29E−03 | 32.57% |
| ME02064P1-07-$T_2$ | 13.26 | 0.561088966 | 54 | 7 | 1.165372 | 16 | 3.87E−06 | 89.52% |
| ME02064P1-09-$T_2$ | 12.23 | 0.654850534 | 54 | 7.33 | 1.141553 | 17 | 1.99E−04 | 66.84% |
| ME02064P1-10-$T_2$ | 15.63 | 0.570291003 | 40 | 12.46 | 0.845552 | 32 | 1.36E−03 | 25.43% |
| ME02064P1-15-$T_2$ | 11.84 | 0.607966 | 42 | 8.64 | 0.959856 | 30 | 3.20E−03 | 36.95% |

*SGI (Salt Growth Index) = seedling area × Fv/Fm (photosynthesis efficiency)

Summary of Results:
Ectopic expression of Clone 375587P1 under the control of the 35S promoter enhances tolerance to salt stress.

Example 15: ME02064P2; Clone 375578P2—Amino Acids 188 to 498 of SEQ ID No. 140

Wild-type *Arabidopsis thaliana* Wassilewskija was transformed with a Ti plasmid carrying the 35S promoter and a nucleic acid encoding Ceres Clone 375578P2 (amino acids 188 to 498 of SEQ ID NO: 140), a 5' truncation variant of Ceres Clone 375578 described above in Example 1. Eight ME02064P2 transgenic lines were investigated for tolerance to salt. Four transgenic lines, ME02064P2-01-$T_2$, ME02064CP2-04-$T_2$, ME02064P2-05-$T_2$, ME02064P2-06-$T_2$ ME02064P2-07-$T_2$, ME02064P2-$T_2$-08 and ME02064P2-09-$T_2$ did show statistically significant salt tolerance in quantitative assays as compared to non-transgenic control seedlings; and one transgenic lines, ME02064P2-10-$T_2$, showed statistically significant reduction in salt tolerance as compared to non-transgenic control seedlings.

Table 15 shows that, when grown on MS agar plates containing 100 mM NaCl, the T2-generation SGI value for: ME02064P2-01-$T_2$ seedlings as compared to non-transgenic control seedlings was 1.62%, ME02064P2-04-$T_2$ seedlings as compared to non-transgenic control seedlings was 20.31%, ME02064P2-05-$T_2$ seedlings as compared to non-transgenic control seedlings was 31.24%, ME02064P2-06-$T_2$ seedlings as compared to non-transgenic control seedlings was 41.14%, ME02064P2-07-$T_2$ seedlings as compared to non-transgenic control seedlings was 15.91%, ME02064P2-08-$T_2$ seedlings as compared to non-transgenic control seedlings was 40.82%, ME02064P2-09-$T_2$ seedlings as compared to non-transgenic control seedlings was 135.79%, and ME02064P2-10-$T_2$ was −12.36% as compared to non-transgenic control seedlings.

When grown on MS agar plates containing 100 mM NaCl, ME02064P2-01-$T_2$, ME02064P2-04-$T_2$, ME02064P2-05-$T_2$, ME02064P2-06-$T_2$, ME02064P2-07-$T_2$, ME02064P2-08-$T_2$ and ME02064P2-09-$T_2$ transgenic plants showed significantly greater seedling area and SGI relative to non-transgenic plants. However as shown in Table 3, the T2-generation SGI value for ME02064P2-10-$T_2$ seedlings showed a decrease in SGI compared to non-transgenic control seedlings.

TABLE 15

Validation assay of ME02064P2 on salt tolerance in one generation

| ME Events | SGI* of transgenics | | | SGI of pooled non-transgenics | | | P value | % of SGI increase |
|---|---|---|---|---|---|---|---|---|
| | Avg | SE | N | Avg | SE | N | | |
| ME02064P2-01-$T_2$ | 9.84 | 0.687493743 | 53 | 9.68 | 1.261045 | 19 | 0.4567634 | 1.62% |
| ME02064P2-04-$T_2$ | 5.2 | 0.558723451 | 47 | 4.32 | 0.560634 | 25 | 0.1357713 | 20.31% |
| ME02064P2-05-$T_2$ | 8.42 | 0.714218299 | 45 | 6.41 | 0.623421 | 27 | 0.0190578 | 31.24% |
| ME02064P2-06-$T_2$ | 8.56 | 0.515029349 | 48 | 6.07 | 0.654098 | 24 | 1.88E−03 | 41.14% |
| ME02064P2-07-$T_2$ | 12.3 | 0.647077232 | 47 | 10.61 | 0.8768 | 25 | 6.29E−02 | 15.91% |
| ME02064P2-08-$T_2$ | 9.16 | 0.724681422 | 37 | 6.51 | 0.73405 | 35 | 6.08E−03 | 40.82% |
| ME02064P2-09-$T_2$ | 5.72 | 0.489863069 | 47 | 2.43 | 0.182583 | 24 | 1.19E−08 | 135.79% |
| ME02064P2-10-$T_2$ | 9.32 | 0.908174851 | 21 | 10.63 | 0.70877 | 51 | 0.1289273 | 12.36% |

*SGI (Salt Growth Index) = seedling area × Fv/Fm (photosynthesis efficiency)

Summary of Results:
Ectopic expression of Clone 375587P2 under the control of the 35S promoter enhances tolerance to salt stress. Ceres Clone 375578P2 retains the α-β domains of Ceres Clone 375578 located within amino acid residues 137-157 of SEQ ID NO: 140) but does not retain the δ-Γ domains of Ceres Clone 375578 of SEQ ID NO: 140.

Example 16: ME10681; Clone 335348 SEQ ID No. 141

Wild-type *Arabidopsis thaliana* Wassilewskija was transformed with a Ti plasmid carrying the 35S promoter operatively linked to Ceres cDNA 335348 (SEQ ID NO: 141). Wildtype Ws seedlings showed necrotic lesions and stunted growth on plates containing 100 or 150 μM SA, whereas the transgenic plants showed significantly better growth.

Three transformed lines, ME10681-01, ME10681-02 and ME10681-05, were quantitatively studied by growth on MS agar plates containing 100 μM SA. After 14 days, plates were scanned using an EPSON color scanner or fluorescence scanner and SAGI calculated for each plant. The data is summarized in Table 16.

When grown on MS agar plates containing 100 μM SA, ME10681-02-$T_2$ and ME10681-05-$T_2$ transgenic plants showed significantly increased seedling area and SAGI relative to non-transgenic plants. However ME10681-01-$T_2$ showed a slight decrease in SAGI relative to non-transgenic plants. As shown in Table 12, the $T_2$ generation SAGI value for ME10681-01-$T_2$, ME10681-02-$T_2$ and ME10681-05-$T_2$ seedlings was −3.29%, 17.65% and 51.84%, respectively. The differences between transgenic and non-transgenic seedlings have statistically significant P values for lines ME10681-02-$T_2$ and ME10681-05-$T_2$, and clearly demonstrate enhanced tolerance to oxidative stress is a result of the ectopic expression of Ceres cDNA 36505846 in the ME10681 transformant lines.

TABLE 16

Salicylic acid validation assay of ME10681 in one generation

| ME Events | Seedling area of transgenics | | | Seedling area of pooled non-transgenics | | | P value | % Seedling area increase |
| --- | --- | --- | --- | --- | --- | --- | --- | --- |
| | Avg | SE | N | Avg | SE | N | | |
| ME10681-01-$T_2$ | 0.56 | 0.096445 | 18 | 0.58 | 0.061856 | 53 | 0.434159 | −3.29% |
| ME10681-02-$T_2$ | 0.67 | 0.06042 | 38 | 0.38 | 0.079644 | 32 | 0.002198 | 17.65% |
| ME10681-05-$T_2$ | 0.68 | 0.072271 | 43 | 0.45 | 0.108539 | 25 | 0.039761 | 51.84% |

Summary of Results:
In sum, ectopic expression of Ceres Clone 335348 under the control of the 35S promoter enhances oxidative stress tolerance that causes necrotic lesions and stunted growth in wild-type WS seedlings.

Example 17: ME24091; Clone 106263; SEQ ID No. 136

Wild-type *Arabidopsis thaliana* Wassilewskija was transformed with a Ti plasmid carrying the 35S promoter operatively linked to Ceres cDNA 016263 (SEQ ID NO: 135). Wildtype Ws seedlings showed necrotic lesions and stunted growth on plates containing 100 or 150 μM SA, whereas the transgenic plants showed significantly better growth.

Ten transformed lines, ME24091-01-$T_2$, ME24091-02-$T_2$, ME24091-03-$T_2$, ME24091-04-$T_2$ ME24091-05-$T_2$, ME24091-06-$T_2$ ME24091-07-$T_2$, ME24091-08-$T_2$, ME24091-09-$T_2$ and ME24091-10-$T_2$, were quantitatively studied by growth on MS agar plates containing 100 μM SA. After 14 days, plates were scanned using an EPSON color scanner or fluorescence scanner and SAGI calculated for each plant.

When grown on MS agar plates containing 100 μM SA, ME24091-01-$T_2$, ME24091-02-$T_2$, ME24091-03-$T_2$, ME24091-04-01-$T_3$, ME24091-04-$T_2$, ME24091-05-01-$T_3$, ME24091-05-$T_2$, ME24091-06-01, ME24091-06, ME24091-07-01, ME24091-07, ME24091-08-01, ME24091-08, ME24091-09-01, ME24091-09, ME24091-10-01 and ME24091-10 transgenic plants showed significantly increased seedling area and SAGI relative to non-transgenic plants. As shown in Table 17, the $T_2$ generation SAGI value for ME24091-01, ME24091-02, ME24091-03, ME24091-04 ME24091-05, ME24091-06 ME24091-07, ME24091-08, ME24091-09 and ME24091-10 seedlings increased by 119.47%, 198.00% and 133.67%, 241.50%, 143.70% and 248.12%, 186.59%, 188.86%, 285.42% and 180.46% respectively. The differences between transgenic and non-transgenic seedlings have statistically significant P values for transgenic lines ME24091-01, ME24091-02, ME24091-03, ME24091-04-01, ME24091-04 ME24091-05-01, ME24091-05, ME24091-06-01, ME24091-06, ME24091-07-01, ME24091-07, ME24091-08, ME24091-09-01, ME24091-09, and ME24091-10, and clearly demonstrate that the enhanced tolerance to oxidative stress is a result of the ectopic expression of Ceres Clone 106263 in the ME24091 transformant lines.

TABLE 17

Salicylic acid validation assay of ME24091 in two generations

| ME Events | Seedling area of transgenics | | | Seedling area of pooled non-transgenics | | | P value | % Seedling area increase |
| --- | --- | --- | --- | --- | --- | --- | --- | --- |
| | Avg | SE | N | Avg | SE | N | | |
| ME24091-01-$T_2$ | 0.69 | 0.055882059 | 29 | 0.58 | 0.070002209 | 38 | 0.105475324 | 19.47% |
| ME24091-02-$T_2$ | 0.44 | 0.050576014 | 41 | 0.22 | 0.054717602 | 27 | 0.002577564 | 98.00% |
| ME24091-03-$T_2$ | 0.58 | 0.054269056 | 43 | 0.44 | 0.085715224 | 26 | 0.076183067 | 33.67% |
| ME24091-04-$T_2$ | 0.54 | 0.050859903 | 45 | 0.22 | 0.077668008 | 19 | 0.000634704 | 141.50% |
| ME24091-04-01-$T_3$ | 0.39 | 0.07715765 | 20 | 0.24 | 0.07271465 | 20 | 0.081950663 | 61.93% |
| ME24091-05-$T_2$ | 0.55 | 0.048581793 | 42 | 0.38 | 0.072915009 | 27 | 0.029849118 | 43.70% |
| ME24091-05-01-$T_3$ | 0.38 | 0.068463201 | 21 | 0.15 | 0.05109963 | 30 | 0.005958129 | 144.90% |
| ME24091-06-$T_2$ | 0.71 | 0.049360913 | 39 | 0.29 | 0.063969074 | 23 | 1.13831E−06 | 148.12% |
| ME24091-06-01-$T_2$ | 0.49 | 0.073404661 | 19 | 0.22 | 0.063271768 | 22 | 0.004691952 | 118.19% |
| ME24091-07-$T_2$ | 0.69 | 0.054095931 | 37 | 0.37 | 0.07390372 | 25 | 0.000414138 | 86.59% |
| ME24091-07-01-$T_3$ | 0.49 | 0.052850446 | 33 | 0.19 | 0.049649799 | 22 | 5.3153E−05 | 162.61% |
| ME24091-08-$T_2$ | 0.64 | 0.059981819 | 24 | 0.34 | 0.071776729 | 23 | 0.00111815 | 88.86% |
| ME24091-08-01-$T_3$ | 0.44 | 0.050181996 | 27 | 0.40 | 0.074557785 | 26 | 0.306877156 | 11.48% |
| ME24091-09-$T_2$ | 0.81 | 0.056031311 | 38 | 0.29 | 0.067403065 | 22 | 5.88685E−08 | 185.42% |
| ME24091-09-01-$T_3$ | 0.45 | 0.055439617 | 36 | 0.28 | 0.05131548 | 31 | 0.0116714 | 62.95% |
| ME24091-10-$T_2$ | 0.56 | 0.048643058 | 39 | 0.31 | 0.062146975 | 29 | 0.001240527 | 80.46% |
| ME24091-10-01-$T_3$ | 0.36 | 0.051198395 | 31 | 0.26 | 0.066281225 | 22 | 0.114418402 | 39.44% |

Summary of Results:
In sum, ectopic expression of Ceres cDNA Clone 106263 under the control of the 35S promoter enhances oxidative stress tolerance that causes necrotic lesions and stunted growth in wild-type Ws seedlings.

Example 18: Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., *Proc. Natl. Acad. Sci. USA,* 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Missouri, USA was used to determine BLAST sequence identity and E-value. The BLASTP version 2.0 program includes the following parameters: 1) an E-value cutoff of 1.0e-5; 2) a word size of 5; and 3) the –postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of 10-5 and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID Nos. 2, 35, 41, 43, 44, 45, 86, 109, 135, 136, 138, 140, 141, 142, 143 and to amino acids X-Y of SEQ ID NO: 140 and to amino acids X-Y of SEQ ID NO: 140 are shown in FIGS. 1-6 and the Sequence Listing.

Example 19: Determination of Functional Homologs by Hidden Markov Models

Hidden Markov Models (HMMs) were generated by the program HMMER 2.3.2. To generate each HMM, the default HMMER 2.3.2 program parameters, conFigured for glocal alignments, were used.

An HMM was generated using the sequences shown in FIG. 1 as input. These sequences were input into the model and the HMM bit score for each sequence is shown in the Sequence Listing. Additional sequences were input into the model, and the HMM bit scores for the additional sequences are shown in the Sequence Listing. The results indicate that these additional sequences are functional homologs of SEQ ID NO: 86.

HMMs were also generated using the sequences shown in FIGS. 2-6 as input. These sequences were input into the respective models and the corresponding HMM bit score for each sequence is shown in the Sequence Listing. Additional sequences were input into the models, and the HMM bit scores for the additional sequences are shown in the Sequence Listing. The results indicate that these additional sequences are functional homologs of the groups in FIGS. 2-6.

In an alternative embodiment, the HMM is generated with the proviso that none of the amino acids specifically described in PCT/US2007/06544 are used. In particular the following amino acids appearing in the Sequence Listing of PCT/US2007/06544 are excluded: SEQ ID NO:99, SEQ ID NO:100, SEQ ID NO:102, SEQ ID NO:103, SEQ ID NO:104, SEQ ID NO:180, SEQ ID NO:252, SEQ ID NO:298, SEQ ID NO:300, SEQ ID NO:301, SEQ ID NO:306 and SEQ ID NO:312.

REFERENCES

The following references are cited in the Specification. Each of the references from the patent and periodical literature cited herein is hereby expressly incorporated in its entirety by such citation.

Zhang et al. (2004) *Plant Physiol.* 135:615.
Salomon et al. (1984) *EMBO J.* 3:141.
Herrera-Estrella et al. (1983) *EMBO J.* 2:987.
Escudero et al. (1996) *Plant J.* 10:355.
Ishida et al. (1996) *Nature Biotechnology* 14:745.
May et al. (1995) *Bio/Technology* 13:486)
Armaleo et al. (1990) *Current Genetics* 17:97.
Smith. T. F. and Waterman, M. S. (1981) *Adv. App. Math.* 2:482.
Needleman and Wunsch (1970) *J. Mol. Biol.* 48:443.
Pearson and Lipman (1988) *Proc. Natl. Acad. Sci.* (*USA*) 85:2444.
Yamauchi et al. (1996) *Plant Mol Biol.* 30:321-9.
Xu et al. (1995) *Plant Mol. Biol.* 27:237.
Yamamoto et al. (1991) *Plant Cell* 3:371.
P. Tijessen, "Hybridization with Nucleic Acid Probes" In Laboratory Techniques in Biochemistry and Molecular Biology, P. C. vand der Vliet, ed., c. 1993 by Elsevier, Amsterdam.
Bonner et al., (1973) *J. Mol. Biol.* 81:123.
Sambrook et al., Molecular Cloning: A Laboratory Manual, Second Edition, Cold Spring Harbor Laboratory Press, 1989, New York.
Shizuya et al. (1992) *Proc. Natl. Acad. Sci. USA*, 89: 8794-8797.
Hamilton et al. (1996) *Proc. Natl. Acad. Sci. USA*, 93: 9975-9979.
Burke et al. (1987) *Science*, 236:806-812.
Sternberg N. et al. (1990) *Proc Natl Acad Sci USA.*, 87:103-7.
Bradshaw et al. (1995) *Nucl Acids Res*, 23: 4850-4856.
Frischauf et al. (1983) *J. Mol Biol*, 170: 827-842.
Huynh et al., Glover N M (ed) DNA Cloning: A practical Approach, Vol. 1 Oxford: IRL Press (1985).
Walden et al. (1990) *Mol Cell Biol* 1: 175-194.
Vissenberg et al. (2005) *Plant Cell Physiol* 46:192.
Husebye et al. (2002) *Plant Physiol* 128:1180.
Plesch et al. (2001) *Plant J* 28:455.
Weising et al. (1988) *Ann. Rev. Genet.*, 22:421.
Christou (1995) *Euphytica*, v. 85, n. 1-3:13-27.
Newell (2000)
Griesbach (1987) *Plant Sci.* 50:69-77.
Fromm et al. (1985) *Proc. Natl. Acad. Sci. USA* 82:5824.
Paszkowski et al. (1984) *EMBO J.* 3:2717.
Klein et al. (1987) *Nature* 327:773.
Willmitzer, L. (1993) Transgenic Plants. In: iotechnology, A Multi-Volume Comprehensive treatise (H. J. Rehm, G. Reed, A. Püler, P. Stadler, eds., Vol. 2, 627-659, VCH Weinheim-New York-Basel-Cambridge).
*Crit. Rev. Plant. Sci.* 4:1-46.
Fromm et al. (1990) *Biotechnology* 8:833-844.
Cho et al. (2000) *Planta* 210:195-204.
Brootghaerts et al. (2005) *Nature* 433:629-633.
Lincoln et al. (1998) *Plant Mol. Biol. Rep.* 16:1-4.
Lacomme et al. (2001), "Genetically Engineered Viruses" (C. J. A. Ring and E. D. Blair, Eds).
Pp. 59-99, BIOS Scientific Publishers, Ltd. Oxford, U K.
Huh G H, Damsz B, Matsumoto T K, Reddy M P, Rus A M, Ibeas J I, Narasimhan M L, Bressan R A, Hasegawa P M, 2002, Salt causes ion disequilibrium-induced programmed cell death in yeast and plants. *Plant J* 29(5): 649-59.
Kang D K, Li X M, Ochi K, Horinouchi S, 1999, Possible involvement of cAMP in aerial mycelium formation and secondary metabolism in *Streptomyces griseus*. Microbiology, 145 (Pt 5):1161-72.
Kerk D, Bulgrien J, Smith D W, Gribskov M, 2003, *Arabidopsis* proteins containing similarity to the universal stress protein domain of bacteria. *Plant Physiol.* 131(3): 1209-19.
Zhu J K, 2001, Cell signaling under salt, water and cold stresses. *Curr Opin Plant Biol.* 4(5):401-6.
Susstrunk U, Pidoux J, Taubert S, Ullmann A, Thompson C J, 1998, Pleiotropic effects of cAMP on germination, antibiotic biosynthesis and morphological development in *Streptomyces coelicolor. Mol Microbiol* 30(1):33-46.
Davletova S, Schlauch K, Coutu J, Mittler R., 2005, The zinc-finger protein Zat12 plays a central role in reactive oxygen and abiotic stress signaling in *Arabidopsis. Plant Physiol* 139(2):847-56.
Fowler S G, Cook D, Thomashow M F., 2005, Low temperature induction of *Arabidopsis* CBF1, 2, and 3 is gated by the circadian clock. *Plant Physiol* 137(3):961-8.

Nachin L, Nannmark U, Nystom T (2005) Differential roles of the universal stress proteins of *Escherichia coli* in oxidative stress resistance, adhesion and motility *J Bacteriol* 187(18):6265-72.

Rizhsky L, Davletova S, Liang H, Mittler R, 2004, The zinc finger protein Zat12 is required for cytosolic ascorbate peroxidase 1 expression during oxidative stress in *Arabidopsis. J Biol Chem.* 19; 279(12):11736-43.

Vogel J T, Zarka D G, Van Buskirk H A, Fowler S G, Thomashow M F, 2005, Roles of the CBF2 and ZAT12 transcription factors in configuring the low temperature transcriptome of *Arabidopsis. Plant J.* 41(2):195-211.

Sanchez-Barrena M J, Martinez-Ripoll M, Zhu J K, Albert A., 2005, The structure of the *Arabidopsis thaliana* SOS3: molecular mechanism of sensing calcium for salt stress response *J Mol Biol.* 345(5):1253-64.

Griffen, H. G, and Gasson, M. J. (1995) The Gene (aroK) Encoding Shikimate Kinase I from *E. coli.* DNA Seq., 5(3):195-197.

Susstrunk et al. (1998) *Mol Microbiol,* 30(1):33-46

Kang et al. (1999) *Microbiology,* 145:1161-72.

Sauter M, Rzewuski G, Marwedel T, Lorbiecke R (2002) The novel ethylene-regulated gene OsUsp1 from rice encodes a member of a plant protein family related to prokaryotic universal stress proteins. *J Exp Bot* 53 (379): 2325-31.

Kasuga et al. (1999) *Nature Biotech* 17: 287-291.

Rus et al. (2001) PNAS 98:14150-14155.

Shi et al. (2000) PNAS 97:6896-6901.

Apse et al. (1999) Science 285:1256-1258.

Zhang et al. (2001) PNAS 98:12832-12836.

Berthomieu et al. (2003) EMBO J 22:2004-2014.

Ren et al. (2005) Nat Genet. 37:1029-30

Davletova et al (2005) Plant Physiol. 139:847-56

The invention claimed is:

1. A plant cell transformed with an exogenous nucleic acid said exogenous nucleic acid comprising a heterologous promoter operably linked to a nucleotide sequence encoding a polypeptide wherein said polypeptide has 95 percent or greater sequence identity to the amino acid sequence of SEQ ID NO:141 or SEQ ID NO:143, and wherein overexpression of said polypeptide in a transformed plant grown from said transformed plant cell has an increased level of tolerance to salinity or oxidative stress as compared to the corresponding level of tolerance to salinity or oxidative stress of a control plant of the same species cultivated under the same conditions that does not comprise said exogenous nucleic acid.

2. The transformed plant cell of claim 1, wherein the polynucleotide sequence encodes a polypeptide comprising an amino acid sequence having 97 percent or greater sequence identity to the amino acid sequence of SEQ ID NO:141 or SEQ ID NO:143.

3. The transformed plant cell of claim 1, wherein the polynucleotide sequence encodes a polypeptide comprising an amino acid sequence having 98 percent or greater sequence identity to the amino acid sequence of SEQ ID NO:141 or SEQ ID NO:143.

4. A transgenic plant comprising the plant cell of claim 1.

5. The transgenic plant of claim 4, wherein said plant is a member of a species selected from the group consisting of *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), and *Pennisetum glaucum* (pearl millet).

6. A seed tissue or vegetative tissue comprising the plant cell of claim 1, wherein said seed tissue or vegetative tissue comprises the exogenous nucleic acid.

7. A food or feed product comprising the seed or vegetative tissue of claim 6, wherein the food or feed product comprises the exogenous nucleic acid.

8. The transformed plant cell of claim 1, wherein the polynucleotide sequence encodes a polypeptide comprising the amino acid sequence of SEQ ID NO:141 or SEQ ID NO:143.

9. The transgenic plant of claim 4, wherein the polynucleotide sequence encodes a polypeptide comprising the amino acid sequence of SEQ ID NO:141 or SEQ ID NO:143.

10. A seed produced by the transgenic plant of claim 4, wherein the seed comprises the exogenous nucleic acid.

* * * * *